US012590147B2

(12) United States Patent
Trkulja et al.

(10) Patent No.: US 12,590,147 B2
(45) Date of Patent: Mar. 31, 2026

(54) TRPV1 EPITOPES AND ANTIBODIES

(71) Applicant: OBLIQUE THERAPEUTICS AB, Gothenburg (SE)

(72) Inventors: Carolina Trkulja, Hökerum (SE); Max Davidson, Gothenburg (SE); Owe Orwar, Hovås (SE)

(73) Assignee: OBLIQUE THERAPEUTICS AB, Gothenburg (SE)

( * ) Notice: Subject to any disclaimer, the term of this patent is extended or adjusted under 35 U.S.C. 154(b) by 922 days.

(21) Appl. No.: 17/784,127

(22) PCT Filed: Dec. 10, 2020

(86) PCT No.: PCT/EP2020/085629
§ 371 (c)(1),
(2) Date: Jun. 10, 2022

(87) PCT Pub. No.: WO2021/116341
PCT Pub. Date: Jun. 17, 2021

(65) Prior Publication Data
US 2023/0322916 A1      Oct. 12, 2023

(30) Foreign Application Priority Data

Dec. 10, 2019      (GB) ..................................... 1918103

(51) Int. Cl.
*C07K 16/28*        (2006.01)
*A61K 47/68*        (2017.01)

(52) U.S. Cl.
CPC .......... *C07K 16/28* (2013.01); *A61K 47/6811* (2017.08); *A61K 47/6849* (2017.08); *C07K*

2317/34 (2013.01); *C07K 2317/565* (2013.01); *C07K 2317/76* (2013.01)

(58) Field of Classification Search
None
See application file for complete search history.

(56) References Cited

U.S. PATENT DOCUMENTS

2011/0104301 A1      5/2011   Ahern et al.

FOREIGN PATENT DOCUMENTS

| CN | 104520331 A | 4/2014 |
| CN | 105348381 A | 2/2016 |
| CN | 107531792 A | 1/2018 |
| EP | 1493438 | 1/2005 |

(Continued)

OTHER PUBLICATIONS

Kussie et al., A single engineered amino acid substitution changes antibody fine specificity.J Immunol. Jan. 1, 1994;152(1):146-52. (Year: 1994).*

(Continued)

*Primary Examiner* — Aurora M Fontainhas
(74) *Attorney, Agent, or Firm* — Meunier Carlin & Curfman LLC

(57)        ABSTRACT

The present invention relates to antibodies that bind to TRPV1. The invention also relates to certain epitopes of the protein TRPV1. The invention also relates to immunoconjugates and compositions comprising such antibodies. The invention also provides methods of producing such antibodies. The invention further provides the use of such antibodies for therapeutic purposes, for example in the treatment of pain.

10 Claims, 18 Drawing Sheets

Figure 1:
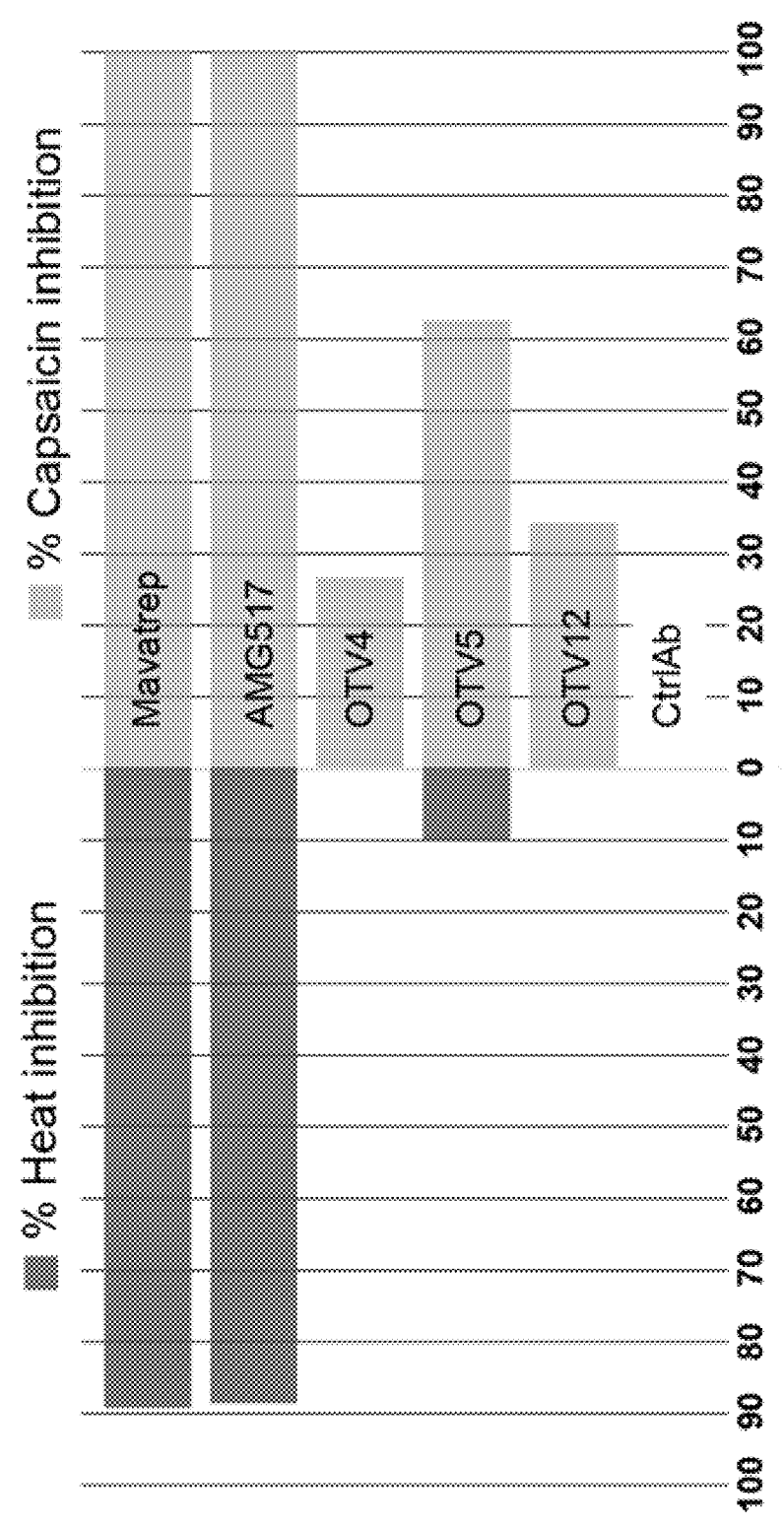

Specification includes a Sequence Listing.

(56) References Cited

FOREIGN PATENT DOCUMENTS

| | | |
|---|---|---|
| JP | 2011153106 A | 8/2011 |
| WO | 9909140 A1 | 2/1999 |
| WO | 99/37675 | 7/1999 |
| WO | 0063415 A1 | 10/2000 |
| WO | 2007/066068 | 6/2007 |
| WO | 2009155932 A2 | 12/2009 |
| WO | 2013109829 A1 | 7/2013 |
| WO | 2013181543 A1 | 12/2013 |
| WO | 2016/156545 | 10/2016 |
| WO | 2018/042010 | 3/2018 |
| WO | 2018065599 A1 | 4/2018 |

OTHER PUBLICATIONS

Edwards et al., The remarkable flexibility of the human antibody repertoire; isolation of over one thousand different antibodies to a single protein, BLyS. J Mol Biol. Nov. 14, 2003;334(1):103-18 (Year: 2003).*

Koenig et al., Mutational landscape of antibody variable domains reveals a switch modulating the interdomain conformational dynamics and antigen binding. PNAS Jan. 24, 2017 114 (4) E486-E495; first published Jan. 5, 2017; (Year: 2017).*

Chen et al., Enhancement and destruction of antibody function by somatic mutation: unequal occurrence is controlled by V gene combinatorial associations. EMBO J. Jun. 15, 1995;14(12):2784-94. (Year: 1995).*

GenPept—Accession No. AAX84657, submitted Mar. 28, 2005.

Fischer, M.J.M., et al., Direct evidence for functional TRPV1/TRPA1 heteromers, European Journal of Physiology (2014) 466(12):2229-2241.

Dyachenko, I.A., et al., Biological Activity of a Polypeptide Modulator of TRPV1 Receptor, Doklady Biological Sciences (2015) 465(2):1-3.

Finkelstein, A.V., et al., Protein physics: A course of lectures with colored and stereoscopic illustrations and problems, Textbook / A.V. Finkelstein, O.B. Ptitsyn.—4th ed., Corr. M.: KDU, 2012, p. 23.

Yarilin, A.A., Fundamentals of Immunology: Textbook.—Moscow Medicine (1999) 608:171-173.

Lana Klionsky et al, "A Polyclonal Antibody to the Prepare Loop of Transient Receptor Potential Vanilloid Type 1 Blocks Channel Activation", The Journal of Pharmacology and Experimental Therapeutics, vol. 319, No. 1, Jan. 1, 2006.

Caterina M J et al, "The vanilloid receptor: a molecular gateway to the pain pathway", Annual Review of Neuroscience, Annual Reviews Inc., Palo Alto, CA, US, vol. 24, Jan. 1, 2001.

Catarina H. J. et al., "Impaired Nociception and Pain Sensation in Mice Lacking the Capsaicin Receptor", Jan. 1, 2000.

Haustrate Aurélien et al, "Monoclonal Antibodies Targeting Ion Channels and Their Therapeutic Potential", Jun. 5, 2019.

Andreev Yaroslav A. et al, "Analgesic Compound from Sea Anemone Heteractis crispa Is the First Polypeptide Inhibitor of Vanilloid Receptor 1 (TRPV1)", Aug. 1, 2008.

International Search Report and Written Opinion in PCT/EP2020/085629. Mailed Apr. 21, 2021. 20 pages.

Chen et al., In Vitro and in Vivo Assays for the Discovery of Analgesic Drugs Targeting TRP Channels. Chapter 18 in TRP Channels, ed. Zhu, M.X., CRC Press/Taylor & Francis, 2011. 8 pages.

Gavva, N. R. et al., Pharmacological blockade of the vanilloid receptor TRPV1 elicits marked hyperthermia in humans. Pain (2008), 136(1-2):202-210.

Manitpisitkul P., et al. Multiple-dose double-blind randomized study to evaluate the safety, pharmacokinetics, pharmacodynamics and analgesic efficacy of the TRPV1 antagonist JNi-39439335 (mavatrep). Scand. J. Pain (2018), 18(2):151-164.

Wegrzyn, I., et al., An Optofluidic Temperature Probe. Sensors (Switzerland) (2013), 13(4):4289-4302.

Nikolaev, M. V. et al., TRPV1 activation power can switch an action mode for its polypeptide ligands. PLoS One (2017) 12:1-16.

Kamei et al. Eur. J. Pharmacol. Role of vanilloid VR1 receptor in thermal allodynia and hyperalgesia in diabetic mice. (2001), 422:83-86.

Papakosta et al., The chimeric approach reveals that differences in the TRPV1 pore domain determine species-specific sensitivity to block of heat activation. The Journal of Biological Chemistry (2011), 286(45):39663-39672.

Jungholm, et al., "Modality-selective mAbs targeting the TRPV1 ion channel" poster presented by Oscar Jungholm, Dec. 10, 2019, at the conference Antibody Engineering & Therapeutics (San Diego, US). 1 page.

Cui et al., Selective disruption of high sensitivity heat activation but not capsaicin activation of TRPV1 channels by pore turret mutations. Journal of General Physiology (2012), 139: 273-283.

Han et al., Development of ELISA to measure TRPVI protein in rat tissues. Journal of Neuroscience Methods, (2011), 200(2):144-152.

Xia et al., TRPV1 Signaling: Mechanistic Understanding and Therapeutic Potential. Current Topics in Medicinal Chemistry, (2011), 11(17):2180-2191.

Martinez-Garcia et al. Differential expression and localization of transient receptor potential vanilloid 1 in rabbit and human eyes. Histol. Histopathol., (2013), 28:1507-1516.

Lucchese et al., How a single amino acid change may alter the immunological information of a peptide. Frontiers in Bioscience, (2012), 4(5):1843-1852.

Rudikoff et al., Single amino acid substitution altering antigen-binding specificity. P. N. A. S., (1982), 79:1979-1983.

Szallasi, A et al., Targeting TRPV1 for pain relief: limits, losers and laurels. Exp. Rev. Invest. Drugs, (2012), 21(9):1351-1369 (2012).

Oblique Therapeutics AB website at http://obliquet.com/portfolio/atrpv1-in-pain. accessed Nov. 2018.

Altshuler E.P et al., Generation of recombinant antibodies and means for increasing their affinity, Advances in Biological Chemistry, 2010, vol. 50, pp. 203-258, see pp. 207-208.

Filippovich Yu.B et al., Biochemical basis of human life. Textbook for universities. Moscow: Vlados, 2005. 407 p.:ill.; see pp. 49-50, 70. English translation included.

Roitt A., Brostoff J., Male D. Immunology. Translated from English-M.: Mir, 2000. -592 p., ill.; see p. 151. English translation included.

Tani et al, Analysis of metabolisms and transports of xylitol using xylose- and xylitol-assimilating *Saccharomyces cerevisiae*, Journal of Bioscience and Bioengineering, vol. 123, Issue 5, May 2017, pp. 613-620.

* cited by examiner

TRPV1 EPITOPES AND ANTIBODIES

REFERENCE TO SEQUENCE LISTING

The Sequence Listing submitted Jan. 10, 2023, as a text file named "10414-081US1_2022_12_09 ST25.txt," created on Dec. 9, 2022, and having a size of 156,500 bytes is hereby incorporated by reference pursuant to 37 C.F.R. § 1.52 (e) (5).

This invention relates generally to the field of epitopes and antibodies, in particular epitopes of the protein TRPV1 and antibodies that bind to TRPV1. Such anti-TRPV1 antibodies have therapeutic uses, such as in the treatment of pain. Antibody-based compositions and methods and uses of the invention also extend to the use of conjugates and other therapeutic combinations, kits and methods.

TRPV1 (transient receptor potential vanilloid type 1) is an ion channel that is sensitive to noxious stimuli such as low pH, high temperatures (T≥42° C.), capsaicin, and inflammatory mediators. TRPV1 has been studied for almost two decades due to its involvement in pain sensation. Several attempts have been made to block the activity of the receptor as a new mode of action for pain therapies, but these attempts have not been successful.

It is well known in the art that capsaicin is an activator of TRPV1 and can cause pain. Capsaicin is routinely used in the art in models to assess TRPV1 activation and pain. Assessing inhibition of capsaicin-induced TRPV1 activation is a well-known model system for assessing the potential of agents to treat pain. Such model systems are described, for example, by Chen et al. (2011) (Chen et al., in *TRP Channels*, ed. MX, Z., 1-14, CRC Press/Taylor & Francis, 2011).

Due to the complexity of its activation mechanisms (as mentioned above it can be activated several stimuli including low pH, high temperatures (T≥42° C.), capsaicin, and inflammatory mediators), the majority of compounds targeting TRPV1 have produced adverse effects such as hyperthermia or loss of heat sensation.

For example, the compound AMG 517 is a potent TRPV1 small molecule antagonist developed by Amgen which inhibits capsaicin, pH and temperature activation of TRPV1. It was terminated after Phase 1 studies where it caused marked hyperthermia in subjects treated for molar extraction (Gavva, N. R. et al. *Pain* (2008), 136 (1-2), 202-210).

Another small molecule TRPV1 antagonist, Mavatrep, developed by Johnson & Johnson has shown efficacy in a Phase 1b study of chronic pain including subjects with knee osteoarthritis, though several subjects reported side-effects of feeling hot and some experiencing minor thermal burns (Manitpisitkul P, et al. *Scand. J. Pain* (2018), 18(2):151-164).

Antibodies that bind to TRPV1 have previously been generated (Klionsky et al., *The Journal of Pharmacology and Experimental Therapeutics* (2006), Vol. 319 (1), pages 192-198), but these antibodies either do not inhibit capsaicin-induced activity of TRPV1 at all or, where an antibody is reported as inhibiting capsaicin-induced activity of TRPV1, an equivalent degree of inhibition of heat-induced activity of TRPV1 is also reported.

There is thus a need for improved treatments of pain. TRPV1 is a clinically and genetically validated target. Successful targeting of TRPV1 could provide a long sought-after solution to providing pain relief at its source.

In particular, identifying epitopes on TRPV1, the targeting of which would lead to the preferential inhibition of capsaicin activation of TRPV1 as opposed to heat-induced activation of TRPV1 would be particularly beneficial. This would guide the identification and generation of agents, such as antibodies, that bind to TRPV1 and reduce capsaicin activation of TRPV1 without, or with reduced, heat-related side effects that have been observed with previous small molecule TRPV1 antagonists (e.g. AMG 517 and Mavatrep as described above).

The present inventors have addressed this need by identifying certain epitopes (or regions) in the extracellular region of TRPV1 that are particularly useful to target, e.g. with antibodies, in order to preferentially inhibit capsaicin-induced activation of TRPV1 as opposed to heat-induced activation of TRPV1. The extracellular region of TRPV1 is of course the region (or part) of TRPV1 that is exposed at (or accessible at, e.g. accessible by antibodies at) the extracellular side (or extracellular surface) of a cell when TRPV1 is expressed on (or at) the surface of a cell. The inventors have identified and generated isolated peptides that correspond to (or correspond essentially) to such epitopes. The inventors have also used such isolated peptides to generate antibodies that preferentially inhibit capsaicin activation of TRPV1 as opposed to heat-induced activation of TRPV1.

Thus, in one aspect, the present invention provides an isolated peptide comprising an amino acid sequence selected from the group consisting of (or comprising): SEQ ID NO:2 (OTV3) or a sequence substantially homologous thereto, SEQ ID NO:3 (OTV4) or a sequence substantially homologous thereto, SEQ ID NO:4 (OTV5) or a sequence substantially homologous thereto, SEQ ID NO:5 (OTV6) or a sequence substantially homologous thereto, SEQ ID NO:6 (OTV7) or a sequence substantially homologous thereto, SEQ ID NO:7 (OTV8) or a sequence substantially homologous thereto, SEQ ID NO:8 (OTV9) or a sequence substantially homologous thereto, SEQ ID NO:9 (OTV10) or a sequence substantially homologous thereto, SEQ ID NO:10 (OTV11) or a sequence substantially homologous thereto, SEQ ID NO:11 (OTV12) or a sequence substantially homologous thereto, SEQ ID NO:12 (OTV13) or a sequence substantially homologous thereto, SEQ ID NO:13 (OTV14) or a sequence substantially homologous thereto and SEQ ID NO:14 (OTV15) or a sequence substantially homologous thereto.

As discussed elsewhere herein, such isolated peptides may be used as antigenic peptides to generate antibodies that inhibit TRPV1 activation. Typically, such antibodies inhibit capsaicin-induced activation of TRPV1, typically as opposed to heat-induced activation of TRPV1.

Unless otherwise clear from the context, references to "isolated peptides" or "peptides" of the invention may alternatively be considered references to "isolated epitopes" or "isolated antigenic epitopes".

In some preferred embodiments, the present invention provides an isolated peptide comprising an amino acid sequence selected from the group consisting of (or comprising): SEQ ID NO:3 (OTV4) or a sequence substantially homologous thereto, SEQ ID NO:4 (OTV5) or a sequence substantially homologous thereto, SEQ ID NO:6 (OTV7) or a sequence substantially homologous thereto, SEQ ID NO:8 (OTV9), SEQ ID NO:11 (OTV12) or a sequence substantially homologous thereto and SEQ ID NO:12 (OTV13) or a sequence substantially homologous thereto.

In some preferred embodiments, the present invention provides an isolated peptide comprising an amino acid sequence selected from the group consisting of (or comprising): SEQ ID NO:3 (OTV4) or a sequence substantially homologous thereto, SEQ ID NO:4 (OTV5) or a sequence substantially homologous thereto, and SEQ ID NO: 11 (OTV12) or a sequence substantially homologous thereto.

3                                                4

In some preferred embodiments, the present invention provides an isolated peptide comprising an amino acid sequence selected from the group consisting of (or comprising): SEQ ID NO:2 (OTV3) or a sequence substantially homologous thereto, SEQ ID NO:3 (OTV4) or a sequence substantially homologous thereto, and SEQ ID NO:4 (OTV5) or a sequence substantially homologous thereto.

In some embodiments, the present invention provides an isolated peptide comprising an amino acid sequence selected from the group consisting of (or comprising): SEQ ID NO:2 (OTV3), SEQ ID NO:3 (OTV4), SEQ ID NO:4 (OTV5), SEQ ID NO:5 (OTV6), SEQ ID NO:6 (OTV7), SEQ ID NO:7 (OTV8), SEQ ID NO:8 (OTV9), SEQ ID NO:9 (OTV10), SEQ ID NO:10 (OTV11), SEQ ID NO:11 (OTV12), SEQ ID NO:12 (OTV13), SEQ ID NO:13 (OTV14) and SEQ ID NO:14 (OTV15).

In some preferred embodiments, the present invention provides an isolated peptide comprising an amino acid sequence selected from the group consisting of (or comprising): SEQ ID NO:3 (OTV4), SEQ ID NO:4 (OTV5), SEQ ID NO:6 (OTV7), SEQ ID NO:8 (OTV9), SEQ ID NO:11 (OTV12), and SEQ ID NO:12 (OTV13).

In some preferred embodiments, the present invention provides an isolated peptide comprising an amino acid sequence selected from the group consisting of (or comprising): SEQ ID NO:3 (OTV4), SEQ ID NO:4 (OTV5) and SEQ ID NO:11 (OTV12).

In some preferred embodiments, the present invention provides an isolated peptide comprising an amino acid sequence selected from the group consisting of (or comprising): SEQ ID NO:2 (OTV3), SEQ ID NO:3 (OTV4) and SEQ ID NO:4 (OTV5).

In some embodiments, the present invention provides an isolated peptide consisting of an amino acid sequence selected from the group consisting of: SEQ ID NO:2 (OTV3) or a sequence substantially homologous thereto, SEQ ID NO:3 (OTV4) or a sequence substantially homologous thereto, SEQ ID NO:4 (OTV5) or a sequence substantially homologous thereto, SEQ ID NO:5 (OTV6) or a sequence substantially homologous thereto, SEQ ID NO:6 (OTV7) or a sequence substantially homologous thereto, SEQ ID NO:7 (OTV8) or a sequence substantially homologous thereto, SEQ ID NO:8 (OTV9) or a sequence substantially homologous thereto, SEQ ID NO:9 (OTV10) or a sequence substantially homologous thereto, SEQ ID NO:10 (OTV11) or a sequence substantially homologous thereto, SEQ ID NO:11 (OTV12) or a sequence substantially homologous thereto, SEQ ID NO:12 (OTV13) or a sequence substantially homologous thereto, SEQ ID NO:13 (OTV14) or a sequence substantially homologous thereto, and SEQ ID NO:14 (OTV15) or a sequence substantially homologous thereto. Preferred isolated peptides (and groups of isolated peptides) are disclosed elsewhere herein.

In some embodiments, the present invention provides an isolated peptide consisting of an amino acid sequence selected from the group consisting of: SEQ ID NO:2 (OTV3), SEQ ID NO:3 (OTV4), SEQ ID NO:4 (OTV5), SEQ ID NO:5 (OTV6), SEQ ID NO:6 (OTV7), SEQ ID NO:7 (OTV8), SEQ ID NO:8 (OTV9), SEQ ID NO:9 (OTV10), SEQ ID NO:10 (OTV11), SEQ ID NO:11 (OTV12), SEQ ID NO:12 (OTV13), SEQ ID NO:13 (OTV14) and SEQ ID NO:14 (OTV15). Preferred isolated peptides (and groups of isolated peptides) are disclosed elsewhere herein.

In some embodiments, the isolated peptide may comprise one or more additional amino acids at the N- and/or C-terminus. In some preferred embodiments, the isolated peptide may comprise one or more additional amino acids at the N-terminus. In some preferred embodiments, the isolated peptide may comprise one or more additional amino acids at the C-terminus. In some preferred embodiments, the isolated peptide may comprise one or more additional amino acids at the N-terminus and at the C-terminus. In some preferred embodiments, the isolated peptide may comprise a cysteine (C) residue at the N- and/or at the C-terminus (or an additional cysteine (C) residue at the N- and/or at the C-terminus). In some embodiments, the isolated peptide may comprise a cysteine (C) residue at the N-terminus. In some embodiments, the isolated peptide may comprise a cysteine (C) residue at the C-terminus. In some preferred embodiments, the isolated peptide may comprise a cysteine (C) residue at the N- and C-terminus. The provision of a cysteine residue at a terminus of the isolated peptide can permit convenient attachment to a peptide carrier, e.g. as discussed elsewhere herein. The provision of cysteine residues at both the N- and C-termini provides a convenient means for cyclization of the peptide, if desired.

In some embodiments, the isolated peptide may comprise one or more additional modifications at the N- and/or C-terminus. For example, in some embodiments the isolated peptide may be C-terminally amidated. In some embodiments, the isolated peptide may have a modification (chemical group or linker) that may be used to attach (or link or connect) the peptide to a peptide carrier. In some embodiments, the modification (chemical group or linker) that may be used to attach (or link or connect) the peptide to a peptide carrier is a propargyl (Pra) group. A modification (chemical group or linker) that may be used to attach (or link or connect) the peptide to a peptide carrier may be at the N- and/or C-terminus. In some embodiments, a modification (chemical group or linker such as a propargyl group) that may be used to attach (or link or connect) the peptide to a peptide carrier is at the N-terminus of the isolated peptide.

In some embodiments, the present invention provides an isolated peptide comprising an amino acid sequence selected from the group consisting of (or comprising): SEQ ID NO:16 (OTV3) or a sequence substantially homologous thereto, SEQ ID NO:17 (OTV4) or a sequence substantially homologous thereto, SEQ ID NO:18 (OTV5) or a sequence substantially homologous thereto, SEQ ID NO:19 (OTV6) or a sequence substantially homologous thereto, SEQ ID NO:20 (OTV7) or a sequence substantially homologous thereto, SEQ ID NO:21 (OTV8) or a sequence substantially homologous thereto, SEQ ID NO:22 (OTV9) or a sequence substantially homologous thereto, SEQ ID NO:23 (OTV10) or a sequence substantially homologous thereto, SEQ ID NO:24 (OTV11) or a sequence substantially homologous thereto, SEQ ID NO:25 (OTV12) or a sequence substantially homologous thereto, SEQ ID NO:26 (OTV13) or a sequence substantially homologous thereto, SEQ ID NO:27 (OTV14) or a sequence substantially homologous thereto, and SEQ ID NO:28 (OTV15) or a sequence substantially homologous thereto.

In some preferred embodiments, the present invention provides an isolated peptide comprising an amino acid sequence selected from the group consisting of (or comprising): SEQ ID NO:17 (OTV4) or a sequence substantially homologous thereto, SEQ ID NO:18 (OTV5) or a sequence substantially homologous thereto SEQ ID NO:20 (OTV7) or a sequence substantially homologous thereto, SEQ ID NO:22 (OTV9) or a sequence substantially homologous thereto, SEQ ID NO:25 (OTV12) or a sequence substantially homologous thereto, and SEQ ID NO:26 (OTV13) or a sequence substantially homologous thereto.

In some preferred embodiments, the present invention provides an isolated peptide comprising an amino acid sequence selected from the group consisting of (or comprising): SEQ ID NO:17 (OTV4) or a sequence substantially homologous thereto, SEQ ID NO:18 (OTV5) or a sequence substantially homologous thereto, and SEQ ID NO:25 (OTV12) or a sequence substantially homologous thereto.

In some preferred embodiments, the present invention provides an isolated peptide comprising an amino acid sequence selected from the group consisting of (or comprising): SEQ ID NO:16 (OTV3) or a sequence substantially homologous thereto, SEQ ID NO:17 (OTV4) or a sequence substantially homologous thereto, and SEQ ID NO:18 (OTV5) or a sequence substantially homologous thereto.

In some embodiments, the present invention provides an isolated peptide comprising an amino acid sequence selected from the group consisting of (or comprising): SEQ ID NO:16 (OTV3), SEQ ID NO:17 (OTV4), SEQ ID NO:18 (OTV5), SEQ ID NO:19 (OTV6), SEQ ID NO:20 (OTV7), SEQ ID NO:21 (OTV8), SEQ ID NO:22 (OTV9), SEQ ID NO:23 (OTV10), SEQ ID NO:24 (OTV11), SEQ ID NO:25 (OTV12), SEQ ID NO:26 (OTV13), SEQ ID NO:27 (OTV14), and SEQ ID NO:28 (OTV15).

In some preferred embodiments, the present invention provides an isolated peptide comprising an amino acid sequence selected from the group consisting of (or comprising): SEQ ID NO:17 (OTV4), SEQ ID NO:18 (OTV5), SEQ ID NO:20 (OTV7), SEQ ID NO:22 (OTV9), SEQ ID NO:25 (OTV12), and SEQ ID NO:26 (OTV13).

In some preferred embodiments, the present invention provides an isolated peptide comprising an amino acid sequence selected from the group consisting of (or comprising): SEQ ID NO:17 (OTV4), SEQ ID NO:18 (OTV5), and SEQ ID NO:25 (OTV12).

In some preferred embodiments, the present invention provides an isolated peptide comprising an amino acid sequence selected from the group consisting of (or comprising): SEQ ID NO:16 (OTV3), SEQ ID NO:17 (OTV4), and SEQ ID NO:18 (OTV5).

In some embodiments, the present invention provides an isolated peptide consisting of an amino acid sequence selected from the group consisting of: SEQ ID NO:16 (OTV3) or a sequence substantially homologous thereto, SEQ ID NO:17 (OTV4) or a sequence substantially homologous thereto, SEQ ID NO:18 (OTV5) or a sequence substantially homologous thereto, SEQ ID NO:19 (OTV6) or a sequence substantially homologous thereto, SEQ ID NO:20 (OTV7) or a sequence substantially homologous thereto, SEQ ID NO:21 (OTV8) or a sequence substantially homologous thereto, SEQ ID NO:22 (OTV9) or a sequence substantially homologous thereto, SEQ ID NO:23 (OTV10) or a sequence substantially homologous thereto, SEQ ID NO:24 (OTV11) or a sequence substantially homologous thereto, SEQ ID NO:25 (OTV12) or a sequence substantially homologous thereto, SEQ ID NO:26 (OTV13) or a sequence substantially homologous thereto, SEQ ID NO:27 (OTV14) or a sequence substantially homologous thereto, and SEQ ID NO:28 (OTV15) or a sequence substantially homologous thereto. Preferred isolated peptides (and groups of isolated peptides) are disclosed elsewhere herein.

In some embodiments, the present invention provides an isolated peptide consisting of an amino acid sequence selected from the group consisting of: SEQ ID NO:16 (OTV3), SEQ ID NO:17 (OTV4), SEQ ID NO:18 (OTV5), SEQ ID NO:19 (OTV6), SEQ ID NO:20 (OTV7), SEQ ID NO:21 (OTV8), SEQ ID NO:22 (OTV9), SEQ ID NO:23 (OTV10), SEQ ID NO:24 (OTV11), SEQ ID NO:25

(OTV12), SEQ ID NO:26 (OTV13), SEQ ID NO:27 (OTV14), and SEQ ID NO:28 (OTV15). Preferred isolated peptides (and groups of isolated peptides) are disclosed elsewhere herein.

In some embodiments, the present invention provides an isolated peptide consisting of an amino acid sequence selected from the group consisting of: SEQ ID NO:16 (OTV3), SEQ ID NO:17 (OTV4) and SEQ ID NO:18 (OTV5).

In some embodiments, an isolated peptide comprising (or consisting of) an amino acid sequence of SEQ ID NO:4 or SEQ ID NO:18 (OTV5 sequences), or a sequence substantially homologous thereto, is preferred.

In some embodiments, an isolated peptide comprising (or consisting of) an amino acid sequence of SEQ ID NO:2 or SEQ ID NO:16 (OTV3 sequences), or a sequence substantially homologous thereto, is preferred.

In some embodiments, an isolated peptide comprising (or consisting of) an amino acid sequence of SEQ ID NO:3 or SEQ ID NO:17 (OTV4 sequences), or a sequence substantially homologous thereto, is preferred.

In the context of the isolated peptide sequences of the invention, a sequence "substantially homologous" to a given amino acid sequence may be a sequence containing 1, 2, 3, 4, 5 or 6 (preferably 1, 2 or 3) amino acid substitutions or deletions or additions compared to the given amino acid sequence, or a sequence having at least 70% sequence identity to the given amino acid sequence, or a sequence having at least 6 consecutive amino acids of the given amino acid sequence. Other examples of "substantially homologous" sequences are described elsewhere herein in relation to amino acid sequences that are "substantially homologous" to isolated peptides and these examples of "substantially homologous" sequence are also applicable to the specific peptide sequences mentioned above.

In some preferred embodiments, amino acid sequences that are "substantially homologous" to isolated peptides are sequences having, or sequences comprising, a sequence that has, 1, 2, or 3 amino acid substitutions or additions or deletions (preferably 1 or 2, more preferably 1) compared with the amino acid sequence of the given isolated peptide.

Amino acid sequences that are "substantially homologous" to isolated peptides include sequences that comprise (or consist of) at least 5 or at least 6 consecutive amino acids of the isolated peptides (or comprise or consist of at least 7, at least 8, at least 9, at least 10, at least 11, at least 12, at least 15, at least 20, at least 25 or at least 30 consecutive amino acids of the isolated peptide). Six amino acids is a typical length of peptide/protein sequence that is recognized or bound by an antibody.

Amino acid sequences that are "substantially homologous" to isolated peptides include sequences having, or sequences comprising (or consisting of) a sequence that has, at least 50%, at least 55%, at least 60%, at least 65%, at least 70%, at least 75%, at least 80%, at least 85%, at least 90%, at least 95%, or at least 98% sequence identity to the given isolated peptide sequence. Sequence identities of at least 70%, at least 75%, at least 80%, at least 85%, at least 90%, at least 95%, or at least 98% are preferred.

Alterations in the amino acid sequences can be with conservative or non-conservative amino acids. Preferably said alterations are conservative amino acid substitutions.

A "conservative amino acid substitution", as used herein, is one in which the amino acid residue is replaced with another amino acid residue having a similar side chain. Families of amino acid residues having similar side chains have been defined in the art, including basic side chains (e.g.

lysine, arginine, histidine), acidic side chains (e.g. aspartic acid, glutamic acid), uncharged polar side chains (e.g. asparagine, glutamine, serine, threonine, tyrosine, cysteine), nonpolar side chains (e.g. glycine, cysteine, alanine, valine, leucine, isoleucine, proline, phenylalanine, methionine, tryptophan), beta-branched side chains (e.g. threonine, valine, isoleucine) and aromatic side chains (e.g. tyrosine, phenylalanine, tryptophan, histidine).

The term "substantially homologous" also includes modifications or chemical equivalents of the amino acid sequences of the present invention that perform substantially the same function as the proteins of the invention in substantially the same way. For example, any substantially homologous isolated peptide should typically retain the ability to act as peptide or epitope to (or against) which antibodies which bind to TRPV1 can be generated (or raised).

Methods of carrying out the above described manipulation of amino acids (e.g. to generate "substantially homologous" sequences) are well known to a person skilled in the art.

In some embodiments, the isolated peptides do not contain any internal cysteine residues. By "internal" residue is meant a residue at a position other than the N-terminal and/or C-terminal residue. Thus, in some embodiments, a sequence that is "substantially homologous" to a given amino acid sequence does not have a cysteine (C) residue as the substituting or additional amino acid.

Homology (e.g. sequence identity) may be assessed by any convenient method. However, for determining the degree of homology (e.g. identity) between sequences, computer programs that make multiple alignments of sequences are useful, for instance Clustal W (Thompson, Higgins, Gibson, *Nucleic Acids Res.,* 22:4673-4680, 1994). If desired, the Clustal W algorithm can be used together with BLOSUM 62 scoring matrix (Henikoff and Henikoff, *Proc. Natl. Acad. Sci. USA,* 89:10915-10919, 1992) and a gap opening penalty of 10 and gap extension penalty of 0.1, so that the highest order match is obtained between two sequences wherein at least 50% of the total length of one of the sequences is involved in the alignment. Other methods that may be used to align sequences are the alignment method of Needleman and Wunsch (Needleman and Wunsch, *J. Mol. Biol.,* 48:443, 1970) as revised by Smith and Waterman (Smith and Waterman, *Adv. Appl. Math.,* 2:482, 1981) so that the highest order match is obtained between the two sequences and the number of identical amino acids is determined between the two sequences. Other methods to calculate the percentage identity between two amino acid sequences are generally art recognized and include, for example, those described by Carillo and Lipton (Carillo and Lipton, *SIAM J. Applied Math.,* 48:1073, 1988) and those described in Computational Molecular Biology, Lesk, e.d. Oxford University Press, New York, 1988, Biocomputing: Informatics and Genomics Projects.

Generally, computer programs will be employed for such calculations. Programs that compare and align pairs of sequences, like ALIGN (Myers and Miller, *CABIOS,* 4:11-17, 1988), FASTA (Pearson and Lipman, *Proc. Natl. Acad. Sci. USA,* 85:2444-2448, 1988; Pearson, *Methods in Enzymology,* 183:63-98, 1990) and gapped BLAST (Altschul et al., *Nucleic Acids Res.,* 25:3389-3402, 1997), BLASTP, BLASTN, or GCG (Devereux, Haeberli, Smithies, *Nucleic Acids Res.,* 12:387, 1984) are also useful for this purpose. Furthermore, the Dali server at the European Bioinformatics institute offers structure-based alignments of protein sequences (Holm, *Trends in Biochemical Sciences,* 20:478-

480, 1995; Holm, *J. Mol. Biol.,* 233:123-38, 1993; Holm, *Nucleic Acid Res.,* 26:316-9, 1998).

By way of providing a reference point, sequences according to the present invention having 65%, 70%, 75%, 80%, 85%, 90%, 95%, 96%, 97%, 98% or 99% homology, sequence identity etc. may be determined using the ALIGN program with default parameters (for instance available on Internet at the GENESTREAM network server, IGH, Montpellier, France).

In some embodiments, the present invention provides an isolated peptide that comprises (or consists of) an elongated, truncated or cyclic version of an isolated peptide sequence disclosed herein (or a sequence substantially homologous thereto). In some embodiments, an isolated peptide may be elongated and cyclic (i.e. cyclized). In some embodiments, an isolated peptide may be truncated and cyclic (i.e. cyclized). Elongated, truncated and cyclic versions of peptides are discussed elsewhere herein.

An isolated peptide of the invention may comprise (or consist of) an elongated version of an isolated peptide sequence disclosed herein, or an elongated version of an amino acid sequence substantially homologous to an isolated peptide sequence disclosed herein. For example, one or more additional amino acids (e.g. at least 2, at least 3, at least 4, at least 5, at least 6, at least 7, at least 8 or at 9, at least 10, at least 15 or at least 20 amino acids, or 1-5 or 1-10 or 1-20 amino acids) may be present at one end or both ends of the isolated peptide sequence (or sequence substantially homologous thereto).

An isolated peptide of the invention may comprise (or consist of) a truncated version of an isolated peptide sequence disclosed herein, or a truncated version of an isolated peptide sequence disclosed herein. For example, one or more amino acids (e.g. at least 2, at least 3, at least 4, at least 5, at least 6, at least 7, at least 8 or at 9, at least 10 amino acids, or 1-5 or 1-10 amino acids) may be absent from one end or both ends of the isolated peptide sequence (or sequence substantially homologous thereto).

In some embodiments, isolated peptides may be at least 5, at least 6, at least 7, at least 8, at least 9 or at least 10 amino acids in length, for example 6 to 10, 6 to 12, 6 to 15, 6 to 20, 6 to 25, 6 to 30, 6 to 40, 6 to 50, 6 to 60, or 6 to 75 amino acids in length. Isolated peptides may be, for example, 5 to 7, 5 to 8, 5 to 9, 5 to 10, 5 to 15, 5 to 20, 5 to 25, 5 to 30, 5 to 40, 5 to 50, 5 to 60, 5 to 70, 5 to 75 amino acids in length. Isolated peptides may be, for example, 8 to 10, 8 to 15, 8 to 20, 8 to 25, 8 to 30, 8 to 40, 8 to 50, 8 to 60, 8 to 70, 8 to 75 amino acids in length.

In some embodiments, isolated peptides may be ≤50 amino acids in length, e.g. ≤45, ≤40, ≤35, ≤30, ≤25, ≤20, ≤15 or ≤10 amino acids in length (e.g. 5-10, 5-15, 5-20, 5-25, 5-30, 5-35, 5-40, 5-45, 5-50, 6-10, 6-15, 6-20, 6-25, 6-30, 6-35, 6-40, 6-45, 6-50, 8-10, 8-15, 8-20, 8-25, 8-30, 8-35, 8-40, 8-45, 8-50, 10-15, 10-20, 10-25, 10-30, 10-35, 10-40, 10-45, 10-50, 15-20, 15-25, 15-30, 15-35, 15-40, 15-45, 15-50, 20-25, 20-30, 20-35, 25-30, 25-35 or 25-40, 25-45, 25-50, 30-35, 30-40, 30-45, 30-50, 35-40, 35-45, 35-50, 40-45, 40-50 or 45-50 amino acids in length).

In some embodiments, isolated peptides may be <39 amino acids in length, e.g. ≤38, ≤35, ≤30, ≤25, ≤20, ≤15, ≤10 amino acids in length (e.g. 5-10, 5-15, 5-20, 5-25, 5-30, 5-35, 5-38, 6-10, 6-15, 6-20, 6-25, 6-30, 6-35, 6-38, 8-10, 8-15, 8-20, 8-25, 8-30, 8-32, 8-35, 8-38, 10-15, 10-20, 10-25, 10-30, 10-32, 10-35, 10-38, 15-20, 15-25, 15-30, 15-32, 15-35, 15-38, 20-25, 20-30, 20-35, 25-30, 25-35 or 25-38 amino acids in length). In some embodiments, isolated peptides may be 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 amino acids in length.

In some embodiments, isolated peptides may be <24 amino acids in length, e.g. ≤23, ≤20, ≤15, ≤10 amino acids in length (e.g. 5-10, 5-15, 5-20, 5-23, 6-10, 6-15, 6-20, 6-23, 8-10, 8-15, 8-20, 8-23, 10-15, 10-20, 10-23, 15-20, 15-23 or 20-23 amino acids in length).

In some embodiments, the isolated peptides may be linear peptides (or linear epitopes).

In some embodiments, the isolated peptides may be conformational peptides (or conformational epitopes).

In some embodiments, the isolated peptides may be cyclic (or cyclized) peptides (or cyclic or cyclized epitopes).

In some preferred embodiments, isolated peptides based on SEQ ID NO:2 or SEQ ID NO:16 (or sequences substantially homologous thereto), or based on SEQ ID NO:3 or SEQ ID NO:17 (or sequences substantially homologous thereto), or based on SEQ ID NO:5 or SEQ ID NO:19 (or sequences substantially homologous thereto), or based on SEQ ID NO:6 or SEQ ID NO:20 (or sequences substantially homologous thereto), or based on SEQ ID NO:7 or SEQ ID NO:21 (or sequences substantially homologous thereto), or based on SEQ ID NO:8 or SEQ ID NO:22 (or sequences substantially homologous thereto), or based on SEQ ID NO:9 or SEQ ID NO:23 (or sequences substantially homologous thereto), or based on SEQ ID NO:10 or SEQ ID NO:24 (or sequences substantially homologous thereto), or based on SEQ ID NO: 11 or SEQ ID NO:25 (or sequences substantially homologous thereto), or based on SEQ ID NO:12 or SEQ ID NO:26 (or sequences substantially homologous thereto) are linear peptides.

In some preferred embodiments, isolated peptides based on SEQ ID NO:4 or SEQ ID NO:18 (or sequences substantially homologous thereto), or based on SEQ ID NO:13 or SEQ ID NO:27 (or sequences substantially homologous thereto), or based on SEQ ID NO:14 or SEQ ID NO:28 (or sequences substantially homologous thereto) are cyclic peptides.

Methods for synthesising peptides are well known in the art. A common technique used for preparing linear peptides (e.g. to be used for immunization and antibody generation) is Fmoc SPPS (Solid Phase Peptide Synthesis). In SPPS, small porous beads are treated with functional linkers on which peptide chains can be built using repeated cycles of wash-coupling-wash. The synthesized peptide is then released from the beads using chemical cleavage. For synthesis of cyclic peptides, common methods utilize cyclization by formation of a disulphide bridge (where the bridge is formed bridge by two cysteines of the peptide, e.g. one at the N-terminus and one at the C-terminus), or by formation of a "head-to-tail" bridge where the bridge consists of a typical peptide bond. Cyclic peptides can be formed on a solid support.

Other methods for synthesising peptides include using other chemical synthesis procedures, in vitro translation, or by introducing a suitable expression vector into cells.

In some embodiments, the isolated peptide does not comprise (or does not consist of) the amino acid sequence EDGKNNSLPMESTPHKCRGSACKP (SEQ ID NO:30).

In some embodiments, the isolated peptide does not comprise (or does not consist of) the amino acid sequence TLIEDGKNDSLPSESTSHRWRGPACRPPDSSYNS-LYSTC (SEQ ID NO:31).

In some embodiments, the isolated peptide does not comprise (or does not consist of) the amino acid sequence SLPSESTSH (SEQ ID NO:32).

Isolated peptides in accordance with the present invention of course do not include the full-length TRPV1 protein (i.e. wild-type TRPV1 protein), or any other full-length (wild-type) protein in the TRPV superfamily, or any other full-length (wild-type) proteins. Isolated peptides in accordance with the present invention thus do not include full-length SEQ ID NO:1.

Isolated peptides of the present invention, although corresponding to (or corresponding essentially to) regions (or epitopes) of the full-length TRPV1 protein (e.g. as described elsewhere herein), do not themselves occur in nature (i.e. they do not have naturally occurring counterparts or do not occur in isolation in nature). Thus, the isolated peptides of the invention can be considered to be artificial peptides, or synthetic peptides, or man-made peptides, or non-native peptides.

A further aspect of the invention provides a conjugate. Typically the conjugate is configured to be used for the production of antibodies. The conjugate may comprise at least one isolated peptide as defined above coupled to (i.e. linked to or connected to or bonded to), or admixed with, a peptide carrier.

Thus, in one aspect, the invention provides a conjugate comprising an isolated peptide of the invention. Conjugates typically comprise an isolated peptide of the invention and a peptide carrier, wherein said isolated peptide is coupled to, or admixed with, said peptide carrier. Peptide carriers typically enhance immunogenicity. This may be useful as, in some cases, short peptides which provide (or represent or correspond to) an antigenic epitope are, by themselves, too small to induce an immune response.

Peptide carriers are typically large macromolecules such as proteins, polysaccharides or polymeric amino acids. In some embodiments, the peptide carrier is selected from the group consisting of keyhole limpet hemocyanin (KLH), ovalbumin (OVA), serum albumins (e.g. bovine serum albumin, BSA), polylysine and the like. KLH is typically preferred.

The coupling of an isolated peptide of the invention to a peptide carrier can, for example, be a covalent coupling or a disulphide bridge. In some embodiments, an isolated peptide of the invention may be provided with an (additional) cysteine residue at its N- or C-terminus (e.g. as described elsewhere herein). Such a cysteine residue typically facilitates coupling of the isolated peptide to a peptide carrier (e.g. KLH). In some embodiments, the isolated peptide may have a modification (e.g. a chemical group such as a propargyl group) that permits coupling of the isolated peptide to a peptide carrier. In some embodiments, the isolated peptide is coupled to a peptide carrier via standard cross-linking agent (e.g. glutaraldehyde). Methods of linking isolated peptides to peptide carriers are well known in the art.

In one embodiment, the present invention provides an isolated peptide comprising an amino acid sequence of SEQ ID NO:2 (OTV3) or a sequence substantially homologous thereto. Substantially homologous sequences are described elsewhere herein.

In a preferred embodiment, the present invention provides an isolated peptide comprising an amino acid sequence of SEQ ID NO:2 (OTV3).

In one embodiment, the present invention provides an isolated peptide consisting of an amino acid sequence of SEQ ID NO:2 (OTV3) or a sequence substantially homologous thereto. Substantially homologous sequences are described elsewhere herein.

In one embodiment, the present invention provides an isolated peptide consisting of an amino acid sequence of SEQ ID NO:2 (OTV3).

In one embodiment, the present invention provides an isolated peptide comprising an amino acid sequence of SEQ ID NO:16 (OTV3) or a sequence substantially homologous thereto. Substantially homologous sequences are described elsewhere herein.

In a preferred embodiment, the present invention provides an isolated peptide comprising an amino acid sequence of SEQ ID NO:16 (OTV3).

In one embodiment, the present invention provides an isolated peptide consisting of an amino acid sequence of SEQ ID NO:16 (OTV3) or a sequence substantially homologous thereto. Substantially homologous sequences are described elsewhere herein.

In one embodiment, the present invention provides an isolated peptide consisting of an amino acid sequence of SEQ ID NO:16 (OTV3).

In some embodiments, isolated peptides based on SEQ ID NO:2 or SEQ ID NO:16 (or sequences substantially homologous thereto) are at least 25 amino acids in length, or at least 30 amino acids in length, or at least 32 amino acids in length (e.g. are 25-35, 25-38, 25-45, 25-55, 25-65 or 25 to 75 amino acids in length). In some embodiments, isolated peptides based on SEQ ID NO:2 or SEQ ID NO:16 (or sequences substantially homologous thereto) are less than 39 amino acids in length, are less than 38 amino acids in length, or less than 37 amino acids in length, or less than 36 amino acids in length, or less than 35 amino acids in length, or less than 34 amino acids in length, or less than 33 amino acids in length (e.g. are 20-25 or 20-30 or 20-32 or 20-38 or 25-30 or 25-32 or 25-38 or 30-38 or amino acids in length). In some embodiments, isolated peptides based on SEQ ID NO:2 or SEQ ID NO:16 (or sequences substantially homologous thereto) are 29-35 amino acids in length. In some embodiments, isolated peptides based on SEQ ID NO:2 or SEQ ID NO:16 (or sequences substantially homologous thereto) do not contain any internal cysteine residues. By "internal" residue is meant a residue at a position other than the N-terminal and/or C-terminal residue. In some embodiments, isolated peptides based on SEQ ID NO:2 or SEQ ID NO:16 (or sequences substantially homologous thereto) have an N-terminal cysteine residue.

In some embodiments, isolated peptides substantially homologous to SEQ ID NO:2 or SEQ ID NO:16 have 1, 2 or 3 amino acid substitutions, deletions or additions as compared to SEQ ID NO:2 or SEQ ID NO:16 themselves.

Preferably, isolated peptides based on SEQ ID NO:2 or SEQ ID NO:16 (or sequences substantially homologous thereto) are linear peptides.

In one aspect, the invention provides a conjugate comprising an isolated peptide comprising (or consisting of) SEQ ID NO:2 (or a sequence substantially homologous thereto) or comprising (or consisting of) SEQ ID NO:16 (or a sequence substantially homologous thereto) and (e.g. coupled to) a peptide carrier. Peptide carriers are described elsewhere herein. In a preferred embodiment the peptide carrier is KLH. In a preferred embodiment, the invention provides a conjugate comprising an isolated peptide consisting of SEQ ID NO:16 coupled to the peptide carrier KLH (preferably via the N-terminal cysteine residue of SEQ ID NO:16).

In one embodiment, the present invention provides an isolated peptide comprising an amino acid sequence of SEQ ID NO:3 (OTV4) or a sequence substantially homologous thereto. Substantially homologous sequences are described elsewhere herein.

In a preferred embodiment, the present invention provides an isolated peptide comprising an amino acid sequence of SEQ ID NO:3 (OTV4).

In one embodiment, the present invention provides an isolated peptide consisting of an amino acid sequence of SEQ ID NO:3 (OTV4) or a sequence substantially homologous thereto. Substantially homologous sequences are described elsewhere herein.

In one embodiment, the present invention provides an isolated peptide consisting of an amino acid sequence of SEQ ID NO:3 (OTV4).

In one embodiment, the present invention provides an isolated peptide comprising an amino acid sequence of SEQ ID NO:17 (OTV4) or a sequence substantially homologous thereto. Substantially homologous sequences are described elsewhere herein.

In a preferred embodiment, the present invention provides an isolated peptide comprising an amino acid sequence of SEQ ID NO:17 (OTV4).

In one embodiment, the present invention provides an isolated peptide consisting of an amino acid sequence of SEQ ID NO:17 (OTV4) or a sequence substantially homologous thereto. Substantially homologous sequences are described elsewhere herein.

In one embodiment, the present invention provides an isolated peptide consisting of an amino acid sequence of SEQ ID NO:17 (OTV4).

In some embodiments, isolated peptides based on SEQ ID NO:3 or SEQ ID NO:17 (or sequences substantially homologous thereto) are at least 25 amino acids in length, or at least 30 amino acids in length, or at least 32 amino acids in length (e.g. are 25-35, 25-38, 25-45, 25-55, 25-65 or 25 to 75 amino acids in length). In some embodiments, isolated peptides based on SEQ ID NO:3 or SEQ ID NO:17 (or sequences substantially homologous thereto) are less than 39 amino acids in length, are less than 38 amino acids in length, or less than 37 amino acids in length, or less than 36 amino acids in length, or less than 35 amino acids in length, or less than 34 amino acids in length, or less than 33 amino acids in length (e.g. are 20-25 or 20-30 or 20-32 or 20-38 or 25-30 or 25-32 or 25-38 or 30-38 amino acids in length). In some embodiments, isolated peptides based on SEQ ID NO:3 or SEQ ID NO:17 (or sequences substantially homologous thereto) are 29-35 amino acids in length. In some embodiments, isolated peptides based on SEQ ID NO:3 or SEQ ID NO:17 (or sequences substantially homologous thereto) do not contain any internal cysteine residues. By "internal" residue is meant a residue at a position other than the N-terminal and/or C-terminal residue. In some embodiments, the cysteine at position 23 of SEQ ID NO:3 or at position 24 of SEQ ID NO:17 is substituted for a different amino acid residue. In other embodiments, isolated peptides based on SEQ ID NO:3 or SEQ ID NO:17 (or sequences substantially homologous thereto) contain at least one (e.g. 1) internal cysteine residue (e.g. at position 23 of SEQ ID NO:3 or at position 24 of SEQ ID NO:17). In some embodiments, isolated peptides based on SEQ ID NO:3 or SEQ ID NO:17 (or sequences substantially homologous thereto) have an N-terminal cysteine residue.

In some embodiments, isolated peptides substantially homologous to SEQ ID NO:3 or SEQ ID NO:17 have 1, 2 or 3 amino acid substitutions, deletions or additions as compared to SEQ ID NO:3 or SEQ ID NO:17 themselves.

Preferably, isolated peptides based on SEQ ID NO:3 or SEQ ID NO:17 (or sequences substantially homologous thereto) are linear peptides.

In one aspect, the invention provides a conjugate comprising an isolated peptide comprising (or consisting of) SEQ ID NO:3 (or a sequence substantially homologous thereto) or comprising (or consisting of) SEQ ID NO:17 (or a sequence substantially homologous thereto) and (e.g. coupled to) a peptide carrier. Peptide carriers are described elsewhere herein. In a preferred embodiment the peptide carrier is KLH. In a preferred embodiment, the invention provides a conjugate comprising an isolated peptide consisting of SEQ ID NO:17 coupled to the peptide carrier KLH (preferably via the N-terminal cysteine residue of SEQ ID NO:17).

In one embodiment, the present invention provides an isolated peptide comprising an amino acid sequence of SEQ ID NO:4 (OTV5) or a sequence substantially homologous thereto. Substantially homologous sequences are described elsewhere herein.

In a preferred embodiment, the present invention provides an isolated peptide comprising an amino acid sequence of SEQ ID NO:4 (OTV5).

In one embodiment, the present invention provides an isolated peptide consisting of an amino acid sequence of SEQ ID NO:4 (OTV5) or a sequence substantially homologous thereto. Substantially homologous sequences are described elsewhere herein.

In one embodiment, the present invention provides an isolated peptide consisting of an amino acid sequence of SEQ ID NO:4 (OTV5).

In one embodiment, the present invention provides an isolated peptide comprising an amino acid sequence of SEQ ID NO:18 (OTV5) or a sequence substantially homologous thereto. Substantially homologous sequences are described elsewhere herein.

In a preferred embodiment, the present invention provides an isolated peptide comprising an amino acid sequence of SEQ ID NO:18 (OTV5).

In one embodiment, the present invention provides an isolated peptide consisting of an amino acid sequence of SEQ ID NO:18 (OTV5) or a sequence substantially homologous thereto. Substantially homologous sequences are described elsewhere herein.

In one embodiment, the present invention provides an isolated peptide consisting of an amino acid sequence of SEQ ID NO:18 (OTV5).

In some embodiments, isolated peptides based on SEQ ID NO:4 or SEQ ID NO:18 (or sequences substantially homologous thereto) are at least 25 amino acids in length, or at least 30 amino acids in length, or at least 32 amino acids in length (e.g. are 25-35, 25-45, 25-55, 25-65 or 25 to 75 amino acids in length). In some embodiments, isolated peptides based on SEQ ID NO:4 or SEQ ID NO:18 (or sequences substantially homologous thereto) are less than 39 amino acids in length, are less than 38 amino acids in length, or less than 37 amino acids in length, or less than 36 amino acids in length, or less than 35 amino acids in length, or less than 34 amino acids in length, or less than 33 amino acids in length (e.g. are 20-25 or 20-30 or 20-31 or 25-30 or 25-32 or 20-38 or 25-38 or 30-38 amino acids in length). In some embodiments, isolated peptides based on SEQ ID NO:4 or SEQ ID NO:18 (or sequences substantially homologous thereto) are 29-35 amino acids in length. In some embodiments, isolated peptides based on SEQ ID NO:4 or SEQ ID NO:18 (or sequences substantially homologous thereto) do not contain any internal cysteine residues. By "internal" residue is meant a residue at a position other than the N-terminal and/or C-terminal residue. In some embodiments, isolated peptides based on SEQ ID NO:4 or SEQ ID NO:18 (or sequences substantially homologous thereto) have an N-terminal cysteine residue and a C-terminal cysteine residue. In some embodiments, a further modification may be present at the N- and/or C-terminus (e.g. a propargyl group at the N-terminus and/or a C-terminal amide group).

In some embodiments, isolated peptides substantially homologous to SEQ ID NO:4 or SEQ ID NO:18 have 1, 2 or 3 amino acid substitutions, deletions or additions as compared to SEQ ID NO:4 or SEQ ID NO:18 themselves.

Preferably, isolated peptides based on SEQ ID NO:4 or SEQ ID NO:18 (or sequences substantially homologous thereto) are cyclic peptides. Preferably such peptides are cyclized via a disulphide bond between N- and C-terminal cysteine residues.

In one aspect, the invention provides a conjugate comprising an isolated peptide comprising (or consisting of) SEQ ID NO:4 (or a sequence substantially homologous thereto) or comprising (or consisting of) SEQ ID NO:18 (or a sequence substantially homologous thereto) and (e.g. coupled to) a peptide carrier. Peptide carriers are described elsewhere herein. In a preferred embodiment the peptide carrier is KLH. In a preferred embodiment, the invention provides a conjugate comprising an isolated peptide consisting of SEQ ID NO:18 coupled to the peptide carrier KLH (preferably via the propargyl group of SEQ ID NO:18).

In one embodiment, the present invention provides an isolated peptide comprising an amino acid sequence of SEQ ID NO:5 (OTV6) or a sequence substantially homologous thereto. Substantially homologous sequences are described elsewhere herein.

In a preferred embodiment, the present invention provides an isolated peptide comprising an amino acid sequence of SEQ ID NO:5 (OTV6).

In one embodiment, the present invention provides an isolated peptide consisting of an amino acid sequence of SEQ ID NO:5 (OTV6) or a sequence substantially homologous thereto. Substantially homologous sequences are described elsewhere herein.

In one embodiment, the present invention provides an isolated peptide consisting of an amino acid sequence of SEQ ID NO:5 (OTV6).

In one embodiment, the present invention provides an isolated peptide comprising an amino acid sequence of SEQ ID NO:19 (OTV6) or a sequence substantially homologous thereto. Substantially homologous sequences are described elsewhere herein.

In a preferred embodiment, the present invention provides an isolated peptide comprising an amino acid sequence of SEQ ID NO:19 (OTV6).

In one embodiment, the present invention provides an isolated peptide consisting of an amino acid sequence of SEQ ID NO:19 (OTV6) or a sequence substantially homologous thereto. Substantially homologous sequences are described elsewhere herein.

In one embodiment, the present invention provides an isolated peptide consisting of an amino acid sequence of SEQ ID NO:19 (OTV6).

In some embodiments, isolated peptides based on SEQ ID NO:5 or SEQ ID NO:19 (or sequences substantially homologous thereto) are <24 amino acids in length or <20 amino acids in length <15 amino acids in length <10 amino acids in length (e.g. are 5-10, 5-12, 5-15, 5-20, 5-23 or 8-23 or 10-23 or 15-23 or 20-23 or 5-10 or 8-10 or 10-15 or 5-15 or 8-15 or 10-15 or 5-20 or 8-20 or 10-20 amino acids in length). In some embodiments, isolated peptides based on SEQ ID NO:5 or SEQ ID NO:19 (or sequences substantially homologous thereto) are less than 39 amino acids in length, are less than 38 amino acids in length, or less than 37 amino acids in length, or less than 36 amino acids in length, or less than 35 amino acids in length, or less than 34 amino acids in length, or less than 33 amino acids in length (e.g. are 5-10, 5-15, 5-20, 5-25 or 5-30 or 5-32 or 5-38 or 8-10, 8-15, 8-20, 8-25 or 8-30 or 8-32 or 8-38 or 10-38 or 15-38 or 20-38 or 20-25 or 20-30 or 20-32 or 25-30 or 25-32 or 25-38 or 30-38 amino acids in length). In some embodiments, isolated peptides based on SEQ ID NO:5 or SEQ ID NO:19 (or sequences substantially homologous thereto) are 5-11 amino acids in length. In some embodiments, isolated peptides based on SEQ ID NO:5 or SEQ ID NO:19 (or sequences substantially homologous thereto) do not contain any internal cysteine residues. By "internal" residue is meant a residue at a position other than the N-terminal and/or C-terminal residue. In some embodiments, isolated peptides based on SEQ ID NO:5 or SEQ ID NO:19 (or sequences substantially homologous thereto) have an N-terminal cysteine residue.

In some embodiments, isolated peptides substantially homologous to SEQ ID NO:5 or SEQ ID NO:19 have 1, 2 or 3 amino acid substitutions, deletions or additions as compared to SEQ ID NO:5 or SEQ ID NO:19 themselves.

Preferably, isolated peptides based on SEQ ID NO:5 or SEQ ID NO:19 (or sequences substantially homologous thereto) are linear peptides.

In one aspect, the invention provides a conjugate comprising an isolated peptide comprising (or consisting of) SEQ ID NO:5 (or a sequence substantially homologous thereto) or comprising (or consisting of) SEQ ID NO:19 (or a sequence substantially homologous thereto) and (e.g. coupled to) a peptide carrier. Peptide carriers are described elsewhere herein. In a preferred embodiment the peptide carrier is KLH. In a preferred embodiment, the invention provides a conjugate comprising an isolated peptide consisting of SEQ ID NO:19 coupled to the peptide carrier KLH (preferably via the N-terminal cysteine residue of SEQ ID NO:19).

In one embodiment, the present invention provides an isolated peptide comprising an amino acid sequence of SEQ ID NO:6 (OTV7) or a sequence substantially homologous thereto. Substantially homologous sequences are described elsewhere herein.

In a preferred embodiment, the present invention provides an isolated peptide comprising an amino acid sequence of SEQ ID NO:6 (OTV7).

In one embodiment, the present invention provides an isolated peptide consisting of an amino acid sequence of SEQ ID NO:6 (OTV7) or a sequence substantially homologous thereto. Substantially homologous sequences are described elsewhere herein.

In one embodiment, the present invention provides an isolated peptide consisting of an amino acid sequence of SEQ ID NO:6 (OTV7).

In one embodiment, the present invention provides an isolated peptide comprising an amino acid sequence of SEQ ID NO:20 (OTV7) or a sequence substantially homologous thereto. Substantially homologous sequences are described elsewhere herein.

In a preferred embodiment, the present invention provides an isolated peptide comprising an amino acid sequence of SEQ ID NO:20 (OTV7).

In one embodiment, the present invention provides an isolated peptide consisting of an amino acid sequence of SEQ ID NO:20 (OTV7) or a sequence substantially homologous thereto. Substantially homologous sequences are described elsewhere herein.

In one embodiment, the present invention provides an isolated peptide consisting of an amino acid sequence of SEQ ID NO:20 (OTV7).

In some embodiments, isolated peptides based on SEQ ID NO:6 or SEQ ID NO:20 (or sequences substantially homologous thereto) are <24 amino acids in length or <20 amino acids in length <15 amino acids in length <10 amino acids in length (e.g. are 5-23 or 8-23 or 10-23 or 15-23 or 16-23 or 20-23 or 5-10 or 8-10 or 10-15 or 5-15 or 8-15 or 10-15 or 5-20 or 8-20 of 16-20 or 10-20 amino acids in length). In some embodiments, isolated peptides based on SEQ ID NO:6 or SEQ ID NO:20 (or sequences substantially homologous thereto) are less than 39 amino acids in length, are less than 38 amino acids in length, or less than 37 amino acids in length, or less than 36 amino acids in length, or less than 35 amino acids in length, or less than 34 amino acids in length, or less than 33 amino acids in length (e.g. are 12-20 or 12-25 or 12-30 or 12-32 or 12-38 or 16-20 or 16-25 or 16-30 or 16-32 or 16-38 or 20-25 or 20-30 or 20-32 or 25-30 or 25-32 or 25-38 or 30-38 amino acids in length). In some embodiments, isolated peptides based on SEQ ID NO:6 or SEQ ID NO:20 (or sequences substantially homologous thereto) are 13-19 amino acids in length. In some embodiments, isolated peptides based on SEQ ID NO:6 or SEQ ID NO:20 (or sequences substantially homologous thereto) do not contain any internal cysteine residues. By "internal" residue is meant a residue at a position other than the N-terminal and/or C-terminal residue. In some embodiments, isolated peptides based on SEQ ID NO:6 or SEQ ID NO:20 (or sequences substantially homologous thereto) have an N-terminal cysteine residue.

In some embodiments, isolated peptides substantially homologous to SEQ ID NO:6 or SEQ ID NO:20 have 1, 2 or 3 amino acid substitutions, deletions or additions as compared to SEQ ID NO:6 or SEQ ID NO:20 themselves.

Preferably, isolated peptides based on SEQ ID NO:6 or SEQ ID NO:20 (or sequences substantially homologous thereto) are linear peptides.

In one aspect, the invention provides a conjugate comprising an isolated peptide comprising (or consisting of) SEQ ID NO:6 (or a sequence substantially homologous thereto) or comprising (or consisting of) SEQ ID NO:20 (or a sequence substantially homologous thereto) and (e.g. coupled to) a peptide carrier. Peptide carriers are described elsewhere herein. In a preferred embodiment the peptide carrier is KLH. In a preferred embodiment, the invention provides a conjugate comprising an isolated peptide consisting of SEQ ID NO:20 coupled to the peptide carrier KLH (preferably via the N-terminal cysteine residue of SEQ ID NO:20).

In one embodiment, the present invention provides an isolated peptide comprising an amino acid sequence of SEQ ID NO:7 (OTV8) or a sequence substantially homologous thereto. Substantially homologous sequences are described elsewhere herein.

In a preferred embodiment, the present invention provides an isolated peptide comprising an amino acid sequence of SEQ ID NO:7 (OTV8).

In one embodiment, the present invention provides an isolated peptide consisting of an amino acid sequence of SEQ ID NO:7 (OTV8) or a sequence substantially homologous thereto. Substantially homologous sequences are described elsewhere herein.

In one embodiment, the present invention provides an isolated peptide consisting of an amino acid sequence of SEQ ID NO:7 (OTV8).

In one embodiment, the present invention provides an isolated peptide comprising an amino acid sequence of SEQ ID NO:21 (OTV8) or a sequence substantially homologous thereto. Substantially homologous sequences are described elsewhere herein.

In a preferred embodiment, the present invention provides an isolated peptide comprising an amino acid sequence of SEQ ID NO:21 (OTV8).

In one embodiment, the present invention provides an isolated peptide consisting of an amino acid sequence of SEQ ID NO:21 (OTV8) or a sequence substantially homologous thereto. Substantially homologous sequences are described elsewhere herein.

In one embodiment, the present invention provides an isolated peptide consisting of an amino acid sequence of SEQ ID NO:21 (OTV8).

In some embodiments, isolated peptides based on SEQ ID NO:7 or SEQ ID NO:21 (or sequences substantially homologous thereto) are less than 39 amino acids in length, are less than 38 amino acids in length, or less than 37 amino acids in length, or less than 36 amino acids in length, or less than 35 amino acids in length, or less than 34 amino acids in length, or less than 33 amino acids in length (e.g. are 20-25 or 20-30 or 20-32 or 20-38 or 25-30 or 25-32 or 25-38 or 30-38 or 24-30 or 24-38 amino acids in length). In some embodiments, isolated peptides based on SEQ ID NO:7 or SEQ ID NO:21 (or sequences substantially homologous thereto) are 21-27 amino acids in length. In some embodiments, isolated peptides based on SEQ ID NO:7 or SEQ ID NO:21 (or sequences substantially homologous thereto) do not contain any internal cysteine residues. By "internal" residue is meant a residue at a position other than the N-terminal and/or C-terminal residue. In some embodiments, isolated peptides based on SEQ ID NO:7 or SEQ ID NO:21 (or sequences substantially homologous thereto) have an N-terminal cysteine residue.

In some embodiments, isolated peptides substantially homologous to SEQ ID NO:7 or SEQ ID NO:21 have 1, 2 or 3 amino acid substitutions, deletions or additions as compared to SEQ ID NO:7 or SEQ ID NO:21 themselves.

Preferably, isolated peptides based on SEQ ID NO:7 or SEQ ID NO:21 (or sequences substantially homologous thereto) are linear peptides.

In one aspect, the invention provides a conjugate comprising an isolated peptide comprising (or consisting of) SEQ ID NO:7 (or a sequence substantially homologous thereto) or comprising (or consisting of) SEQ ID NO:21 (or a sequence substantially homologous thereto) and (e.g. coupled to) a peptide carrier. Peptide carriers are described elsewhere herein. In a preferred embodiment the peptide carrier is KLH. In a preferred embodiment, the invention provides a conjugate comprising an isolated peptide consisting of SEQ ID NO:21 coupled to the peptide carrier KLH (preferably via the N-terminal cysteine residue of SEQ ID NO:21).

In one embodiment, the present invention provides an isolated peptide comprising an amino acid sequence of SEQ ID NO:8 (OTV9) or a sequence substantially homologous thereto. Substantially homologous sequences are described elsewhere herein.

In a preferred embodiment, the present invention provides an isolated peptide comprising an amino acid sequence of SEQ ID NO:8 (OTV9).

In one embodiment, the present invention provides an isolated peptide consisting of an amino acid sequence of SEQ ID NO:8 (OTV9) or a sequence substantially homologous thereto. Substantially homologous sequences are described elsewhere herein.

In one embodiment, the present invention provides an isolated peptide consisting of an amino acid sequence of SEQ ID NO:8 (OTV9).

In one embodiment, the present invention provides an isolated peptide comprising an amino acid sequence of SEQ ID NO:22 (OTV9) or a sequence substantially homologous thereto. Substantially homologous sequences are described elsewhere herein.

In a preferred embodiment, the present invention provides an isolated peptide comprising an amino acid sequence of SEQ ID NO:22 (OTV9).

In one embodiment, the present invention provides an isolated peptide consisting of an amino acid sequence of SEQ ID NO:22 (OTV9) or a sequence substantially homologous thereto. Substantially homologous sequences are described elsewhere herein.

In one embodiment, the present invention provides an isolated peptide consisting of an amino acid sequence of SEQ ID NO:22 (OTV9).

In some embodiments, isolated peptides based on SEQ ID NO:8 or SEQ ID NO:22 (or sequences substantially homologous thereto) are less than 39 amino acids in length, are less than 38 amino acids in length, or less than 37 amino acids in length, or less than 36 amino acids in length, or less than 35 amino acids in length, or less than 34 amino acids in length, or less than 33 amino acids in length (e.g. are 20-25 or 20-30 or 20-32 or 20-38 or 25-30 or 25-32 or 25-38 or 30-38 or 24-30 or 24-38 amino acids in length). In some embodiments, isolated peptides based on SEQ ID NO:8 or SEQ ID NO:22 (or sequences substantially homologous thereto) are 21-27 amino acids in length. In some embodiments, isolated peptides based on SEQ ID NO:8 or SEQ ID NO:22 (or sequences substantially homologous thereto) do not contain any internal cysteine residues. By "internal" residue is meant a residue at a position other than the N-terminal and/or C-terminal residue. In some embodiments, isolated peptides based on SEQ ID NO:8 or SEQ ID NO:22 (or sequences substantially homologous thereto) have a C-terminal cysteine residue.

In some embodiments, isolated peptides substantially homologous to SEQ ID NO:8 or SEQ ID NO:22 have 1, 2 or 3 amino acid substitutions, deletions or additions as compared to SEQ ID NO:8 or SEQ ID NO:22 themselves.

Preferably, isolated peptides based on SEQ ID NO:8 or SEQ ID NO:22 (or sequences substantially homologous thereto) are linear peptides.

In one aspect, the invention provides a conjugate comprising an isolated peptide comprising (or consisting of) SEQ ID NO:8 (or a sequence substantially homologous thereto) or comprising (or consisting of) SEQ ID NO:22 (or a sequence substantially homologous thereto) and (e.g. coupled to) a peptide carrier. Peptide carriers are described elsewhere herein. In a preferred embodiment the peptide carrier is KLH. In a preferred embodiment, the invention provides a conjugate comprising an isolated peptide consisting of SEQ ID NO:22 coupled to the peptide carrier KLH (preferably via the N-terminal cysteine residue of SEQ ID NO:22).

In one embodiment, the present invention provides an isolated peptide comprising an amino acid sequence of SEQ ID NO:9 (OTV10) or a sequence substantially homologous thereto. Substantially homologous sequences are described elsewhere herein.

In a preferred embodiment, the present invention provides an isolated peptide comprising an amino acid sequence of SEQ ID NO:9 (OTV10).

In one embodiment, the present invention provides an isolated peptide consisting of an amino acid sequence of SEQ ID NO:9 (OTV10) or a sequence substantially homologous thereto. Substantially homologous sequences are described elsewhere herein.

In one embodiment, the present invention provides an isolated peptide consisting of an amino acid sequence of SEQ ID NO:9 (OTV10).

In one embodiment, the present invention provides an isolated peptide comprising an amino acid sequence of SEQ ID NO:9 (OTV10) or a sequence substantially homologous thereto. Substantially homologous sequences are described elsewhere herein.

In a preferred embodiment, the present invention provides an isolated peptide comprising an amino acid sequence of SEQ ID NO:23 (OTV10).

In one embodiment, the present invention provides an isolated peptide consisting of an amino acid sequence of SEQ ID NO:23 (OTV10) or a sequence substantially homologous thereto. Substantially homologous sequences are described elsewhere herein.

In one embodiment, the present invention provides an isolated peptide consisting of an amino acid sequence of SEQ ID NO:23 (OTV10).

In some embodiments, isolated peptides based on SEQ ID NO:9 or SEQ ID NO:23 (or sequences substantially homologous thereto) are <24 amino acids in length or <20 amino acids in length <15 amino acids in length <10 amino acids in length (e.g. are 5-23 or 8-23 or 10 to 23 or 15 to 23 or 16-23 or 20-23 or 5-10 or 8-10 or 10-15 or 5-15 or 8-15 or 10-15 or 5-20 or 8-20 or 10-20 or 16-20 amino acids in length). In some embodiments, isolated peptides based on SEQ ID NO:9 or SEQ ID NO:23 (or sequences substantially homologous thereto) are less than 39 amino acids in length, are less than 38 amino acids in length, or less than 37 amino acids in length, or less than 36 amino acids in length, or less than 35 amino acids in length, or less than 34 amino acids in length, or less than 33 amino acids in length (e.g. are 12-20 or 12-25 or 12-30 or 12-32 or 12-38 or 16-20 or 16-25 or 16-30 or 16-32 or 16-38 or 20-25 or 20-30 or 20-32 or 20-38 or 25-30 or 25-32 or 25-38 or 30-38 or 16-30 or 16-38 amino acids in length). In some embodiments, isolated peptides based on SEQ ID NO:9 or SEQ ID NO:23 (or sequences substantially homologous thereto) are 13-19 amino acids in length. In some embodiments, isolated peptides based on SEQ ID NO:9 or SEQ ID NO:23 (or sequences substantially homologous thereto) do not contain any internal cysteine residues. By "internal" residue is meant a residue at a position other than the N-terminal and/or C-terminal residue. In some embodiments, isolated peptides based on SEQ ID NO:9 or SEQ ID NO:23 (or sequences substantially homologous thereto) has a C-terminal cysteine residue.

In some embodiments, isolated peptides substantially homologous to SEQ ID NO:9 or SEQ ID NO:23 have 1, 2 or 3 amino acid substitutions, deletions or additions as compared to SEQ ID NO:9 or SEQ ID NO:23 themselves.

Preferably, isolated peptides based on SEQ ID NO:9 or SEQ ID NO:23 (or sequences substantially homologous thereto) are linear peptides.

In one aspect, the invention provides a conjugate comprising an isolated peptide comprising (or consisting of) SEQ ID NO:9 (or a sequence substantially homologous thereto) or comprising (or consisting of) SEQ ID NO:23 (or a sequence substantially homologous thereto) and (e.g. coupled to) a peptide carrier. Peptide carriers are described elsewhere herein. In a preferred embodiment the peptide carrier is KLH. In a preferred embodiment, the invention provides a conjugate comprising an isolated peptide consisting of SEQ ID NO:23 coupled to the peptide carrier KLH (preferably via the C-terminal cysteine residue of SEQ ID NO:23).

In one embodiment, the present invention provides an isolated peptide comprising an amino acid sequence of SEQ ID NO:10 (OTV11) or a sequence substantially homologous thereto. Substantially homologous sequences are described elsewhere herein.

In a preferred embodiment, the present invention provides an isolated peptide comprising an amino acid sequence of SEQ ID NO:10 (OTV11).

In one embodiment, the present invention provides an isolated peptide consisting of an amino acid sequence of SEQ ID NO:10 (OTV11) or a sequence substantially homologous thereto. Substantially homologous sequences are described elsewhere herein.

In one embodiment, the present invention provides an isolated peptide consisting of an amino acid sequence of SEQ ID NO:10 (OTV11).

In one embodiment, the present invention provides an isolated peptide comprising an amino acid sequence of SEQ ID NO:24 (OTV11) or a sequence substantially homologous thereto. Substantially homologous sequences are described elsewhere herein.

In a preferred embodiment, the present invention provides an isolated peptide comprising an amino acid sequence of SEQ ID NO:24 (OTV11).

In one embodiment, the present invention provides an isolated peptide consisting of an amino acid sequence of SEQ ID NO:24 (OTV11) or a sequence substantially homologous thereto. Substantially homologous sequences are described elsewhere herein.

In one embodiment, the present invention provides an isolated peptide consisting of an amino acid sequence of SEQ ID NO:24 (OTV11).

In some embodiments, isolated peptides based on SEQ ID NO:10 or SEQ ID NO:24 (or sequences substantially homologous thereto) are <24 amino acids in length or <20 amino acids in length <15 amino acids in length <10 amino acids in length (e.g. are 5-23 or 8-23 or 10 to 23 or 15 to 23 or 20-23 or 5-10 or 8-10 or 10-15 or 5-15 or 8-15 or 10-15 or 5-20 or 8-20 or 10-20 amino acids in length). In some embodiments, isolated peptides based on SEQ ID NO:10 or SEQ ID NO:24 (or sequences substantially homologous thereto) are less than 39 amino acids in length, are less than 38 amino acids in length, or less than 37 amino acids in length, or less than 36 amino acids in length, or less than 35 amino acids in length, or less than 34 amino acids in length, or less than 33 amino acids in length (e.g. are 5-10, 5-15, 5-20, 5-25 or 5-30 or 5-32 or 5-30 or 8-10, 8-15, 8-20, 8-25 or 8-30 or 8-32 or 8-38 or 10-38 or 15-38 or 20-38 or 20-25 or 20-30 or 20-32 or 25-30 or 25-32 or 25-38 or 30-38 amino acids in length). In some embodiments, isolated peptides based on SEQ ID NO:10 or SEQ ID NO:24 (or sequences substantially homologous thereto) are 5-11 amino acids in length. In some embodiments, isolated peptides based on SEQ ID NO:10 or SEQ ID NO:24 (or sequences substantially homologous thereto) do not contain any internal cysteine residues. By "internal" residue is meant a residue at a position other than the N-terminal and/or C-terminal residue. In some embodiments, isolated peptides based on SEQ ID NO:10 or SEQ ID NO:24 (or sequences substantially homologous thereto) have a C-terminal cysteine residue.

In some embodiments, isolated peptides substantially homologous to SEQ ID NO:10 or SEQ ID NO:24 have 1, 2 or 3 amino acid substitutions, deletions or additions as compared to SEQ ID NO:10 or SEQ ID NO:24 themselves.

Preferably, isolated peptides based on SEQ ID NO:10 or SEQ ID NO:24 (or sequences substantially homologous thereto) are linear peptides.

In one aspect, the invention provides a conjugate comprising an isolated peptide comprising (or consisting of) SEQ ID NO:10 (or a sequence substantially homologous thereto) or comprising (or consisting of) SEQ ID NO:24 (or a sequence substantially homologous thereto) and (e.g. coupled to) a peptide carrier. Peptide carriers are described elsewhere herein. In a preferred embodiment the peptide carrier is KLH. In a preferred embodiment, the invention provides a conjugate comprising an isolated peptide consisting of SEQ ID NO:24 coupled to the peptide carrier KLH (preferably via the C-terminal cysteine residue of SEQ ID NO:24).

In one embodiment, the present invention provides an isolated peptide comprising an amino acid sequence of SEQ ID NO:11 (OTV12) or a sequence substantially homologous thereto. Substantially homologous sequences are described elsewhere herein.

In a preferred embodiment, the present invention provides an isolated peptide comprising an amino acid sequence of SEQ ID NO:11 (OTV12).

In one embodiment, the present invention provides an isolated peptide consisting of an amino acid sequence of SEQ ID NO: 11 (OTV12) or a sequence substantially homologous thereto. Substantially homologous sequences are described elsewhere herein.

In one embodiment, the present invention provides an isolated peptide consisting of an amino acid sequence of SEQ ID NO: 11 (OTV12).

In one embodiment, the present invention provides an isolated peptide comprising an amino acid sequence of SEQ ID NO:25 (OTV12) or a sequence substantially homologous thereto. Substantially homologous sequences are described elsewhere herein.

In a preferred embodiment, the present invention provides an isolated peptide comprising an amino acid sequence of SEQ ID NO:25 (OTV12).

In one embodiment, the present invention provides an isolated peptide consisting of an amino acid sequence of SEQ ID NO:25 (OTV12) or a sequence substantially homologous thereto. Substantially homologous sequences are described elsewhere herein.

In one embodiment, the present invention provides an isolated peptide consisting of an amino acid sequence of SEQ ID NO:25 (OTV12).

In some embodiments, isolated peptides based on SEQ ID NO:11 or SEQ ID NO:25 (or sequences substantially homologous thereto) are <24 amino acids in length or <20 amino acids in length <15 amino acids in length <10 amino acids in length (e.g. are 5-23 or 8-23 or 10-23 or 15-23 or 20-23 or 5-10 or 8-10 or 10-15 or 5-13 or 8-13 or 10-13 or 5-15 or 8-15 or 5-20 or 8-20 or 10-20 or 13-15 or 13-20 amino acids in length). In some embodiments, isolated peptides based on SEQ ID NO:11 or SEQ ID NO:25 (or sequences substantially homologous thereto) are less than 39 amino acids in length, are less than 38 amino acids in length, or less than 37 amino acids in length, or less than 36 amino acids in length, or less than 35 amino acids in length, or less than 34 amino acids in length, or less than 33 amino acids in length (e.g. are 5-10 or 5-15 or 5-25 or 5-30 or 5-32 or 5-30 or 5-38 or 8-32 or 8-38 or 10-38 or 13-15 or 13-20 or 13-25 or 13-30 or 13-32 or 13-38 or 15-38 or 20-38 or 20-25 or 20-30 or 20-32 or 25-30 or 25-32 or 25-38 or 30-38 amino acids in length). In some embodiments, isolated peptides based on SEQ ID NO:11 or SEQ ID NO:25 (or sequences substantially homologous thereto) are 10-16 amino acids in length). In some embodiments, isolated peptides based on SEQ ID NO: 11 or SEQ ID NO:25 (or sequences substantially homologous thereto) do not contain any internal cysteine residues. By "internal" residue is meant a residue at a position other than the N-terminal and/or C-terminal residue. In some embodiments, isolated peptides based on SEQ ID NO:11 or SEQ ID NO:25 (or sequences substantially homologous thereto) have a C-terminal cysteine residue.

In some embodiments, isolated peptides substantially homologous to SEQ ID NO: 11 or SEQ ID NO:25 have 1, 2 or 3 amino acid substitutions, deletions or additions as compared to SEQ ID NO: 11 or SEQ ID NO:25 themselves.

Preferably, isolated peptides based on SEQ ID NO: 11 or SEQ ID NO:25 (or sequences substantially homologous thereto) are linear peptides.

In one aspect, the invention provides a conjugate comprising an isolated peptide comprising (or consisting of) SEQ ID NO:11 (or a sequence substantially homologous thereto) or comprising (or consisting of) SEQ ID NO:25 (or a sequence substantially homologous thereto) and (e.g. coupled to) a peptide carrier. Peptide carriers are described elsewhere herein. In a preferred embodiment the peptide carrier is KLH. In a preferred embodiment, the invention provides a conjugate comprising an isolated peptide consisting of SEQ ID NO:25 coupled to the peptide carrier KLH (preferably via the C-terminal cysteine residue of SEQ ID NO:25).

In one embodiment, the present invention provides an isolated peptide comprising an amino acid sequence of SEQ ID NO:12 (OTV13) or a sequence substantially homologous thereto. Substantially homologous sequences are described elsewhere herein.

In a preferred embodiment, the present invention provides an isolated peptide comprising an amino acid sequence of SEQ ID NO:12 (OTV13).

In one embodiment, the present invention provides an isolated peptide consisting of an amino acid sequence of SEQ ID NO:12 (OTV13) or a sequence substantially homologous thereto. Substantially homologous sequences are described elsewhere herein.

In one embodiment, the present invention provides an isolated peptide consisting of an amino acid sequence of SEQ ID NO:12 (OTV13).

In one embodiment, the present invention provides an isolated peptide comprising an amino acid sequence of SEQ ID NO:26 (OTV13) or a sequence substantially homologous thereto. Substantially homologous sequences are described elsewhere herein.

In a preferred embodiment, the present invention provides an isolated peptide comprising an amino acid sequence of SEQ ID NO:26 (OTV13).

In one embodiment, the present invention provides an isolated peptide consisting of an amino acid sequence of SEQ ID NO:26 (OTV13) or a sequence substantially homologous thereto. Substantially homologous sequences are described elsewhere herein.

In one embodiment, the present invention provides an isolated peptide consisting of an amino acid sequence of SEQ ID NO:26 (OTV13).

In some embodiments, isolated peptides based on SEQ ID NO:12 or SEQ ID NO:26 (or sequences substantially homologous thereto) are <24 amino acids in length or <20 amino acids in length <15 amino acids in length <10 amino acids in length (e.g. are 5-23 or 8-23 or 10-23 or 15-23 or 20-23 or 5-10 or 8-10 or 10-15 or 5-13 or 8-13 or 10-13 or 5-15 or 8-15 or 5-20 or 8-20 or 10-20 or 13-15 or 13-20 amino acids in length). In some embodiments, isolated peptides based on SEQ ID NO:12 or SEQ ID NO:26 (or sequences substantially homologous thereto) are less than 39 amino acids in length, are less than 38 amino acids in length, or less than 37 amino acids in length, or less than 36 amino acids in length, or less than 35 amino acids in length, or less than 34 amino acids in length, or less than 33 amino acids in length (e.g. are 5-10 or 5-15 or 5-25 or 5-30 or 5-32 or 5-30 or 5-38 or 8-32 or 8-38 or 10-38 13-15 or 13-20 or 13-25 or 13-30 or 13-32 or 13-38 or 15-38 or 20-38 or 20-25 or 20-30 or 20-32 or 25-30 or 25-32 or 25-38 or 30-38 amino acids in length). In some embodiments, isolated peptides based on SEQ ID NO:12 or SEQ ID NO:26 (or sequences substantially homologous thereto) are less than 39 amino acids in length, are 10-16 amino acids in length. In some embodiments, isolated peptides based on SEQ ID NO:12 or SEQ ID NO:26 (or sequences substantially homologous thereto) do not contain any internal cysteine residues. By "internal" residue is meant a residue at a position other than the N-terminal and/or C-terminal residue. In some embodiments, isolated peptides based on SEQ ID NO:12 or SEQ ID NO:26 (or sequences substantially homologous thereto) have an N-terminal cysteine residue.

In some embodiments, isolated peptides substantially homologous to SEQ ID NO:12 or SEQ ID NO:26 have 1, 2 or 3 amino acid substitutions, deletions or additions as compared to SEQ ID NO:12 or SEQ ID NO:26 themselves.

Preferably, isolated peptides based on SEQ ID NO:12 or SEQ ID NO:26 (or sequences substantially homologous thereto) are linear peptides.

In one aspect, the invention provides a conjugate comprising an isolated peptide comprising (or consisting of) SEQ ID NO:12 (or a sequence substantially homologous thereto) or comprising (or consisting of) SEQ ID NO:26 (or a sequence substantially homologous thereto) and (e.g. coupled to) a peptide carrier. Peptide carriers are described elsewhere herein. In a preferred embodiment the peptide carrier is KLH. In a preferred embodiment, the invention provides a conjugate comprising an isolated peptide consisting of SEQ ID NO:26 coupled to the peptide carrier KLH (preferably via the N-terminal cysteine residue of SEQ ID NO:26).

In one embodiment, the present invention provides an isolated peptide comprising an amino acid sequence of SEQ ID NO:13 (OTV14) or a sequence substantially homologous thereto. Substantially homologous sequences are described elsewhere herein.

In a preferred embodiment, the present invention provides an isolated peptide comprising an amino acid sequence of SEQ ID NO:13 (OTV14).

In one embodiment, the present invention provides an isolated peptide consisting of an amino acid sequence of SEQ ID NO:13 (OTV14) or a sequence substantially homologous thereto. Substantially homologous sequences are described elsewhere herein.

In one embodiment, the present invention provides an isolated peptide consisting of an amino acid sequence of SEQ ID NO:13 (OTV14).

In one embodiment, the present invention provides an isolated peptide comprising an amino acid sequence of SEQ ID NO:27 (OTV14) or a sequence substantially homologous thereto. Substantially homologous sequences are described elsewhere herein.

In a preferred embodiment, the present invention provides an isolated peptide comprising an amino acid sequence of SEQ ID NO:27 (OTV14).

In one embodiment, the present invention provides an isolated peptide consisting of an amino acid sequence of SEQ ID NO:27 (OTV14) or a sequence substantially homologous thereto. Substantially homologous sequences are described elsewhere herein.

In one embodiment, the present invention provides an isolated peptide consisting of an amino acid sequence of SEQ ID NO:27 (OTV14).

Preferably, isolated peptides based on SEQ ID NO:13 or SEQ ID NO:27 (or sequences substantially homologous thereto) comprise the amino sequences (or motifs) IED and/or (preferably "and") NYD. The amino acid sequence IED is found at positions 11-13 of SEQ ID NO:13 and at positions 12-14 of SEQ ID NO:27. The amino acid sequence NYD is found at positions 4-6 of SEQ ID NO:13 and at positions 5-7 of SEQ ID NO:27.

Preferably, in isolated peptides based on SEQ ID NO:13 or SEQ ID NO:27 (or sequences substantially homologous thereto) there is no more than one (preferably no) amino acid substitution or deletion within the IED motif and/or no more than one (preferably no) amino acid substitution or deletion within the NYD motif.

The OTV14 peptide (represented by SEQ ID NOs: 13 and 27) is a conformational epitope. The IED motif in these sequences corresponds to amino acid positions 599-601 of TRPV1 (SEQ ID NO:1) and the NYD motif in these sequences corresponds to amino acid positions 653-655 of TRPV1 (SEQ ID NO:1). Without wishing to be bound by theory, the other residues (i.e. the residues other than the IED and NYD motifs) act as spacers, believed to force the force the side-chains of the IED and NYD motifs into a specific conformation that mimics the actual conformation in a structural model of the full TRPV1 sequence.

In some embodiments, isolated peptides based on SEQ ID NO:13 or SEQ ID NO:27 (or sequences substantially homologous thereto) are <24 amino acids in length or <20 amino acids in length or <15 amino acids in length (e.g. are 5-23 or 8-23 or 10 to 23 or 15 to 23 or 20-23 or 5-10 or 8-10 or 5-11 or 8-11 or 10-15 or 11-15 or 5-15 or 8-15 or 5-20 or 8-20 or 10-20 or 11-20 amino acids in length). In some embodiments, isolated peptides based on SEQ ID NO:13 or SEQ ID NO:27 (or sequences substantially homologous thereto) are less than 39 amino acids in length, are less than 38 amino acids in length, or less than 37 amino acids in length, or less than 36 amino acids in length, or less than 35 amino acids in length, or less than 34 amino acids in length, or less than 33 amino acids in length (e.g. are 5-15 or 10-15 or 10-20 or 10-30 or 10-35 or 10-38 or 20-25 or 20-30 or 20-32 or 25-30 or 25-32 or 25-38 or 30-38 amino acids in length). In some embodiments, isolated peptides based on SEQ ID NO:13 or SEQ ID NO:27 (or sequences substantially homologous thereto) are 12-18 amino acids in length. In some embodiments, isolated peptides based on SEQ ID NO:13 or SEQ ID NO:27 (or sequences substantially homologous thereto) do not contain any internal cysteine residues. By "internal" residue is meant a residue at a position other than the N-terminal and/or C-terminal residue. In some embodiments, isolated peptides based on SEQ ID NO:13 or SEQ ID NO:27 (or sequences substantially homologous thereto) have an N-terminal cysteine residue and a C-terminal cysteine residue. In some embodiments, a further modification may be present at the N- and/or C-terminus (e.g. a propargyl group at the N-terminus and/or a C-terminal amide group).

In some embodiments, isolated peptides substantially homologous to SEQ ID NO:13 or SEQ ID NO:27 have 1, 2 or 3 amino acid substitutions, deletions or additions as compared to SEQ ID NO:13 or SEQ ID NO:27 themselves.

Preferably, isolated peptides based on SEQ ID NO:13 or SEQ ID NO:27 (or sequences substantially homologous thereto) are cyclic peptides. Preferably such peptides are cyclized via a disulphide bond between N- and C-terminal cysteine residues.

In one aspect, the invention provides a conjugate comprising an isolated peptide comprising (or consisting of) SEQ ID NO:13 (or a sequence substantially homologous thereto) or comprising (or consisting of) SEQ ID NO:27 (or a sequence substantially homologous thereto) and (e.g. coupled to) a peptide carrier. Peptide carriers are described elsewhere herein. In a preferred embodiment the peptide carrier is KLH. In a preferred embodiment, the invention provides a conjugate comprising an isolated peptide consisting of SEQ ID NO:27 coupled to the peptide carrier KLH (preferably via the propargyl group of SEQ ID NO:28).

In one aspect, the invention provides an isolated peptide comprising the amino acid sequence (or motif) NYD and the amino acid sequence (or motif) IED, wherein the amino acid sequence NYD is positioned N-terminally with respect to the amino acid sequence IED and preferably the NYD and IED sequences are separated by one or more amino acid residues (e.g. separated by 3, 4 or 5 amino acid resides, preferably by 4 amino acid residues, e.g. separated by the amino acid sequence PDGS (SEQ ID NO:38)). Such isolated peptides may further comprise one or more (e.g. 1, 2 or 3) amino acid residues positioned N-terminally with respect to the NYD sequence and/or (preferably "and") one or more (e.g. 1, 2 or 3) amino acid residues positioned C-terminally with respect to the IED sequence. The discussion elsewhere herein in relation to preferred features and properties of isolated peptides of the invention (e.g. preferred lengths and modifications) may be applied, mutatis mutandis, to this aspect for the invention. In another aspect, the present invention provides a conjugate comprising (i) an isolated peptide comprising the amino acid sequence (or motif) NYD and the amino acid sequence (or motif) IED, wherein the amino acid sequence NYD is positioned N-terminally with respect to the amino acid sequence IED and (ii) a peptide carrier. In preferred embodiments, the isolated peptide is as described elsewhere herein.

In one embodiment, the present invention provides an isolated peptide comprising an amino acid sequence of SEQ ID NO:14 (OTV15) or a sequence substantially homologous thereto. Substantially homologous sequences are described elsewhere herein.

In a preferred embodiment, the present invention provides an isolated peptide comprising an amino acid sequence of SEQ ID NO:14 (OTV15).

In one embodiment, the present invention provides an isolated peptide consisting of an amino acid sequence of SEQ ID NO:14 (OTV15) or a sequence substantially homologous thereto. Substantially homologous sequences are described elsewhere herein.

In one embodiment, the present invention provides an isolated peptide consisting of an amino acid sequence of SEQ ID NO:14 (OTV15).

In one embodiment, the present invention provides an isolated peptide comprising an amino acid sequence of SEQ ID NO:28 (OTV15) or a sequence substantially homologous thereto. Substantially homologous sequences are described elsewhere herein.

In a preferred embodiment, the present invention provides an isolated peptide comprising an amino acid sequence of SEQ ID NO:28 (OTV15).

In one embodiment, the present invention provides an isolated peptide consisting of an amino acid sequence of SEQ ID NO:28 (OTV15) or a sequence substantially homologous thereto. Substantially homologous sequences are described elsewhere herein.

In one embodiment, the present invention provides an isolated peptide consisting of an amino acid sequence of SEQ ID NO:28 (OTV15).

In some embodiments, isolated peptides based on SEQ ID NO:14 or SEQ ID NO:28 (or sequences substantially homologous thereto) comprise the amino sequence ESTSH. In some embodiments, isolated peptides based on SEQ ID NO:14 or SEQ ID NO:28 (or sequences substantially homologous thereto) are <24 amino acids in length or <20 amino acids in length <15 amino acids in length <10 amino acids in length (e.g. are 5-23 or 8-23 or 10 to 23 or 15 to 23 or 20-23 or 5-10 or 8-10 or 5-11 or 8-11 or 10-15 or 11-15 or 5-15 or 8-15 or 5-20 or 8-20 or 10-20 or 11-20 amino acids in length). In some embodiments, isolated peptides based on SEQ ID NO:14 or SEQ ID NO:28 (or sequences substantially homologous thereto) are less than 39 amino acids in length, are less than 38 amino acids in length, or less than 37 amino acids in length, or less than 36 amino acids in length, or less than 35 amino acids in length, or less than 34 amino acids in length, or less than 33 amino acids in length (e.g. are 5-15 or 10-15 or 10-20 or 10-30 or 10-35 or 10-38 or 20-25 or 20-30 or 20-32 or 25-30 or 25-32 or 25-38 or 30-38 amino acids in length). In some embodiments, isolated peptides based on SEQ ID NO:14 or SEQ ID NO:28 (or sequences substantially homologous thereto) are 8-14 amino acids in length. In some embodiments, isolated peptides based on SEQ ID NO:14 or SEQ ID NO:28 (or sequences substantially homologous thereto) do not contain any internal cysteine residues. By "internal" residue is meant a residue at a position other than the N-terminal and/or C-terminal residue. In some embodiments, isolated peptides based on SEQ ID NO:14 or SEQ ID NO:28 (or sequences substantially homologous thereto) have an N-terminal cysteine residue and a C-terminal cysteine residue. In some embodiments, a further modification may be present at the N- and/or C-terminus (e.g. a propargyl group at the N-terminus and/or a C-terminal amide group).

In some embodiments, isolated peptides substantially homologous to SEQ ID NO:14 or SEQ ID NO:28 have 1, 2 or 3 amino acid substitutions, deletions or additions as compared to SEQ ID NO:14 or SEQ ID NO:28 themselves.

Preferably, isolated peptides based on SEQ ID NO:14 or SEQ ID NO:28 (or sequences substantially homologous thereto) are cyclic peptides. Preferably such peptides are cyclized via a disulphide bond between N- and C-terminal cysteine residues.

In one aspect, the invention provides a conjugate comprising an isolated peptide comprising (or consisting of) SEQ ID NO:14 (or a sequence substantially homologous thereto) or comprising (or consisting of) SEQ ID NO:28 (or a sequence substantially homologous thereto) and (e.g.

coupled to) a peptide carrier. Peptide carriers are described elsewhere herein. In a preferred embodiment the peptide carrier is KLH. In a preferred embodiment, the invention provides a conjugate comprising an isolated peptide consisting of SEQ ID NO:28 coupled to the peptide carrier KLH (preferably via the propargyl group of SEQ ID NO:28).

In some embodiments, isolated peptides (or conjugates) in accordance with the invention may be present in a solution or in a suspension. Thus, in one aspect the present invention provides a composition comprising an isolated peptide of the invention, and optionally an acceptable (e.g. a pharmaceutically acceptable) diluent, buffer, preservative and/or excipient.

In some embodiments, isolated peptides (or conjugates) may be present on (i.e. attached to or bound to) a solid support (e.g. a bead or microbead or plate or microtitre plate). Thus, in one aspect the present invention provides a solid support, having attached thereto (either directly or indirectly attached thereto) an isolated peptide or conjugate of the invention.

Isolated peptides (and conjugates) of the invention are typically suitable for use in the identification (or generation or raising) of antibodies that bind to TRPV1 (preferably human TRPV1). For example, isolated peptides of the present invention are typically suitable for use as antigenic epitopes for the identification (or the generation or the raising) of antibodies. The identification (or the generation or the raising) of antibodies using isolated peptides of the invention may be done by any suitable means and the skilled person is familiar with suitable techniques (e.g. as discussed elsewhere herein). For example, isolated peptides (and conjugates) of the invention are typically suitable for use in the identification (or generation or raising) of polyclonal antibodies that bind to TRPV1 (e.g. polyclonal antibodies raised in an animal such as a rabbit that has been immunized with an isolated peptide (or conjugate) of the invention), or in in the identification (or generation or raising) of monoclonal antibodies using standard hybridoma technology or phage display. Put another way, isolated peptides (and conjugates) of the invention typically represent (or correspond to or correspond essentially to) useful epitopes of TRPV1 to target with anti-TRPV1 antibodies.

In some embodiments, isolated peptides (and conjugates) of the invention are suitable for use in the identification (or generation or raising) of antibodies that bind to TRPV1 (preferably human TRPV1) and inhibit capsaicin-induced activation of TRPV1.

In some embodiments, isolated peptides (and conjugates) of the invention are suitable for use in the identification (or generation or raising) of antibodies that bind to TRPV1 (preferably human TRPV1) and do not significantly inhibit heat-induced activation of TRPV1.

In some embodiments, isolated peptides (and conjugates) of the invention are suitable for use in the identification (or generation or raising) of antibodies that bind to TRPV1 (preferably human TRPV1) and preferentially inhibit capsaicin-induced activation of TRPV1 as opposed to heat-induced activation of TRPV1. In some such embodiments, isolated peptides OTV4, OTV5 and OTV12 are preferred. In some such embodiments, isolated peptides OTV3, OTV4 and OTV5 are preferred. In some embodiments, OTV5 is preferred. In some embodiments, OTV4 is preferred. In some embodiments, OTV3 is preferred.

Isolated peptides (and conjugates) of the invention correspond to (or correspond essentially to) epitopes (or regions or portions) of TRPV1 (preferably human TRPV1, SEQ ID NO:1) that are positioned in the region of TRPV1 (preferably human TRPV1, SEQ ID NO:1) from amino acid residue 599 to amino acid residue 656.

In some embodiments, isolated peptides of the invention have an amino acid residue other than cysteine (C) (preferably a serine (S)) at the position that corresponds to C621 of human TRPV1 (SEQ ID NO:1).

In some embodiments, isolated peptides of the invention comprise the amino acid sequence IEDGKN (SEQ ID NO:33) or a sequence containing 1, 2 or 3 amino acid substitutions or deletions or additions compared to SEQ ID NO:33.

In some embodiments, isolated peptides of the invention comprise the amino acid sequence LPSEST (SEQ ID NO:34) or a sequence containing 1, 2 or 3 amino acid substitutions or deletions or additions compared to SEQ ID NO:34.

In some embodiments, isolated peptides of the invention comprise the amino acid sequence PPDSSYNS (SEQ ID NO:35) or a sequence containing 1, 2 or 3 amino acid substitutions or deletions or additions compared to SEQ ID NO:35.

In some embodiments, isolated peptides of the invention comprise the amino acid sequence RWRGPA (SEQ ID NO:36) or a sequence containing 1, 2 or 3 amino acid substitutions or deletions or additions compared to SEQ ID NO:36.

In some embodiments, isolated peptides of the invention comprise the amino acid sequence RGPASR (SEQ ID NO:37) or a sequence containing 1, 2 or 3 amino acid substitutions or deletions or additions compared to SEQ ID NO:37.

Nucleic acid molecules comprising (or consisting of) nucleotide sequences that encode the isolated peptides of the present invention as defined herein, or nucleic acid molecules substantially homologous thereto, form yet further aspects of the invention.

The term "substantially homologous" as used herein in connection with an nucleic acid sequence includes sequences having at least 65%, 70% or 75%, preferably at least 80%, and even more preferably at least 85%, 90%, 95%, 96%, 97%, 98% or 99%, sequence identity to the starting nucleic acid sequence.

The term "nucleic acid sequence" or "nucleic acid molecule" as used herein refers to a sequence of nucleoside or nucleotide monomers composed of naturally occurring bases, sugars and intersugar (backbone) linkages. The term also includes modified or substituted sequences comprising non-naturally occurring monomers or portions thereof. The nucleic acid sequences of the present invention may be deoxyribonucleic acid sequences (DNA) or ribonucleic acid sequences (RNA) and may include naturally occurring bases including adenine, guanine, cytosine, thymidine and uracil. The sequences may also contain modified bases. Examples of such modified bases include aza and deaza adenine, guanine, cytosine, thymidine and uracil; and xanthine and hypoxanthine. The nucleic acid molecules may be double stranded or single stranded. The nucleic acid molecules may be wholly or partially synthetic or recombinant.

In another aspect, the present invention provides a composition comprising an isolated peptide (or conjugate) of the invention. Such compositions may further comprise (e.g. be in admixture with) a suitable diluent, carrier, excipient and/or preservative (e.g. a pharmaceutically acceptable diluent, carrier, excipient and/or preservative).

As indicated above, isolated peptides (and conjugates) of the invention are typically suitable for use in the identification (or generation or raising) of antibodies that bind to TRPV1 (preferably human TRPV1) and preferentially inhibit capsaicin-induced activation of TRPV1 as opposed to heat-induced activation of TRPV1.

Thus, in one aspect, the present invention provides an antibody, for example an isolated antibody, which binds to (or specifically recognises or specifically binds) TRPV1, wherein said antibody preferentially inhibits capsaicin-induced activation of TRPV1 as opposed to heat-induced activation of TRPV1.

In preferred embodiments, the TRPV1 (transient receptor potential vanilloid type 1) is human TRPV1 (hTRPV1). The amino acid sequence of human TRPV1 is set forth herein as SEQ ID NO:1.

In some embodiments, antibodies of the invention bind to an epitope of TRPV1 that is located in an extracellular region of the TRPV1 protein. In some embodiments, antibodies bind to an epitope of TRPV1 in the region of TRPV1 defined by amino acid residues 599-656 of TRPV1 (SEQ ID NO:1). In some embodiments, the entire epitope bound lies within this region of TRPV1. In some embodiments, at least one amino acid of the epitope bound lies within this region of TRPV1.

In preferred embodiments, antibodies of the invention bind to (or are capable of binding to) an isolated peptide or conjugate of the invention. Preferred isolated peptides and conjugates and preferred groups of isolated peptides and conjugates are defined elsewhere herein. In preferred embodiments, antibodies of the invention bind to a preferred isolated peptide or conjugate as described elsewhere herein. The ability of an antibody to bind to an isolated peptide can be assessed by any appropriate means and skilled person is familiar with suitable methods (e.g. an ELISA assay to assess whether or not a given isolated peptide can compete with full length TRPV1 for antibody binding).

Although preferred antibodies of the invention bind to (or are capable of binding to) an isolated peptide or conjugate of the invention, they of course also typically bind to full-length (or wild-type or native) TRPV1 (preferably human TRPV1).

In some embodiments, the full-length (or wild-type or native) TRPV1 (preferably human TRPV1) is TRPV1 that is expressed on cells, preferably on mammalian cells (e.g. on adherent Chinese hamster ovary (CHO) cells). In some embodiments, antibodies of the present invention are capable of binding to TRPV1 that is heterologously expressed on cells (e.g. CHO cells). In some embodiments, antibodies of the present invention are capable of binding to TRPV1 that is expressed on cells, wherein the TRPV1 is expressed from an inducible expression system (such as a tetracycline regulated expression system e.g. as described in the Example section herein). TRPV1 is typically expressed on (or at) the surface of cells. The binding of an antibody of the invention to TRPV1 may be assessed by any suitable means, and the skilled person will be familiar with suitable methods (e.g. flow cytometry (such as FACS) or immuno-cytochemistry or using a functional assay e.g. as described elsewhere herein).

The isolated peptides of the present invention correspond to, or correspond essentially to, certain regions or epitopes of full-length TRPV1 (preferably human TRPV1, SEQ ID NO:1).

More specifically, the isolated peptides of SEQ ID NO:2 and SEQ ID NO:16 (OTV3 peptides) correspond essentially to residues 599-630 of human TRPV1 (SEQ ID NO:1).

The isolated peptide SEQ ID NO:3 (an OTV4 peptide) corresponds to residues 599-630 of human TRPV1 (SEQ ID NO:1). The isolated peptide SEQ ID NO:17 (an OTV4 peptide) corresponds essentially to residues 599-630 of human TRPV1 (SEQ ID NO:1).

The isolated peptides of SEQ ID NO:4 and SEQ ID NO:18 (OTV5 peptides) correspond essentially to residues 599-630 of human TRPV1 (SEQ ID NO:1).

The isolated peptide of SEQ ID NO:5 (an OTV6 peptide) corresponds to residues 599-606 of human TRPV1 (SEQ ID NO:1). The isolated peptide of SEQ ID NO:19 (an OTV6 peptide) corresponds essentially to residues 599-606 of human TRPV1 (SEQ ID NO:1).

The isolated peptide SEQ ID NO:6 (an OTV7 peptide) corresponds to residues 599-614 of human TRPV1 (SEQ ID NO:1). The isolated peptide SEQ ID NO:20 (an OTV7 peptide) corresponds essentially to residues 599-614 of human TRPV1 (SEQ ID NO:1).

The isolated peptides of SEQ ID NO:7 and SEQ ID NO:21 (OTV8 peptides) correspond essentially to residues 599-622 of human TRPV1 (SEQ ID NO:1).

The isolated peptides of SEQ ID NO:8 and SEQ ID NO:22 (OTV9 peptides) correspond essentially to residues 607-630 of human TRPV1 (SEQ ID NO:1).

The isolated peptides of SEQ ID NO:9 and SEQ ID NO:23 (OTV10 peptides) correspond essentially to residues 615-630 of human TRPV1 (SEQ ID NO:1).

The isolated peptide of SEQ ID NO:10 (an OTV11 peptide) corresponds to residues 623-630 of human TRPV1 (SEQ ID NO:1). The isolated peptide of SEQ ID NO:24 (an OTV11 peptide) corresponds essentially to residues 623-630 of human TRPV1 (SEQ ID NO:1).

The isolated peptides of SEQ ID NO:11 and SEQ ID NO:25 (OTV12 peptides) correspond essentially to residues 631-643 of human TRPV1 (SEQ ID NO:1).

The isolated peptide of SEQ ID NO:12 (an OTV13 peptide) corresponds to residues 644-656 of human TRPV1 (SEQ ID NO:1). The isolated peptide of SEQ ID NO:26 (an OTV13 peptide) corresponds essentially to residues 644-656 of human TRPV1 (SEQ ID NO:1).

The isolated peptides of SEQ ID NOs:13 and 27 (OTV14 peptides) comprise amino acid sequences (or motifs), IED and NYD, that correspond to residues in TRPV1 (SEQ ID NO:1). More specifically, the IED sequence within SEQ ID NOs: 13 and 27 corresponds to residues 599-601 of TRPV1 (SEQ ID NO:1) and the NYD sequence within SEQ ID NOs:13 and 27 corresponds to residues 653-655 of TRPV1 (SEQ ID NO:1).

The isolated peptide of SEQ ID NO:14 (an OTV15 peptide) corresponds to residues 610-620 of human TRPV1 (SEQ ID NO:1). The isolated peptide of SEQ ID NO:28 (an OTV15 peptide) corresponds essentially to residues 610-620 of human TRPV1 (SEQ ID NO:1).

By "corresponds to" is meant that the amino sequence (SEQ ID NO:) of the isolated peptide matches the amino acid sequence of the stated region or epitope of human TRPV1 (SEQ ID NO:1). By "corresponds essentially to" is meant that the amino acid sequence of the isolated peptide (SEQ ID NO:) is identifiable as being based on (or derived from or a modified form of) the sequence of the stated region or epitope of human TRPV1 (SEQ ID NO:1). For example, an isolated peptide having a sequence that "corresponds essentially to" the stated region or epitope of human TRPV1 (SEQ ID NO:1) typically has one or more (e.g. 1, 2, 3, 4 or 5, preferably 1, 2 or 3) amino acid substitutions, additions or deletions as compared to an isolated peptide that corresponds to (i.e. exactly corresponds to) the sequence of the stated region or epitope of human TRPV1 (SEQ ID NO:1). Thus, an isolated peptide having a sequence that "corresponds essentially to" the stated region or epitope of human TRPV1 (SEQ ID NO:1) may be considered to be a "substantially homologous" isolated peptide sequence as defined elsewhere herein.

In some embodiments, antibodies of the invention bind to TRPV1 at an epitope that is in the region defined by amino acid residues 599-630, amino acid residues 599-606, amino acid residues 599-614, amino acid residues 599-622, amino acid residues 607-630, amino acid residues 615-630, amino acid residues 623-630, amino acid residues 631-643, amino acid residues 644-656, or amino acid residues 610-620 of TRPV1 (SEQ ID NO:1), or bind to TRPV1 at an epitope in the region defined by amino acid residues 599-601 and residues 653-655 of TRPV1 (SEQ ID NO:1). In some embodiments, the entire epitope bound lies within one of these regions of TRPV1. In some embodiments, at least one amino acid of the epitope bound lies within one of these regions of TRPV1.

In some embodiments, antibodies of the invention bind to TRPV1 at an epitope of TRPV1 that is in the region defined by amino acid residues 599-630, amino acid residues 599-614, amino acid residues 607-630, amino acid residues 631-643, or amino acid residues 644-656 of TRPV1 (SEQ ID NO:1).

In some embodiments, antibodies of the invention bind to TRPV1 at an epitope of TRPV1 that is in the region defined by amino acid residues 599-630, or 631-643 of TRPV1 (SEQ ID NO:1).

In some embodiments, antibodies of the invention that bind to TRPV1 at an epitope of TRPV1 that is in the region defined by amino acid residues 599-630 of TRPV1 (SEQ ID NO:1) are preferred.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:
(a) a variable heavy (VH) CDR1 that has the amino acid sequence of SEQ ID NO:41 or SEQ ID NO:77, or a sequence substantially homologous thereto,
(b) a VH CDR2 that has the amino acid sequence of SEQ ID NO:42 or SEQ ID NO:78, or a sequence substantially homologous thereto, and
(c) a VH CDR3 that has the amino acid sequence of SEQ ID NO:43 or SEQ ID NO:79, or a sequence substantially homologous thereto; and/or (preferably "and")
wherein said light chain variable region comprises:
(d) a variable light (VL) CDR1 that has the amino acid sequence of SEQ ID NO:91 or preferably SEQ ID NO:92, or a sequence substantially homologous thereto,
(e) a VL CDR2 that has the amino acid sequence of SEQ ID NO:45 or SEQ ID NO:81, or a sequence substantially homologous thereto, and
(f) a VL CDR3 that has the amino acid sequence of SEQ ID NO:46 or SEQ ID NO:82, or a sequence substantially homologous thereto. Substantially homologous sequences are described elsewhere herein. Preferably, said substantially homologous sequence is a sequence containing 1, 2 or 3 amino acid substitutions compared to the given CDR sequence, or said substantially homologous sequence is a sequence containing conservative amino acid substitutions of the given CDR sequence.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:
(a) a variable heavy (VH) CDR1 that has the amino acid sequence of SEQ ID NO:41 or SEQ ID NO:77,
(b) a VH CDR2 that has the amino acid sequence of SEQ ID NO:42 or SEQ ID NO:78, and
(c) a VH CDR3 that has the amino acid sequence of SEQ ID NO:43 or SEQ ID NO:79, and/or (preferably "and")
wherein said light chain variable region comprises:
(d) a variable light (VL) CDR1 that has the amino acid sequence of SEQ ID NO:91 or preferably SEQ ID NO:92,
(e) a VL CDR2 that has the amino acid sequence of SEQ ID NO:45 or SEQ ID NO:81, and
(f) a VL CDR3 that has the amino acid sequence of SEQ ID NO:46 or SEQ ID NO:82.

In some embodiments of the present invention, the VL CDR1 has or comprises an amino acid sequence of SEQ ID NO: 91 (K S S Q S L L $X_8$ S $X_{10}$ $X_{11}$ $X_{12}$ $X_{13}$ $X_{14}$ $X_{15}$ $X_{16}$ $X_{17}$). In these embodiments $X_8$, $X_{10}$, $X_{11}$, $X_{12}$, $X_{13}$, $X_{14}$, $X_{15}$ and $X_{16}$ can be any amino acid, and $X_{17}$ can be any amino acid or no amino acid. Preferably one or more, most preferably all, of these X residues are selected from the following group: $X_8$ is D or Y; $X_{10}$ is A or S; $X_{11}$ is G or N; $X_{12}$ is K or Q; $X_{13}$ is T or K; $X_{14}$ is Y or N; $X_{15}$ is L or C, $X_{16}$ is N or L; $X_{17}$ is A or is no amino acid. Thus, a preferred VL CDR1 has or comprises the amino acid sequence of SEQ ID NO: 92. For example, preferred VL CDR1 sequences of this embodiment have or comprise SEQ ID NOs: 44, 62 or 80.

In embodiments of the invention where one or more of the CDR sequences contain an $X_X$ residue, then CDRs with sequences which are substantially homologous thereto containing 1, 2 or 3, preferably 1 or 2 (more preferably 1), altered amino acids or amino acid substitutions compared with a given CDR sequence are also encompassed by the invention. In some such embodiments said alterations or substitutions in amino acid residues can include one or more of the $X_X$ residues or can be at residues other than the $X_X$ residues. In other such embodiments said alterations are in a mixture of the $X_X$ residues and the non-$X_X$ residues.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:
(a) a variable heavy (VH) CDR1 that has the amino acid sequence of SEQ ID NO:41, or a sequence substantially homologous thereto,
(b) a VH CDR2 that has the amino acid sequence of SEQ ID NO:42, or a sequence substantially homologous thereto, and
(c) a VH CDR3 that has the amino acid sequence of SEQ ID NO:43, or a sequence substantially homologous thereto; and/or (preferably "and")
wherein said light chain variable region comprises:
(d) a variable light (VL) CDR1 that has the amino acid sequence of SEQ ID NO:91 or preferably SEQ ID NO:92, or a sequence substantially homologous thereto, (e) a VL CDR2 that has the amino acid sequence of SEQ ID NO:45, or a sequence substantially homologous thereto, and
(f) a VL CDR3 that has the amino acid sequence of SEQ ID NO:46, or a sequence substantially homologous thereto. Substantially homologous sequences are described elsewhere herein. Preferably, said substantially homologous sequence is a sequence containing 1, 2 or 3 amino acid substitutions compared to the given CDR sequence, or said substantially homologous sequence is a sequence containing conservative amino acid substitutions of the given CDR sequence.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:77, or a sequence substantially homologous thereto, (b) a VH CDR2 that has the amino acid sequence of SEQ ID NO:78, or a sequence substantially homologous thereto, and (c) a VH CDR3 that has the amino acid sequence of SEQ ID NO:79, or a sequence substantially homologous thereto; and/or (preferably "and")

wherein said light chain variable region comprises:

(d) a variable light (VL) CDR1 that has the amino acid sequence of SEQ ID NO:91 or preferably SEQ ID NO:92, or a sequence substantially homologous thereto, (e) a VL CDR2 that has the amino acid sequence of SEQ ID NO:81, or a sequence substantially homologous thereto, and (f) a VL CDR3 that has the amino acid sequence of SEQ ID NO:82, or a sequence substantially homologous thereto. Substantially homologous sequences are described elsewhere herein. Preferably, said substantially homologous sequence is a sequence containing 1, 2 or 3 amino acid substitutions compared to the given CDR sequence, or said substantially homologous sequence is a sequence containing conservative amino acid substitutions of the given CDR sequence.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:440 or preferably SEQ ID NO:441, or a sequence substantially homologous thereto, (b) a VH CDR2 that has the amino acid sequence of SEQ ID NO:442 or preferably SEQ ID NO:443, or a sequence substantially homologous thereto, and (c) a VH CDR3 that has the amino acid sequence of SEQ ID NO:444 or preferably SEQ ID NO:445, or a sequence substantially homologous thereto; and/or (preferably "and")

wherein said light chain variable region comprises:

(d) a variable light (VL) CDR1 that has the amino acid sequence of SEQ ID NO:446 or preferably SEQ ID NO:447, or a sequence substantially homologous thereto, (e) a VL CDR2 that has the amino acid sequence of SEQ ID NO:107, SEQ ID NO:127, SEQ ID NO:147, SEQ ID NO:167, SEQ ID NO:187, SEQ ID NO:207, SEQ ID NO:227, SEQ ID NO:247 or SEQ ID NO:267, or a sequence substantially homologous thereto, and (f) a VL CDR3 that has the amino acid sequence of SEQ ID NO:108, SEQ ID NO:128, SEQ ID NO:148, SEQ ID NO:168, SEQ ID NO:188, SEQ ID NO:208, SEQ ID NO:228, SEQ ID NO:248 or SEQ ID NO:268, or a sequence substantially homologous thereto. Substantially homologous sequences are described elsewhere herein. Preferably, said substantially homologous sequence is a sequence containing 1, 2 or 3 amino acid substitutions compared to the given CDR sequence, or said substantially homologous sequence is a sequence containing conservative amino acid substitutions of the given CDR sequence.

In some embodiments of the present invention, the VH CDR1 has or comprises an amino acid sequence of SEQ ID NO: 440 (S D $X_3$ A W N). In these embodiments $X_3$ can be any amino acid. Preferably the $X_3$ residue is F or Y. Thus, a preferred VH CDR1 has or comprises the amino acid sequence of SEQ ID NO: 441. For example, preferred VH CDR1 sequences of this embodiment have or comprise SEQ ID NOs: 103, 123, 143, 163, 183, 203, 223, 243 or 263.

In some embodiments of the present invention, the VH CDR2 has or comprises an amino acid sequence of SEQ ID NO: 442 ($X_1$ I T Y S $X_6$ $X_7$ T N $X_{10}$ N P S L $X_{15}$ S). In these embodiments $X_1$, $X_6$, $X_7$, $X_{10}$ and $X_{15}$ can be any amino acid. Preferably one or more, most preferably all, of these X residues are selected from the following group: $X_1$ is Y or F; $X_6$ is G or D; $X_7$ is Y or H or N; $X_{10}$ is Y or F; $X_{15}$ is K or I or R. Thus, a preferred VH CDR2 has or comprises the amino acid sequence of SEQ ID NO: 443. For example, preferred VH CDR2 sequences of this embodiment have or comprise SEQ ID NOs: 104, 124, 144, 164, 184, 204, 224, 244 or 264.

In some embodiments of the present invention, the VH CDR3 has or comprises an amino acid sequence of SEQ ID NO: 444 (S $X_2$ $X_3$ $X_4$ F D Y). In these embodiments $X_2$, $X_3$ and $X_4$ can be any amino acid. Preferably one or more, most preferably all, of these X residues are selected from the following group: $X_2$ is T or G; $X_3$ is T or A or N; $X_4$ is Y or F. Thus, a preferred VH CDR3 has or comprises the amino acid sequence of SEQ ID NO: 445. For example, preferred VH CDR3 sequences of this embodiment have or comprise SEQ ID NOs: 105, 125, 145, 165, 185, 205, 225, 245 or 265.

In some embodiments of the present invention, the VL CDR1 has or comprises an amino acid sequence of SEQ ID NO: 446 (R S S Q $X_5$ $X_6$ $X_7$ H S D G N T Y L E). In these embodiments $X_5$, $X_6$ and $X_7$ can be any amino acid. Preferably one or more, most preferably all, of these X residues are selected from the following group: $X_5$ is S or T; $X_6$ is I or V; $X_7$ is L or V or I. Thus, a preferred VL CDR1 has or comprises the amino acid sequence of SEQ ID NO: 447. For example, preferred VL CDR1 sequences of this embodiment have or comprise SEQ ID NOs: 106, 126, 146, 166, 186, 206, 226, 246 or 266.

Certain preferred combinations of VH CDR sequences and VL CDR sequences are set forth in each of the rows numbered 1-45 in Table W below:

TABLE W

| | VH CDR1 (SEQ ID NO:) | VH CDR2 (SEQ ID NO:) | VH CDR3 (SEQ ID NO:) | VL CDR1 (SEQ ID NO:) | VL CDR2 (SEQ ID NO:) | VL CDR3 (SEQ ID NO:) |
|---|---|---|---|---|---|---|
| 1 | 440 | 104 | 105 | 106 | 107 | 108 |
| 2 | 440 | 124 | 125 | 126 | 127 | 128 |
| 3 | 440 | 144 | 145 | 146 | 147 | 148 |
| 4 | 440 | 164 | 165 | 166 | 167 | 168 |
| 5 | 440 | 184 | 185 | 186 | 187 | 188 |
| 6 | 440 | 204 | 205 | 206 | 207 | 208 |
| 7 | 440 | 224 | 225 | 226 | 227 | 228 |
| 8 | 440 | 244 | 245 | 246 | 247 | 248 |
| 9 | 440 | 264 | 265 | 266 | 267 | 268 |

TABLE W-continued

| | VH CDR1 (SEQ ID NO:) | VH CDR2 (SEQ ID NO:) | VH CDR3 (SEQ ID NO:) | VL CDR1 (SEQ ID NO:) | VL CDR2 (SEQ ID NO:) | VL CDR3 (SEQ ID NO:) |
|---|---|---|---|---|---|---|
| 10 | 103 | 442 | 105 | 106 | 107 | 108 |
| 11 | 123 | 442 | 125 | 126 | 127 | 128 |
| 12 | 143 | 442 | 145 | 146 | 147 | 148 |
| 13 | 163 | 442 | 165 | 166 | 167 | 168 |
| 14 | 183 | 442 | 185 | 186 | 187 | 188 |
| 15 | 203 | 442 | 205 | 206 | 207 | 208 |
| 16 | 223 | 442 | 225 | 226 | 227 | 228 |
| 17 | 243 | 442 | 245 | 246 | 247 | 248 |
| 18 | 263 | 442 | 265 | 266 | 267 | 268 |
| 19 | 103 | 104 | 444 | 106 | 107 | 108 |
| 20 | 123 | 124 | 444 | 126 | 127 | 128 |
| 21 | 143 | 144 | 444 | 146 | 147 | 148 |
| 22 | 163 | 164 | 444 | 166 | 167 | 168 |
| 23 | 183 | 184 | 444 | 186 | 187 | 188 |
| 24 | 203 | 204 | 444 | 206 | 207 | 208 |
| 25 | 223 | 224 | 444 | 226 | 227 | 228 |
| 26 | 243 | 244 | 444 | 246 | 247 | 248 |
| 27 | 263 | 264 | 444 | 266 | 267 | 268 |
| 28 | 103 | 104 | 105 | 446 | 107 | 108 |
| 29 | 123 | 124 | 125 | 446 | 127 | 128 |
| 30 | 143 | 144 | 145 | 446 | 147 | 148 |
| 31 | 163 | 164 | 165 | 446 | 167 | 168 |
| 32 | 183 | 184 | 185 | 446 | 187 | 188 |
| 33 | 203 | 204 | 205 | 446 | 207 | 208 |
| 34 | 223 | 224 | 225 | 446 | 227 | 228 |
| 35 | 243 | 244 | 245 | 446 | 247 | 248 |
| 36 | 263 | 264 | 265 | 446 | 267 | 268 |
| 37 | 440 | 442 | 444 | 446 | 107 | 108 |
| 38 | 440 | 442 | 444 | 446 | 127 | 128 |
| 39 | 440 | 442 | 444 | 446 | 147 | 148 |
| 40 | 440 | 442 | 444 | 446 | 167 | 168 |
| 41 | 440 | 442 | 444 | 446 | 187 | 188 |
| 42 | 440 | 442 | 444 | 446 | 207 | 208 |
| 43 | 440 | 442 | 444 | 446 | 227 | 228 |
| 44 | 440 | 442 | 444 | 446 | 247 | 248 |
| 45 | 440 | 442 | 444 | 446 | 267 | 268 |

In embodiments of the invention set forth in Table W, preferably the consensus sequence as set forth as SEQ ID NO:440 is a sequence as set forth as SEQ ID NO:441. In embodiments of the invention set forth in Table W, preferably the consensus sequence as set forth as SEQ ID NO:442 is a sequence as set forth as SEQ ID NO:443. In embodiments of the invention set forth in Table W, preferably the consensus sequence as set forth as SEQ ID NO:444 is a sequence as set forth as SEQ ID NO:445. In embodiments of the invention set forth in Table W, preferably the consensus sequence as set forth as SEQ ID NO:446 is a sequence as set forth as SEQ ID NO:447. In some embodiments of the invention set forth in Table W, the combinations of CDR sequences set out in rows 37-45 are preferred. In some embodiments, sequences substantially homologous to the specific sequences recited in Table W may be employed instead of the specific sequences themselves.

In some embodiments, the antibody of the invention comprises at least one heavy chain variable region that comprises three CDRs and at least one light chain variable region that comprises three CDRs, wherein said heavy chain variable region comprises a VH CDR1 that has the amino acid sequence of SEQ ID NO:440 or preferably SEQ ID NO:441, a VH CDR2 that has the amino acid sequence of SEQ ID NO:442 or preferably SEQ ID NO:443 and a VH CDR3 that has the amino acid sequence of SEQ ID NO:444 or preferably SEQ ID NO:445, and/or (preferably "and") wherein said light chain variable region comprises a VL CDR1 that has the amino acid sequence of SEQ ID NO:446 or preferably SEQ ID NO:447. In some such embodiments, preferably the light chain variable region comprises a VL CDR2 that has the amino acid sequence of SEQ ID NO:107 and a VL CDR3 that has the amino acid sequence of SEQ ID NO:108, or the light chain variable region comprises a VL CDR2 that has the amino acid sequence of SEQ ID NO:127 and a VL CDR3 that has the amino acid sequence of SEQ ID NO:128, or the light chain variable region comprises a VL CDR2 that has the amino acid sequence of SEQ ID NO:147 and a VL CDR3 that has the amino acid sequence of SEQ ID NO:148, or the light chain variable region comprises a VL CDR2 that has the amino acid sequence of SEQ ID NO:167 and a VL CDR3 that has the amino acid sequence of SEQ ID NO:168, or the light chain variable region comprises a VL CDR2 that has the amino acid sequence of SEQ ID NO:187 and a VL CDR3 that has the amino acid sequence of SEQ ID NO:188, or the light chain variable region comprises a VL CDR2 that has the amino acid sequence of SEQ ID NO:207 and a VL CDR3 that has the amino acid sequence of SEQ ID NO:208, or the light chain variable region comprises a VL CDR2 that has the amino acid sequence of SEQ ID NO:227 and a VL CDR3 that has the amino acid sequence of SEQ ID NO:228, or the light chain variable region comprises a VL CDR2 that has the amino acid sequence of SEQ ID NO:247 and a VL CDR3 that has the amino acid sequence of SEQ ID NO:248, or the light chain variable region comprises a VL CDR2 that has the amino acid sequence of SEQ ID NO:267 and a VL CDR3 that has the amino acid sequence of SEQ ID NO:268. In some embodiments, sequences substantially homologous to the specific sequences recited in this paragraph may be employed instead of the specific sequences themselves.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:103, SEQ ID NO:123, SEQ ID NO:143, SEQ ID NO:163, SEQ ID NO:183, SEQ ID NO:203, SEQ ID NO:223, SEQ ID NO:243, SEQ ID NO:263, SEQ ID NO:283, SEQ ID NO:303, SEQ ID NO:323, SEQ ID NO:363, SEQ ID NO:383, SEQ ID NO:403, SEQ ID NO:41, SEQ ID NO:59 or SEQ ID NO:77, or a sequence substantially homologous thereto, (b) a VH CDR2 that has the amino acid sequence of SEQ ID NO: 104, SEQ ID NO:124, SEQ ID NO:144, SEQ ID NO:164, SEQ ID NO:184, SEQ ID NO:204, SEQ ID NO:224, SEQ ID NO:244, SEQ ID NO:264, SEQ ID NO:284, SEQ ID NO:304, SEQ ID NO:324, SEQ ID NO:364, SEQ ID NO:384, SEQ ID NO:404, SEQ ID NO:42, SEQ ID NO:60 or SEQ ID NO:78, or a sequence substantially homologous thereto, and (c) a VH CDR3 that has the amino acid sequence of SEQ ID NO: 105, SEQ ID NO:125, SEQ ID NO:145, SEQ ID NO:165, SEQ ID NO:185, SEQ ID NO:205, SEQ ID NO:225, SEQ ID NO:245, SEQ ID NO:265, SEQ ID NO:285, SEQ ID NO:305, SEQ ID NO:325, SEQ ID NO:365, SEQ ID NO:385, SEQ ID NO:405, SEQ ID NO:43, SEQ ID NO:61 or SEQ ID NO:79, or a sequence substantially homologous thereto; and/or (preferably "and")

wherein said light chain variable region comprises:

(d) a variable light (VL) CDR1 that has the amino acid sequence of SEQ ID NO:448 or preferably SEQ ID NO:449, or a sequence substantially homologous thereto, (e) a VL CDR2 that has the amino acid sequence of SEQ ID NO:107, SEQ ID NO:127, SEQ ID NO:147, SEQ ID NO:167, SEQ ID NO:187, SEQ ID NO:207, SEQ ID NO:227, SEQ ID NO:247, SEQ ID NO:267, SEQ ID NO:287, SEQ ID NO:307, SEQ ID NO:327, SEQ ID NO:367, SEQ ID NO:387, SEQ ID NO:407, SEQ ID NO:45, SEQ ID NO:63 or SEQ ID NO:81, or a sequence substantially homologous thereto, and (f) a VL CDR3 that has the amino acid sequence of SEQ ID NO:108, SEQ ID NO:128, SEQ ID NO:148, SEQ ID NO:168, SEQ ID NO:188, SEQ ID NO:208, SEQ ID NO:228, SEQ ID NO:248 or SEQ ID NO:268, SEQ ID NO:288, 308, SEQ ID NO:328, SEQ ID NO:368, SEQ ID NO:388, SEQ ID NO:408, SEQ ID NO:46, SEQ ID NO:64 or SEQ ID NO:82, or a sequence substantially homologous thereto. Substantially homologous sequences are described elsewhere herein. Preferably, said substantially homologous sequence is a sequence containing 1, 2 or 3 amino acid substitutions compared to the given CDR sequence, or said substantially homologous sequence is a sequence containing conservative amino acid substitutions of the given CDR sequence.

In some embodiments of the present invention, the VL CDR1 has or comprises an amino acid sequence of SEQ ID NO: 448 ($X_1$ S S Q $X_5$ $X_6$ $X_7$ $X_8$ S $X_{10}$ $X_{11}$ $X_{12}$ $X_{13}$ $X_{14}$ $X_{15}$ L $X_{17}$). In these embodiments $X_1$, $X_5$, $X_6$, $X_7$, $X_8$, $X_{10}$, $X_{11}$, $X_{13}$, $X_{14}$, $X_{15}$ and $X_{17}$ can be any amino acid, and $X_{12}$ can be any amino acid or no amino acid. Preferably one or more, most preferably all, of these X residues are selected from the following group: $X_1$ is R or K; $X_5$ is S or T; $X_6$ is L or V or I; $X_7$ is L or V or I; $X_8$ is H or D or Y; $X_{10}$ is S or A or D; $X_{11}$ is G or N; $X_{13}$ is K or N; $X_{14}$ is T or N; $X_{15}$ is Y or C; $X_{17}$ is A or N or E; $X_{12}$ is Q or no amino acid. Thus, a preferred VL CDR1 has or comprises the amino acid sequence of SEQ ID NO: 449. For example, preferred VL CDR1 sequences of this embodiment have or comprise SEQ ID NOs: 106, 126, 146, 166, 186, 206, 226, 246, 266, 286, 306, 326, 366, 386, 406, 44, 62 or 80.

Certain preferred combinations of VH CDR sequences and VL CDR sequences are set forth in each of the rows numbered 1-18 in Table Y below:

TABLE Y

| VH CDR1 (SEQ ID NO:) | VH CDR2 (SEQ ID NO:) | VH CDR3 (SEQ ID NO:) | VL CDR1 (SEQ ID NO:) | VL CDR2 (SEQ ID NO:) | VL CDR3 (SEQ ID NO:) |
|---|---|---|---|---|---|
| 1 | 103 | 104 | 105 | 448 | 107 | 108 |
| 2 | 123 | 124 | 125 | 448 | 127 | 128 |
| 3 | 143 | 144 | 145 | 448 | 147 | 148 |
| 4 | 163 | 164 | 165 | 448 | 167 | 168 |
| 5 | 183 | 184 | 185 | 448 | 187 | 188 |
| 6 | 203 | 204 | 205 | 448 | 207 | 208 |
| 7 | 223 | 224 | 225 | 448 | 227 | 228 |
| 8 | 243 | 244 | 245 | 448 | 247 | 248 |
| 9 | 263 | 264 | 265 | 448 | 267 | 268 |
| 10 | 283 | 284 | 285 | 448 | 287 | 288 |
| 11 | 303 | 304 | 305 | 448 | 307 | 308 |
| 12 | 323 | 324 | 325 | 448 | 327 | 328 |
| 13 | 363 | 364 | 365 | 448 | 367 | 368 |
| 14 | 383 | 384 | 385 | 448 | 387 | 388 |
| 15 | 403 | 404 | 405 | 448 | 407 | 408 |

TABLE Y-continued

| VH CDR1 (SEQ ID NO:) | VH CDR2 (SEQ ID NO:) | VH CDR3 (SEQ ID NO:) | VL CDR1 (SEQ ID NO:) | VL CDR2 (SEQ ID NO:) | VL CDR3 (SEQ ID NO:) |
|---|---|---|---|---|---|
| 16 | 41 | 42 | 43 | 448 | 45 | 46 |
| 17 | 59 | 60 | 61 | 448 | 63 | 64 |
| 18 | 77 | 78 | 79 | 448 | 81 | 82 |

In embodiments of the invention set forth in Table Y, preferably the consensus sequence as set forth as SEQ ID NO:448 is a sequence as set forth as SEQ ID NO:449. In some embodiments, sequences substantially homologous to the specific sequences recited in Table Y may be employed instead of the specific sequences themselves.

In some embodiments, the antibody of the invention comprises at least one heavy chain variable region that comprises three CDRs and at least one light chain variable region that comprises three CDRs, wherein said heavy chain variable region comprises a VL CDR1 that has the amino acid sequence of SEQ ID NO:448 or preferably SEQ ID NO:449 (or a sequence substantially homologous thereto). In some such embodiments, preferably the light chain variable region comprises a VL CDR2 and a VL CDR3 and the heavy chain variable region comprises a VH CDR1, a VH CDR2 and a VH CDR3, wherein said CDRs have amino acid sequences as set forth in a given row selected from row numbers 1-18 of Table Y above (or sequences substantially homologous thereto). Put another way, in some such embodiments, in addition to having a VL CDR1 that has the amino acid sequence of SEQ ID NO:448 or preferably SEQ ID NO:449 (or a sequence substantially homologous thereto), preferably the light chain variable region comprises a combination of a VL CDR2, a VL CDR3 and the heavy chain variable region comprises combination of a VH CDR1, a VH CDR2 and a VH CDR3, wherein said VL CDR2, VL CDR3, VH CDR1, VH CDR2 and VH CDR3 have amino acid sequences as set forth in combination (i.e. together) in rows of Table Y above.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:41, SEQ ID NO:59, SEQ ID NO:103, SEQ ID NO:123, SEQ ID NO:143, SEQ ID NO:163, SEQ ID NO:183, SEQ ID NO:203, SEQ ID NO:223, SEQ ID NO:243, SEQ ID NO:263, SEQ ID NO:283, SEQ ID NO:303, or SEQ ID NO:403, or a sequence substantially homologous thereto, (b) a VH CDR2 that has the amino acid sequence of SEQ ID NO:42, SEQ ID NO:60, SEQ ID NO: 104, SEQ ID NO:124, SEQ ID NO:144, SEQ ID NO:164, SEQ ID NO:184, SEQ ID NO:204, SEQ ID NO:224, SEQ ID NO:244, SEQ ID NO:264, SEQ ID NO:284, SEQ ID NO:304, or SEQ ID NO:404, or a sequence substantially homologous thereto, and (c) a VH CDR3 that has the amino acid sequence of SEQ ID NO:43, SEQ ID NO:61, SEQ ID NO: 105, SEQ ID NO:125, SEQ ID NO:145, SEQ ID NO:165, SEQ ID NO:185, SEQ ID NO:205, SEQ ID NO:225, SEQ ID NO:245, SEQ ID NO:265, SEQ ID NO:285, SEQ ID NO:305, or SEQ ID NO:405, or a sequence substantially homologous thereto; and/or (preferably "and")

wherein said light chain variable region comprises:

(d) a VL CDR1 that has the amino acid sequence of SEQ ID NO:44, SEQ ID NO:62, SEQ ID NO:106, SEQ ID NO:126, SEQ ID NO:146, SEQ ID NO:166, SEQ ID NO:186, SEQ ID NO:206, SEQ ID NO:226, SEQ ID NO:246, SEQ ID NO:266, SEQ ID NO:286, SEQ ID NO:306, or SEQ ID NO:406, or a sequence substantially homologous thereto, (e) a VL CDR2 that has the amino acid sequence of SEQ ID NO:45, SEQ ID NO:63, SEQ ID NO:107, SEQ ID NO:127, SEQ ID NO:147, SEQ ID NO:167, SEQ ID NO:187, SEQ ID NO:207, SEQ ID NO:227, SEQ ID NO:247, SEQ ID NO:267, SEQ ID NO:287, SEQ ID NO:307, or SEQ ID NO:407, or a sequence substantially homologous thereto, and (f) a VL CDR3 that has the amino acid sequence of SEQ ID NO:450 or preferably SEQ ID NO: 451, or a sequence substantially homologous thereto. Substantially homologous sequences are described elsewhere herein. Preferably, said substantially homologous sequence is a sequence containing 1, 2 or 3 amino acid substitutions compared to the given CDR sequence, or said substantially homologous sequence is a sequence containing conservative amino acid substitutions of the given CDR sequence.

In some embodiments of the present invention, the VL CDR3 has or comprises an amino acid sequence of SEQ ID NO: 450 ($X_1$ Q G $X_4$ H $X_6$ P $X_8$ T). In these embodiments $X_1$, $X_4$ and $X_6$ can be any amino acid, and $X_8$ can be any amino acid or no amino acid. Preferably one or more, most preferably all, of these X residues are selected from the following group: $X_1$ is W or F or S; $X_4$ is T or S; $X_6$ is F or V; $X_8$ is P or Y or is no amino acid. Thus, a preferred VL CDR3 has or comprises the amino acid sequence of SEQ ID NO: 451. For example, preferred VL CDR3 sequences of this embodiment have or comprise SEQ ID NOs: SEQ ID NO:46, SEQ ID NO:64, SEQ ID NO:108, SEQ ID NO:128, SEQ ID NO:148, SEQ ID NO:168, SEQ ID NO:188, SEQ ID NO:208, SEQ ID NO:228, SEQ ID NO:248, SEQ ID NO:268, SEQ ID NO:288, SEQ ID NO:308, or SEQ ID NO:408.

Certain preferred combinations of VH CDR sequences and VL CDR sequences are set forth in each of the rows numbered 1-14 in Table AA below:

TABLE AA

| | VH CDR1 (SEQ ID NO:) | VH CDR2 (SEQ ID NO:) | VH CDR3 (SEQ ID NO:) | VL CDR1 (SEQ ID NO:) | VL CDR2 (SEQ ID NO:) | VL CDR3 (SEQ ID NO:) |
|---|---|---|---|---|---|---|
| 1 | 103 | 104 | 105 | 106 | 107 | 450 |
| 2 | 123 | 124 | 125 | 126 | 127 | 450 |
| 3 | 143 | 144 | 145 | 146 | 147 | 450 |
| 4 | 163 | 164 | 165 | 166 | 167 | 450 |
| 5 | 183 | 184 | 185 | 186 | 187 | 450 |
| 6 | 203 | 204 | 205 | 206 | 207 | 450 |
| 7 | 223 | 224 | 225 | 226 | 227 | 450 |
| 8 | 243 | 244 | 245 | 246 | 247 | 450 |
| 9 | 263 | 264 | 265 | 266 | 267 | 450 |
| 10 | 283 | 284 | 285 | 286 | 287 | 450 |
| 11 | 303 | 304 | 305 | 306 | 307 | 450 |
| 12 | 403 | 404 | 405 | 406 | 407 | 450 |
| 13 | 41 | 42 | 43 | 44 | 45 | 450 |
| 14 | 59 | 60 | 61 | 62 | 63 | 450 |

In embodiments of the invention set forth in Table AA, preferably the consensus sequence as set forth as SEQ ID NO:450 is a sequence as set forth as SEQ ID NO:451. In some embodiments, sequences substantially homologous to the specific sequences recited in Table AA may be employed instead of the specific sequences themselves.

In some embodiments, the antibody of the invention comprises at least one heavy chain variable region that comprises three CDRs and at least one light chain variable region that comprises three CDRs, wherein said heavy chain variable region comprises a VL CDR3 that has the amino acid sequence of SEQ ID NO:450 or preferably SEQ ID NO:451 (or a sequence substantially homologous thereto). In some such embodiments, preferably the light chain variable region comprises a VL CDR1 and a VL CDR2 and the heavy chain variable region comprises a VH CDR1, a VH CDR2 and a VH CDR3, wherein said CDRs have amino acid sequences as set forth in a given row selected from row numbers 1-14 of Table AA above (or sequences substantially homologous thereto). Put another way, in some such embodiments, in addition to having a VL CDR3 that has the amino acid sequence of SEQ ID NO:450 or preferably SEQ ID NO:451 (or a sequence substantially homologous thereto), preferably the light chain variable region comprises a combination of a VL CDR1, a VL CDR2 and the heavy chain variable region comprises combination of a VH CDR1, a VH CDR2 and a VH CDR3, wherein said VL CDR1, VL CDR2, VH CDR1, VH CDR2 and VH CDR3 have amino acid sequences as set forth in combination (i.e. together) in rows of Table AA above.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:77, SEQ ID NO:363, or SEQ ID NO:383, or a sequence substantially homologous thereto, (b) a VH CDR2 that has the amino acid sequence of SEQ ID NO:42, SEQ ID NO:78, SEQ ID NO:364, or SEQ ID NO:384, or a sequence substantially homologous thereto, and (c) a VH CDR3 that has the amino acid sequence of SEQ ID NO:79, SEQ ID NO:365, or 385, or a sequence substantially homologous thereto; and/or (preferably "and")

wherein said light chain variable region comprises:

(d) a VL CDR1 that has the amino acid sequence of SEQ ID NO:80, SEQ ID NO:366, SEQ ID NO:386, or a sequence substantially homologous thereto, (e) a VL CDR2 that has the amino acid sequence of SEQ ID NO:81, SEQ ID NO:367, SEQ ID NO:387, or a sequence substantially homologous thereto, and (f) a VL CDR3 that has the amino acid sequence of SEQ ID NO:452 or preferably SEQ ID NO: 439, or a sequence substantially homologous thereto. Substantially homologous sequences are described elsewhere herein. Preferably, said substantially homologous sequence is a sequence containing 1, 2 or 3 amino acid substitutions compared to the given CDR sequence, or said substantially homologous sequence is a sequence containing conservative amino acid substitutions of the given CDR sequence.

In some embodiments of the present invention, the VL CDR3 has or comprises an amino acid sequence of SEQ ID NO: 452 (Q Q Y Y $X_5$ Y P $X_8$ $X_9$). In these embodiments $X_5$ and $X_8$ can be any amino acid, and $X_9$ can be any amino acid or no amino acid. Preferably one or more, most preferably all, of these X residues are selected from the following group: $X_5$ is Y or S; $X_8$ is P or T; $X_9$ is T or is no amino acid. Thus, a preferred VL CDR3 has or comprises the amino acid sequence of SEQ ID NO: 439. For example, preferred VL CDR3 sequences of this embodiment have or comprise SEQ ID NOs: 82, SEQ ID NO:368, or SEQ ID NO:388.

Certain preferred combinations of VH CDR sequences and VL CDR sequences are set forth in each of the rows numbered 1-3 in Table CC below:

TABLE CC

| | VH CDR1 (SEQ ID NO:) | VH CDR2 (SEQ ID NO:) | VH CDR3 (SEQ ID NO:) | VL CDR1 (SEQ ID NO:) | VL CDR2 (SEQ ID NO:) | VL CDR3 (SEQ ID NO:) |
|---|---|---|---|---|---|---|
| 1 | 77 | 78 | 79 | 80 | 81 | 452 |
| 2 | 363 | 364 | 365 | 366 | 367 | 452 |
| 3 | 383 | 384 | 385 | 386 | 387 | 452 |

In embodiments of the invention set forth in Table CC, preferably the consensus sequence as set forth as SEQ ID NO:452 is a sequence as set forth as SEQ ID NO:439. In some embodiments, sequences substantially homologous to the specific sequences recited in Table CC may be employed instead of the specific sequences themselves.

In some embodiments, the antibody of the invention comprises at least one heavy chain variable region that comprises three CDRs and at least one light chain variable region that comprises three CDRs, wherein said heavy chain variable region comprises a VL CDR3 that has the amino acid sequence of SEQ ID NO:452 or preferably SEQ ID NO:439 (or a sequence substantially homologous thereto). In some such embodiments, preferably the light chain variable region comprises a VL CDR1 and a VL CDR2 and the heavy chain variable region comprises a VH CDR1, a VH CDR2 and a VH CDR3, wherein said CDRs have amino acid sequences as set forth in a given row selected from row numbers 1-3 of Table CC above (or sequences substantially homologous thereto). Put another way, in some such embodiments, in addition to having a VL CDR3 that has the amino acid sequence of SEQ ID NO:452 or preferably SEQ ID NO:439 (or a sequence substantially homologous thereto), preferably the light chain variable region comprises a combination of a VL CDR1, a VL CDR2 and the heavy chain variable region comprises combination of a VH CDR1, a VH CDR2 and a VH CDR3, wherein said VL CDR1, VL CDR2, VH CDR1, VH CDR2 and VH CDR3 have amino acid sequences as set forth in combination (i.e. together) in rows of Table CC above.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:103, SEQ ID NO:123, SEQ ID NO:143, SEQ ID NO:163, SEQ ID NO:183, SEQ ID NO:203, SEQ ID NO:223, SEQ ID NO:243, SEQ ID NO:263, or SEQ ID NO:303, or a sequence substantially homologous thereto, (b) a VH CDR2 that has the amino acid sequence of SEQ ID NO: 104, SEQ ID NO:124, SEQ ID NO:144, SEQ ID NO:164, SEQ ID NO:184, SEQ ID NO:204, SEQ ID NO:224, SEQ ID NO:244, SEQ ID NO:264, SEQ ID NO:304, or a sequence substantially homologous thereto, and (c) a VH CDR3 that has the amino acid sequence of SEQ ID NO: 105, SEQ ID NO:125, SEQ ID NO:145, SEQ ID NO:165, SEQ ID NO:185, SEQ ID NO:205, SEQ ID NO:225, SEQ ID NO:245, SEQ ID NO:265, or SEQ ID NO:305, or a sequence substantially homologous thereto; and/or (preferably "and")

wherein said light chain variable region comprises:

(d) a VL CDR1 that has the amino acid sequence of SEQ ID NO:106, SEQ ID NO:126, SEQ ID NO:146, SEQ ID NO:166, SEQ ID NO:186, SEQ ID NO:206, SEQ ID NO:226, SEQ ID NO:246, SEQ ID NO:266, SEQ ID NO:306, or a sequence substantially homologous thereto, (e) a VL CDR2 that has the amino acid sequence of SEQ ID NO:107, or a sequence substantially homologous thereto, and (f) a VL CDR3 that has the amino acid sequence of SEQ ID NO:108, SEQ ID NO:128, SEQ ID NO:148, SEQ ID NO:168, SEQ ID NO:188, SEQ ID NO:208, SEQ ID NO:228, SEQ ID NO:248, SEQ ID NO:268, SEQ ID NO:308, or a sequence substantially homologous thereto. Substantially homologous sequences are described elsewhere herein. Preferably, said substantially homologous sequence is a sequence containing 1, 2 or 3 amino acid substitutions compared to the given CDR sequence, or said substantially homologous sequence is a sequence containing conservative amino acid substitutions of the given CDR sequence.

Certain preferred combinations of VH CDR sequences and VL CDR sequences are set forth in each of the rows numbered 1-10 in Table DD below:

TABLE DD

| | VH CDR1 (SEQ ID NO:) | VH CDR2 (SEQ ID NO:) | VH CDR3 (SEQ ID NO:) | VL CDR1 (SEQ ID NO:) | VL CDR2 (SEQ ID NO:) | VL CDR3 (SEQ ID NO:) |
|---|---|---|---|---|---|---|
| 1 | 103 | 104 | 105 | 106 | 107 | 108 |
| 2 | 123 | 124 | 125 | 126 | 107 | 128 |
| 3 | 143 | 144 | 145 | 146 | 107 | 148 |
| 4 | 163 | 164 | 165 | 166 | 107 | 168 |
| 5 | 183 | 184 | 185 | 186 | 107 | 188 |
| 6 | 203 | 204 | 205 | 206 | 107 | 208 |
| 7 | 223 | 224 | 225 | 226 | 107 | 228 |
| 8 | 243 | 244 | 245 | 246 | 107 | 248 |
| 9 | 263 | 264 | 265 | 266 | 107 | 268 |
| 10 | 303 | 304 | 305 | 306 | 107 | 308 |

In some embodiments, sequences substantially homologous to the specific sequences recited in Table DD may be employed instead of the specific sequences themselves.

In some embodiments, the antibody of the invention comprises at least one heavy chain variable region that comprises three CDRs and at least one light chain variable region that comprises three CDRs, wherein said light chain variable region comprises a VL CDR2 that has the amino acid sequence of SEQ ID NO:107 (or a sequence substantially homologous thereto). In some such embodiments, preferably the light chain variable region comprises a VL CDR1 and a VL CDR3 and the heavy chain variable region comprises a VH CDR1, a VH CDR2 and a VH CDR3, wherein said CDRs have amino acid sequences as set forth in a given row selected from row numbers 1-10 of Table DD above (or sequences substantially homologous thereto). Put another way, in some such embodiments, in addition to having a VL CDR2 that has the amino acid sequence of SEQ ID NO:107 (or a sequence substantially homologous thereto), preferably the light chain variable region comprises a combination of a VL CDR1, a VL CDR3 and the heavy chain variable region comprises combination of a VH CDR1, a VH CDR2 and a VH CDR3, wherein said VL CDR1, VL CDR3, VH CDR1, VH CDR2 and VH CDR3 have amino acid sequences as set forth in combination (i.e. together) in rows of Table DD above.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:77, SEQ ID NO:323, SEQ ID NO:363, or SEQ ID NO:383, or a sequence substantially homologous thereto, (b) a VH CDR2 that has the amino acid sequence of SEQ ID NO: 78, SEQ ID NO:324, SEQ ID NO:364, or SEQ ID NO:384, or a sequence substantially homologous thereto, and (c) a VH CDR3 that has the amino acid sequence of SEQ ID NO: 79, SEQ ID NO:325, SEQ ID NO:365, or SEQ ID NO:385, or a sequence substantially homologous thereto; and/or (preferably "and")

wherein said light chain variable region comprises:

(d) a VL CDR1 that has the amino acid sequence of SEQ ID NO:80, SEQ ID NO:326, SEQ ID NO:366, or SEQ ID NO:386, or a sequence substantially homologous thereto, (e) a VL CDR2 that has the amino acid sequence of SEQ ID NO:81, or a sequence substantially homologous thereto, and (f) a VL CDR3 that has the amino acid sequence of SEQ ID NO:82, SEQ ID NO:328, SEQ ID NO:368, or SEQ ID NO:388, or a sequence substantially homologous thereto. Substantially homologous sequences are described elsewhere herein. Preferably, said substantially homologous sequence is a sequence containing 1, 2 or 3 amino acid substitutions compared to the given CDR sequence, or said substantially homologous sequence is a sequence containing conservative amino acid substitutions of the given CDR sequence.

Certain preferred combinations of VH CDR sequences and VL CDR sequences are set forth in each of the rows numbered 1-4 in Table EE below:

TABLE EE

| | VH CDR1 (SEQ ID NO:) | VH CDR2 (SEQ ID NO:) | VH CDR3 (SEQ ID NO:) | VL CDR1 (SEQ ID NO:) | VL CDR2 (SEQ ID NO:) | VL CDR3 (SEQ ID NO:) |
|---|---|---|---|---|---|---|
| 1 | 77 | 78 | 79 | 80 | 81 | 82 |
| 2 | 323 | 324 | 325 | 326 | 81 | 328 |
| 3 | 363 | 364 | 365 | 366 | 81 | 368 |
| 4 | 383 | 384 | 385 | 386 | 81 | 388 |

In some embodiments, sequences substantially homologous to the specific sequences recited in Table EE may be employed instead of the specific sequences themselves.

In some embodiments, the antibody of the invention comprises at least one heavy chain variable region that comprises three CDRs and at least one light chain variable region that comprises three CDRs, wherein said light chain variable region comprises a VL CDR2 that has the amino acid sequence of SEQ ID NO:81 (or a sequence substantially homologous thereto). In some such embodiments, preferably the light chain variable region comprises a VL CDR1 and a VL CDR3 and the heavy chain variable region comprises a VH CDR1, a VH CDR2 and a VH CDR3, wherein said CDRs have amino acid sequences as set forth in a given row selected from row numbers 1-4 of Table EE above (or sequences substantially homologous thereto). Put another way, in some such embodiments, in addition to having a VL CDR2 that has the amino acid sequence of SEQ ID NO:81 (or a sequence substantially homologous thereto), preferably the light chain variable region comprises a combination of a VL CDR1, a VL CDR3 and the heavy chain variable region comprises combination of a VH CDR1, a VH CDR2 and a VH CDR3, wherein said VL CDR1, VL CDR3, VH CDR1, VH CDR2 and VH CDR3 have amino acid sequences as set forth in combination (i.e. together) in rows of Table EE above.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:41, SEQ ID NO:59, SEQ ID NO:283, or SEQ ID NO:403, or a sequence substantially homologous thereto, (b) a VH CDR2 that has the amino acid sequence of SEQ ID NO: 42, SEQ ID NO:60, SEQ ID NO:284, or SEQ ID NO:404, or a sequence substantially homologous thereto, and (c) a VH CDR3 that has the amino acid sequence of SEQ ID NO: 43, SEQ ID NO:61, SEQ ID NO:285, or SEQ ID NO:405, or a sequence substantially homologous thereto; and/or (preferably "and")

wherein said light chain variable region comprises:

(d) a VL CDR1 that has the amino acid sequence of SEQ ID NO:44, SEQ ID NO:62, SEQ ID NO:286, or SEQ ID NO:406, or a sequence substantially homologous thereto, (e) a VL CDR2 that has the amino acid sequence of SEQ ID NO:45, or a sequence substantially homologous thereto, and (f) a VL CDR3 that has the amino acid sequence of SEQ ID NO:46, SEQ ID NO:64, SEQ ID NO:288, or SEQ ID NO:408, or a sequence substantially homologous thereto. Substantially homologous sequences are described elsewhere herein. Preferably, said substantially homologous sequence is a sequence containing 1, 2 or 3 amino acid substitutions compared to the given CDR sequence, or said substantially homologous sequence is a sequence containing conservative amino acid substitutions of the given CDR sequence.

Certain preferred combinations of VH CDR sequences and VL CDR sequences are set forth in each of the rows numbered 1-4 in Table FF below:

TABLE FF

| | VH CDR1 (SEQ ID NO:) | VH CDR2 (SEQ ID NO:) | VH CDR3 (SEQ ID NO:) | VL CDR1 (SEQ ID NO:) | VL CDR2 (SEQ ID NO:) | VL CDR3 (SEQ ID NO:) |
|---|---|---|---|---|---|---|
| 1 | 41 | 42 | 43 | 44 | 45 | 46 |
| 2 | 59 | 60 | 61 | 62 | 45 | 64 |
| 3 | 283 | 284 | 285 | 286 | 45 | 288 |
| 4 | 403 | 404 | 405 | 406 | 45 | 408 |

In some embodiments, sequences substantially homologous to the specific sequences recited in Table FF may be employed instead of the specific sequences themselves.

In some embodiments, the antibody of the invention comprises at least one heavy chain variable region that comprises three CDRs and at least one light chain variable region that comprises three CDRs, wherein said light chain variable region comprises a VL CDR2 that has the amino acid sequence of SEQ ID NO:45 (or a sequence substantially homologous thereto). In some such embodiments, preferably the light chain variable region comprises a VL CDR1 and a VL CDR3 and the heavy chain variable region comprises a VH CDR1, a VH CDR2 and a VH CDR3, wherein said CDRs have amino acid sequences as set forth in a given row selected from row numbers 1-4 of Table FF above (or sequences substantially homologous thereto). Put another way, in some such embodiments, in addition to having a VL CDR2 that has the amino acid sequence of SEQ ID NO:45 (or a sequence substantially homologous thereto), preferably the light chain variable region comprises a combination of a VL CDR1, a VL CDR3 and the heavy chain variable region comprises combination of a VH CDR1, a VH CDR2 and a VH CDR3, wherein said VL CDR1, VL CDR3, VH CDR1, VH CDR2 and VH CDR3 have amino acid sequences as set forth in combination (i.e. together) in rows of Table FF above.

In some embodiments, the antibody of the invention comprises at least one heavy chain variable region that comprises three CDRs and at least one light chain variable region that comprises three CDRs, wherein said light chain variable region comprises a VL CDR1 that has the amino acid sequence of SEQ ID NO:91 (or preferably SEQ ID NO:92). In some such embodiments, preferably the VL CDR2, VL CDR3, VH CDR1, VH CDR2 and VH CDR3 (e.g. combinations thereof) have amino acid sequences as defined elsewhere herein.

In some embodiments, the antibody of the invention comprises at least one heavy chain variable region that comprises three CDRs and at least one light chain variable region that comprises three CDRs, wherein said heavy chain variable region comprises a VH CDR1 that has the amino acid sequence of SEQ ID NO:440 (or preferably SEQ ID NO:441). In some such embodiments, preferably the VL CDR1, VL CDR2, VL CDR3, VH CDR2 and VH CDR3 (e.g. combinations thereof) have amino acid sequences as defined elsewhere herein.

In some embodiments, the antibody of the invention comprises at least one heavy chain variable region that comprises three CDRs and at least one light chain variable region that comprises three CDRs, wherein said heavy chain variable region comprises a VH CDR2 that has the amino acid sequence of SEQ ID NO:442 (or preferably SEQ ID NO:443). In some such embodiments, preferably the VL CDR1, VL CDR2, VL CDR3, VH CDR1 and VH CDR3 (e.g. combinations thereof) have amino acid sequences as defined elsewhere herein.

In some embodiments, the antibody of the invention comprises at least one heavy chain variable region that comprises three CDRs and at least one light chain variable region that comprises three CDRs, wherein said heavy chain variable region comprises a VH CDR3 that has the amino acid sequence of SEQ ID NO:444 (or preferably SEQ ID NO:445). In some such embodiments, preferably the VL CDR1, VL CDR2, VL CDR3, VH CDR1 and VH CDR2 (e.g. combinations thereof) have amino acid sequences as defined elsewhere herein.

In some embodiments, the antibody of the invention comprises at least one heavy chain variable region that comprises three CDRs and at least one light chain variable region that comprises three CDRs, wherein said light chain variable region comprises a VL CDR1 that has the amino acid sequence of SEQ ID NO:446 (or preferably SEQ ID NO:447). In some such embodiments, preferably the VL CDR2, VL CDR3, VH CDR1, VH CDR2 and VH CDR3 (e.g. combinations thereof) have amino acid sequences as defined elsewhere herein.

In some embodiments, the antibody of the invention comprises at least one heavy chain variable region that comprises three CDRs and at least one light chain variable region that comprises three CDRs, wherein said light chain variable region comprises a VL CDR1 that has the amino acid sequence of SEQ ID NO:448 (or preferably SEQ ID NO:449). In some such embodiments, preferably the VL CDR2, VL CDR3, VH CDR1, VH CDR2 and VH CDR3 (e.g. combinations thereof) have amino acid sequences as defined elsewhere herein.

In some embodiments, the antibody of the invention comprises at least one heavy chain variable region that comprises three CDRs and at least one light chain variable region that comprises three CDRs, wherein said light chain variable region comprises a VL CDR3 that has the amino acid sequence of SEQ ID NO:450 (or preferably SEQ ID NO:451). In some such embodiments, preferably the VL CDR1, VL CDR2, VH CDR1, VH CDR2 and VH CDR3 (e.g. combinations thereof) have amino acid sequences as defined elsewhere herein.

In some embodiments, the antibody of the invention comprises at least one heavy chain variable region that comprises three CDRs and at least one light chain variable region that comprises three CDRs, wherein said light chain variable region comprises a VL CDR3 that has the amino acid sequence of SEQ ID NO:452 (or preferably SEQ ID NO:439). In some such embodiments, preferably the VL CDR1, VL CDR2, VH CDR1, VH CDR2 and VH CDR3 (e.g. combinations thereof) have amino acid sequences as defined elsewhere herein.

In some embodiments, the antibody of the invention comprises at least one heavy chain variable region that comprises three CDRs and at least one light chain variable region that comprises three CDRs, wherein said light chain variable region comprises a VL CDR2 that has the amino acid sequence of SEQ ID NO:107 or SEQ ID NO:81 or SEQ ID NO: 45 (or a sequence substantially homologous thereto). In some such embodiments, preferably the VL CDR1, VL CDR3, VH CDR1, VH CDR2 and VH CDR3 (e.g. combinations thereof) have amino acid sequences as defined elsewhere herein.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:41, or a sequence substantially homologous thereto, (b) a VH CDR2 that has the amino acid sequence of SEQ ID NO:42, or a sequence substantially homologous thereto, and (c) a VH CDR3 that has the amino acid sequence of SEQ ID NO:43, or a sequence substantially homologous thereto; and/or wherein said light chain variable region comprises:

(d) a variable light (VL) CDR1 that has the amino acid sequence of SEQ ID NO:44, or a sequence substantially homologous thereto, (e) a VL CDR2 that has the amino acid sequence of SEQ ID NO:45, or a sequence substantially homologous thereto, and (f) a VL CDR3 that has the amino acid sequence of SEQ ID NO:46, or a sequence substantially homologous thereto. Substantially homologous sequences are described elsewhere herein. Preferably, said substantially homologous sequence is a sequence containing 1, 2 or 3 amino acid substitutions compared to the given CDR sequence, or said substantially homologous sequence is a sequence containing conservative amino acid substitutions of the given CDR sequence.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:41, (b) a VH CDR2 that has the amino acid sequence of SEQ ID NO:42, and (c) a VH CDR3 that has the amino acid sequence of SEQ ID NO:43; and/or wherein said light chain variable region comprises:

(d) a variable light (VL) CDR1 that has the amino acid sequence of SEQ ID NO:44, (e) a VL CDR2 that has the amino acid sequence of SEQ ID NO:45, and (f) a VL CDR3 that has the amino acid sequence of SEQ ID NO:46.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:41, or a sequence substantially homologous thereto, (b) a VH CDR2 that has the amino acid sequence of SEQ ID NO:42, or a sequence substantially homologous thereto, and (c) a VH CDR3 that has the amino acid sequence of SEQ ID NO:43, or a sequence substantially homologous thereto; and wherein said light chain variable region comprises:

(d) a variable light (VL) CDR1 that has the amino acid sequence of SEQ ID NO:44, or a sequence substantially homologous thereto, (e) a VL CDR2 that has the amino acid sequence of SEQ ID NO:45, or a sequence substantially homologous thereto, and (f) a VL CDR3 that has the amino acid sequence of SEQ ID NO:46, or a sequence substantially homologous thereto. Substantially homologous sequences are described elsewhere herein. Preferably, said substantially homologous sequence is a sequence containing 1, 2 or 3 amino acid substitutions compared to the given CDR sequence, or said substantially homologous sequence is a sequence containing conservative amino acid substitutions of the given CDR sequence.

In a preferred embodiment, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:41, (b) a VH CDR2 that has the amino acid sequence of SEQ ID NO:42, and (c) a VH CDR3 that has the amino acid sequence of SEQ ID NO:43; and wherein said light chain variable region comprises:

(d) a variable light (VL) CDR1 that has the amino acid sequence of SEQ ID NO:44, (e) a VL CDR2 that has the amino acid sequence of SEQ ID NO:45, and (f) a VL CDR3 that has the amino acid sequence of SEQ ID NO:46.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:77, or a sequence substantially homologous thereto, (b) a VH CDR2 that has the amino acid sequence of SEQ ID NO:78, or a sequence substantially homologous thereto, and (c) a VH CDR3 that has the amino acid sequence of SEQ ID NO:79, or a sequence substantially homologous thereto; and/or wherein said light chain variable region comprises:

(d) a variable light (VL) CDR1 that has the amino acid sequence of SEQ ID NO:80, or a sequence substantially homologous thereto, (e) a VL CDR2 that has the amino acid sequence of SEQ ID NO:81, or a sequence substantially homologous thereto, and (f) a VL CDR3 that has the amino acid sequence of SEQ ID NO:82, or a sequence substantially homologous thereto. Substantially homologous sequences are described elsewhere herein. Preferably, said substantially homologous sequence is a sequence containing 1, 2 or 3 amino acid substitutions compared to the given CDR sequence, or said substantially homologous sequence is a sequence containing conservative amino acid substitutions of the given CDR sequence.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:77, (b) a VH CDR2 that has the amino acid sequence of SEQ ID NO:78, and (c) a VH CDR3 that has the amino acid sequence of SEQ ID NO:79; and/or wherein said light chain variable region comprises:

(d) a variable light (VL) CDR1 that has the amino acid sequence of SEQ ID NO:80, (e) a VL CDR2 that has the amino acid sequence of SEQ ID NO:81, and (f) a VL CDR3 that has the amino acid sequence of SEQ ID NO:82.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:77, or a sequence substantially homologous thereto, (b) a VH CDR2 that has the amino acid sequence of SEQ ID NO:78, or a sequence substantially homologous thereto, and (c) a VH CDR3 that has the amino acid sequence of SEQ ID NO:79, or a sequence substantially homologous thereto; and wherein said light chain variable region comprises:

(d) a variable light (VL) CDR1 that has the amino acid sequence of SEQ ID NO:80, or a sequence substantially homologous thereto, (e) a VL CDR2 that has the amino acid sequence of SEQ ID NO:81, or a sequence substantially homologous thereto, and (f) a VL CDR3 that has the amino acid sequence of SEQ ID NO:82, or a sequence substantially homologous thereto. Substantially homologous sequences are described elsewhere herein. Preferably, said substantially homologous sequence is a sequence containing 1, 2 or 3 amino acid substitutions compared to the given CDR sequence, or said substantially homologous sequence is a sequence containing conservative amino acid substitutions of the given CDR sequence.

In a preferred embodiment, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:77, (b) a VH CDR2 that has the amino acid sequence of SEQ ID NO:78, and (c) a VH CDR3 that has the amino acid sequence of SEQ ID NO:79; and wherein said light chain variable region comprises:

(d) a variable light (VL) CDR1 that has the amino acid sequence of SEQ ID NO:80, (e) a VL CDR2 that has the amino acid sequence of SEQ ID NO:81, and (f) a VL CDR3 that has the amino acid sequence of SEQ ID NO:82.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:103, or a sequence substantially homologous thereto, (b) a VH CDR2 that has the amino acid sequence of SEQ ID NO:104, or a sequence substantially homologous thereto, and (c) a VH CDR3 that has the amino acid sequence of SEQ ID NO:105, or a sequence substantially homologous thereto; and/or (preferably "and")

wherein said light chain variable region comprises:

(d) a variable light (VL) CDR1 that has the amino acid sequence of SEQ ID NO:106, or a sequence substantially homologous thereto, (e) a VL CDR2 that has the amino acid sequence of SEQ ID NO:107, or a sequence substantially homologous thereto, and (f) a VL CDR3 that has the amino acid sequence of SEQ ID NO:108, or a sequence substantially homologous thereto. Substantially homologous sequences are described elsewhere herein. Preferably, said substantially homologous sequence is a sequence containing 1, 2 or 3 amino acid substitutions compared to the given CDR sequence, or said substantially homologous sequence is a sequence containing conservative amino acid substitutions of the given CDR sequence.

In some embodiments, the antibody comprises at least one heavy chain variable region that comprises a VH CDR1 of SEQ ID NO:103, a VH CDR2 of SEQ ID NO:104, and a VH CDR3 of SEQ ID NO:105, and/or (preferably "and") at least one light chain variable region that comprises a VL CDR1 of SEQ ID NO:106, a VL CDR2 of SEQ ID NO:107, and a VL CDR3 of SEQ ID NO:108.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:123, or a sequence substantially homologous thereto, (b) a VH CDR2 that has the amino acid sequence of SEQ ID NO:124, or a sequence substantially homologous thereto, and (c) a VH CDR3 that has the amino acid sequence of SEQ ID NO:125, or a sequence substantially homologous thereto; and/or (preferably "and")

wherein said light chain variable region comprises:

(d) a variable light (VL) CDR1 that has the amino acid sequence of SEQ ID NO:126, or a sequence substantially homologous thereto, (e) a VL CDR2 that has the amino acid sequence of SEQ ID NO:127, or a sequence substantially homologous thereto, and (f) a VL CDR3 that has the amino acid sequence of SEQ ID NO:128, or a sequence substantially homologous thereto. Substantially homologous sequences are described elsewhere herein. Preferably, said substantially homologous sequence is a sequence containing 1, 2 or 3 amino acid substitutions compared to the given CDR sequence, or said substantially homologous sequence is a sequence containing conservative amino acid substitutions of the given CDR sequence.

In some embodiments, the antibody comprises at least one heavy chain variable region that comprises a VH CDR1 of SEQ ID NO:123, a VH CDR2 of SEQ ID NO:124, and a VH CDR3 of SEQ ID NO:125, and/or (preferably "and") at least one light chain variable region that comprises a VL CDR1 of SEQ ID NO:126, a VL CDR2 of SEQ ID NO:127, and a VL CDR3 of SEQ ID NO:128.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:143, or a sequence substantially homologous thereto, (b) a VH CDR2 that has the amino acid sequence of SEQ ID NO:144, or a sequence substantially homologous thereto, and (c) a VH CDR3 that has the amino acid sequence of SEQ ID NO:145, or a sequence substantially homologous thereto; and/or (preferably "and")

wherein said light chain variable region comprises:

(d) a variable light (VL) CDR1 that has the amino acid sequence of SEQ ID NO:146, or a sequence substantially homologous thereto, (e) a VL CDR2 that has the amino acid sequence of SEQ ID NO:147, or a sequence substantially homologous thereto, and (f) a VL CDR3 that has the amino acid sequence of SEQ ID NO:148, or a sequence substantially homologous thereto. Substantially homologous sequences are described elsewhere herein. Preferably, said substantially homologous sequence is a sequence containing 1, 2 or 3 amino acid substitutions compared to the given CDR sequence, or said substantially homologous sequence is a sequence containing conservative amino acid substitutions of the given CDR sequence.

In some embodiments, the antibody comprises at least one heavy chain variable region that comprises a VH CDR1 of SEQ ID NO:143, a VH CDR2 of SEQ ID NO:144, and a VH CDR3 of SEQ ID NO:145, and/or (preferably "and") at least one light chain variable region that comprises a VL CDR1 of SEQ ID NO:146, a VL CDR2 of SEQ ID NO:147, and a VL CDR3 of SEQ ID NO:148.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:183, or a sequence substantially homologous thereto, (b) a VH CDR2 that has the amino acid sequence of SEQ ID NO:184, or a sequence substantially homologous thereto, and (c) a VH CDR3 that has the amino acid sequence of SEQ ID NO:185, or a sequence substantially homologous thereto; and/or (preferably "and")

wherein said light chain variable region comprises:

(d) a variable light (VL) CDR1 that has the amino acid sequence of SEQ ID NO:186, or a sequence substantially homologous thereto, (e) a VL CDR2 that has the amino acid sequence of SEQ ID NO:187, or a sequence substantially homologous thereto, and (f) a VL CDR3 that has the amino acid sequence of SEQ ID NO:188, or a sequence substantially homologous thereto. Substantially homologous sequences are described elsewhere herein. Preferably, said substantially homologous sequence is a sequence containing 1, 2 or 3 amino acid substitutions compared to the given CDR sequence, or said substantially homologous sequence is a sequence containing conservative amino acid substitutions of the given CDR sequence.

In some embodiments, the antibody comprises at least one heavy chain variable region that comprises a VH CDR1 of SEQ ID NO:183, a VH CDR2 of SEQ ID NO:184, and a VH CDR3 of SEQ ID NO:185, and/or (preferably "and") at least one light chain variable region that comprises a VL CDR1 of SEQ ID NO:186, a VL CDR2 of SEQ ID NO:187, and a VL CDR3 of SEQ ID NO:188.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:203, or a sequence substantially homologous thereto, (b) a VH CDR2 that has the amino acid sequence of SEQ ID NO:204, or a sequence substantially homologous thereto, and (c) a VH CDR3 that has the amino acid sequence of SEQ ID NO:205, or a sequence substantially homologous thereto; and/or (preferably "and")

wherein said light chain variable region comprises:

(d) a variable light (VL) CDR1 that has the amino acid sequence of SEQ ID NO:206, or a sequence substantially homologous thereto, (e) a VL CDR2 that has the amino acid sequence of SEQ ID NO:207, or a sequence substantially homologous thereto, and (f) a VL CDR3 that has the amino acid sequence of SEQ ID NO:208, or a sequence substantially homologous thereto. Substantially homologous sequences are described elsewhere herein. Preferably, said substantially homologous sequence is a sequence containing 1, 2 or 3 amino acid substitutions compared to the given CDR sequence, or said substantially homologous sequence is a sequence containing conservative amino acid substitutions of the given CDR sequence.

In some embodiments, the antibody comprises at least one heavy chain variable region that comprises a VH CDR1 of SEQ ID NO:203, a VH CDR2 of SEQ ID NO:204, and a VH CDR3 of SEQ ID NO:205, and/or (preferably "and") at least one light chain variable region that comprises a VL CDR1 of SEQ ID NO:206, a VL CDR2 of SEQ ID NO:207, and a VL CDR3 of SEQ ID NO:208.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:223, or a sequence substantially homologous thereto, (b) a VH CDR2 that has the amino acid sequence of SEQ ID NO:224, or a sequence substantially homologous thereto, and (c) a VH CDR3 that has the amino acid sequence of SEQ ID NO:225, or a sequence substantially homologous thereto; and/or (preferably "and")

wherein said light chain variable region comprises:

(d) a variable light (VL) CDR1 that has the amino acid sequence of SEQ ID NO:226, or a sequence substantially homologous thereto, (e) a VL CDR2 that has the amino acid sequence of SEQ ID NO:227, or a sequence substantially homologous thereto, and (f) a VL CDR3 that has the amino acid sequence of SEQ ID NO:228, or a sequence substantially homologous thereto. Substantially homologous sequences are described elsewhere herein. Preferably, said substantially homologous sequence is a sequence containing 1, 2 or 3 amino acid substitutions compared to the given CDR sequence, or said substantially homologous sequence is a sequence containing conservative amino acid substitutions of the given CDR sequence.

In some embodiments, the antibody comprises at least one heavy chain variable region that comprises a VH CDR1 of SEQ ID NO:223, a VH CDR2 of SEQ ID NO:224, and a VH CDR3 of SEQ ID NO:225, and/or (preferably "and") at least one light chain variable region that comprises a VL CDR1 of SEQ ID NO:226, a VL CDR2 of SEQ ID NO:227, and a VL CDR3 of SEQ ID NO:228.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:283, or a sequence substantially homologous thereto, (b) a VH CDR2 that has the amino acid sequence of SEQ ID NO:284, or a sequence substantially homologous thereto, and (c) a VH CDR3 that has the amino acid sequence of SEQ ID NO:285, or a sequence substantially homologous thereto; and/or (preferably "and")

wherein said light chain variable region comprises:

(d) a variable light (VL) CDR1 that has the amino acid sequence of SEQ ID NO:286, or a sequence substantially homologous thereto, (e) a VL CDR2 that has the amino acid sequence of SEQ ID NO:287, or a sequence substantially homologous thereto, and (f) a VL CDR3 that has the amino acid sequence of SEQ ID NO:288, or a sequence substantially homologous thereto. Substantially homologous sequences are described elsewhere herein. Preferably, said substantially homologous sequence is a sequence containing 1, 2 or 3 amino acid substitutions compared to the given CDR sequence, or said substantially homologous sequence is a sequence containing conservative amino acid substitutions of the given CDR sequence.

In some embodiments, the antibody comprises at least one heavy chain variable region that comprises a VH CDR1 of SEQ ID NO:283, a VH CDR2 of SEQ ID NO:284, and a VH CDR3 of SEQ ID NO:285, and/or (preferably "and") at least one light chain variable region that comprises a VL CDR1 of SEQ ID NO:286, a VL CDR2 of SEQ ID NO:287, and a VL CDR3 of SEQ ID NO:288.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:303, or a sequence substantially homologous thereto, (b) a VH CDR2 that has the amino acid sequence of SEQ ID NO:304, or a sequence substantially homologous thereto, and (c) a VH CDR3 that has the amino acid sequence of SEQ ID NO:305, or a sequence substantially homologous thereto; and/or (preferably "and")

wherein said light chain variable region comprises:

(d) a variable light (VL) CDR1 that has the amino acid sequence of SEQ ID NO:306, or a sequence substantially homologous thereto, (e) a VL CDR2 that has the amino acid sequence of SEQ ID NO:307, or a sequence substantially homologous thereto, and (f) a VL CDR3 that has the amino acid sequence of SEQ ID NO:308, or a sequence substantially homologous thereto. Substantially homologous sequences are described elsewhere herein. Preferably, said substantially homologous sequence is a sequence containing 1, 2 or 3 amino acid substitutions compared to the given CDR sequence, or said substantially homologous sequence is a sequence containing conservative amino acid substitutions of the given CDR sequence.

In some embodiments, the antibody comprises at least one heavy chain variable region that comprises a VH CDR1 of SEQ ID NO:303, a VH CDR2 of SEQ ID NO:304, and a VH CDR3 of SEQ ID NO:305, and/or (preferably "and") at least one light chain variable region that comprises a VL CDR1 of SEQ ID NO:306, a VL CDR2 of SEQ ID NO:307, and a VL CDR3 of SEQ ID NO:308.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:323, or a sequence substantially homologous thereto, (b) a VH CDR2 that has the amino acid sequence of SEQ ID NO:324, or a sequence substantially homologous thereto, and (c) a VH CDR3 that has the amino acid sequence of SEQ ID NO:325, or a sequence substantially homologous thereto; and/or (preferably "and")

wherein said light chain variable region comprises:

(d) a variable light (VL) CDR1 that has the amino acid sequence of SEQ ID NO:326, or a sequence substantially homologous thereto, (e) a VL CDR2 that has the amino acid sequence of SEQ ID NO:327, or a sequence substantially homologous thereto, and (f) a VL CDR3 that has the amino acid sequence of SEQ ID NO:328, or a sequence substantially homologous thereto. Substantially homologous sequences are described elsewhere herein. Preferably, said substantially homologous sequence is a sequence containing 1, 2 or 3 amino acid substitutions compared to the given CDR sequence, or said substantially homologous sequence is a sequence containing conservative amino acid substitutions of the given CDR sequence.

In some embodiments, the antibody comprises at least one heavy chain variable region that comprises a VH CDR1 of SEQ ID NO:323, a VH CDR2 of SEQ ID NO:324, and a VH CDR3 of SEQ ID NO:325, and/or (preferably "and") at least one light chain variable region that comprises a VL CDR1 of SEQ ID NO:326, a VL CDR2 of SEQ ID NO:327, and a VL CDR3 of SEQ ID NO:328.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:343, or a sequence substantially homologous thereto, (b) a VH CDR2 that has the amino acid sequence of SEQ ID NO:344, or a sequence substantially homologous thereto, and (c) a VH CDR3 that has the amino acid sequence of SEQ ID NO:345, or a sequence substantially homologous thereto; and/or (preferably "and")

wherein said light chain variable region comprises:

(d) a variable light (VL) CDR1 that has the amino acid sequence of SEQ ID NO:346, or a sequence substantially homologous thereto, (e) a VL CDR2 that has the amino acid sequence of SEQ ID NO:347, or a sequence substantially homologous thereto, and (f) a VL CDR3 that has the amino acid sequence of SEQ ID NO:348, or a sequence substantially homologous thereto. Substantially homologous sequences are described elsewhere herein. Preferably, said substantially homologous sequence is a sequence containing 1, 2 or 3 amino acid substitutions compared to the given CDR sequence, or said substantially homologous sequence is a sequence containing conservative amino acid substitutions of the given CDR sequence.

In some embodiments, the antibody comprises at least one heavy chain variable region that comprises a VH CDR1 of SEQ ID NO:343, a VH CDR2 of SEQ ID NO:344, and a VH CDR3 of SEQ ID NO:345, and/or (preferably "and") at least one light chain variable region that comprises a VL CDR1 of SEQ ID NO:346, a VL CDR2 of SEQ ID NO:347, and a VL CDR3 of SEQ ID NO:348.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:363, or a sequence substantially homologous thereto, (b) a VH CDR2 that has the amino acid sequence of SEQ ID NO:364, or a sequence substantially homologous thereto, and (c) a VH CDR3 that has the amino acid sequence of SEQ ID NO:365, or a sequence substantially homologous thereto; and/or (preferably "and")

wherein said light chain variable region comprises:

(d) a variable light (VL) CDR1 that has the amino acid sequence of SEQ ID NO:366, or a sequence substantially homologous thereto, (e) a VL CDR2 that has the amino acid sequence of SEQ ID NO:367, or a sequence substantially homologous thereto, and (f) a VL CDR3 that has the amino acid sequence of SEQ ID NO:368, or a sequence substantially homologous thereto. Substantially homologous sequences are described elsewhere herein. Preferably, said substantially homologous sequence is a sequence containing 1, 2 or 3 amino acid substitutions compared to the given CDR sequence, or said substantially homologous sequence is a sequence containing conservative amino acid substitutions of the given CDR sequence.

In some embodiments, the antibody comprises at least one heavy chain variable region that comprises a VH CDR1 of SEQ ID NO:363, a VH CDR2 of SEQ ID NO:364, and a VH CDR3 of SEQ ID NO:365, and/or (preferably "and") at least one light chain variable region that comprises a VL CDR1 of SEQ ID NO:366, a VL CDR2 of SEQ ID NO:367, and a VL CDR3 of SEQ ID NO:368.

In some embodiments, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:423, or a sequence substantially homologous thereto, (b) a VH CDR2 that has the amino acid sequence of SEQ ID NO:424, or a sequence substantially homologous thereto, and (c) a VH CDR3 that has the amino acid sequence of SEQ ID NO:425, or a sequence substantially homologous thereto; and/or (preferably "and")

wherein said light chain variable region comprises:

(d) a variable light (VL) CDR1 that has the amino acid sequence of SEQ ID NO:426, or a sequence substantially homologous thereto, (e) a VL CDR2 that has the amino acid sequence of SEQ ID NO:427, or a sequence substantially homologous thereto, and (f) a VL CDR3 that has the amino acid sequence of SEQ ID NO:428, or a sequence substantially homologous thereto. Substantially homologous sequences are described elsewhere herein. Preferably, said substantially homologous sequence is a sequence containing 1, 2 or 3 amino acid substitutions compared to the given CDR sequence, or said substantially homologous sequence is a sequence containing conservative amino acid substitutions of the given CDR sequence.

In some embodiments, the antibody comprises at least one heavy chain variable region that comprises a VH CDR1 of SEQ ID NO:423, a VH CDR2 of SEQ ID NO:424, and a VH CDR3 of SEQ ID NO:425, and/or (preferably "and") at least one light chain variable region that comprises a VL CDR1 of SEQ ID NO:426, a VL CDR2 of SEQ ID NO:427, and a VL CDR3 of SEQ ID NO:428.

Certain preferred embodiments of the invention provide an antibody comprising a VH domain that has the amino acid sequence of SEQ ID NO:39 or 57 or 75, or a sequence substantially homologous thereto, and/or a VL domain that has the amino acid sequence of SEQ ID NO: 40 or 58 or 76, or a sequence substantially homologous thereto.

Further preferred embodiments provide an antibody comprising a VH domain that has the amino acid sequence of SEQ ID NO: 39 or 57 or 75 and a VL domain that comprises 3 light chain CDRs. Preferably said light chain CDRs have SEQ ID NOs 44, 45 and 46; or 80, 81 and 82.

Further preferred embodiments provide an antibody comprising a VL domain that has the amino acid sequence of SEQ ID NO: 40 or 58 or 76 and a VH domain that comprises 3 heavy chain CDRs. Preferably said heavy chain CDRs have SEQ ID NOs 41, 42 and 43; or 77, 78 or 79.

In one embodiment the invention provides an antibody comprising a VH domain that has the amino acid sequence of SEQ ID NO: 39 or a sequence substantially homologous thereto, and/or a VL domain that has the amino acid sequence of SEQ ID NO: 40 or a sequence substantially homologous thereto.

In a preferred embodiment, the present invention provides an antibody, wherein the light chain variable region has the amino acid sequence of SEQ ID NO:40, or a sequence having at least 80% sequence identity thereto (e.g. at least 85%, 90%, 95% or 98%) and/or wherein the heavy chain variable region has the amino acid sequence of SEQ ID NO:39, or a sequence having at least 80% sequence identity thereto (e.g. at least 85%, 90%, 95% or 98%).

In a preferred embodiment, the present invention provides an antibody, wherein the light chain variable region has the amino acid sequence of SEQ ID NO:40 and/or wherein the heavy chain variable region has the amino acid sequence of SEQ ID NO:39.

In a preferred embodiment, the present invention provides an antibody, wherein the light chain variable region has the amino acid sequence of SEQ ID NO:40 and wherein the heavy chain variable region has the amino acid sequence of SEQ ID NO:39.

In one embodiment the invention provides an antibody comprising a VH domain that has the amino acid sequence of SEQ ID NO: 57 or a sequence substantially homologous thereto, and/or a VL domain that has the amino acid sequence of SEQ ID NO: 58 or a sequence substantially homologous thereto.

In a preferred embodiment, the present invention provides an antibody, wherein the light chain variable region has the amino acid sequence of SEQ ID NO:58, or a sequence having at least 80% sequence identity thereto (e.g. at least 85%, 90%, 95% or 98%) and/or wherein the heavy chain variable region has the amino acid sequence of SEQ ID NO:57, or a sequence having at least 80% sequence identity thereto (e.g. at least 85%, 90%, 95% or 98%).

In a preferred embodiment, the present invention provides an antibody, wherein the light chain variable region has the amino acid sequence of SEQ ID NO:58 and/or wherein the heavy chain variable region has the amino acid sequence of SEQ ID NO:57.

In a preferred embodiment, the present invention provides an antibody, wherein the light chain variable region has the amino acid sequence of SEQ ID NO:58 and wherein the heavy chain variable region has the amino acid sequence of SEQ ID NO:57.

In one embodiment the invention provides an antibody comprising a VH domain that has the amino acid sequence of SEQ ID NO: 75 or a sequence substantially homologous thereto, and/or a VL domain that has the amino acid sequence of SEQ ID NO: 76 or a sequence substantially homologous thereto.

In a preferred embodiment, the present invention provides an antibody, wherein the light chain variable region has the amino acid sequence of SEQ ID NO:76, or a sequence having at least 80% sequence identity thereto (e.g. at least 85%, 90%, 95% or 98%) and/or wherein the heavy chain variable region has the amino acid sequence of SEQ ID NO:75, or a sequence having at least 80% sequence identity thereto (e.g. at least 85%, 90%, 95% or 98%).

In a preferred embodiment, the present invention provides an antibody, wherein the light chain variable region has the amino acid sequence of SEQ ID NO:76 and/or wherein the heavy chain variable region has the amino acid sequence of SEQ ID NO:75.

In a preferred embodiment, the present invention provides an antibody, wherein the light chain variable region has the amino acid sequence of SEQ ID NO:76 and wherein the heavy chain variable region has the amino acid sequence of SEQ ID NO:75.

In one embodiment the invention provides an antibody comprising a VH domain that has the amino acid sequence of SEQ ID NO: 101 or a sequence substantially homologous thereto (e.g. a sequence having at least 80% sequence identity thereto, for example at least 85%, 90%, 95% or 98% sequence identity thereto), and/or (preferably "and") a VL domain that has the amino acid sequence of SEQ ID NO: 102 or a sequence substantially homologous thereto (e.g. a sequence having at least 80% sequence identity thereto, for example at least 85%, 90%, 95% or 98% sequence identity thereto). In a preferred embodiment, the present invention provides an antibody, wherein the light chain variable region has the amino acid sequence of SEQ ID NO:102 and/or (preferably "and") wherein the heavy chain variable region has the amino acid sequence of SEQ ID NO:101.

In one embodiment the invention provides an antibody comprising a VH domain that has the amino acid sequence of SEQ ID NO: 121 or a sequence substantially homologous thereto (e.g. a sequence having at least 80% sequence identity thereto, for example at least 85%, 90%, 95% or 98% sequence identity thereto), and/or (preferably "and") a VL domain that has the amino acid sequence of SEQ ID NO: 122 or a sequence substantially homologous thereto (e.g. a sequence having at least 80% sequence identity thereto, for example at least 85%, 90%, 95% or 98% sequence identity thereto). In a preferred embodiment, the present invention provides an antibody, wherein the light chain variable region has the amino acid sequence of SEQ ID NO:122 and/or (preferably "and") wherein the heavy chain variable region has the amino acid sequence of SEQ ID NO:121.

In one embodiment the invention provides an antibody comprising a VH domain that has the amino acid sequence of SEQ ID NO: 141 or a sequence substantially homologous thereto (e.g. a sequence having at least 80% sequence identity thereto, for example at least 85%, 90%, 95% or 98% sequence identity thereto), and/or (preferably "and") a VL domain that has the amino acid sequence of SEQ ID NO: 142 or a sequence substantially homologous thereto (e.g. a sequence having at least 80% sequence identity thereto, for example at least 85%, 90%, 95% or 98% sequence identity thereto). In a preferred embodiment, the present invention provides an antibody, wherein the light chain variable region has the amino acid sequence of SEQ ID NO:142 and/or (preferably "and") wherein the heavy chain variable region has the amino acid sequence of SEQ ID NO:141.

In one embodiment the invention provides an antibody comprising a VH domain that has the amino acid sequence of SEQ ID NO: 161 or a sequence substantially homologous thereto (e.g. a sequence having at least 80% sequence identity thereto, for example at least 85%, 90%, 95% or 98% sequence identity thereto), and/or (preferably "and") a VL domain that has the amino acid sequence of SEQ ID NO: 162 or a sequence substantially homologous thereto (e.g. a sequence having at least 80% sequence identity thereto, for example at least 85%, 90%, 95% or 98% sequence identity thereto). In a preferred embodiment, the present invention provides an antibody, wherein the light chain variable region has the amino acid sequence of SEQ ID NO:162 and/or (preferably "and") wherein the heavy chain variable region has the amino acid sequence of SEQ ID NO:161.

In one embodiment the invention provides an antibody comprising a VH domain that has the amino acid sequence of SEQ ID NO: 181 or a sequence substantially homologous thereto (e.g. a sequence having at least 80% sequence identity thereto, for example at least 85%, 90%, 95% or 98% sequence identity thereto), and/or (preferably "and") a VL domain that has the amino acid sequence of SEQ ID NO: 182 or a sequence substantially homologous thereto (e.g. a sequence having at least 80% sequence identity thereto, for example at least 85%, 90%, 95% or 98% sequence identity thereto). In a preferred embodiment, the present invention provides an antibody, wherein the light chain variable region has the amino acid sequence of SEQ ID NO:182 and/or (preferably "and") wherein the heavy chain variable region has the amino acid sequence of SEQ ID NO:181.

In one embodiment the invention provides an antibody comprising a VH domain that has the amino acid sequence of SEQ ID NO: 201 or a sequence substantially homologous thereto (e.g. a sequence having at least 80% sequence identity thereto, for example at least 85%, 90%, 95% or 98% sequence identity thereto), and/or (preferably "and") a VL domain that has the amino acid sequence of SEQ ID NO: 202 or a sequence substantially homologous thereto (e.g. a sequence having at least 80% sequence identity thereto, for example at least 85%, 90%, 95% or 98% sequence identity thereto). In a preferred embodiment, the present invention provides an antibody, wherein the light chain variable region has the amino acid sequence of SEQ ID NO:202 and/or (preferably "and") wherein the heavy chain variable region has the amino acid sequence of SEQ ID NO:201.

In one embodiment the invention provides an antibody comprising a VH domain that has the amino acid sequence of SEQ ID NO: 221 or a sequence substantially homologous thereto (e.g. a sequence having at least 80% sequence identity thereto, for example at least 85%, 90%, 95% or 98% sequence identity thereto), and/or (preferably "and") a VL domain that has the amino acid sequence of SEQ ID NO: 222 or a sequence substantially homologous thereto (e.g. a sequence having at least 80% sequence identity thereto, for example at least 85%, 90%, 95% or 98% sequence identity thereto). In a preferred embodiment, the present invention provides an antibody, wherein the light chain variable region has the amino acid sequence of SEQ ID NO:222 and/or (preferably "and") wherein the heavy chain variable region has the amino acid sequence of SEQ ID NO:221.

In one embodiment the invention provides an antibody comprising a VH domain that has the amino acid sequence of SEQ ID NO: 241 or a sequence substantially homologous thereto (e.g. a sequence having at least 80% sequence identity thereto, for example at least 85%, 90%, 95% or 98% sequence identity thereto), and/or (preferably "and") a VL domain that has the amino acid sequence of SEQ ID NO: 242 or a sequence substantially homologous thereto (e.g. a sequence having at least 80% sequence identity thereto, for example at least 85%, 90%, 95% or 98% sequence identity thereto). In a preferred embodiment, the present invention provides an antibody, wherein the light chain variable region has the amino acid sequence of SEQ ID NO:242 and/or (preferably "and") wherein the heavy chain variable region has the amino acid sequence of SEQ ID NO:241.

In one embodiment the invention provides an antibody comprising a VH domain that has the amino acid sequence of SEQ ID NO: 261 or a sequence substantially homologous thereto (e.g. a sequence having at least 80% sequence identity thereto, for example at least 85%, 90%, 95% or 98% sequence identity thereto), and/or (preferably "and") a VL domain that has the amino acid sequence of SEQ ID NO: 262 or a sequence substantially homologous thereto (e.g. a sequence having at least 80% sequence identity thereto, for example at least 85%, 90%, 95% or 98% sequence identity thereto). In a preferred embodiment, the present invention provides an antibody, wherein the light chain variable region has the amino acid sequence of SEQ ID NO:262 and/or (preferably "and") wherein the heavy chain variable region has the amino acid sequence of SEQ ID NO:261.

In one embodiment the invention provides an antibody comprising a VH domain that has the amino acid sequence of SEQ ID NO: 281 or a sequence substantially homologous thereto (e.g. a sequence having at least 80% sequence identity thereto, for example at least 85%, 90%, 95% or 98% sequence identity thereto), and/or (preferably "and") a VL domain that has the amino acid sequence of SEQ ID NO: 282 or a sequence substantially homologous thereto (e.g. a sequence having at least 80% sequence identity thereto, for example at least 85%, 90%, 95% or 98% sequence identity thereto). In a preferred embodiment, the present invention provides an antibody, wherein the light chain variable region has the amino acid sequence of SEQ ID NO:282 and/or (preferably "and") wherein the heavy chain variable region has the amino acid sequence of SEQ ID NO:281.

In one embodiment the invention provides an antibody comprising a VH domain that has the amino acid sequence of SEQ ID NO: 301 or a sequence substantially homologous thereto (e.g. a sequence having at least 80% sequence identity thereto, for example at least 85%, 90%, 95% or 98% sequence identity thereto), and/or (preferably "and") a VL domain that has the amino acid sequence of SEQ ID NO: 302 or a sequence substantially homologous thereto (e.g. a sequence having at least 80% sequence identity thereto, for example at least 85%, 90%, 95% or 98% sequence identity thereto). In a preferred embodiment, the present invention provides an antibody, wherein the light chain variable region has the amino acid sequence of SEQ ID NO:302 and/or (preferably "and") wherein the heavy chain variable region has the amino acid sequence of SEQ ID NO:301.

In one embodiment the invention provides an antibody comprising a VH domain that has the amino acid sequence of SEQ ID NO: 321 or a sequence substantially homologous thereto (e.g. a sequence having at least 80% sequence identity thereto, for example at least 85%, 90%, 95% or 98% sequence identity thereto), and/or (preferably "and") a VL domain that has the amino acid sequence of SEQ ID NO: 322 or a sequence substantially homologous thereto (e.g. a sequence having at least 80% sequence identity thereto, for example at least 85%, 90%, 95% or 98% sequence identity thereto). In a preferred embodiment, the present invention provides an antibody, wherein the light chain variable region has the amino acid sequence of SEQ ID NO:322 and/or (preferably "and") wherein the heavy chain variable region has the amino acid sequence of SEQ ID NO:321.

In one embodiment the invention provides an antibody comprising a VH domain that has the amino acid sequence of SEQ ID NO: 341 or a sequence substantially homologous thereto (e.g. a sequence having at least 80% sequence identity thereto, for example at least 85%, 90%, 95% or 98% sequence identity thereto), and/or (preferably "and") a VL domain that has the amino acid sequence of SEQ ID NO: 342 or a sequence substantially homologous thereto (e.g. a sequence having at least 80% sequence identity thereto, for example at least 85%, 90%, 95% or 98% sequence identity thereto). In a preferred embodiment, the present invention provides an antibody, wherein the light chain variable region has the amino acid sequence of SEQ ID NO:342 and/or (preferably "and") wherein the heavy chain variable region has the amino acid sequence of SEQ ID NO:341.

In one embodiment the invention provides an antibody comprising a VH domain that has the amino acid sequence of SEQ ID NO: 361 or a sequence substantially homologous thereto (e.g. a sequence having at least 80% sequence identity thereto, for example at least 85%, 90%, 95% or 98% sequence identity thereto), and/or (preferably "and") a VL domain that has the amino acid sequence of SEQ ID NO: 362 or a sequence substantially homologous thereto (e.g. a sequence having at least 80% sequence identity thereto, for example at least 85%, 90%, 95% or 98% sequence identity thereto). In a preferred embodiment, the present invention provides an antibody, wherein the light chain variable region has the amino acid sequence of SEQ ID NO:362 and/or (preferably "and") wherein the heavy chain variable region has the amino acid sequence of SEQ ID NO:361.

In one embodiment the invention provides an antibody comprising a VH domain that has the amino acid sequence of SEQ ID NO: 381 or a sequence substantially homologous thereto (e.g. a sequence having at least 80% sequence identity thereto, for example at least 85%, 90%, 95% or 98% sequence identity thereto), and/or (preferably "and") a VL domain that has the amino acid sequence of SEQ ID NO: 382 or a sequence substantially homologous thereto (e.g. a sequence having at least 80% sequence identity thereto, for example at least 85%, 90%, 95% or 98% sequence identity thereto). In a preferred embodiment, the present invention provides an antibody, wherein the light chain variable region has the amino acid sequence of SEQ ID NO:382 and/or (preferably "and") wherein the heavy chain variable region has the amino acid sequence of SEQ ID NO:381.

In one embodiment the invention provides an antibody comprising a VH domain that has the amino acid sequence of SEQ ID NO: 401 or a sequence substantially homologous thereto (e.g. a sequence having at least 80% sequence identity thereto, for example at least 85%, 90%, 95% or 98% sequence identity thereto), and/or (preferably "and") a VL domain that has the amino acid sequence of SEQ ID NO: 402 or a sequence substantially homologous thereto (e.g. a sequence having at least 80% sequence identity thereto, for example at least 85%, 90%, 95% or 98% sequence identity thereto). In a preferred embodiment, the present invention provides an antibody, wherein the light chain variable region has the amino acid sequence of SEQ ID NO:402 and/or (preferably "and") wherein the heavy chain variable region has the amino acid sequence of SEQ ID NO:401.

In one embodiment the invention provides an antibody comprising a VH domain that has the amino acid sequence of SEQ ID NO: 421 or a sequence substantially homologous thereto (e.g. a sequence having at least 80% sequence identity thereto, for example at least 85%, 90%, 95% or 98% sequence identity thereto), and/or (preferably "and") a VL domain that has the amino acid sequence of SEQ ID NO: 422 or a sequence substantially homologous thereto (e.g. a sequence having at least 80% sequence identity thereto, for example at least 85%, 90%, 95% or 98% sequence identity thereto). In a preferred embodiment, the present invention provides an antibody, wherein the light chain variable region has the amino acid sequence of SEQ ID NO:422 and/or (preferably "and") wherein the heavy chain variable region has the amino acid sequence of SEQ ID NO:421.

Other preferred embodiments are Ig (e.g. IgG) forms of antibodies described herein, e.g. IgG forms of the OT-Ab3, OT-Ab2 and OT-Ab1 antibodies (or antibodies based thereon), preferably full length IgG forms. Other preferred embodiments are Ig (e.g. IgG) forms of the OT-Ab3, OT-Ab2, OT-Ab1, 32C8-1, 33C9-1, 34C11-1, 40B10-1, 41B5-1, 43D6-1, 44E8-1, 46B7-1, 46D9-1, 12C9-1, 12G6-1, 15D8-1, 16F1-1, 17E11-1, 17E9-1, 18E10-1 and R4P1-C1 antibodies (or antibodies based thereon), preferably full length IgG forms. In some embodiments, the IgG is $IgG_1$ or $IgG_2$ (e.g. $IgG_{2b}$). Thus, in some embodiments the antibody is an Ig antibody comprising CDR sequences and/or a heavy chain variable region and/or a light chain variable region as described herein. It is of course understood that full IgG antibodies will typically comprise two substantially identical heavy chains and two substantially identical light chains.

In some embodiments, antibodies based on the OT-Ab3, OT-Ab2 and OT-Ab1 antibody sequences set forth in Tables A, B and C herein are preferred. In some embodiments, antibodies based on the OT-Ab1 antibody sequences set forth in Table C are preferred.

In some embodiments, antibodies based on the OT-Ab3, OT-Ab2, OT-Ab1, 32C8-1, 33C9-1, 34C11-1, 40B10-1, 41B5-1, 43D6-1, 44E8-1, 46B7-1, 46D9-1, 12C9-1, 12G6-1, 15D8-1, 16F1-1, 17E11-1, 17E9-1, 18E10-1 and R4P1-C1 antibody sequences set forth in Tables A-C and E-U herein are preferred.

Some examples of antibodies of the present invention are the monoclonal antibodies OT-Ab3, OT-Ab2 and OT-Ab1, sequences of which are shown in Tables A, B and C herein. The monoclonal antibodies OT-Ab3, OT-Ab2 and OT-Ab1 were identified using hybridoma technology, with an OTV5 peptide (SEQ ID NO:18) as the immunogen. The CDR domains, VH and VL domains are shown in Tables A, B and C herein. Antibodies comprising these CDR domains or VH and VL domains (or sequences substantially homologous thereto) are preferred aspects of the invention.

Other examples of antibodies of the present invention are the monoclonal antibodies 32C8-1, 33C9-1, 34C11-1, 40B10-1, 41B5-1, 43D6-1, 44E8-1, 46B7-1 and 46D9-1, sequences of which are shown in Tables E-M herein. The monoclonal antibodies 32C8-1, 33C9-1, 34C11-1, 40B10-1, 41B5-1, 43D6-1, 44E8-1, 46B7-1 and 46D9-1 were identified using hybridoma technology, with an OTV3 peptide (SEQ ID NO:16) as the immunogen. The CDR domains, VH and VL domains are shown in Tables E-M herein. Antibodies comprising these CDR domains or VH and VL domains (or sequences substantially homologous thereto) are preferred aspects of the invention.

Other examples of antibodies of the present invention are the monoclonal antibodies 12C9-1, 12G6-1, 15D8-1, 16F1-1, 17E11-1, 17E9-1 and 18E10-1, sequences of which are shown in Tables N-T herein. The monoclonal antibodies 12C9-1, 12G6-1, 15D8-1, 16F1-1, 17E11-1, 17E9-1 and 18E10-1 were identified using hybridoma technology, with an OTV4 peptide (SEQ ID NO:17) as the immunogen. The CDR domains, VH and VL domains are shown in Tables N-T herein. Antibodies comprising these CDR domains or VH and VL domains (or sequences substantially homologous thereto) are preferred aspects of the invention.

Another example of an antibody of the present invention is the monoclonal antibody R4P1-C1, sequences of which are shown in Table U herein. This monoclonal antibody was identified using phage display technology as described in the example section herein. The CDR domains, VH and VL domains are shown in Table U herein. Antibodies comprising these CDR domains or VH and VL domains (or sequences substantially homologous thereto) are preferred aspects of the invention.

Typically, the monoclonal antibodies OT-Ab3, OT-Ab2, OT-Ab1, 32C8-1, 33C9-1, 34C11-1, 40B10-1, 41B5-1, 43D6-1, 44E8-1, 46B7-1, 46D9-1, 12C9-1, 12G6-1, 15D8-1, 16F1-1, 17E11-1, 17E9-1, 18E10-1 and/or R4P1-C1 (or antibodies based thereon, e.g. antibodies having substantially homologous sequences thereto) bind to (or are capable of binding to, e.g. specifically binding to) an epitope of TRPV1 in the region of TRPV1 defined by amino acid residues 599-630 of TRPV1 (SEQ ID NO:1). In some embodiments, the entire epitope bound lies within this region of TRPV1. In some embodiments, at least one amino acid of the epitope bound lies within this region of TRPV1.

Certain examples of substantially homologous sequences are sequences that have at least 65% identity to the amino acid sequences disclosed. In certain embodiments, the antibodies of the invention comprise at least one light chain variable region that includes an amino acid sequence region of at least about 65%, 70% or 75%, more preferably at least about 80%, more preferably at least about 85%, more preferably at least about 90% or 95% and most preferably at least about 97%, 98% or 99% amino acid sequence identity to the amino acid sequence of SEQ ID NO:40, 58, 76, 102, 122, 142, 162, 182, 202, 222, 242, 262, 282, 302, 322, 342, 362, 382, 402, or 422; and/or at least one heavy chain variable region that includes an amino acid sequence region of at least about 65%, 70% or 75%, more preferably at least about 80%, more preferably at least about 85%, more preferably at least about 90% or 95% and most preferably at least about 97%, 98% or 99% amino acid sequence identity to the amino acid sequence of SEQ ID NO:39, 57, 75, 101, 121, 141, 161, 181, 201, 221, 241, 261, 281, 301, 321, 341, 361, 381, 401, or 421.

Other preferred examples of substantially homologous sequences are sequences containing conservative amino acid substitutions of the amino acid sequences disclosed.

Other preferred examples of substantially homologous sequences are sequences containing 1, 2 or 3, preferably 1 or 2 (more preferably 1), altered amino acids in one or more of the CDR regions disclosed. Such alterations might be conserved or non-conserved amino acid substitutions, or a mixture thereof.

In some such embodiments, preferred alterations are conservative amino acid substitutions.

In all embodiments, antibodies containing substantially homologous sequences retain the ability to bind to TRPV1. Preferably, antibodies containing substantially homologous sequences retain one or more (preferably all) of the properties described in relation to the OT-Ab3 and/or OT-Ab2 and/or OT-Ab1 antibodies. Preferably, antibodies containing substantially homologous sequences retain one or more (preferably all) of the properties described in relation to the 32C8-1 and/or 33C9-1 and/or 34C11-1 and/or 40B10-1 and/or 41B5-1 and/or 43D6-1 and/or 44E8-1 and/or 46B7-1 and/or 46D9-1 and/or 12C9-1 and/or 12G6-1 and/or 15D8-1 and/or 16F1-1 and/or 17E11-1 and/or 17E9-1 and/or 18E10-1 and/or R4P1-C1 antibodies.

Further examples of substantially homologous amino acid sequences in accordance with the present invention are described elsewhere herein.

The CDRs of antibodies of the invention are preferably separated by appropriate framework regions such as those found in naturally occurring antibodies and/or effective engineered antibodies. Thus, the $V_H$, $V_L$ and individual CDR sequences of the invention are preferably provided within or incorporated into an appropriate framework or scaffold to enable antigen binding. Such framework sequences or regions may correspond to naturally occurring framework regions, FR1, FR2, FR3 and/or FR4, as appropriate to form an appropriate scaffold, or may correspond to consensus framework regions, for example identified by comparing various naturally occurring framework regions. Alternatively, non-antibody scaffolds or frameworks, e.g. T cell receptor frameworks can be used.

Appropriate sequences that can be used for framework regions are well known and documented in the art and any of these may be used. Preferred sequences for framework regions are one or more of the framework regions making up the $V_H$ and/or $V_L$ domains of the invention, i.e. one or more of the framework regions of the OT-Ab3, OT-Ab2, or OT-Ab1 antibodies, or one or more of the framework regions of the 32C8-1, 33C9-1, 34C11-1, 40B10-1, 41B5-1, 43D6-1, 44E8-1, 46B7-1, 46D9-1, 12C9-1, 12G6-1, 15D8-1, 16F1-1, 17E11-1, 17E9-1, 18E10-1, or R4P1-C1 antibodies, as disclosed in Tables A-C and E-U, herein, or framework regions substantially homologous thereto, and in particular framework regions that allow the maintenance of antigen specificity, for example framework regions that result in substantially the same or the same 3D structure of the antibody.

In certain preferred embodiments, all four of the variable light chain (SEQ ID NOs:51, 52, 53 and 54) and/or variable heavy chain (SEQ ID NOs:47, 48, 49 and 50) framework regions (FR), as appropriate, or FR regions substantially homologous thereto, are found in the antibodies of the invention.

In other preferred embodiments, all four of the variable light chain (SEQ ID NOs:69, 70, 71 and 72) and/or variable heavy chain (SEQ ID NOs:65, 66, 67 and 68) framework regions (FR), as appropriate, or FR regions substantially homologous thereto, are found in the antibodies of the invention.

In other preferred embodiments, all four of the variable light chain (SEQ ID NOs:87, 88, 89 and 90) and/or variable heavy chain (SEQ ID NOs:83, 84, 85 and 86) framework regions (FR), as appropriate, or FR regions substantially homologous thereto, are found in the antibodies of the invention.

In other preferred embodiments, all four of the variable light chain (SEQ ID NOs:113, 114, 115 and 116) and/or variable heavy chain (SEQ ID NOs:109, 110, 111 and 112) framework regions (FR), as appropriate, or FR regions substantially homologous thereto, are found in the antibodies of the invention.

In other preferred embodiments, all four of the variable light chain (SEQ ID NOs:133, 134, 135 and 136) and/or variable heavy chain (SEQ ID NOs:129, 130, 131 and 132) framework regions (FR), as appropriate, or FR regions substantially homologous thereto, are found in the antibodies of the invention.

In other preferred embodiments, all four of the variable light chain (SEQ ID NOs:153, 154, 155 and 156) and/or variable heavy chain (SEQ ID NOs:149, 150, 151 and 152) framework regions (FR), as appropriate, or FR regions substantially homologous thereto, are found in the antibodies of the invention.

In other preferred embodiments, all four of the variable light chain (SEQ ID NOs:173, 174, 175 and 176) and/or variable heavy chain (SEQ ID NOs:169, 170, 171 and 172) framework regions (FR), as appropriate, or FR regions substantially homologous thereto, are found in the antibodies of the invention.

In other preferred embodiments, all four of the variable light chain (SEQ ID NOs:193, 194, 195 and 196) and/or variable heavy chain (SEQ ID NOs:189, 190, 191 and 192) framework regions (FR), as appropriate, or FR regions substantially homologous thereto, are found in the antibodies of the invention.

In other preferred embodiments, all four of the variable light chain (SEQ ID NOs:213, 214, 215 and 216) and/or variable heavy chain (SEQ ID NOs:209, 210, 211 and 212) framework regions (FR), as appropriate, or FR regions substantially homologous thereto, are found in the antibodies of the invention.

In other preferred embodiments, all four of the variable light chain (SEQ ID NOs:233, 234, 235 and 236) and/or variable heavy chain (SEQ ID NOs:229, 230, 231 and 232) framework regions (FR), as appropriate, or FR regions substantially homologous thereto, are found in the antibodies of the invention.

In other preferred embodiments, all four of the variable light chain (SEQ ID NOs:253, 254, 255 and 256) and/or variable heavy chain (SEQ ID NOs:249, 250, 251 and 252) framework regions (FR), as appropriate, or FR regions substantially homologous thereto, are found in the antibodies of the invention.

In other preferred embodiments, all four of the variable light chain (SEQ ID NOs:273, 274, 275 and 276) and/or variable heavy chain (SEQ ID NOs:269, 270, 271 and 272) framework regions (FR), as appropriate, or FR regions substantially homologous thereto, are found in the antibodies of the invention.

In other preferred embodiments, all four of the variable light chain (SEQ ID NOs:293, 294, 295 and 296) and/or variable heavy chain (SEQ ID NOs:289, 290, 291 and 292) framework regions (FR), as appropriate, or FR regions substantially homologous thereto, are found in the antibodies of the invention.

In other preferred embodiments, all four of the variable light chain (SEQ ID NOs:313, 314, 315 and 315) and/or variable heavy chain (SEQ ID NOs:309, 310, 311 and 312) framework regions (FR), as appropriate, or FR regions substantially homologous thereto, are found in the antibodies of the invention.

In other preferred embodiments, all four of the variable light chain (SEQ ID NOs:333, 334, 335 and 336) and/or variable heavy chain (SEQ ID NOs:329, 330, 331 and 332) framework regions (FR), as appropriate, or FR regions substantially homologous thereto, are found in the antibodies of the invention.

In other preferred embodiments, all four of the variable light chain (SEQ ID NOs:353, 354, 355 and 356) and/or variable heavy chain (SEQ ID NOs:349, 350, 351 and 352) framework regions (FR), as appropriate, or FR regions substantially homologous thereto, are found in the antibodies of the invention.

In other preferred embodiments, all four of the variable light chain (SEQ ID NOs:373, 374, 375 and 376) and/or variable heavy chain (SEQ ID NOs:369, 370, 371 and 372) framework regions (FR), as appropriate, or FR regions substantially homologous thereto, are found in the antibodies of the invention.

In other preferred embodiments, all four of the variable light chain (SEQ ID NOs:393, 394, 395 and 396) and/or variable heavy chain (SEQ ID NOs:389, 390, 391 and 392) framework regions (FR), as appropriate, or FR regions substantially homologous thereto, are found in the antibodies of the invention.

In other preferred embodiments, all four of the variable light chain (SEQ ID NOs:413, 414, 415 and 416) and/or variable heavy chain (SEQ ID NOs:409, 410, 411 and 412) framework regions (FR), as appropriate, or FR regions substantially homologous thereto, are found in the antibodies of the invention.

In other preferred embodiments, all four of the variable light chain (SEQ ID NOs:433, 434, 435 and 436) and/or variable heavy chain (SEQ ID NOs:429, 430, 431 and 432) framework regions (FR), as appropriate, or FR regions substantially homologous thereto, are found in the antibodies of the invention.

In some embodiments, VH domains and/or VL domains of the invention may additionally comprise a signal peptide at their N-terminal end (e.g. positioned immediately N-terminally with respect to the VH or VL domain). However, such signal peptides are typically absent from the antibody itself (e.g. absent from the mature antibody or isolated antibody product) as they are typically cleaved off.

In some embodiments, a VH domain comprising SEQ ID NO:39 (or sequence substantially homologous thereto) further comprises at its N-terminal end a signal peptide of SEQ ID NO:93. In some embodiments, a VL domain comprising SEQ ID NO:40 (or sequence substantially homologous thereto) further comprises at its N-terminal end a signal peptide of SEQ ID NO:94.

In some embodiments, a VH domain comprising SEQ ID NO:57 (or sequence substantially homologous thereto) further comprises at its N-terminal end a signal peptide of SEQ ID NO:95. In some embodiments, a VL domain comprising SEQ ID NO:58 (or sequence substantially homologous thereto) further comprises at its N-terminal end a signal peptide of SEQ ID NO:96.

In some embodiments, a VH domain comprising SEQ ID NO:75 (or sequence substantially homologous thereto) further comprises at its N-terminal end a signal peptide of SEQ ID NO:97. In some embodiments, a VL domain comprising SEQ ID NO:76 (or sequence substantially homologous thereto) further comprises at its N-terminal end a signal peptide of SEQ ID NO:98.

In some embodiments, a VH domain comprising SEQ ID NO:101 (or sequence substantially homologous thereto) further comprises at its N-terminal end a signal peptide of SEQ ID NO:117. In some embodiments, a VL domain comprising SEQ ID NO:102 (or sequence substantially homologous thereto) further comprises at its N-terminal end a signal peptide of SEQ ID NO:118.

In some embodiments, a VH domain comprising SEQ ID NO:121 (or sequence substantially homologous thereto) further comprises at its N-terminal end a signal peptide of SEQ ID NO:137. In some embodiments, a VL domain comprising SEQ ID NO:122 (or sequence substantially homologous thereto) further comprises at its N-terminal end a signal peptide of SEQ ID NO:138.

In some embodiments, a VH domain comprising SEQ ID NO:141 (or sequence substantially homologous thereto) further comprises at its N-terminal end a signal peptide of SEQ ID NO:157. In some embodiments, a VL domain comprising SEQ ID NO:142 (or sequence substantially homologous thereto) further comprises at its N-terminal end a signal peptide of SEQ ID NO:158.

In some embodiments, a VH domain comprising SEQ ID NO:161 (or sequence substantially homologous thereto) further comprises at its N-terminal end a signal peptide of SEQ ID NO:177. In some embodiments, a VL domain comprising SEQ ID NO:162 (or sequence substantially homologous thereto) further comprises at its N-terminal end a signal peptide of SEQ ID NO:178.

In some embodiments, a VH domain comprising SEQ ID NO:181 (or sequence substantially homologous thereto) further comprises at its N-terminal end a signal peptide of SEQ ID NO:197. In some embodiments, a VL domain comprising SEQ ID NO:182 (or sequence substantially homologous thereto) further comprises at its N-terminal end a signal peptide of SEQ ID NO:198.

In some embodiments, a VH domain comprising SEQ ID NO:201 (or sequence substantially homologous thereto) further comprises at its N-terminal end a signal peptide of SEQ ID NO:217. In some embodiments, a VL domain comprising SEQ ID NO:202 (or sequence substantially homologous thereto) further comprises at its N-terminal end a signal peptide of SEQ ID NO:218.

In some embodiments, a VH domain comprising SEQ ID NO:221 (or sequence substantially homologous thereto) further comprises at its N-terminal end a signal peptide of SEQ ID NO:237. In some embodiments, a VL domain comprising SEQ ID NO:222 (or sequence substantially homologous thereto) further comprises at its N-terminal end a signal peptide of SEQ ID NO:238.

In some embodiments, a VH domain comprising SEQ ID NO:241 (or sequence substantially homologous thereto) further comprises at its N-terminal end a signal peptide of SEQ ID NO:257. In some embodiments, a VL domain comprising SEQ ID NO:242 (or sequence substantially homologous thereto) further comprises at its N-terminal end a signal peptide of SEQ ID NO:258.

In some embodiments, a VH domain comprising SEQ ID NO:261 (or sequence substantially homologous thereto) further comprises at its N-terminal end a signal peptide of SEQ ID NO:277. In some embodiments, a VL domain comprising SEQ ID NO:262 (or sequence substantially homologous thereto) further comprises at its N-terminal end a signal peptide of SEQ ID NO:278.

In some embodiments, a VH domain comprising SEQ ID NO:281 (or sequence substantially homologous thereto) further comprises at its N-terminal end a signal peptide of SEQ ID NO:297. In some embodiments, a VL domain comprising SEQ ID NO:282 (or sequence substantially homologous thereto) further comprises at its N-terminal end a signal peptide of SEQ ID NO:298.

In some embodiments, a VH domain comprising SEQ ID NO:301 (or sequence substantially homologous thereto) further comprises at its N-terminal end a signal peptide of SEQ ID NO:317. In some embodiments, a VL domain comprising SEQ ID NO:302 (or sequence substantially homologous thereto) further comprises at its N-terminal end a signal peptide of SEQ ID NO:318.

In some embodiments, a VH domain comprising SEQ ID NO:321 (or sequence substantially homologous thereto) further comprises at its N-terminal end a signal peptide of SEQ ID NO:337. In some embodiments, a VL domain comprising SEQ ID NO:322 (or sequence substantially homologous thereto) further comprises at its N-terminal end a signal peptide of SEQ ID NO:338.

In some embodiments, a VH domain comprising SEQ ID NO:341 (or sequence substantially homologous thereto) further comprises at its N-terminal end a signal peptide of SEQ ID NO:357. In some embodiments, a VL domain comprising SEQ ID NO:342 (or sequence substantially homologous thereto) further comprises at its N-terminal end a signal peptide of SEQ ID NO:358.

In some embodiments, a VH domain comprising SEQ ID NO:361 (or sequence substantially homologous thereto) further comprises at its N-terminal end a signal peptide of SEQ ID NO:377. In some embodiments, a VL domain comprising SEQ ID NO:362 (or sequence substantially homologous thereto) further comprises at its N-terminal end a signal peptide of SEQ ID NO:378.

In some embodiments, a VH domain comprising SEQ ID NO:381 (or sequence substantially homologous thereto) further comprises at its N-terminal end a signal peptide of SEQ ID NO:397. In some embodiments, a VL domain comprising SEQ ID NO:382 (or sequence substantially homologous thereto) further comprises at its N-terminal end a signal peptide of SEQ ID NO:398.

In some embodiments, a VH domain comprising SEQ ID NO:401 (or sequence substantially homologous thereto) further comprises at its N-terminal end a signal peptide of SEQ ID NO:417. In some embodiments, a VL domain comprising SEQ ID NO:402 (or sequence substantially homologous thereto) further comprises at its N-terminal end a signal peptide of SEQ ID NO:418.

In some embodiments, a VH domain comprising SEQ ID NO:421 (or sequence substantially homologous thereto)

further comprises at its N-terminal end a signal peptide of SEQ ID NO:437. In some embodiments, a VL domain comprising SEQ ID NO:422 (or sequence substantially homologous thereto) further comprises at its N-terminal end a signal peptide of SEQ ID NO:438.

As indicated above, in this aspect of the invention, antibodies inhibit capsaicin-induced activation of TRPV1.

In some embodiments, inhibition of capsaicin-induced activation of TRPV1 is any measurable or significant inhibition, more preferably a statistically significant inhibition (e.g. as compared to a control with no antibody or as compared to a control with an antibody that does not bind to TRPV1).

In some embodiments, the level of inhibition (or amount of inhibition) of capsaicin-induced activation of TRPV1 observed with (or caused by or elicited by) a control (e.g. a control antibody that does not bind to (or does not specifically bind to) TRPV1) represents (or is set as) the zero inhibition level (or zero inhibition value or 0% inhibition level or value). Thus, in some embodiments, the % inhibitions of capsaicin-induced activation of TRPV1 discussed elsewhere herein are as compared to (or relative to) the inhibition observed with (or caused by or elicited by) a control antibody (e.g. a control antibody that does not bind to TRPV1).

In some embodiments, inhibition of capsaicin-induced activation of TRPV1 is an inhibition of at least 5%, at least 10%, at least 15%, preferably at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or 100%.

In some embodiments, inhibition of capsaicin-induced activation of TRPV1 is an inhibition of up to 5%, up to 10%, up to 15%, up to 20%, up to 25%, up to 30%, up to 35%, up to 40%, up to 45%, up to 50%, up to 55%, up to 60%, up to 65%, up to 70%, up to 75%, up to 80%, up to 85%, up to 90%, up to 95% or up to 100%.

Thus, in some embodiments, inhibition of capsaicin-induced activation of TRPV1 is an inhibition of 5%-100%, 10%-100%, 15%-100%, 20%-100%, 25%-100%, 30%-100%, 35%-100%, 40%-100%, 45%-100%, 50%-100%, 55%-100%, 60%-100%, 65%-100%, 70%-100%, 75%-100%, 80%-100%, 85%-100%, 90%-100% or 95%-100%.

In some embodiments, inhibition of capsaicin-induced activation of TRPV1 is an inhibition of 5%-75%, 10%-75%, 15%-75%, 20%-75%, 25%-75%, 30%-75%, 35%-75%, 40%-75%, 45%-75%, 50%-75%, 55%-75%, 60%-75%, 65%-75% or 70%-75%.

In some embodiments, inhibition of capsaicin-induced activation of TRPV1 is an inhibition of 5%-50%, 10%-50%, 15%-50%, 20%-50%, 25%-50%, 30%-50%, 35%-50%, 40%-50% or 45%-50%.

In some embodiments, inhibition of capsaicin-induced activation of TRPV1 is an inhibition of 5%-25%, 10%-25%, 15%-25% or 20%-25%.

In some preferred embodiments, inhibition of capsaicin-induced activation of TRPV1 is an inhibition of at least 20%, or at least 25%, at least 30%, at least 35%, at least 40%, at least 45%, at least 50%, at least 55%, at least 60%, at least 65%, at least 70%, at least 75%, at least 80%, at least 85%, at least 90%, at least 95% or 100%.

In some embodiments, antibodies of the invention have an IC50 with respect to inhibition of capsaicin-induced activation of TRPV1 of $\leq 5$ µM, $\leq 1$ µM, $\leq 900$ nM, $\leq 800$ nM, $\leq 700$ nM, $\leq 600$ nM, $\leq 500$ nM, $\leq 400$ nM, $\leq 300$ nM, $\leq 200$ nM, $\leq 100$ nM, $\leq 75$ nM, $\leq 50$ nM, $\leq 25$ nM, $\leq 10$ nM, $\leq 5$ nM, $\leq 2$ nM, ≤1 nM, ≤500 pM, ≤400 pM, ≤300 pM, ≤200 pM, ≤100 pM, ≤50 pM, ≤25 pM, ≤10 pM, ≤5 pM, ≤2 pM or ≤1 pM. Preferably, the IC50 is ≤1 μM, for example ≤750 nM, ≤500 nM, ≤400 nM, ≤300 nM, ≤200 nM, ≤100 nM, ≤75 nM, ≤50 nM, ≤25 nM, ≤10 nM or ≤5 nM. In some embodiments, the IC50 value may be in the range of 1 pM-≤5 μM, for example 1 pM-1 μM, 1 pM-500 nM, 1 pM-100 nM, 1 pM-50 nM, 500 pM-10 μM, 500 pM-1 μM, 500 pM-500 nM, 500 pM-100 nM, 500 pM-50 nM, 1 nM-10 μM, 1 nM-1 μM, 1 nM-500 nM, 1 nM-100 nM, 1 nM-50 nM, 10 nM-10 μM, 10 nM-1 μM, 10 nM-500 nM, 10 nM-100 nM, 10 nM-50 nM, 100 nM-10 μM, 100 nM-1 μM, or 100 nM-500 nM. In some embodiments, the IC50 value may be up to 5 μM, or up to 1 μM, or up to 900 nM, or up to 800 nM, or up to 700 nM, or up to 600 nM, or up to 500 nM, or up to 400 nM, or up to 300 nM, or up to 200 nM, or up to 100 nM, or up to 50 nM or up to 10 nM. An IC50 value represents the half maximal inhibitory concentration of a substance for a biological process under study, in the context of the present invention the half maximal inhibitory concentration of an antibody for the inhibition of capsaicin-induced activation of TRPV1. IC50 values in the context of the present invention may be alternatively viewed as half maximal inhibitory concentration of an antibody for the inhibition of capsaicin-induced cellular TRPV1-mediated $Ca^{2+}$ influx. IC50 values may be calculated by any suitable means (and be based on any suitable tests, methods or assays, for example methods as described herein). For example, IC50 values may be established (or calculated) based on the results of a FLIPR method. A particularly preferred FLIPR method is described in the Example section herein.

As indicated above, in this aspect of the invention, antibodies preferentially inhibit capsaicin-induced activation of TRPV1 as opposed to heat-induced activation of TRPV1.

In some embodiments, the inhibition of heat-induced activation of TRPV1 (if any) by an antibody of the invention is substantially the same as (or not significantly different from or analogous to or comparable to) the inhibition of heat-induced activation of TRPV1 observed with (or caused by or elicited by) a control (e.g. a control antibody that does not bind to (or does not specifically bind to) TRPV1). In some embodiments, the level of inhibition (or amount of inhibition) of heat-induced activation of TRPV1 observed with (or caused by or elicited by) a control (e.g. a control antibody that does not bind to (or does not specifically bind to) TRPV1) represents (or is set as) the zero inhibition level (or zero inhibition value or 0% inhibition level or value). Thus, in some embodiments, the % inhibitions of heat-induced activation of TRPV1 discussed elsewhere herein are as compared to (or relative to) the inhibition observed with (or caused by or elicited by) a control antibody (e.g. a control antibody that does not bind to TRPV1).

In some embodiments, antibodies of the present invention inhibit heat-induced activation of TRPV1 by no more than 25%, or by no more than 20%, or by no more than 15%, preferably by no more than 10%, by no more than 5%, by no more than 4%, by no more than 3%, by no more than 2%, or by no more than 1% or by 0%.

Thus, in some embodiments, antibodies of the present invention inhibit heat-induced activation of TRPV1 by 0%-25%, 0%-20%, 0%-10%, 0%-5%, 0%-4%, 0%-3%, 0%-2%, 0%-1% or 0%.

In some preferred embodiments, antibodies of the present invention cause (or elicit) no measurable inhibition of heat-induced activation of TRPV1 or no significant inhibition (preferably no statistically significant inhibition) of heat-induced activation of TRPV1.

In some embodiments, the above inhibitions are as determined when the antibody is used at a concentration in the micromolar (μM), nanomolar (nM) or picomolar (pM) range, preferably the nanomolar (nM) or picomolar (pM) range. Thus, in some embodiments, the above inhibitions are as determined when the antibody is used at a concentration of ≤10 μM, ≤5 μM, ≤1 μM, ≤900 nM, ≤800 nM, ≤700 nM, ≤600 nM, ≤500 nM, ≤400 nM, ≤300 nM, ≤200 nM, ≤100 nM, ≤75 nM, ≤50 nM, ≤25 nM, ≤10 nM, ≤5 nM, ≤2 nM, ≤1 nM, ≤500 pM, ≤400 pM, ≤300 pM, ≤200 pM, ≤100 pM, ≤50 pM, ≤25 pM, ≤10 pM, ≤5 pM, ≤2 pM or ≤1 pM. Thus, in some embodiments, the above inhibitions are as determined when the antibody is used at a concentration of 1 pM-≤10 μM, for example 1 pM-1 μM, 1 pM-500 nM, 1 pM-100 nM, 1 pM-50 nM, 500 pM-10 μM, 500 pM-1 μM, 500 pM-500 nM, 500 pM-100 nM, 500 pM-50 nM, 1 nM-10 μM, 1 nM-1 μM, 1 nM-500 nM, 1 nM-100 nM, 1 nM-50 nM, 10 nM-10 μM, 10 nM-1 μM, 10 nM-500 nM, 10 nM-100 nM, 10 nM-50 nM, 100 nM-10 μM, 100 nM-1 μM, or 100 nM-500 nM. In some embodiments, the above inhibitions are as determined when the antibody is used at a concentration of up to 5 μM, or up to 1 μM, or up to 900 nM, or up to 800 nM, or up to 700 nM, or up to 600 nM, or up to 400 nM, or up to 300 nM, or up to 200 nM, or up to 100 nM, or up to 50 nM or up to 10 nM.

In some embodiments, the above inhibitions (e.g. % inhibitions) and concentrations apply when the antibody is a polyclonal antibody (e.g. a rabbit polyclonal antibody). In some embodiments, the above inhibitions (e.g. % inhibitions) and concentrations apply when the antibody is a monoclonal antibody (e.g. a mouse monoclonal antibody).

As indicated above, in this aspect of the invention antibodies preferentially inhibit capsaicin-induced activation of TRPV1 as opposed to heat-induced activation of TRPV1. This means that the given antibody inhibits (or is capable of inhibiting) capsaicin-induced activation of TRPV1 to a greater extent than it inhibits (or is capable of inhibiting) heat-induced activation of TRPV1. Thus, if a given antibody inhibits capsaicin-induced activation of TRPV1 by X %, that antibody will inhibit heat-induced activation of TRPV1 by <X %.

In some embodiments, the % inhibition (or % inhibition value) of capsaicin-induced activation of TRPV1 is at least 5% higher, but typically at least 10% higher, preferably at least 20% higher, at least 30% higher, at least 40% higher, at least 50% higher, at least 60% higher, at least 70% higher, at least 80% higher, at least 90% or even 100% higher than the % inhibition (or % inhibition value) of heat-induced activation of TRPV1.

In some embodiments, the % inhibition (or % inhibition value) of capsaicin-induced activation of TRPV1 is at least 20% and the % inhibition (or % inhibition value) of heat-induced activation of TRPV1 is ≤10% or is ≤5% or is 0%. In some embodiments, the % inhibition (or % inhibition value) of capsaicin-induced activation of TRPV1 is at least 40% and the % inhibition (or % inhibition value) of heat-induced activation of TRPV1 is ≤10% or is 55% or is 0%. In some embodiments, the % inhibition (or % inhibition value) of capsaicin-induced activation of TRPV1 is at least 60% and the % inhibition (or % inhibition value) of heat-induced activation of TRPV1 is ≤10% or is ≤5% or is 0%. In some embodiments, the % inhibition (or % inhibition value) of capsaicin-induced activation of TRPV1 is at least 80% and the % inhibition (or % inhibition value) of heat-induced activation of TRPV1 is ≤10% or is 55% or is 0%.

In some embodiments, the % inhibition (or % inhibition value) of capsaicin-induced activation of TRPV1 is at least 40% and the % inhibition (or % inhibition value) of heat-induced activation of TRPV1 is ≤25% or is ≤20% or is 15% or is ≤10% or is ≤5% or is 0%. In some embodiments, the % inhibition (or % inhibition value) of capsaicin-induced activation of TRPV1 is at least 60% and the % inhibition (or % inhibition value) of heat-induced activation of TRPV1 is ≤25% or is ≤20% or is 15% or is ≤10% or is ≤5% or is 0%. In some embodiments, the % inhibition (or % inhibition value) of capsaicin-induced activation of TRPV1 is at least 80% and the % inhibition (or % inhibition value) of heat-induced activation of TRPV1 is ≤25% or is ≤20% or is 15% or is ≤10% or is ≤5% or is 0%.

In some embodiments, antibodies preferentially inhibit capsaicin-induced activation of TRPV1 as opposed to heat-induced activation of TRPV1 as determined by performing a test (or assay) to determine (or quantify) the level of (or amount of) inhibition of capsaicin-induced activation of TRPV1 and a test (or assay to) to determine the level of (or amount of) inhibition of heat-induced activation of TRPV1. Suitable assays are described elsewhere herein.

In some embodiments, antibodies preferentially inhibit (or are capable of inhibiting) capsaicin-induced activation of TRPV1 as opposed to heat-induced activation of TRPV1 as determined when the antibody is used at the same concentration in both such assays (i.e. the same concentration of antibody is used in the test to determine the level of inhibition of capsaicin-induced activation of TRPV1 as is used in the test to determine the level of inhibition of heat-induced activation of TRPV1).

In some embodiments, antibodies preferentially inhibit capsaicin-induced activation of TRPV1 as opposed to heat-induced activation of TRPV1 as determined when the antibody is used at least a 1.5 times, at least a 2 times, at least a 3 times, at least a 4 times, preferably at least a 5 times, (e.g. a 1.5, 2, 3, 4, 5, 6, 7, 8, 9 or 10 times or a 2-5, 3-5, or 4-5 times) higher concentration in the test to determine the level of inhibition of heat-induced activation of TRPV1 concentration than is used in test the to determine the level of inhibition of capsaicin-induced activation of TRPV1.

In some embodiments, for antibodies that bind to an isolated peptide of SEQ ID NO:3 or SEQ ID NO:17 (OTV4 peptides) (or isolated peptides substantially homologous thereto) or that bind to an epitope of TRPV1 that corresponds to (or corresponds essentially to) such an isolated peptide, the inhibition of capsaicin-induced activation of TRPV1 is an inhibition of at least 10%, at least 15%, at least 20%, at least 25%, at least 30%, at least 35%, at least 40% or at least 45% or at least 50%.

In some embodiments, for antibodies that bind to an isolated peptide of SEQ ID NO:3 or SEQ ID NO:17 (or isolated peptides substantially homologous thereto) or that bind to an epitope of TRPV1 that corresponds to (or corresponds essentially to) such an isolated peptide, the inhibition of capsaicin-induced activation of TRPV1 is an inhibition of up to 10%, up to 15%, up to 20%, up to 25%, up to 30%, up to 35%, up to 40%, up to 45% or up to 50%.

In some embodiments, the above-mentioned % inhibitions of capsaicin-induced activation of TRPV1 for antibodies that bind to an isolated peptide of SEQ ID NO:3 or SEQ ID NO:17 (or isolated peptides substantially homologous thereto) or that bind to an epitope of TRPV1 that corresponds to (or corresponds essentially to) such an isolated peptide are as determined when said antibody (e.g. a polyclonal antibody such as a rabbit polyclonal antibody) is used at a concentration of 50 nM to 1 μM or 100 nM to 1 μM, e.g. 400 nM to 500 nM, or about 500 nM (e.g. 533 nM).

In some embodiments, for antibodies that bind to an isolated peptide of SEQ ID NO:3 or SEQ ID NO:17 (or isolated peptides substantially homologous thereto) or that bind to an epitope of TRPV1 that corresponds to (or corresponds essentially to) such an isolated peptide, inhibition of heat-induced activation of TRPV1 is by no more than 5%, by no more than 4%, by no more than 3%, by no more than 2% or by no more than 1%, preferably 0%, preferably there is no measurable (or no significant) inhibition of heat-induced activation of TRPV1.

Thus, in some embodiments, for antibodies that bind to an isolated peptide of SEQ ID NO:3 or SEQ ID NO:17 (or isolated peptides substantially homologous thereto) or that bind to an epitope of TRPV1 that corresponds to (or corresponds essentially to) such an isolated peptide, the inhibition of heat-induced activation of TRPV1 is 0%-5%, 0%-4%, 0%-3%, 0%-2%, 0%-1% or preferably 0%.

In some embodiments, the above-mentioned % inhibitions of heat-induced activation of TRPV1 for antibodies that bind to an isolated peptide of SEQ ID NO:3 or SEQ ID NO:17 (or isolated peptides substantially homologous thereto) or that bind to an epitope of TRPV1 that corresponds to (or corresponds essentially to) such an isolated peptide are as determined when said antibody (e.g. a polyclonal antibody such as a rabbit polyclonal antibody) is used at a concentration of 50 nM to 1 μM or 100 nM to 10 μM, e.g. 200 nM to 3 μM, or about 300 nM (e.g. 270 nM) or about 3 μM (e.g. 2.7 μM).

In some embodiments, for antibodies that bind to an isolated peptide of SEQ ID NO:3 or SEQ ID NO:17 (or isolated peptides substantially homologous thereto) or that bind to an epitope of TRPV1 that corresponds to (or corresponds essentially to) such an isolated peptide, no more than 5%, no more than 4%, no more than 3%, no more than 2% or no more than 1%, preferably 0%, preferably no measurable (or no significant) inhibition of heat-induced activation of TRPV1 is observed when the antibody is used at about a 5 times higher concentration than an antibody concentration that inhibits capsaicin-induced activation of TRPV1 by at least 10%, at least 15%, at least 20%, at least 25%, at least 30%, at least 35%, at least 40% or at least 45% or at least 50%.

In some embodiments, for antibodies that bind to an isolated peptide of SEQ ID NO:3 or SEQ ID NO:17 (or isolated peptides substantially homologous thereto) or that bind to an epitope of TRPV1 that corresponds to (or corresponds essentially to) such an isolated peptide, no more than 5%, no more than 4%, no more than 3%, no more than 2% or no more than 1%, preferably 0%, preferably no measurable (or no significant) inhibition of heat-induced activation of TRPV1 is observed when said antibody is used at a concentration of about 3 μM (e.g. 2.7 μM) and at least 10%, at least 15%, preferably at least 20%, at least 25%, at least 30%, at least 35%, at least 40% or at least 45% or at least 50% inhibition of capsaicin-induced activation of TRPV1 is observed when said antibody is used at a concentration of about 500 nM (e.g. 533 nM).

In some embodiments, for antibodies that bind to an isolated peptide of SEQ ID NO:3 or SEQ ID NO:17 (or isolated peptides substantially homologous thereto) or that bind to an epitope of TRPV1 that corresponds to (or corresponds essentially to) such an isolated peptide, no more than 5% inhibition of heat-induced activation of TRPV1 is observed when said antibody is used at a concentration of about 3 μM (e.g. 2.7 μM) and at least 20% inhibition of capsaicin-induced activation of TRPV1 is observed when said antibody is used at a concentration of about 500 nM (e.g. 533 nM).

In some embodiments, for antibodies that bind to an isolated peptide of SEQ ID NO:4 or SEQ ID NO:18 (OTV5 peptides) (or isolated peptides substantially homologous thereto) or that bind to an epitope of TRPV1 that corresponds to (or corresponds essentially to) such an isolated peptide, the inhibition of capsaicin-induced activation of TRPV1 is at least 20%, at least 25%, at least 30%, at least 35%, at least 40% or at least 45%, at least 50%, at least 55%, at least 60%, at least 65%, at least 70% or at least 75%.

In some embodiments, for antibodies that bind to an isolated peptide of SEQ ID NO:4 or SEQ ID NO:18 (or isolated peptides substantially homologous thereto) or that bind to an epitope of TRPV1 that corresponds to (or corresponds essentially to) such an isolated peptide, the inhibition of capsaicin-induced activation of TRPV1 is an inhibition of up to 20%, up to 25%, up to 30%, up to 35%, up to 40%, up to 45%, up to 50%, up to 55%, up to 60%, up to 65%, up to 70% or up to 75%.

In some embodiments, the above-mentioned % inhibitions of capsaicin-induced activation of TRPV1 for antibodies that bind to an isolated peptide of SEQ ID NO:4 or SEQ ID NO:18 (or isolated peptides substantially homologous thereto) or that bind to an epitope of TRPV1 that corresponds to (or corresponds essentially to) such an isolated peptide are as determined when said antibody (e.g. a polyclonal antibody such as a rabbit polyclonal antibody) is used at a concentration of 100 pM to 100 nM, e.g. 1 nM to 20 nM, or about 10 nM (e.g. 13.3 nM).

In some embodiments, for antibodies that bind to an isolated peptide of SEQ ID NO:4 or SEQ ID NO:18 (or isolated peptides substantially homologous thereto) or that bind to an epitope of TRPV1 that corresponds to (or corresponds essentially to) such an isolated peptide, inhibition of heat-induced activation of TRPV1 is by no more than 15%, preferably by no more than 10%, by no more than 5%, by no more than 4%, by no more than 3%, by no more than 2% or by no more than 1%, preferably 0%, preferably there is no measurable (or no significant) inhibition of heat-induced activation of TRPV1.

Thus, in some embodiments, for antibodies that bind to an isolated peptide of SEQ ID NO:4 or SEQ ID NO:18 (or isolated peptides substantially homologous thereto) or that bind to an epitope of TRPV1 that corresponds to (or corresponds essentially to) such an isolated peptide, the inhibition of heat-induced activation of TRPV1 is 0%-15%, preferably 0%-10%, 0%-5%, 0%-4%, 0%-3%, 0%-2%, 0%-1% or preferably 0%.

In some embodiments, the above-mentioned % inhibitions of heat-induced activation of TRPV1 for antibodies that bind to an isolated peptide of SEQ ID NO:4 or SEQ ID NO:18 (or isolated peptides substantially homologous thereto) or that bind to an epitope of TRPV1 that corresponds to (or corresponds essentially to) such an isolated peptide are as determined when said antibody (e.g. a polyclonal antibody such as a rabbit polyclonal antibody) is used at a concentration of 1 nM to 100 nM, e.g. 5 nM to 75 nM, or about 5 nM (e.g. 6.7 nM) or about 50 nM (e.g. 67 nM).

In some embodiments, for antibodies that bind to an isolated peptide of SEQ ID NO:4 or SEQ ID NO:18 (or isolated peptides substantially homologous thereto) or that bind to an epitope of TRPV1 that corresponds to (or corresponds essentially to) such an isolated peptide, no more than 15%, preferably no more than 10%, no more than 5%, no more than 4%, no more than 3%, no more than 2% or no more than 1%, preferably 0%, preferably no measurable (or no significant) inhibition of heat-induced activation of TRPV1 is observed when the antibody is used at about a 5 times higher concentration than an antibody concentration that inhibits capsaicin-induced activation of TRPV1 by at least 20%, at least 25%, at least 30%, at least 35%, at least 40% or at least 45% or at least 50%.

In some embodiments, for antibodies that bind to an isolated peptide of SEQ ID NO:4 or SEQ ID NO:18 (or isolated peptides substantially homologous thereto) or that bind to an epitope of TRPV1 that corresponds to (or corresponds essentially to) such an isolated peptide, no more than 15%, preferably no more than 10%, no more than 5%, no more than 4%, no more than 3%, no more than 2% or no more than 1%, preferably 0%, preferably no measurable (or no significant) inhibition of heat-induced activation of TRPV1 is observed when said antibody is used at a concentration of about 50 nM (e.g. 67 nM) and at least 20%, at least 25%, at least 30%, at least 35%, at least 40% or at least 45% or at least 50% inhibition of capsaicin-induced activation of TRPV1 is observed when said antibody is used at a concentration of about 10 nM (e.g. 13.3 nM).

In some embodiments, for antibodies that bind to an isolated peptide of SEQ ID NO:4 or SEQ ID NO:18 (or isolated peptides substantially homologous thereto) or that bind to an epitope of TRPV1 that corresponds to (or corresponds essentially to) such an isolated peptide, no more than 5%, no more than 4%, no more than 3%, no more than 2% or no more than 1%, preferably 0%, preferably no measurable (or no significant) inhibition of heat-induced activation of TRPV1 is observed when said antibody is used at a concentration of about 5 nM (e.g. 6.7 nM) and at least 15%, at least 20%, at least 25%, at least 30%, at least 35%, at least 40% or at least 45% or at least 50% inhibition of capsaicin-induced activation of TRPV1 is observed when said antibody is used at a concentration of about 1 nM (e.g. 1.33 nM).

In some embodiments, for antibodies that bind to an isolated peptide of SEQ ID NO:4 or SEQ ID NO:18 (or isolated peptides substantially homologous thereto) or that bind to an epitope of TRPV1 that corresponds to (or corresponds essentially to) such an isolated peptide, no more than 5% inhibition of heat-induced activation of TRPV1 is observed when said antibody is used at a concentration of about 5 nM (e.g. 6.7 nM) at least 10% inhibition of capsaicin-induced activation of TRPV1 is observed when said antibody is used at a concentration of about 1 nM (e.g. 1.33 nM).

In some embodiments, for antibodies that bind to an isolated peptide of SEQ ID NO:11 or SEQ ID NO:25 (OTV12 peptides) (or isolated peptides substantially homologous thereto) or that bind to an epitope of TRPV1 that corresponds to (or corresponds essentially to) such an isolated peptide, the inhibition of capsaicin-induced activation of TRPV1 is an inhibition of at least 10%, at least 15%, at least 20%, at least 25%, at least 30%, at least 35% or at least 40%.

In some embodiments, for antibodies that bind to an isolated peptide of SEQ ID NO:11 or SEQ ID NO:25 (or isolated peptides substantially homologous thereto) or that bind to an epitope of TRPV1 that corresponds to (or corresponds essentially to) such an isolated peptide, the inhibition of capsaicin-induced activation of TRPV1 is an inhibition of up to 10%, up to 15%, up to 20%, up to 25%, up to 30%, up to 35% or up to 40%.

In some embodiments, the above-mentioned % inhibitions of capsaicin-induced activation of TRPV1 for antibodies that bind to an isolated peptide of SEQ ID NO:11 or SEQ ID NO:25 (or isolated peptides substantially homologous thereto) or that bind to an epitope of TRPV1 that corresponds to (or corresponds essentially to) such an isolated peptide are as determined when said antibody (e.g. a polyclonal antibody such as a rabbit polyclonal antibody) is used at a concentration of 10 pM to 100 nM, e.g. 100 pM to 20 nM, or about 10 nM (e.g. 13.3 nM).

In some embodiments, for antibodies that bind to an isolated peptide of SEQ ID NO:11 or SEQ ID NO:25 (or isolated peptides substantially homologous thereto) or that bind to an epitope of TRPV1 that corresponds to (or corresponds essentially to) such an isolated peptide, inhibition of heat-induced activation of TRPV1 is by no more than 5%, by no more than 4%, by no more than 3%, by no more than 2% or by no more than 1%, preferably 0%, preferably there is no measurable (or no significant) inhibition of heat-induced activation of TRPV1.

Thus, in some embodiments, for antibodies that bind to an isolated peptide of SEQ ID NO:11 or SEQ ID NO:25 (or isolated peptides substantially homologous thereto) or that bind to an epitope of TRPV1 that corresponds to (or corresponds essentially to) such an isolated peptide, the inhibition of heat-induced activation of TRPV1 is 0%-5%, 0%-4%, 0%-3%, 0%-2%, 0%-1% or preferably 0%.

In some embodiments, the above-mentioned % inhibitions of heat-induced activation of TRPV1 for antibodies that bind to an isolated peptide of SEQ ID NO: 11 or SEQ ID NO:25 (or isolated peptides substantially homologous thereto) or that bind to an epitope of TRPV1 that corresponds to (or corresponds essentially to) such an isolated peptide are as determined when said antibody (e.g. a polyclonal antibody such as a rabbit polyclonal antibody) is used at a concentration of 100 pM to 500 nM, e.g. 500 pM to 100 nM, or about 1 nM (e.g. 0.67 nM) or about 50 nM (e.g. 67 nM).

In some embodiments, for antibodies that bind to an isolated peptide of SEQ ID NO:11 or SEQ ID NO:25 (or isolated peptides substantially homologous thereto) or that bind to an epitope of TRPV1 that corresponds to (or corresponds essentially to) such an isolated peptide, no more than 5%, no more than 4%, no more than 3%, no more than 2% or no more than 1%, preferably 0%, preferably no measurable (or no significant) inhibition of heat-induced activation of TRPV1 is observed when the antibody is used at about a 5 times higher concentration than an antibody concentration that inhibits capsaicin-induced activation of TRPV1 by at least 10%, at least 15%, at least 20%, at least 25%, at least 30%, at least 35%, at least 40% or at least 45% or at least 50%.

In some embodiments, for antibodies that bind to an isolated peptide of SEQ ID NO:11 or SEQ ID NO:25 (or isolated peptides substantially homologous thereto) or that bind to an epitope of TRPV1 that corresponds to (or corresponds essentially to) such an isolated peptide, no more than 5%, no more than 4%, no more than 3%, preferably no more than 2% or no more than 1%, preferably no measurable (or no significant) inhibition of heat-induced activation of TRPV1 is observed when said antibody is used at a concentration of about 50 nM (e.g. 67 nM) and at least 20%, at least 25%, at least 30%, at least 35%, at least 40% or at least 45% or at least 50% inhibition of capsaicin-induced activation of TRPV1 is observed when said antibody is used at a concentration of about 10 nM (e.g. 13.3 nM).

In some embodiments, for antibodies that bind to an isolated peptide of SEQ ID NO:11 or SEQ ID NO:25 (or isolated peptides substantially homologous thereto) or that bind to an epitope of TRPV1 that corresponds to (or corresponds essentially to) such an isolated peptide, no more than 5% inhibition of heat-induced activation of TRPV1 is observed when said antibody is used at a concentration of about 50 nM (e.g. 67 nM) and at least 20% inhibition of capsaicin-induced activation of TRPV1 is observed when said antibody is used at a concentration of about 10 nM (e.g. 13.3 nM).

In some embodiments, for antibodies based on the OT-Ab3, OT-Ab2 and OT-Ab1 antibodies of the invention (e.g. those having the CDR sequences and/or VH domain and/or VL domain sequences thereof, or sequences substantially homologous thereto), the inhibition of capsaicin-induced activation of TRPV1 is at least 20%, at least 25%, at least 30%, at least 35%, at least 40% or at least 45%, at least 50%, at least 55%, at least 60%, at least 65%, at least 70%, at least 75% or at least 80%.

In some embodiments, for antibodies based on the OT-Ab3, OT-Ab2 and OT-Ab1 antibodies of the invention (e.g. those having the CDR sequences and/or VH domain and/or VL domain sequences thereof, or sequences substantially homologous thereto), the inhibition of capsaicin-induced activation of TRPV1 is an inhibition of up to 30%, up to 35%, up to 40%, up to 45%, up to 50%, up to 55%, up to 60%, up to 65%, up to 70%, up to 75%, up to 80% or up to 90%.

In some embodiments, the above-mentioned % inhibitions of capsaicin-induced activation of TRPV1 for antibodies based on the OT-Ab3, OT-Ab2 and OT-Ab1 antibodies of the invention (e.g. those having the CDR sequences and/or VH domain and/or VL domain sequences thereof, or sequences substantially homologous thereto) are as determined when said antibody (e.g. a monoclonal antibody such as a mouse monoclonal antibody) is used at a concentration of 100 nM to 1 μM, e.g. 100 nM to 500 nM (e.g. 243 nM for antibodies based on OT-Ab1 or e.g. 166 nM for antibodies based on OT-Ab2 or e.g. 326 nM for antibodies based on OT-Ab3).

In some embodiments, for antibodies based on the OT-Ab3, OT-Ab2 and OT-Ab1 antibodies of the invention (e.g. those having the CDR sequences and/or VH domain and/or VL domain sequences thereof, or sequences substantially homologous thereto), inhibition of heat-induced activation of TRPV1 is by no more than 15%, preferably by no more than 10%, by no more than 5%, by no more than 4%, by no more than 3%, by no more than 2% or by no more than 1%, preferably 0%, preferably there is no measurable (or no significant) inhibition of heat-induced activation of TRPV1.

Thus, in some embodiments, for antibodies based on the OT-Ab3, OT-Ab2 and OT-Ab1 antibodies of the invention (e.g. those having the CDR sequences and/or VH domain and/or VL domain sequences thereof, or sequences substantially homologous thereto) (e.g. a monoclonal antibody such as a mouse monoclonal antibody), the inhibition of heat-induced activation of TRPV1 is 0%-15%, preferably 0%-10%, 0%-5%, 0%-4%, 0%-3%, 0%-2%, 0%-1% or preferably 0%.

In some embodiments, the above-mentioned % inhibitions of heat-induced activation of TRPV1 for antibodies based on the OT-Ab3, OT-Ab2 and OT-Ab1 antibodies of the invention (e.g. those having the CDR sequences and/or VH domain and/or VL domain sequences thereof, or sequences substantially homologous thereto) are as determined when said antibody (e.g. a monoclonal antibody such as a mouse monoclonal antibody) is used at a concentration of 100 nM to 1 μM, e.g. 100 nM to 500 nM (e.g. 243 nM for antibodies based on OT-Ab1 or e.g. 166 nM for antibodies based on OT-Ab2 or e.g. 326 nM for antibodies based on OT-Ab3).

In some embodiments, for antibodies based on the OT-Ab3, OT-Ab2 and OT-Ab1 antibodies of the invention (e.g. those having the CDR sequences and/or VH domain and/or VL domain sequences thereof, or sequences substantially homologous thereto), no more than 15%, preferably no more than 10%, no more than 5%, no more than 4%, no more than 3%, no more than 2% or no more than 1%, preferably 0%, preferably no measurable (or no significant) inhibition of heat-induced activation of TRPV1 is observed when the antibody is used at a concentration that inhibits capsaicin-induced activation of TRPV1 by at least 25%, preferably at least 30%, at least 35%, at least 40% or at least 45%, at least 50%, at least 55%, at least 60%, at least 65%, at least 70%, at least 75% or at least 80%.

In some embodiments, for antibodies based on the OT-Ab3, OT-Ab2 and OT-Ab1 antibodies of the invention (e.g. those having the CDR sequences and/or VH domain and/or VL domain sequences thereof, or sequences substantially homologous thereto), no more than 15%, preferably no more than 10%, no more than 5%, no more than 4%, no more than 3%, no more than 2% or no more than 1%, preferably 0%, preferably no measurable (or no significant) inhibition of heat-induced activation of TRPV1 is observed when said antibody is used at a concentration of 100 nM to 1 μM, e.g. 100 nM to 500 nM (e.g. 243 nM for antibodies based on OT-Ab1 or e.g. 166 nM for antibodies based on OT-Ab2 or e.g. 326 nM for antibodies based on OT-Ab3), and at least 25%, preferably at least 30%, at least 35%, at least 40% or at least 45%, at least 50%, at least 55%, at least 60%, at least 65%, at least 70%, at least 75% or at least 80% inhibition of capsaicin-induced activation of TRPV1 is observed when said antibody is used at a concentration of 100 nM to 1 μM, e.g. 100 nM to 500 nM (e.g. 243 nM for antibodies based on OT-Ab1 or e.g. 166 nM for antibodies based on OT-Ab2 or e.g. 326 nM for antibodies based on OT-Ab3).

In some embodiments, for antibodies based on the 16F1-1, 15D8-1, 17E11-1 or 17E9-1 antibodies of the invention (e.g. those having the CDR sequences and/or VH domain and/or VL domain sequences thereof, or sequences substantially homologous thereto), the inhibition of capsaicin-induced activation of TRPV1 is an inhibition of up to 10%, up to 15%, up to 20%, up to 25%, up to 30%, up to 35%, up to 40%, up to 45%, up to 50%, up to 55%, up to 60%, up to 65%, up to 70%, or up to 75%.

In some embodiments, the above-mentioned % inhibitions of capsaicin-induced activation of TRPV1 for antibodies based on the 16F1-1, 15D8-1, 17E11-1 or 17E9-1 antibodies of the invention (e.g. those having the CDR sequences and/or VH domain and/or VL domain sequences thereof, or sequences substantially homologous thereto) are as determined when said antibody (e.g. a monoclonal antibody such as a mouse monoclonal antibody) is used at a concentration of 50 nM to 1 μM or 100 nM to 1 μM, e.g. 50 nM to 500 nM or 100 nM to 500 nM (e.g. 253 nM for antibodies based on 16F1-1 or e.g. 130 nM for antibodies based on 15D8-1 or e.g. 110 nM for antibodies based on 17E11-1 or e.g. 83 nM for antibodies based on 17E9-1).

In some embodiments, for antibodies based on the 15D8-1 or 17E11-1 antibodies of the invention (e.g. those having the CDR sequences and/or VH domain and/or VL domain sequences thereof, or sequences substantially homologous thereto), inhibition of heat-induced activation of TRPV1 is by no more than 15%, preferably by no more than 10%, by no more than 5%, by no more than 4%, by no more than 3%, by no more than 2% or by no more than 1%, preferably 0%, preferably there is no measurable (or no significant) inhibition of heat-induced activation of TRPV1.

Thus, in some embodiments, for antibodies based on the 15D8-1 or 17E11-1 antibodies of the invention (e.g. those having the CDR sequences and/or VH domain and/or VL domain sequences thereof, or sequences substantially homologous thereto) (e.g. a monoclonal antibody such as a mouse monoclonal antibody), the inhibition of heat-induced activation of TRPV1 is 0%-15%, preferably 0%-10%, 0%-5%, 0%-4%, 0%-3%, 0%-2%, 0%-1% or preferably 0%.

In some embodiments, the above-mentioned % inhibitions of heat-induced activation of TRPV1 for antibodies based on the 15D8-1 or 17E11-1 antibodies of the invention (e.g. those having the CDR sequences and/or VH domain and/or VL domain sequences thereof, or sequences substantially homologous thereto) are as determined when said antibody is used at a concentration of 100 nM to 1 μM, e.g. 100 nM to 500 nM (e.g. 200 nM).

In some embodiments, for antibodies based on the 15D8-1 or 17E11-1 antibodies of the invention (e.g. those having the CDR sequences and/or VH domain and/or VL domain sequences thereof, or sequences substantially homologous thereto), no more than 15%, preferably no more than 10%, no more than 5%, no more than 4%, no more than 3%, no more than 2% or no more than 1%, preferably 0%, preferably no measurable (or no significant) inhibition of heat-induced activation of TRPV1 is observed when the antibody is used at a concentration that inhibits capsaicin-induced activation of TRPV1 by at least 25%, preferably at least 30%, at least 35%, at least 40% or at least 45%, at least 50%, at least 55%, at least 60%, at least 65%, at least 70%, or at least 75%.

In some embodiments, for antibodies based on the 15D8-1 or 17E11-1 antibodies of the invention (e.g. those having the CDR sequences and/or VH domain and/or VL domain sequences thereof, or sequences substantially homologous thereto), no more than 15%, preferably no more than 10%, no more than 5%, no more than 4%, no more than 3%, no more than 2% or no more than 1%, preferably 0%, preferably no measurable (or no significant) inhibition of heat-induced activation of TRPV1 is observed when said antibody is used at a concentration of 100 nM to 1 μM, e.g. 100 nM to 500 nM (e.g. 200 nM), and at least 25%, preferably at least 30%, at least 35%, at least 40% or at least 45%, at least 50%, at least 55%, at least 60%, at least 65%, at least 70%, or at least 75% inhibition of capsaicin-induced activation of TRPV1 is observed when said antibody is used at a concentration of 100 nM to 1 μM, e.g. 100 nM to 500 nM or 100 nM to 200 nM (e.g. 130 nM for antibodies based on 15D8-1 or e.g. 110 nM for antibodies based on 17E11-1).

In some embodiments, for antibodies based on the 41E5-1 antibody of the invention (e.g. those having the CDR sequences and/or VH domain and/or VL domain sequences thereof, or sequences substantially homologous thereto), inhibition of heat-induced activation of TRPV1 is by no more than 15%, preferably by no more than 10%, by no more than 5%, by no more than 4%, by no more than 3%, by no more than 2% or by no more than 1%, preferably 0%, preferably there is no measurable (or no significant) inhibition of heat-induced activation of TRPV1.

Thus, in some embodiments, for antibodies based on the 41B5-1 antibody of the invention (e.g. those having the CDR sequences and/or VH domain and/or VL domain sequences thereof, or sequences substantially homologous thereto) (e.g. a monoclonal antibody such as a mouse monoclonal antibody), the inhibition of heat-induced activation of TRPV1 is 0%-15%, preferably 0%-10%, 0%-5%, 0%-4%, 0%-3%, 0%-2%, 0%-1% or preferably 0%.

In some embodiments, the above-mentioned % inhibitions of heat-induced activation of TRPV1 for antibodies based on the 41B5-1 antibody of the invention (e.g. those having the CDR sequences and/or VH domain and/or VL domain sequences thereof, or sequences substantially homologous thereto) are as determined when said antibody is used at a concentration of 100 nM to 1 μM, e.g. 100 nM to 500 nM (e.g. 300 nM).

In some embodiments, for antibodies based on the 46B7-1 antibody of the invention (e.g. those having the CDR sequences and/or VH domain and/or VL domain sequences thereof, or sequences substantially homologous thereto), inhibition of heat-induced activation of TRPV1 is by no more than 25% or no more than 20%.

Thus, in some embodiments, for antibodies based on the 46B7-1 antibody of the invention (e.g. those having the CDR sequences and/or VH domain and/or VL domain sequences thereof, or sequences substantially homologous thereto) (e.g. a monoclonal antibody such as a mouse monoclonal antibody), the inhibition of heat-induced activation of TRPV1 is 0%-25%, 0%-20% or 0%-15%.

In some embodiments, the above-mentioned % inhibitions of heat-induced activation of TRPV1 for antibodies based on the 46B7-1 antibody of the invention (e.g. those having the CDR sequences and/or VH domain and/or VL domain sequences thereof, or sequences substantially homologous thereto) are as determined when said antibody is used at a concentration of 100 nM to 1 μM, e.g. 100 nM to 500 nM (e.g. 367 nM).

In some embodiments, the above-mentioned inhibitions (e.g. % inhibitions) of capsaicin-induced activation of TRPV1 are as determined in a patch-clamp method, e.g. as described elsewhere herein.

In some embodiments, the above-mentioned inhibitions (e.g. % inhibitions) of heat-induced activation of TRPV1 are as determined as described elsewhere herein.

In some embodiments, antibodies based on the 41B5-1, 15D8-1, 46B7-1, 16F1-1 17E11-1 or 17E9-1 antibodies of the invention (e.g. those having the CDR sequences and/or VH domain and/or VL domain sequences thereof, or sequences substantially homologous thereto) (e.g. a monoclonal antibody such as a mouse monoclonal antibody) may have an IC50 with respect to inhibition of capsaicin-induced activation of TRPV1 of ≤1 μM, preferably ≤750 nM, or ≤500 nM. In some such embodiments, the IC50 value may be in the range of 10 nM to 1 μM, for example 50 nM to 1 μM, or 100 nM to 1 μM, or 200 nM to 1 μM, or 10 nM to 750 nM, or 50 nM to 750 nM or 100 nM to 750 nM, or 200 nM to 750 nM, or 10 nM to 500 nM, or 50 nM to 500 nM or 100 nM to 500 nM, or 200 nM to 500 nM. In some such embodiments, the IC50 value may be up to 1 μM, for example up to 750 nM, or up to or up to 500 nM. IC50 values may be established (or calculated) based on the results of any suitable assay or test, for example a FLIPR method, e.g. as described herein. A particularly preferred FLIPR method is described in the Example section herein.

In some embodiments, for antibodies based on the 41B5-1, 15D8-1, 46B7-1 or 17E11-1 antibodies of the invention (e.g. those having the CDR sequences and/or VH domain and/or VL domain sequences thereof, or sequences substantially homologous thereto), no more than 25%, no more than 20%, no more than 15%, no more than 10%, no more than 5%, no more than 4%, no more than 3%, no more than 2% or no more than 1%, preferably 0%, preferably no measurable (or no significant) inhibition of heat-induced activation of TRPV1 is observed when the antibody is used at a concentration that inhibits capsaicin-induced activation of TRPV1 by about 50%.

In some embodiments, for antibodies based on the 41B5-1, 15D8-1 or 17E11-1 antibodies of the invention (e.g. those having the CDR sequences and/or VH domain and/or VL domain sequences thereof, or sequences substantially homologous thereto), no more than 15%, no more than 10%, no more than 5%, no more than 4%, no more than 3%, no more than 2% or no more than 1%, preferably 0%, preferably no measurable (or no significant) inhibition of heat-induced activation of TRPV1 is observed when the antibody is used at a concentration that inhibits capsaicin-induced activation of TRPV1 by about 50%.

In some embodiments, for antibodies based on the 41B5-1, 15D8-1, 46B7-1 or 17E11-1 antibodies of the invention (e.g. those having the CDR sequences and/or VH domain and/or VL domain sequences thereof, or sequences substantially homologous thereto), no more than 25%, no more than 20%, no more than 15%, no more than 10%, no more than 5%, no more than 4%, no more than 3%, no more than 2% or no more than 1%, preferably 0%, preferably no measurable (or no significant) inhibition of heat-induced activation of TRPV1 is observed when said antibody is used at a concentration of 100 nM to 1 μM, e.g. 100 nM to 500 nM (e.g. 200 nM for antibodies based on 15D8-1 or 17E11-1, or e.g. 300 nM for antibodies based on 41B5-1, or e.g. 367 nM for antibodies based on 46B7-1), and about 50% inhibition of capsaicin-induced activation of TRPV1 is observed when said antibody is used at a concentration of 100 nM to 1 μM, e.g. 100 nM to 500 nM or 100 nM to 200 nM (e.g. 170 nM for antibodies based on 41B5-1, or e.g. 70 nM for antibodies based on 15D8-1, or e.g. 200 nM for antibodies based on 46B7-1, or e.g. 230 nM for antibodies based on 17E11-1).

In some embodiments, for antibodies based on the 41B5-1, 15D8-1, 17E11-1 antibodies of the invention, no more than 15%, no more than 10%, no more than 5%, no more than 4%, no more than 3%, no more than 2% or no more than 1%, preferably 0%, preferably no measurable (or no significant) inhibition of heat-induced activation of TRPV1 is observed when said antibody is used at a concentration of 100 nM to 1 μM, e.g. 100 nM to 500 nM (e.g. 200 nM for antibodies based on 15D8-1 or 17E11-1, or e.g. 300 nM for antibodies based on 41B5-1), and about 50% inhibition of capsaicin-induced activation of TRPV1 is observed when said antibody is used at a concentration of 100 nM to 1 μM, e.g. 100 nM to 500 nM or 100 nM to 200 nM (e.g. 170 nM for antibodies based on 41B5-1, or e.g. 70 nM for antibodies based on 15D8-1, or e.g. 230 nM for antibodies based on 17E11-1).

In some embodiments, for antibodies that bind to an isolated peptide of SEQ ID NO:6 or SEQ ID NO:20 (OTV7 peptides) (or isolated peptides substantially homologous thereto) or that bind to an epitope of TRPV1 that corresponds to (or corresponds essentially to) such an isolated peptide, the inhibition of capsaicin-induced activation of TRPV1 is an inhibition of at least 5%, at least 10%, at least 15%, at least 20% or at least 25%. In some embodiments, these % inhibitions (e.g. % inhibitions) of capsaicin-induced activation of TRPV1 are as determined by a calcium imaging method, e.g. as described elsewhere herein.

In some embodiments, for antibodies that bind to an isolated peptide of SEQ ID NO:6 or SEQ ID NO:20 (or isolated peptides substantially homologous thereto) or that bind to an epitope of TRPV1 that corresponds to (or corresponds essentially to) such an isolated peptide, the inhibition of capsaicin-induced activation of TRPV1 is an inhibition of up to 5%, up to 10%, up to 15%, up to 20%, up to 25% or up to 30%. In some embodiments, these % inhibitions (e.g. % inhibitions) of capsaicin-induced activation of TRPV1 are as determined by a calcium imaging method, e.g. as described elsewhere herein.

In some embodiments, the above-mentioned % inhibitions of capsaicin-induced activation of TRPV1 for antibodies that bind to an isolated peptide of SEQ ID NO:6 or SEQ ID NO:20 (or isolated peptides substantially homologous thereto) or that bind to an epitope of TRPV1 that corresponds to (or corresponds essentially to) such an isolated peptide are as determined when said antibody (e.g. a polyclonal antibody such as a rabbit polyclonal antibody) is used at a concentration of 1 nM to 100 nM (e.g. 40 nM). In some embodiments, these % inhibitions (e.g. % inhibitions) of capsaicin-induced activation of TRPV1 are as determined by a calcium imaging method, e.g. as described elsewhere herein.

In some embodiments, for antibodies that bind to an isolated peptide of SEQ ID NO:8 or SEQ ID NO:22 (OTV9 peptides) (or isolated peptides substantially homologous thereto) or that bind to an epitope of TRPV1 that corresponds to (or corresponds essentially to) such an isolated peptide, the inhibition of capsaicin-induced activation of TRPV1 is an inhibition of at least 5%, at least 10%, at least 15%, at least 20% or at least 25%. In some embodiments, these % inhibitions (e.g. % inhibitions) of capsaicin-induced activation of TRPV1 are as determined by a calcium imaging method, e.g. as described elsewhere herein.

In some embodiments, for antibodies that bind to an isolated peptide of SEQ ID NO:8 or SEQ ID NO:22 (or isolated peptides substantially homologous thereto) or that bind to an epitope of TRPV1 that corresponds to (or corresponds essentially to) such an isolated peptide, the inhibition of capsaicin-induced activation of TRPV1 is an inhibition of up to 5%, up to 10%, up to 15%, up to 20%, up to 25% or up to 30%. In some embodiments, these % inhibitions (e.g. % inhibitions) of capsaicin-induced activation of TRPV1 are as determined by a calcium imaging method, e.g. as described elsewhere herein.

In some embodiments, the above-mentioned % inhibitions of capsaicin-induced activation of TRPV1 for antibodies that bind to an isolated peptide of SEQ ID NO:8 or SEQ ID NO:22 (or isolated peptides substantially homologous thereto) or that bind to an epitope of TRPV1 that corresponds to (or corresponds essentially to) such an isolated peptide are as determined when said antibody (e.g. a polyclonal antibody such as a rabbit polyclonal antibody) is used at a concentration of 1 nM to 100 nM (e.g. 8 nM). In some embodiments, these % inhibitions (e.g. % inhibitions) of capsaicin-induced activation of TRPV1 are as determined by a calcium imaging method, e.g. as described elsewhere herein.

In some embodiments, for antibodies that bind to an isolated peptide of SEQ ID NO:12 or SEQ ID NO:26 (OTV13 peptides) (or isolated peptides substantially homologous thereto) or that bind to an epitope of TRPV1 that corresponds to (or corresponds essentially to) such an isolated peptide, the inhibition of capsaicin-induced activation of TRPV1 is an inhibition of at least 5%, at least 10%, at least 15%, at least 20%, at least 25% or at least 30%. In some embodiments, these % inhibitions (e.g. % inhibitions) of capsaicin-induced activation of TRPV1 are as determined by a calcium imaging method, e.g. as described elsewhere herein.

In some embodiments, for antibodies that bind to an isolated peptide of SEQ ID NO:12 or SEQ ID NO:26 (or isolated peptides substantially homologous thereto) or that bind to an epitope of TRPV1 that corresponds to (or corresponds essentially to) such an isolated peptide, the inhibition of capsaicin-induced activation of TRPV1 is an inhibition of up to 5%, up to 10%, up to 15%, up to 20%, up to 25%, up to 30% or up to 35%. In some embodiments, these % inhibitions (e.g. % inhibitions) of capsaicin-induced activation of TRPV1 are as determined by a calcium imaging method, e.g. as described elsewhere herein.

In some embodiments, the above-mentioned % inhibitions of capsaicin-induced activation of TRPV1 for antibodies that bind to an isolated peptide of SEQ ID NO:12 or SEQ ID NO:26 (or isolated peptides substantially homologous thereto) or that bind to an epitope of TRPV1 that corresponds to (or corresponds essentially to) such an isolated peptide are as determined when said antibody (e.g. a polyclonal antibody such as a rabbit polyclonal antibody) is used at a concentration of 1 nM to 100 nM (e.g. 40 nM). In some embodiments, these % inhibitions (e.g. % inhibitions) of capsaicin-induced activation of TRPV1 are as determined by a calcium imaging method, e.g. as described elsewhere herein.

In some embodiments, capsaicin-induced activation of TRPV1 is the TRPV1 activation induced when capsaicin is present (or used at or contacted with TRPV1) at a concentration of 10 nM to 10 μM, for example 100 nM to 1 μM (e.g. a concentration of 100 nM or 1 μM). In some embodiments, capsaicin-induced activation of TRPV1 is the TRPV1 activation induced when capsaicin is present at 100 nM. In some embodiments, capsaicin-induced activation of TRPV1 is the TRPV1 activation induced when capsaicin is present at 300 nM.

Capsaicin-induced activation of TRPV1 and inhibition of capsaicin-induced activation of TRPV1 may be assessed by any appropriate method and the skilled person will be familiar with suitable methods.

In some embodiments, capsaicin-induced activation of TRPV1 and inhibition of capsaicin-induced activation of TRPV1 may be assessed (or be as assessed) using an electrophysiological method, such as a patch-clamp technique. Patch-clamp methods are well-known in the art and also described herein. In accordance with the present invention a reduction (or inhibition or lowering) of capsaicin-induced currents by an antibody of the invention as compared to a control antibody (e.g. a control antibody that does not bind to (or does not specifically bind to) TRPV1) is typically indicative that the antibody inhibits capsaicin-induced activation of TRPV1.

In some embodiments, the patch-clamp method comprises steps of clamping (e.g. with a pipette) a TRPV1 expressing cell (e.g. in a bath) and recording the current (or current signal). Typically, the current (or current signal) is measured (e.g. in parallel tests) in cells stimulated (or incubated) with capsaicin and in cells stimulated with capsaicin and an antibody of the invention and also preferably in cells stimulated (or incubated) with capsaicin and a control antibody (e.g. a control antibody that does not bind to (or does not specifically bind to) TRPV1). A reduction (or inhibition or lowering) of capsaicin-induced currents, e.g. as compared to a control antibody, is typically indicative that the antibody of the invention inhibits capsaicin-induced activation of TRPV1.

In some embodiments, in a patch clamp method whole cell recordings are performed using a microfluidic device for patch clamp recordings together with a patch clamp amplifier. In some embodiments, the cells are Chinese hamster ovary (CHO) cells expressing TRPV1. In some embodiments, bath and pipette solutions contain buffer F and G (as defined elsewhere herein), respectively. In some embodiments, the cells are clamped (e.g. at −60 mV) and the current signals are recorded with a sampling frequency (e.g. of 10 kHz) and low pass filtered (e.g. at 2 kHz). In some embodiments, the patch-clamp recordings are acquired using digital/analogue sampling and acquisition software. In preferred embodiments, current amplitudes are measured by exposing cells to capsaicin (e.g. 100 nM capsaicin), with and without an antibody of the invention or a control antibody. In preferred embodiments, the cells are exposed to 100 nM capsaicin in buffer F (or buffer A) for ~20 s, followed by buffer F (or buffer A) for ~60 s, antibody in buffer F (or buffer A) for ~60 s and then 100 nM capsaicin together with antibody in buffer F (or buffer A) for ~20 s. In preferred embodiments, measurements where the seal resistance shifted largely during treatment were excluded from analysis. In preferred embodiments, the recorded amplitude of the peak during stimulation with antibody+capsaicin is divided by the recorded amplitude of the peak during stimulation with capsaicin. The obtained value may be multiplied by 100 to obtain the cell response during antibody+capsaicin stimulation as a percentage of the control response (capsaicin, i.e. capsaicin only). Thus, in some embodiments, % inhibition of capsaicin induced stimulation (activation) of TRPV1 may be calculated as (1−(recorded amplitude of the peak during stimulation with antibody+capsaicin divided by the recorded amplitude of the peak during stimulation with capsaicin only)×100). Measurements are preferably performed on cells from at least two different cell culture dishes. Particularly preferred patch-clamp methods are described in the Example section herein.

In some embodiments, a patch clamp method comprises stimulating (or activating) TRPV1 expressing cells four times using capsaicin (e.g. 100 nM capsaicin or 300 nM capsaicin). In some such embodiments, hTRPV1 expressing cells are pre-treated with an antibody of the invention prior to the third activation (or stimulation) and antibody is included together with capsaicin during the third activation (or stimulation). In some such embodiments, the first, second and fourth activations (stimulations) are with capsaicin only. The amplitude of the third current peak in the presence of antibody may be compared to the mean of the amplitudes of current peaks two and four. In some embodiments, cells are treated twice with capsaicin alone to obtain peaks 1 and 2, and then are treated with antibody and then antibody together with capsaicin to obtain peak 3, followed by capsaicin alone to obtain peak 4. In some embodiments, the % inhibition may be calculated as (1−((peak 3)/((peak2+peak4)/2)))*100. In some other embodiments, cells are first treated twice with capsaicin alone to obtain peaks 1 and 2, then treated with antibody or vehicle and then antibody or vehicle together with capsaicin to obtain peak 3, followed by capsaicin alone to obtain peak 4. In some such embodiments, the % inhibition may be calculated as (1−((peak3$_{Ab}$/peak2$_{Ab}$)/(peak3$_{veh}$/peak2$_{veh}$)))*100.

In some embodiments, capsaicin-induced activation of TRPV1 and inhibition of capsaicin-induced activation of TRPV1 may be assessed (or be as assessed) using a calcium imaging method. Capsaicin induces calcium uptake.

In some embodiments, capsaicin-induced activation of TRPV1 and inhibition of capsaicin-induced activation of TRPV1 may be assessed (or be as assessed) by (i) loading TRPV1 expressing cells with a calcium indicator (e.g. as described elsewhere herein), (ii) contacting (or incubating) said cells with an antibody of the invention (or a control antibody or a vehicle only (i.e. no antibody) control), and (iii) contacting said cells (i.e. the cells that have been incubated with an antibody of the invention or control in (ii)) with (or exposing said cells to) capsaicin and calcium (Ca$^{2+}$), and (iv) assessing (or determining or measuring) the ability of an antibody of the invention to reduce (or lower or inhibit) capsaicin-induced calcium influx (or uptake) to the cells by measuring (or determining) a signal (e.g. a fluorescence signal) from the calcium indicator (e.g. as compared to a control antibody or a vehicle only control).

Preferred features of such embodiments will be evident from the discussion elsewhere herein and these may be applied mutatis mutandis to the embodiments discussed in this paragraph.

In some calcium imaging methods for assessing capsaicin-induced activation of TRPV1 and inhibition of capsaicin-induced activation of TRPV1 a calcium indicator (e.g. Fluo-3 AM) is used. In some such methods cells (e.g. CHO cells) expressing hTRPV1 are incubated with a calcium indicator to "load" the cells with the calcium indicator (e.g. Fluo-3 AM e.g. 4.4 µM thereof) for e.g. 30 min at e.g. 37° C. and preferably then washed (the calcium indicator remains inside the cells after washing) and then incubated with an antibody of the invention or with a control antibody (e.g. dissolved in PBS) or with no additional agent for e.g. 1 h, at e.g. room temperature. The control antibody is typically an antibody that does not bind to (or does not specifically bind to) TRPV1. Typically, the cells are then contacted with capsaicin (e.g. 1 µM) and Ca$^{2+}$ (e.g. 150 µM) (e.g. the capsaicin and calcium is added to the antibody solution covering the cells) and the calcium content within the cells is monitored (or measured) by measuring the fluorescence intensity (of the calcium indicator), e.g. with a plate reader. Typically, the fluorescence intensity observed after (or during) incubation with capsaicin and calcium where the cells were prior incubated with an antibody of the invention is normalised with respect to the fluorescence intensity observed after (or during) incubation with capsaicin and calcium (Ca$^{2+}$) where the cells were not prior incubated with an antibody of the invention or with any additional agent. If the fluorescence intensity is reduced (or inhibited or lowered) by the incubation with an antibody of the invention prior to the incubation with capsaicin and calcium (Ca$^{2+}$) as compared to when there is no incubation with an antibody of the invention prior to the incubation with capsaicin and calcium (Ca$^{2+}$) (e.g. as compared to when there is an incubation with a control antibody prior to the incubation with capsaicin and calcium (Ca$^{2+}$)), then that is typically indicative that the antibody of the invention inhibits capsaicin-induced activation of TRPV1. A particularly preferred calcium imaging method is described in the Example section herein.

In some embodiments, capsaicin-induced activation of TRPV1 and inhibition of capsaicin-induced activation of TRPV1 may be assessed (or be as assessed) using a Fluorescence Imaging Plate Reader (FLIPR) method.

In certain preferred FLIPR methods (which reflect the FLIPR method used in Example 3 herein), TRPV1 expressing cells (e.g. TRPV1 expressing CHO cells) are cultured in black, clear bottom, microplates (e.g. 96-well microplates). Cells are then loaded with a calcium indicator (e.g. Fluo-3 AM, e.g. 4 µM thereof) by incubating the cells with a calcium indicator (e.g. 4 µM Fluo-3 AM) in a buffer, e.g. HEPES buffer (140 nM NaCl, 5 mM KCl, 1 mM CaCl$_2$, 1 mM MgCl$_2$, 10 mM HEPES, 10 mM D-glucose, pH 7.4) for e.g. 30 minutes at e.g. room temperature. The cells are then washed with a buffer (e.g. HEPES) to remove extracellular calcium indicator (e.g. Fluo-3 AM) (the calcium indicator remains inside the cells after washing). Subsequently, an antibody of the invention that is diluted into a buffer (e.g. a calcium containing buffer such as HEPES) is added to wells, for example 100 μl of the antibody containing buffer is added to the cells in each well (typically serial dilutions of the antibody diluted into buffer (e.g. a calcium containing buffer, such as HEPES) are added to wells, i.e. different concentrations of antibody in different wells). Cells are incubated in the presence of antibody (e.g. for 4 minutes at e.g. room temperature). Fluorescence measurements are typically made by a microplate reader e.g. with excitation at 483 nm (bandwidth 14 nm) and emission at 530 (bandwidth 30 nm). Baseline fluorescence intensity is first measured, then (i.e. subsequently) a fixed amount of capsaicin in a calcium containing buffer (e.g. in 100 μl of buffer) such as HEPES is added to each well (to give a concentration of capsaicin that had been previously established as representing the EC50 value of capsaicin for the batch of cells under study, typically such a concentration is in the sub-micromolar range, for example such a concentration may be in the lower nM range, e.g. 10 nM) and a second fluorescence intensity measurement is performed after a set time (typically within minutes, e.g. 1 to 5 or 1 to 10 or 1 to 20 minutes). The fluorescence intensity (of the calcium indicator) provides a report (or read-out) of the amount of calcium within the cells (and thus on the capsaicin-induced activation of TRPV1). This FLIPR assay relies on there being calcium ($Ca^{2+}$) present in the buffer when capsaicin is added (i.e. relies on calcium being present in the buffer when the cells are exposed to capsaicin) and any suitable calcium containing buffer may be used (the skilled person will be familiar with suitable buffers), for example the above-mentioned HEPES buffer provides sufficient calcium). The antibody of the invention may be in PBS (phosphate buffered saline) prior to dilution (i.e. prior to being diluted) into a buffer (e.g. a calcium containing buffer such as HEPES) for adding to the cells (wells). EC50 is the concentration of a substance that gives half-maximal response of a biological process, in this case TRPV1-mediated $Ca^{2+}$ entry (or TRPV1-mediated $Ca^{2+}$ uptake) into cells. Data may be presented (or obtained or determined) as the Fluorescence rate, which is calculated as fluorescence at a set (or certain) time after addition of capsaicin minus the (baseline) fluorescence measured before capsaicin addition. If a reduction in the fluorescence rate is observed (or measured or determined) as the concentration of the antibody (i.e. of a given antibody being tested) is increased (e.g. at higher (or increased) concentrations in an antibody dilution series), then that is typically indicative that the antibody of the invention inhibits capsaicin-induced activation of TRPV1. The IC50 values for the tested antibodies may be calculated (and the skilled person can readily do this). The IC50 value is the half maximal inhibitory concentration of a substance for a biological process under study, in this case capsaicin induced cellular TRPV1-mediated $Ca^{2+}$ influx (or uptake or entry). A particularly preferred FLIPR method is described in the Example section herein.

As indicated above, certain methods comprise the use of a calcium indicator (e.g. Fluo3-AM). The skilled person is familiar with such indicators. Calcium indicators may be conveniently used to visualise whether or not (or the extent to which) the intracellular concentration (or amount) of calcium ions ($Ca^{2+}$) is increased during (or after) exposure to a particular stimulus (e.g. capsaicin or heat). Such calcium indicators can be loaded into cells (prior to the exposure to a stimulus) and their fluorescence increases upon binding to $Ca^{2+}$ ions (i.e. upon influx of $Ca^{2+}$ ions into the cell, e.g. from a $Ca^{2+}$ ion containing medium or buffer).

Heat-induced activation of TRPV1 is typically the TRPV1 activation induced at (or as determined at) ≥42° C. Thus, in some embodiments, heat-induced activation of TRPV1 is the TRPV1 activation induced at 42° C.-45° C., 42° C.-50° C., 42° C.-60° C., 42° C.-70° C., 42° C.-80° C., 42° C.-90° C. or 42° C.-100° C. In a preferred embodiment, heat-induced activation of TRPV1 is the TRPV1 activation induced at (or as determined at) 42° C.-45° C. In a preferred embodiment, heat-induced activation of TRPV1 is the TRPV1 activation induced at (or as determined at) 42° C. In another preferred embodiment, heat-induced activation of TRPV1 is the TRPV1 activation induced at (or as determined at) 45° C.

Heat-induced activation of TRPV1 (and inhibition of heat-induced activation of TRPV1) may be assessed by any appropriate method and the skilled person will be familiar with suitable methods. Heat (e.g. ≥42° C., preferably 42° C.) induces the opening of the TRPV1 ion channel and leads to an influx of calcium ions ($Ca^{2+}$) into TRPV1 expressing cells. Thus, heat-induced activation of TRPV1 (and inhibition of heat-induced activation of TRPV1) may be assessed by determining whether or not (or the extent to which) the intracellular concentration (or amount) of calcium ions ($Ca^{2+}$) is increased during (or after) heating. A calcium indicator (e.g. Fluo-3 or Fluo3-AM) may be conveniently used to visualise whether or not (or the extent to which) the intracellular concentration (or amount) of calcium ions ($Ca^{2+}$) is increased during (or after) heating. Such calcium indicators can be loaded into cells (prior to the exposure to heat) and their fluorescence increases upon binding to $Ca^{2+}$ ions (i.e. upon influx of $Ca^{2+}$ ions into the cell, e.g. from a $Ca^{2+}$ ion containing medium). This can be visualised by any convenient means e.g. by confocal microscopy.

Whether or not (or the extent to which) a TRPV1 binding antibody is capable of inhibiting heat-induced activation of TRPV1 may be assessed by contacting the TRPV1 expressing cells with said antibody (e.g. by delivering the antibody to the cells using a microfluidic device, e.g. a Biopen as described in the Example section herein) and determining whether or not (or the extent to which) heat-induced activation of TRPV1 is inhibited (or reduced) as compared to the heat-induced activation of TRPV1 in the absence of the antibody (e.g. as compared to the heat-induced activation of TRPV1 observed in the presence of a control antibody that does not bind to (or that does not specifically bind to) TRPV1). The heat (e.g. 42° C.) may be provided using any suitable means, e.g. a laser heating system, e.g. as described in the Example section herein. A reduction (e.g. a significant reduction) in heat-induced activation of TRPV1 in the presence of an anti-TRPV1 antibody indicates that the antibody inhibits heat-induced activation of TRPV1. The absence of a reduction (or no significant reduction) in heat-induced activation of TRPV1 in the presence of an anti-TRPV1 antibody indicates that the antibody does not (or does not significantly) inhibit heat-induced activation of TRPV1. A particularly preferred method of assessing heat-induced activation of TRPV1 (and inhibition of heat-induced activation of TRPV1) is described in the Example section herein.

In some embodiments, heat-induced activation of TRPV1 (and inhibition thereof) may be assessed (or be as assessed) using a method in which TRPV1 expressing cells receive two pulses of heat. In some such embodiments, the cells are first pulsed with heat, followed by a cool-down, followed by administration of (or contacting with) antibody and a heat pulse in combination, followed by a cool-down. The effect of an antibody on heat-induced activation of TRPV1 may be assessed by determining the effect of the antibody on heat-induced influx of calcium ions into the cells. The influx of calcium into the cells (peak amplitude) may be measured using a calcium indicator (e.g. Fluo-3). The ratio of the second (second heat pulse or peak 2) to first (first heat pulse or peak 1) peak amplitude may be calculated for both antibody and vehicle. In some embodiments, the percent of inhibition may be calculated by comparing the ratio for the antibody to the ratio for the vehicle. Thus, in some embodiments, % inhibition may be $(1-((Peak2_{Ab}/Peak1_{Ab})/(peak2_{veh}/peak1_{veh})))*100$.

In some embodiments, antibodies of the present invention may inhibit (or be capable of inhibiting) NADA-induced activation of TRPV1. NADA (N-arachidonoyl dopamine) is a potent natural TRPV1 agonist.

In some embodiments, inhibition of NADA-induced activation of TRPV1 by an antibody of the invention is any measurable or significant inhibition (e.g. as compared to a control with no antibody or as compared to a control with an antibody that does not bind to TRPV1). In some embodiments, the amounts (or levels) of inhibition of NADA-induced activation of TRPV1 (e.g. % inhibitions) are as described elsewhere herein in relation to the inhibition of capsaicin-induced activation of TRPV1.

In some embodiments, NADA-induced activation of TRPV1 is the TRPV1 activation induced when NADA is present (or used at or contacted with TRPV1) at a concentration of 10 nM to 10 µM, for example 100 nM to 1 µM (e.g. a concentration of 100 nM or 1 µM). In some embodiments, NADA-induced activation of TRPV1 is the TRPV1 activation induced when NADA is present at 1 µM.

In some embodiments, the NADA-induced activation of TRPV1 (or inhibition thereof) is as determined in a patch-clamp method, e.g. as described elsewhere herein, with NADA being used instead of capsaicin.

In some embodiments, for antibodies based on the OT-Ab3, OT-Ab2 and OT-Ab1 antibodies (preferably OT-Ab1) of the invention (e.g. those having the CDR sequences and/or VH domain and/or VL domain sequences thereof, or sequences substantially homologous thereto), the inhibition of NADA-induced activation of TRPV1 is at least 10%, at least 15%, at least 20%, at least 25%, at least 30%, at least 35%, at least 40% or at least 45%, at least 50%, at least 55%, at least 60%, at least 65%, at least 70%, at least 75% or at least 80%.

In some embodiments, for antibodies based on the OT-Ab3, OT-Ab2 and OT-Ab1 antibodies (preferably OT-Ab1) of the invention (e.g. those having the CDR sequences and/or VH domain and/or VL domain sequences thereof, or sequences substantially homologous thereto), the inhibition of NADA-induced activation of TRPV1 is an inhibition of up to 30%, up to 35%, up to 40%, up to 45%, up to 50%, up to 55%, up to 60%, up to 65%, up to 70%, up to 75%, up to 80% or up to 90%.

In some embodiments, the above-mentioned % inhibitions of NADA-induced activation of TRPV1 for antibodies based on the OT-Ab3, OT-Ab2 and OT-Ab1 antibodies (preferably OT-Ab1) of the invention (e.g. those having the CDR sequences and/or VH domain and/or VL domain sequences thereof, or sequences substantially homologous thereto) are as determined when said antibody (e.g. a monoclonal antibody such as a mouse monoclonal antibody) is used at a concentration of 100 nM to 1 µM, e.g. 100 nM to 500 nM (e.g. 243 nM for antibodies based on OT-Ab1).

Alternatively viewed, the present invention provides an antibody, for example an isolated antibody, which binds to (or specifically recognises or specifically binds to) TRPV1, wherein said antibody is capable of inhibiting capsaicin-induced activation of TRPV1 to a greater extent than heat-induced activation of TRPV1. Discussion of various features of the antibodies of other aspects of the invention and preferred embodiments apply mutatis mutandis to this aspect of the invention.

Alternatively viewed, the present invention provides an antibody, for example an isolated antibody, which binds to (or specifically recognises or specifically binds) TRPV1, wherein said antibody selectively inhibits capsaicin-induced activation of TRPV1 as opposed to heat-induced activation of TRPV1. Discussion of various features of the antibodies of other aspects of the invention and preferred embodiments apply mutatis mutandis to this aspect of the invention.

Alternatively viewed, in one aspect, the present invention provides an antibody, for example an isolated antibody, which binds to (or specifically recognises or specifically binds to) TRPV1, wherein said antibody preferentially inhibits capsaicin-induced activation of TRPV1 as compared to heat-induced activation of TRPV1. Discussion of various features of the antibodies of other aspects of the invention and preferred embodiments apply mutatis mutandis to this aspect of the invention.

Alternatively viewed, in one aspect, the present invention provides an antibody, for example an isolated antibody, which binds to (or specifically recognises or specifically binds to) TRPV1, wherein said antibody preferentially inhibits capsaicin-induced activation of TRPV1 over heat-induced activation of TRPV1. Discussion of various features of the antibodies of other aspects of the invention and preferred embodiments apply mutatis mutandis to this aspect of the invention.

Alternatively viewed, the present invention provides an antibody, for example an isolated antibody, which binds to (or specifically recognises or specifically binds to) TRPV1, wherein said antibody inhibits capsaicin-induced activation of TRPV1 without significantly inhibiting heat-induced activation of TRPV1. Discussion of various features of the antibodies of other aspects of the invention and preferred embodiments apply mutatis mutandis to this aspect of the invention.

In another aspect, the present invention provides an antibody, for example an isolated antibody, which binds to TRPV1 (or specifically recognises or specifically binds to), wherein said antibody does not significantly inhibit heat-induced activation of TRPV1. Discussion of various features of the antibodies of other aspects of the invention and preferred embodiments apply mutatis mutandis to this aspect of the invention.

In another aspect, the present invention provides an antibody, for example an isolated antibody (e.g. a monoclonal antibody), which binds to (or specifically recognises or specifically binds) TRPV1, wherein said antibody inhibits capsaicin-induced activation of TRPV1. Discussion of various features of the antibodies of other aspects of the invention and preferred embodiments may be applied mutatis mutandis to this aspect of the invention.

In another aspect, the present invention provides an antibody, for example an isolated antibody, which binds to (or specifically recognises or specifically binds to) TRPV1, wherein said antibody binds to an isolated epitope or conjugate of the invention. Discussion of various features of the antibodies of other aspects of the invention and preferred embodiments apply mutatis mutandis to this aspect of the invention.

In another aspect, the present invention provides an antibody, for example an isolated antibody, which binds to (or specifically recognises or specifically binds to) TRPV1, wherein said antibody binds to an epitope of TRPV1 that is in the region of TRPV1 defined by amino acid residues 599-630, amino acid residues 599-606, amino acid residues 599-614, amino acid residues 599-622, amino acid residues 607-630, amino acid residues 615-630, amino acid residues 623-630, amino acid residues 631-643, amino acid residues 644-656, or amino acid residues 610-620 of TRPV1 (SEQ ID NO:1), or bind to TRPV1 at an epitope in the region defined by amino acid residues 599-601 and residues 653-655 of TRPV1 (SEQ ID NO:1). In another aspect, the present invention provides an antibody which binds to an epitope of TRPV1 that is in the region of TRPV1 defined by amino acid residues 599-656 of TRPV1 (SEQ ID NO:1). Discussion of various features of the antibodies of other aspects of the invention and preferred embodiments apply mutatis mutandis to these aspects of the invention.

As used throughout the entire application, the terms "a" and "an" are used in the sense that they mean "at least one", "at least a first", "one or more" or "a plurality" of the referenced components or steps, except in instances wherein an upper limit is thereafter specifically stated. Therefore, an "antibody", as used herein, means "at least a first antibody". The operable limits and parameters of combinations, as with the amounts of any single agent, will be known to those of ordinary skill in the art in light of the present disclosure.

In addition, where the terms "comprise", "comprises", "has" or "having", or other equivalent terms are used herein, then in some more specific embodiments these terms include the term "consists of" or "consists essentially of", or other equivalent terms.

Nucleic acid molecules comprising nucleotide sequences that encode the antibodies of the present invention as defined herein or parts or fragments thereof, or nucleic acid molecules substantially homologous thereto, form yet further aspects of the invention.

Preferred nucleic acid molecules are those encoding a VH region of an antibody of the present invention (e.g., those encoding SEQ ID NOs:39 or 57 or 75, such as SEQ ID NOs:15 or 55 or 73, respectively). Other preferred nucleic acid molecules are those encoding a VL region of an antibody of the present invention (e.g., those encoding SEQ ID NOs:40 or 58 or 76, such as SEQ ID NOs:29 or 56 or 74, respectively).

Thus, preferred nucleic acid molecules comprise sequences which encode a heavy chain variable region (VH) that has the amino acid sequence of SEQ ID NO: 39 or 57 or 75 (which is preferably encoded by SEQ ID NO: 15 or 55 or 73) and/or comprise sequences which encode a light chain variable region (VL) which has the amino acid sequence of SEQ ID NO: 40 or 58 or 76 (which is preferably encoded by SEQ ID NO: 29 or 56 or 74).

Also preferred are nucleic acids which encode the following combinations: SEQ ID NOs: 39 and 40; or SEQ ID NOs: 57 and 58; or SEQ ID NOs 75 and 76. Also preferred are nucleic acid molecules which comprise the following combinations: SEQ ID NOs: 15 and 29; or SEQ ID NOs: 55 and 56; or SEQ ID NOs: 73 and 74.

Other preferred nucleic acid molecules are those encoding a VH region of an antibody of the present invention (e.g., those encoding SEQ ID NOs:101 or 121 or 141 or 161 or 181 or 201 or 221 or 241 or 261 or 281 or 301 or 321 or 341 or 361 or 381 or 401 or 421, such as SEQ ID NOs:99 or 119 or 139 or 159 or 179 or 199 or 219 or 239 or 259 or 279 or 299 or 319 or 339 or 359 or 379 or 399 or 419, respectively). Other preferred nucleic acid molecules are those encoding a VL region of an antibody of the present invention (e.g., those encoding SEQ ID NOs:102 or 122 or 142 or 162 or 182 or 202 or 222 or 242 or 262 or 282 or 302 or 322 or 342 or 362 or 382 or 402 or 422, such as SEQ ID NOs:100 or 120 or 140 or 160 or 180 or 200 or 220 or 240 or 260 or 280 or 300 or 320 or 340 or 360 or 380 or 400 or 420, respectively).

Thus, certain preferred nucleic acid molecules comprise sequences which encode a heavy chain variable region (VH) that has the amino acid sequence of SEQ ID NO: 101 or 121 or 141 or 161 or 181 or 201 or 221 or 241 or 261 or 281 or 301 or 321 or 341 or 361 or 381 or 401 or 421 (which are preferably encoded by SEQ ID NO: 99 or 119 or 139 or 159 or 179 or 199 or 219 or 239 or 259 or 279 or 299 or 319 or 339 or 359 or 379 or 399 or 419) and/or comprise sequences which encode a light chain variable region (VL) which has the amino acid sequence of SEQ ID NO: 102 or 122 or 142 or 162 or 182 or 202 or 222 or 242 or 262 or 282 or 302 or 322 or 342 or 362 or 382 or 402 or 422 (which are preferably encoded by SEQ ID NO: 100 or 120 or 140 or 160 or 180 or 200 or 220 or 240 or 260 or 280 or 300 or 320 or 340 or 360 or 380 or 400 or 420).

Also preferred are nucleic acids which encode the following combinations: SEQ ID NOs: 101 and 102; or SEQ ID NOs: 121 and 122; or SEQ ID NOs 141 and 142; or SEQ ID NOs 161 and 162; or SEQ ID NOs 181 and 182; or SEQ ID NOs 201 and 202; or SEQ ID NOs 221 and 222; or SEQ ID NOs 241 and 242; or SEQ ID NOs 261 and 262; or SEQ ID NOs 281 and 282; or SEQ ID NOs 301 and 302; or SEQ ID NOs 321 and 322; or SEQ ID NOs 341 and 342; or SEQ ID NOs 361 and 362; or SEQ ID NOs 381 and 382; or SEQ ID NOs 401 and 402; or SEQ ID NOs 421 and 422;

Also preferred are nucleic acid molecules which comprise the following combinations: SEQ ID NOs: 99 and 100; or SEQ ID NOs: 119 and 120; or SEQ ID NOs 139 and 140; or SEQ ID NOs 159 and 160; or SEQ ID NOs 179 and 180; or SEQ ID NOs 199 and 200; or SEQ ID NOs 219 and 220; or SEQ ID NOs 239 and 240; or SEQ ID NOs 259 and 260; or SEQ ID NOs 279 and 280; or SEQ ID NOs 299 and 300; or SEQ ID NOs 319 and 320; or SEQ ID NOs 339 and 340; or SEQ ID NOs 359 and 360; or SEQ ID NOs 379 and 380; or SEQ ID NOs 399 and 400; or SEQ ID NOs 419 and 420.

Other preferred nucleic acid molecules comprise sequences that encode IgG forms of the antibodies of the invention.

In another aspect, the present invention provides a set (or plurality) of nucleic acid molecules each comprising a nucleotide sequence, wherein said set of nucleic acid molecules together (or collectively) encode an antibody in accordance with the invention. Such a set of nucleic acid molecules may be characterised in that when the set is expressed (i.e. expressed together) (e.g. in a host cell) an entire antibody of the present invention is expressed and preferably assembled.

The term "substantially homologous" as used herein in connection with an amino acid or nucleic acid sequence includes sequences having at least 65%, 70% or 75%, preferably at least 80%, and even more preferably at least 85%, 90%, 95%, 96%, 97%, 98% or 99%, sequence identity to the amino acid or nucleic acid sequence disclosed. Substantially homologous sequences of the invention thus include single or multiple base or amino acid alterations (additions, substitutions, insertions or deletions) to the sequences of the invention. At the amino acid level preferred substantially homologous sequences contain up to 5, e.g. only 1, 2, 3, 4 or 5, preferably 1, 2 or 3, more preferably 1 or 2, altered amino acids, in one or more of the framework regions and/or one or more of the CDRs making up the sequences of the invention. Said alterations can be with conservative or non-conservative amino acids. Preferably said alterations are conservative amino acid substitutions.

In certain embodiments, if a given starting sequence is relatively short (e.g. four amino acids in length), then fewer amino acid substitutions may be present in sequences substantially homologous thereto as compared with the number of amino acid substitutions that might optionally be made in a sequence substantially homologous to a longer starting sequence. For example, in certain embodiments, a sequence substantially homologous to a starting VH CDR3 sequence in accordance with the present invention, e.g. a starting VH CDR3 sequence which in some embodiments may be four amino acid residues in length, preferably has 1 or 2 (more preferably 1) altered amino acids in comparison with the starting sequence. Accordingly, in some embodiments the number of altered amino acids in substantially homologous sequences (e.g. in substantially homologous CDR sequences) can be tailored to the length of a given starting CDR sequence. For example, different numbers of altered amino acids can be present depending on the length of a given starting CDR sequence such as to achieve a particular % sequence identity in the CDRs, for example a sequence identity of at least 75%, 80%, 85%, 90%, 95%, 96%, 97%, 98% or 99%.

Routine methods in the art such as alanine scanning mutagenesis and/or analysis of crystal structure of the antigen-antibody complex can be used in order to determine which amino acid residues of the CDRs do not contribute or do not contribute significantly to antigen binding and therefore are good candidates for alteration or substitution in the embodiments of the invention involving substantially homologous sequences.

The term "substantially homologous" also includes modifications or chemical equivalents of the amino acid and nucleotide sequences of the present invention that perform substantially the same function as the proteins or nucleic acid molecules of the invention in substantially the same way. For example, any substantially homologous antibody should retain the ability to bind to TRPV1 as described above. Preferably, any substantially homologous antibody should retain one or more (or all) of the functional capabilities of the starting antibody.

Substantially homologous sequences of antibodies of the invention also include, without limitation, for example alterations that do not affect the VH, VL or CDR domains of the antibodies, e.g. antibodies where tag sequences or other components are added that do not contribute to the binding of antigen, or alterations to convert one type or format of antibody molecule or fragment to another type or format of antibody molecule or fragment (e.g. conversion from Fab to scFv or whole antibody or vice versa), or the conversion of an antibody molecule to a particular class or subclass of antibody molecule (e.g. the conversion of an antibody molecule to IgG or a subclass thereof, e.g. $IgG_2$ or $IgG_4$).

Preferably, any substantially homologous antibody should retain the ability to specifically bind to the same (or substantially the same) epitope of TRPV1 as recognized by the antibody in question, for example, the same epitope recognized by the CDR domains of the invention or the VH and VL domains of the invention as described herein. Thus, preferably, any substantially homologous antibody should retain the ability to compete with one or more of the various antibodies of the invention (e.g. one or more of the described polyclonal antibodies or one or more of the described monoclonal antibodies OT-Ab3, OT-Ab2, OT-Ab1, 32C8-1, 33C9-1, 34C11-1, 40B10-1, 41B5-1, 43D6-1, 44E8-1, 46B7-1, 46D9-1, 12C9-1, 12G6-1, 15D8-1, 16F1-1, 17E11-1, 17E9-1, 18E10-1 or R4P1-C1) for binding to TRPV1. Binding to the same epitope/antigen can be readily tested by methods well known and described in the art, e.g. using binding assays, e.g. a competition assay. Retention of other functional properties can also readily be tested by methods well known and described in the art or herein.

Thus, a person skilled in the art will appreciate that binding assays can be used to test whether "substantially homologous" antibodies have the same binding specificities as the antibodies and antibody fragments of the invention, for example, binding assays such as competition assays or ELISA assays as described elsewhere herein. BIAcore assays could also readily be used to establish whether "substantially homologous" antibodies can bind to TRPV1. The skilled person will be aware of other suitable methods and variations.

As outlined below, a competition binding assay can be used to test whether "substantially homologous" antibodies retain the ability to specifically bind to substantially the same epitope (or the same epitope) of TRPV1 as recognized by the antibodies of the invention (e.g. antibodies OT-Ab3, OT-Ab2, OT-Ab1, 32C8-1, 33C9-1, 34C11-1, 40B10-1, 41B5-1, 43D6-1, 44E8-1, 46B7-1, 46D9-1, 12C9-1, 12G6-1, 15D8-1, 16F1-1, 17E11-1, 17E9-1, 18E10-1, or R4P1-C1, or antibodies based on these antibodies), or have the ability to compete with one or more of the various antibodies of the invention (e.g. antibodies OT-Ab3, OT-Ab2, OT-Ab1, 32C8-1, 33C9-1, 34C11-1, 40B10-1, 41B5-1, 43D6-1, 44E8-1, 46B7-1, 46D9-1, 12C9-1, 12G6-1, 15D8-1, 16F1-1, 17E11-1, 17E9-1, 18E10-1, or R4P1-C1, or antibodies based on these antibodies). The method described below is only one example of a suitable competition assay. The skilled person will be aware of other suitable methods and variations.

An exemplary competition assay involves assessing the binding of various effective concentrations of an antibody of the invention to TRPV1 in the presence of varying concentrations of a test antibody (e.g. a substantially homologous antibody). The amount of inhibition of binding induced by the test antibody can then be assessed. A test antibody that shows increased competition with an antibody of the invention at increasing concentrations (i.e. increasing concentrations of the test antibody result in a corresponding reduction in the amount of antibody of the invention binding to TRPV1) is evidence of binding to substantially the same epitope. Preferably, the test antibody significantly reduces the amount of antibody of the invention that binds to TRPV1. Preferably, the test antibody reduces the amount of antibody of the invention that binds to TRPV1 by at least about 60%, 65%, 70%, 75%, 80%, 85%, 90% or 95%. ELISA and flow cytometry assays may be used for assessing inhibition of binding in such a competition assay but other suitable techniques would be well known to a person skilled in the art.

In some embodiments, "substantially homologous" antibodies which retain the ability to specifically bind to substantially the same (or the same) epitope of TRPV1 as recognized by the antibodies of the invention (e.g. antibodies OT-Ab3, OT-Ab2, OT-Ab1, 32C8-1, 33C9-1, 34C11-1, 40B10-1, 41B5-1, 43D6-1, 44E8-1, 46B7-1, 46D9-1, 12C9-1, 12G6-1, 15D8-1, 16F1-1, 17E11-1, 17E9-1, 18E10-1 or R4P1-C1, or antibodies based on these antibodies) or which have the ability to compete with one or more of the various antibodies of the invention (e.g. antibodies OT-Ab3, OT-Ab2 or OT-Ab1, 32C8-1, 33C9-1, 34C11-1, 40B10-1, 41B5-1, 43D6-1, 44E8-1, 46B7-1, 46D9-1, 12C9-1, 12G6-1, 15D8-1, 16F1-1, 17E11-1, 17E9-1, 18E10-1 or R4P1-C1, or antibodies based on these antibodies) are preferred.

The term "competing antibodies", as used herein, refers to antibodies that bind to about, substantially or essentially the same, or even the same, epitope as a "reference antibody". "Competing antibodies" include antibodies with overlapping epitope specificities. Competing antibodies are thus able to effectively compete with a reference antibody for binding to TRPV1. Preferably, the competing antibody can bind to the same epitope as the reference antibody. Alternatively viewed, the competing antibody preferably has the same epitope specificity as the reference antibody.

"Reference antibodies" as used herein include antibodies (e.g. the polyclonal rabbit antibodies described herein) that bind to an isolated peptide of the invention or to an epitope of TRPV1 in accordance with the invention. "Reference antibodies" also include antibodies which can bind to TRPV1 in accordance with the invention which preferably have a VH and a VL domain as defined herein, more preferably a VH domain of SEQ ID NO: 39 and a VL domain of SEQ ID NO: 40, or a VH domain of SEQ ID NO: 57 and a VL domain of SEQ ID NO: 58, a VH domain of SEQ ID NO: 75 and a VL domain of SEQ ID NO: 76, a VH domain of SEQ ID NO: 101 and a VL domain of SEQ ID NO: 102, a VH domain of SEQ ID NO: 121 and a VL domain of SEQ ID NO: 122, a VH domain of SEQ ID NO: 141 and a VL domain of SEQ ID NO: 142, a VH domain of SEQ ID NO: 161 and a VL domain of SEQ ID NO: 162, a VH domain of SEQ ID NO: 181 and a VL domain of SEQ ID NO: 182, a VH domain of SEQ ID NO: 201 and a VL domain of SEQ ID NO: 202, a VH domain of SEQ ID NO: 221 and a VL domain of SEQ ID NO: 222, a VH domain of SEQ ID NO: 241 and a VL domain of SEQ ID NO: 242, a VH domain of SEQ ID NO: 261 and a VL domain of SEQ ID NO: 262, a VH domain of SEQ ID NO: 281 and a VL domain of SEQ ID NO: 282, a VH domain of SEQ ID NO: 301 and a VL domain of SEQ ID NO: 302, a VH domain of SEQ ID NO: 321 and a VL domain of SEQ ID NO: 322, a VH domain of SEQ ID NO: 341 and a VL domain of SEQ ID NO: 342, a VH domain of SEQ ID NO: 361 and a VL domain of SEQ ID NO: 362, a VH domain of SEQ ID NO: 381 and a VL domain of SEQ ID NO: 382, a VH domain of SEQ ID NO: 401 and a VL domain of SEQ ID NO: 402, or a VH domain of SEQ ID NO: 421 and a VL domain of SEQ ID NO: 422. Certain preferred reference antibodies are selected from antibodies OT-Ab3, OT-Ab2, OT-Ab1, 32C8-1, 33C9-1, 34C11-1, 40B10-1, 41B5-1, 43D6-1, 44E8-1, 46B7-1, 46D9-1, 12C9-1, 12G6-1, 15D8-1, 16F1-1, 17E11-1, 17E9-1, 18E10-1 or R4P1-C1, or antibodies based on these antibodies.

As the identification of competing antibodies is determined in comparison to a reference antibody, it will be understood that actually determining the epitope to which either or both antibodies bind is not in any way required in order to identify a competing antibody. However, epitope mapping can be performed using standard techniques, if desired.

In the following descriptions of the compositions, immunoconjugates, pharmaceuticals, combinations, cocktails, kits, first and second medical uses and all methods in accordance with this invention, the terms "antibody" and "immunoconjugate", or an antigen-binding region or fragment thereof, unless otherwise specifically stated or made clear from the scientific terminology, refer to a range of anti-TRPV1 antibodies as well as to the specific antibodies described in the Example section herein.

The terms "antibody" and "immunoglobulin", as used herein, refer broadly to any immunological binding agent that comprises an antigen binding domain, including polyclonal and monoclonal antibodies.

In some embodiments, the antibodies are polyclonal antibodies, e.g. polyclonal antibodies that are generated in (or raised in or isolated from) an animal (e.g. a rabbit such as a specific pathogen free (SPF) rabbit) immunized with an isolated peptide or conjugate (preferably a conjugate) of the present invention. Preferred isolated peptides and conjugates are described elsewhere herein.

In some embodiments, monoclonal antibodies are preferred (e.g. mouse monoclonal or human monoclonal antibodies or humanized monoclonal antibodies or rabbit monoclonal antibodies). Preferred monoclonal antibodies include those based on the OT-Ab3, OT-Ab2 and OT-Ab1 antibodies of the invention (e.g. those having the CDR sequences and/or VH domain and/or VL domain sequences thereof, or sequences substantially homologous thereto). Other preferred monoclonal antibodies include those based on the 32C8-1, 33C9-1, 34C11-1, 40B10-1, 41B5-1, 43D6-1, 44E8-1, 46B7-1, 46D9-1, 12C9-1, 12G6-1, 15D8-1, 16F1-1, 17E11-1, 17E9-1, 18E10-1 or R4P1-C1 antibodies of the invention (e.g. those having the CDR sequences and/or VH domain and/or VL domain sequences thereof, or sequences substantially homologous thereto). In some embodiments, monoclonal antibodies based on the OT-Ab1 antibodies of the invention are preferred.

Depending on the type of constant domain in the heavy chains, whole antibodies are assigned to one of five major classes: IgA, IgD, IgE, IgG, and IgM and the antibodies of the invention may be in any one of these classes. Several of these are further divided into subclasses or isotypes, such as IgG1, IgG2, IgG3, IgG4, and the like. The heavy-chain constant domains that correspond to the difference classes of immunoglobulins are termed $\alpha$, $\delta$, $\varepsilon$, $\gamma$ and $\mu$, respectively. The subunit structures and three-dimensional configurations of different classes of immunoglobulins are well known.

Generally, where whole antibodies rather than antigen binding regions are used in the invention, IgG (e.g. $IgG_1$, IgG2 or $IgG_4$) and/or IgM are preferred because they are the most common antibodies in the physiological situation and because they are most easily made in a laboratory setting.

The "light chains" of mammalian antibodies are assigned to one of two clearly distinct types: kappa ($\kappa$) and lambda ($\lambda$), based on the amino acid sequences of their constant domains and some amino acids in the framework regions of their variable domains.

As will be understood by those in the art, the immunological binding reagents encompassed by the term "antibody" includes or extends to all antibodies and antigen binding fragments thereof, including whole antibodies, dimeric, trimeric and multimeric antibodies; bispecific antibodies; chimeric antibodies; recombinant and engineered antibodies, and fragments thereof.

The term "antibody" is thus used to refer to any antibody-like molecule that has an antigen binding region, and this term includes antibody fragments that comprise an antigen binding domain such as Fab', Fab, F(ab')$_2$, single domain antibodies (DABs), TandAbs dimer, Fv, scFv (single chain Fv), dsFv, ds-scFv, Fd, linear antibodies, minibodies, diabodies, bispecific antibody fragments, bibody, tribody (scFv-Fab fusions, bispecific or trispecific, respectively); sc-diabody; kappa(lamda) bodies (scFv-CL fusions); BiTE (Bispecific T-cell Engager, scFv-scFv tandems to attract T cells); DVD-Ig (dual variable domain antibody, bispecific format); SIP (small immunoprotein, a kind of minibody); SMIP ("small modular immunopharmaceutical" scFv-Fc dimer; DART (ds-stabilized diabody "Dual Affinity ReTargeting"); small antibody mimetics comprising one or more CDRs and the like.

The techniques for preparing and using various antibody-based constructs and fragments are well known in the art. Diabodies, in particular, are further described in EP 404 097 and WO 93/11161; whereas linear antibodies are further described in the art.

In some embodiments, the antibodies of the invention are non-human antibodies (e.g. rabbit or rat or mouse antibodies). In some embodiments, the antibodies of the invention are rabbit antibodies. In some embodiments, the antibodies of the invention are mouse antibodies (e.g. mouse monoclonal antibodies).

In some embodiments, the antibodies of the invention are human antibodies, more preferably fully human antibodies. In this regard, human antibodies generally have at least two potential advantages for use in human therapy. First, the human immune system should not recognize the antibody as foreign. Second, the half-life in the human circulation will be similar to naturally occurring human antibodies, allowing smaller and less frequent doses to be given.

The term "human" as used herein in connection with antibody molecules and binding proteins first refers to antibodies and binding proteins having variable regions (e.g., $V_H$, $V_L$, CDR or FR regions) and, optionally, constant antibody regions, isolated or derived from a human repertoire or derived from or corresponding to sequences found in humans or a human repertoire, e.g., in the human germline or somatic cells.

"Human" antibodies and binding proteins further include amino acid residues not encoded by human sequences, e.g., mutations introduced by random or site directed mutations in vitro, for example mutations introduced by in vitro cloning or PCR. Particular examples of such mutations are mutations that involve conservative substitutions or other mutations in a small number of residues of the antibody or binding protein, e.g., in up to 5, 4, 3, 2 or 1 of the residues of the antibody or binding protein, preferably e.g., in up to 5, 4, 3, 2 or 1 of the residues making up one or more of the CDRs of the antibody or binding protein. Certain examples of such "human" antibodies include antibodies and variable regions that have been subjected to standard modification techniques to reduce the amount of potentially immunogenic sites.

Thus, "human" antibodies include sequences derived from and related to sequences found in humans, but which may not naturally exist within the human antibody germline repertoire in vivo. In addition, human antibodies and binding proteins include proteins comprising human consensus sequences identified from human sequences, or sequences substantially homologous to human sequences.

In addition, human antibodies and binding proteins are not limited to combinations of $V_H$, $V_L$, CDR or FR regions that are themselves found in combination in human antibody molecules. Thus, human antibodies and binding proteins can include or correspond to combinations of such regions that do not necessarily exist naturally in humans (e.g. are not naturally occurring antibodies).

In some embodiments, human antibodies will be fully human antibodies. "Fully human" antibodies, as used herein, are antibodies comprising "human" variable region domains and/or CDRs, without substantial non-human antibody sequences or without any non-human antibody sequences.

For example, antibodies comprising human variable region domains and/or CDRs "without substantial non-human antibody sequences" are antibodies, domains and/or CDRs in which only up to 5, 4, 3, 2 or 1 amino acids are amino acids that are not encoded by human antibody sequences. Thus, "fully human" antibodies are distinguished from "humanized" antibodies, which are based on substantially non-human variable region domains, e.g., mouse variable region domains, in which certain amino acids have been changed to better correspond with the amino acids typically present in human antibodies.

The "fully human" antibodies of the invention may be human variable region domains and/or CDRs without any other substantial antibody sequences, such as being single chain antibodies. Alternatively, the "fully human" antibodies of the invention may be human variable region domains and/or CDRs integral with or operatively attached to one or more human antibody constant regions. Certain preferred fully human antibodies are IgG antibodies with the full complement of IgG constant regions.

In other embodiments, "human" antibodies of the invention will be part-human chimeric antibodies. "Part-human chimeric" antibodies, as used herein, are antibodies comprising "human" variable region domains and/or CDRs operatively attached to, or grafted onto, a constant region of a non-human species, such as rat or mouse. Such part-human chimeric antibodies may be used, for example, in pre-clinical studies, wherein the constant region will preferably be of the same species of animal used in the pre-clinical testing. These part-human chimeric antibodies may also be used, for example, in ex vivo diagnostics, wherein the constant region of the non-human species may provide additional options for antibody detection.

In some embodiments, the antibodies of the invention will be humanized antibodies. "Humanized" antibodies, which are based on substantially non-human variable region domains are antibodies in which certain amino acids have been changed to better correspond with the amino acids typically present in human antibodies. Methods for generating humanized antibodies are well known in the art. For example, humanized antibodies can be accomplished by inserting the appropriate CDRs (e.g. murine CDRs) into a human antibody "scaffold". In some cases, one or more CDR residues may be changed to better correspond with the amino acids typically present in human antibodies.

The term "heavy chain complementarity determining region" ("heavy chain CDR") as used herein refers to regions of hypervariability within the heavy chain variable region ($V_H$ domain) of an antibody molecule. The heavy chain variable region has three CDRs termed heavy chain CDR1, heavy chain CDR2 and heavy chain CDR3 from the amino terminus to carboxy terminus. The heavy chain variable region also has four framework regions (FR1, FR2, FR3 and FR4 from the amino terminus to carboxy terminus). These framework regions separate the CDRs.

The term "heavy chain variable region" ($V_H$ domain) as used herein refers to the variable region of a heavy chain of an antibody molecule.

The term "light chain complementarity determining region" ("light chain CDR") as used herein refers to regions of hypervariability within the light chain variable region ($V_L$ domain) of an antibody molecule. Light chain variable regions have three CDRs termed light chain CDR1, light chain CDR2 and light chain CDR3 from the amino terminus to the carboxy terminus. The light chain variable region also has four framework regions (FR1, FR2, FR3 and FR4 from the amino terminus to carboxy terminus). These framework regions separate the CDRs.

The term "light chain variable region" ($V_L$ domain) as used herein refers to the variable region of a light chain of an antibody molecule.

CDR sequences of certain antibodies of the invention are set forth herein in Tables A-C and E-U. In some other embodiments, CDR sequences of antibodies of the invention may be CDR sequences in the VH domains and VL domains of antibodies of the invention as identified using any suitable method (or tool), for example as identified according to the well-known methods of Kabat (e.g. Kabat, et al., "Sequences of Proteins of Immunological Interest", 5th Ed. Public Health Service, National Institutes of Health, Bethesda, MD, 647-669, 1991) or Chothia (e.g. Chothia C, et al. (1989) Nature, 342:877-883, or AI-Lazikani et al., (1997) JMB 273, 927-948).

Antibodies can be fragmented using conventional techniques. For example, F(ab')$_2$ fragments can be generated by treating the antibody with pepsin. The resulting F(ab')$_2$ fragment can be treated to reduce disulfide bridges to produce Fab' fragments. Papain digestion can lead to the formation of Fab fragments. Fab, Fab' and F(ab')$_2$, scFv, Fv, dsFv, Fd, dAbs, TandAbs, ds-scFv, dimers, minibodies, diabodies, bispecific antibody fragments and other fragments can also be synthesized by recombinant techniques or can be chemically synthesized. Techniques for producing antibody fragments are well known and described in the art.

In certain embodiments, the antibody or antibody fragment of the present invention comprises all or a portion of a heavy chain constant region, such as an IgG1, IgG2, IgG3, IgG4, IgA1, IgA2, IgE, IgM or IgD constant region. Preferably, the heavy chain constant region is an IgG heavy chain constant region, e.g. an IgG2 or an IgG4 heavy chain constant region, or a portion thereof. Furthermore, the antibody or antibody fragment can comprise all or a portion of a kappa light chain constant region or a lambda light chain constant region, or a portion thereof. All or part of such constant regions may be produced naturally or may be wholly or partially synthetic. Appropriate sequences for such constant regions are well known and documented in the art. When a full complement of constant regions from the heavy and light chains are included in the antibodies of the invention, such antibodies are typically referred to herein as "full length" antibodies or "whole" antibodies. Thus, in some embodiments, the antibodies of the invention are Ig (e.g. IgG) antibodies.

The antibodies or antibody fragments can be produced naturally or can be wholly or partially synthetically produced. Thus the antibody may be from any appropriate source, for example recombinant sources and/or produced in transgenic animals or transgenic plants, or in eggs using the IgY technology. Thus, the antibody molecules can be produced in vitro or in vivo.

Preferably, the antibody or antibody fragment comprises an antibody light chain variable region ($V_L$) that comprises three CDR domains and an antibody heavy chain variable region ($V_H$) that comprises three CDR domains. Said VL and VH generally form the antigen binding site.

An "Fv" fragment is the minimum antibody fragment that contains a complete antigen-recognition and binding site. This region has a dimer of one heavy chain and one light chain variable domain in tight, non-covalent association. It is in this configuration that the three hypervariable regions (CDRs) of each variable domain interact to define an antigen-binding site on the surface of the $V_H$-$V_L$ dimer. Collectively, the six hypervariable regions (CDRs) confer antigen-binding specificity to the antibody.

However, it is well documented in the art that the presence of three CDRs from the light chain variable domain and three CDRs from the heavy chain variable domain of an antibody is not always necessary for antigen binding. Thus, constructs smaller than the above classical antibody fragment are known to be effective.

For example, camelid antibodies have an extensive antigen binding repertoire but are devoid of light chains. Also, results with single domain antibodies comprising VH domains alone or VL domains alone show that these domains can bind to antigen with acceptably high affinities. Thus, three CDRs can effectively bind antigen.

Thus, although preferred antibodies of the invention might comprise six CDR regions (three from a light chain and three from a heavy chain), antibodies with fewer than six CDR regions (e.g. 3 CDR regions) are encompassed by the invention. Antibodies with CDRs from only the heavy chain or light chain are also contemplated.

Preferred light chain CDR regions for use in conjunction with the specified heavy chain CDR regions are described elsewhere herein. However, other light chain variable regions that comprise three CDRs for use in conjunction with the heavy chain variable regions of the invention are also contemplated. Appropriate light chain variable regions which can be used in combination with the heavy chain variable regions of the invention and which give rise to an antibody which binds TRPV1 in accordance with the invention can be readily identified by a person skilled in the art.

A yet further aspect of the invention provides an antibody, preferably an isolated antibody, which binds to or specifically recognizes TRPV1 and which has the ability to compete with (i.e. bind to the same or substantially the same epitope as) an antibody of the invention for binding to TRPV1. Other features and properties of other aspects of the invention apply, mutatis mutandis, to this aspect of the invention.

For example, antibodies that can compete with antibodies (e.g. polyclonal antibodies such as those described in the Example section herein) that have been generated against isolated peptides (or conjugates) of the invention for binding to TRPV1 represent a further aspect of the invention.

In some embodiments, the invention provides an antibody, preferably an isolated antibody, which binds to or specifically recognizes TRPV1 and which has the ability to compete with (i.e. bind to the same or substantially the same epitope as) the OT-Ab3, OT-Ab2 and/or OT-Ab1 monoclonal antibodies of the invention (i.e. an antibody comprising the VL of SEQ ID NO:40 and the VH of SEQ ID NO:39, or an antibody comprising the VL of SEQ ID NO:57 and the VH of SEQ ID NO:58, or an antibody comprising the VL of SEQ ID NO:75 and the VH of SEQ ID NO:76) as described herein for binding to TRPV1. In other embodiments, the invention provides an antibody, preferably an isolated antibody, which binds to or specifically recognizes TRPV1 and which has the ability to compete with an antibody comprising the same CDRs as the OT-Ab3, OT-Ab2 and/or OT-Ab1 antibodies (i.e. an antibody comprising VL CDR sequences of SEQ ID NOs: 44, 45 and 46 and VH CDR sequences of SEQ ID NOs: 41, 42 and 43, or an antibody comprising VL CDR sequences of SEQ ID NOs: 62, 63 and 64 and VH CDR sequences of SEQ ID NOs: 59, 60 and 61, or an antibody comprising VL CDR sequences of SEQ ID NOs: 80, 81 and 82 and VH CDR sequences of SEQ ID NOs: 77, 78 and 79, respectively) for binding to TRPV1.

In some embodiments, the invention provides an antibody, preferably an isolated antibody, which binds to or specifically recognizes TRPV1 and which has the ability to compete with (i.e. bind to the same or substantially the same epitope as) the 32C8-1, 33C9-1, 34C11-1, 40B10-1, 41B5-1, 43D6-1, 44E8-1, 46B7-1, 46D9-1, 12C9-1, 12G6-1, 15D8-1, 16F1-1, 17E11-1, 17E9-1, 18E10-1 or R4P1-C1 monoclonal antibodies of the invention (i.e. compete with an antibody comprising VL and VH sequences of these monoclonal antibodies as set out elsewhere herein) as described herein for binding to TRPV1.

In other embodiments, the invention provides an antibody, preferably an isolated antibody, which binds to or specifically recognizes TRPV1 and which has the ability to compete with an antibody comprising the same CDRs as the 32C8-1, 33C9-1, 34C11-1, 40B10-1, 41B5-1, 43D6-1, 44E8-1, 46B7-1, 46D9-1, 12C9-1, 12G6-1, 15D8-1, 16F1-1, 17E11-1, 17E9-1, 18E10-1 or R4P1-C1 monoclonal antibodies of the invention (the CDR sequences of these antibodies are set out elsewhere herein) for binding to TRPV1.

Binding to the same epitope/antigen can be readily tested by methods well known and described in the art, e.g. using binding assays such as a competition assay, e.g. as described elsewhere herein.

Preferably, the above described abilities and properties are observed at a measurable or significant level and more preferably at a statistically significant level, when compared to appropriate control levels. Appropriate significance levels are discussed elsewhere herein. More preferably, one or more of the above described abilities and properties are observed at a level which is measurably better, or more preferably significantly better, when compared to the abilities observed for prior art antibodies.

In any statistical analysis referred to herein, preferably the statistically significant difference over a relevant control or other comparative entity or measurement has a probability value of <0.1, preferably <0.05. Appropriate methods of determining statistical significance are well known and documented in the art and any of these may be used.

In another aspect, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:41 or a sequence substantially homologous thereto, (b) a VH CDR2 that has the amino acid sequence of SEQ ID NO:42 or a sequence substantially homologous thereto, and (c) a VH CDR3 that has the amino acid sequence of SEQ ID NO:43 or a sequence substantially homologous thereto; and/or (preferably "and")

wherein said light chain variable region comprises:

(d) a variable light (VL) CDR1 that has the amino acid sequence of SEQ ID NO:44 or a sequence substantially homologous thereto, (e) a VL CDR2 that has the amino acid sequence of SEQ ID NO:45 or a sequence substantially homologous thereto, and (f) a VL CDR3 that has the amino acid sequence of SEQ ID NO:46 or a sequence substantially homologous thereto;

wherein said substantially homologous sequence is a sequence containing 1, 2 or 3 amino acid substitutions compared to the given CDR sequence, or wherein said substantially homologous sequence is a sequence containing conservative amino acid substitutions of the given CDR sequence.

Preferred embodiments of this aspect of the invention include antibodies comprising one or more of the antibody sequences (e.g. CDR sequences and/or VH domain and/or VL domain sequences) that are described elsewhere herein in connection with other aspects of the present invention. Thus, discussion of various features of the antibodies of other aspects of the invention and preferred embodiments apply mutatis mutandis to this aspect of the invention. In some preferred embodiments of this aspect of the invention, the invention provides an antibody comprising a VH domain that has the amino acid sequence of SEQ ID NO: 39 or a sequence substantially homologous thereto, and/or (preferably "and") a VL domain that has the amino acid sequence of SEQ ID NO: 40 or a sequence substantially homologous thereto. In some preferred embodiments of this aspect of the invention, the invention provides an antibody comprising a VH domain that has the amino acid sequence of SEQ ID NO: 57 or a sequence substantially homologous thereto, and/or (preferably "and") a VL domain that has the amino acid sequence of SEQ ID NO: 58 or a sequence substantially homologous thereto.

In another aspect, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:77 or a sequence substantially homologous thereto, (b) a VH CDR2 that has the amino acid sequence of SEQ ID NO:78 or a sequence substantially homologous thereto, and (c) a VH CDR3 that has the amino acid sequence of SEQ ID NO:79 or a sequence substantially homologous thereto; and/or (preferably "and")

wherein said light chain variable region comprises:

(d) a variable light (VL) CDR1 that has the amino acid sequence of SEQ ID NO:80 or a sequence substantially homologous thereto, (e) a VL CDR2 that has the amino acid sequence of SEQ ID NO:81 or a sequence substantially homologous thereto, and (f) a VL CDR3 that has the amino acid sequence of SEQ ID NO:82 or a sequence substantially homologous thereto;

wherein said substantially homologous sequence is a sequence containing 1, 2 or 3 amino acid substitutions compared to the given CDR sequence, or wherein said substantially homologous sequence is a sequence containing conservative amino acid substitutions of the given CDR sequence.

Preferred embodiments of this aspect of the invention include antibodies comprising one or more of the antibody sequences (e.g. CDR sequences and/or VH domain and/or VL domain sequences) that are described elsewhere herein in connection with other aspects of the present invention. Thus, discussion of various features of the antibodies of other aspects of the invention and preferred embodiments apply mutatis mutandis to this aspect of the invention. In some preferred embodiments of this aspect of the invention, the invention provides an antibody comprising a VH domain that has the amino acid sequence of SEQ ID NO: 75 or a sequence substantially homologous thereto, and/or (preferably "and") a VL domain that has the amino acid sequence of SEQ ID NO: 76 or a sequence substantially homologous thereto.

In another aspect, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:41 or SEQ ID NO:77, or a sequence substantially homologous thereto, (b) a VH CDR2 that has the amino acid sequence of SEQ ID NO:42 or SEQ ID NO:78, or a sequence substantially homologous thereto, and (c) a VH CDR3 that has the amino acid sequence of SEQ ID NO:43 or SEQ ID NO:79, or a sequence substantially homologous thereto; and/or (preferably "and") wherein said light chain variable region comprises:

(d) a variable light (VL) CDR1 that has the amino acid sequence of SEQ ID NO:91 or preferably SEQ ID NO:92, or a sequence substantially homologous thereto, (e) a VL CDR2 that has the amino acid sequence of SEQ ID NO:45 or SEQ ID NO:81, or a sequence substantially homologous thereto, and (f) a VL CDR3 that has the amino acid sequence of SEQ ID NO:46 or SEQ ID NO:82, or a sequence substantially homologous thereto;

wherein said substantially homologous sequence is a sequence containing 1, 2 or 3 amino acid substitutions compared to the given CDR sequence, or said substantially homologous sequence is a sequence containing conservative amino acid substitutions of the given CDR sequence.

Preferred embodiments of this aspect of the invention include antibodies comprising one or more of the antibody sequences (e.g. CDR sequences and/or VH domain and/or VL domain sequences) that are described elsewhere herein in connection with other aspects of the present invention. Thus, discussion of various features of the antibodies of other aspects of the invention and preferred embodiments apply mutatis mutandis to this aspect of the invention.

In another aspect, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:103 or a sequence substantially homologous thereto, (b) a VH CDR2 that has the amino acid sequence of SEQ ID NO:104 or a sequence substantially homologous thereto, and (c) a VH CDR3 that has the amino acid sequence of SEQ ID NO:105 or a sequence substantially homologous thereto; and/or (preferably "and") wherein said light chain variable region comprises:

(d) a variable light (VL) CDR1 that has the amino acid sequence of SEQ ID NO:106 or a sequence substantially homologous thereto, (e) a VL CDR2 that has the amino acid sequence of SEQ ID NO:107 or a sequence substantially homologous thereto, and (f) a VL CDR3 that has the amino acid sequence of SEQ ID NO:108 or a sequence substantially homologous thereto;

wherein said substantially homologous sequence is a sequence containing 1, 2 or 3 amino acid substitutions compared to the given CDR sequence, or wherein said substantially homologous sequence is a sequence containing conservative amino acid substitutions of the given CDR sequence.

Preferred embodiments of this aspect of the invention include antibodies comprising one or more of the antibody sequences (e.g. CDR sequences and/or VH domain and/or VL domain sequences) that are described elsewhere herein in connection with other aspects of the present invention. Thus, discussion of various features of the antibodies of other aspects of the invention and preferred embodiments apply mutatis mutandis to this aspect of the invention. In some preferred embodiments of this aspect of the invention, the invention provides an antibody comprising a VH domain that has the amino acid sequence of SEQ ID NO: 101 or a sequence substantially homologous thereto, and/or (preferably "and") a VL domain that has the amino acid sequence of SEQ ID NO: 102 or a sequence substantially homologous thereto.

In another aspect, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:123 or a sequence substantially homologous thereto, (b) a VH CDR2 that has the amino acid sequence of SEQ ID NO:124 or a sequence substantially homologous thereto, and (c) a VH CDR3 that has the amino acid sequence of SEQ ID NO:125 or a sequence substantially homologous thereto; and/or (preferably "and") wherein said light chain variable region comprises:

(d) a variable light (VL) CDR1 that has the amino acid sequence of SEQ ID NO:126 or a sequence substantially homologous thereto, (e) a VL CDR2 that has the amino acid sequence of SEQ ID NO:127 or a sequence substantially homologous thereto, and (f) a VL CDR3 that has the amino acid sequence of SEQ ID NO:128 or a sequence substantially homologous thereto;

wherein said substantially homologous sequence is a sequence containing 1, 2 or 3 amino acid substitutions compared to the given CDR sequence, or wherein said substantially homologous sequence is a sequence containing conservative amino acid substitutions of the given CDR sequence.

Preferred embodiments of this aspect of the invention include antibodies comprising one or more of the antibody sequences (e.g. CDR sequences and/or VH domain and/or VL domain sequences) that are described elsewhere herein in connection with other aspects of the present invention. Thus, discussion of various features of the antibodies of other aspects of the invention and preferred embodiments apply mutatis mutandis to this aspect of the invention. In some preferred embodiments of this aspect of the invention, the invention provides an antibody comprising a VH domain that has the amino acid sequence of SEQ ID NO: 121 or a sequence substantially homologous thereto, and/or (preferably "and") a VL domain that has the amino acid sequence of SEQ ID NO: 122 or a sequence substantially homologous thereto.

In another aspect, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:143 or a sequence substantially homologous thereto, (b) a VH CDR2 that has the amino acid sequence of SEQ ID NO:144 or a sequence substantially homologous thereto, and (c) a VH CDR3 that has the amino acid sequence of SEQ ID NO:145 or a sequence substantially homologous thereto; and/or (preferably "and")

wherein said light chain variable region comprises:

(d) a variable light (VL) CDR1 that has the amino acid sequence of SEQ ID NO:146 or a sequence substantially homologous thereto, (e) a VL CDR2 that has the amino acid sequence of SEQ ID NO:147 or a sequence substantially homologous thereto, and (f) a VL CDR3 that has the amino acid sequence of SEQ ID NO:148 or a sequence substantially homologous thereto;

wherein said substantially homologous sequence is a sequence containing 1, 2 or 3 amino acid substitutions compared to the given CDR sequence, or wherein said substantially homologous sequence is a sequence containing conservative amino acid substitutions of the given CDR sequence.

Preferred embodiments of this aspect of the invention include antibodies comprising one or more of the antibody sequences (e.g. CDR sequences and/or VH domain and/or VL domain sequences) that are described elsewhere herein in connection with other aspects of the present invention. Thus, discussion of various features of the antibodies of other aspects of the invention and preferred embodiments apply mutatis mutandis to this aspect of the invention. In some preferred embodiments of this aspect of the invention, the invention provides an antibody comprising a VH domain that has the amino acid sequence of SEQ ID NO: 141 or a sequence substantially homologous thereto, and/or (preferably "and") a VL domain that has the amino acid sequence of SEQ ID NO: 142 or a sequence substantially homologous thereto. In some other preferred embodiments of this aspect of the invention, the invention provides an antibody comprising a VH domain that has the amino acid sequence of SEQ ID NO: 161 or a sequence substantially homologous thereto, and/or (preferably "and") a VL domain that has the amino acid sequence of SEQ ID NO: 162 or a sequence substantially homologous thereto. In some other preferred embodiments of this aspect of the invention, the invention provides an antibody comprising a VH domain that has the amino acid sequence of SEQ ID NO: 261 or a sequence substantially homologous thereto, and/or (preferably "and") a VL domain that has the amino acid sequence of SEQ ID NO: 262 or a sequence substantially homologous thereto.

In another aspect, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:183 or a sequence substantially homologous thereto, (b) a VH CDR2 that has the amino acid sequence of SEQ ID NO:184 or a sequence substantially homologous thereto, and (c) a VH CDR3 that has the amino acid sequence of SEQ ID NO:185 or a sequence substantially homologous thereto; and/or (preferably "and")

wherein said light chain variable region comprises:

(d) a variable light (VL) CDR1 that has the amino acid sequence of SEQ ID NO:186 or a sequence substantially homologous thereto, (e) a VL CDR2 that has the amino acid sequence of SEQ ID NO:187 or a sequence substantially homologous thereto, and (f) a VL CDR3 that has the amino acid sequence of SEQ ID NO:188 or a sequence substantially homologous thereto;

wherein said substantially homologous sequence is a sequence containing 1, 2 or 3 amino acid substitutions compared to the given CDR sequence, or wherein said substantially homologous sequence is a sequence containing conservative amino acid substitutions of the given CDR sequence.

Preferred embodiments of this aspect of the invention include antibodies comprising one or more of the antibody sequences (e.g. CDR sequences and/or VH domain and/or VL domain sequences) that are described elsewhere herein in connection with other aspects of the present invention. Thus, discussion of various features of the antibodies of other aspects of the invention and preferred embodiments apply mutatis mutandis to this aspect of the invention. In some preferred embodiments of this aspect of the invention, the invention provides an antibody comprising a VH domain that has the amino acid sequence of SEQ ID NO: 181 or a sequence substantially homologous thereto, and/or (preferably "and") a VL domain that has the amino acid sequence of SEQ ID NO: 182 or a sequence substantially homologous thereto.

In another aspect, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:203 or a sequence substantially homologous thereto, (b) a VH CDR2 that has the amino acid sequence of SEQ ID NO:204 or a sequence substantially homologous thereto, and (c) a VH CDR3 that has the amino acid sequence of SEQ ID NO:205 or a sequence substantially homologous thereto; and/or (preferably "and")

wherein said light chain variable region comprises:

(d) a variable light (VL) CDR1 that has the amino acid sequence of SEQ ID NO:206 or a sequence substantially homologous thereto, (e) a VL CDR2 that has the amino acid sequence of SEQ ID NO:207 or a sequence substantially homologous thereto, and (f) a VL CDR3 that has the amino acid sequence of SEQ ID NO:208 or a sequence substantially homologous thereto;

wherein said substantially homologous sequence is a sequence containing 1, 2 or 3 amino acid substitutions compared to the given CDR sequence, or wherein said substantially homologous sequence is a sequence containing conservative amino acid substitutions of the given CDR sequence.

Preferred embodiments of this aspect of the invention include antibodies comprising one or more of the antibody sequences (e.g. CDR sequences and/or VH domain and/or VL domain sequences) that are described elsewhere herein in connection with other aspects of the present invention. Thus, discussion of various features of the antibodies of other aspects of the invention and preferred embodiments apply mutatis mutandis to this aspect of the invention. In some preferred embodiments of this aspect of the invention, the invention provides an antibody comprising a VH domain that has the amino acid sequence of SEQ ID NO: 201 or a sequence substantially homologous thereto, and/or (preferably "and") a VL domain that has the amino acid sequence of SEQ ID NO: 202 or a sequence substantially homologous thereto. In some other preferred embodiments of this aspect of the invention, the invention provides an antibody comprising a VH domain that has the amino acid sequence of SEQ ID NO: 241 or a sequence substantially homologous thereto, and/or (preferably "and") a VL domain that has the amino acid sequence of SEQ ID NO: 242 or a sequence substantially homologous thereto.

In another aspect, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:223 or a sequence substantially homologous thereto, (b) a VH CDR2 that has the amino acid sequence of SEQ ID NO:224 or a sequence substantially homologous thereto, and (c) a VH CDR3 that has the amino acid sequence of SEQ ID NO:225 or a sequence substantially homologous thereto; and/or (preferably "and")

wherein said light chain variable region comprises:

(d) a variable light (VL) CDR1 that has the amino acid sequence of SEQ ID NO:226 or a sequence substantially homologous thereto, (e) a VL CDR2 that has the amino acid sequence of SEQ ID NO:227 or a sequence substantially homologous thereto, and (f) a VL CDR3 that has the amino acid sequence of SEQ ID NO:228 or a sequence substantially homologous thereto;

wherein said substantially homologous sequence is a sequence containing 1, 2 or 3 amino acid substitutions compared to the given CDR sequence, or wherein said substantially homologous sequence is a sequence containing conservative amino acid substitutions of the given CDR sequence.

Preferred embodiments of this aspect of the invention include antibodies comprising one or more of the antibody sequences (e.g. CDR sequences and/or VH domain and/or VL domain sequences) that are described elsewhere herein in connection with other aspects of the present invention. Thus, discussion of various features of the antibodies of other aspects of the invention and preferred embodiments apply mutatis mutandis to this aspect of the invention. In some preferred embodiments of this aspect of the invention, the invention provides an antibody comprising a VH domain that has the amino acid sequence of SEQ ID NO: 221 or a sequence substantially homologous thereto, and/or (preferably "and") a VL domain that has the amino acid sequence of SEQ ID NO: 222 or a sequence substantially homologous thereto.

In another aspect, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:283 or a sequence substantially homologous thereto, (b) a VH CDR2 that has the amino acid sequence of SEQ ID NO:284 or a sequence substantially homologous thereto, and (c) a VH CDR3 that has the amino acid sequence of SEQ ID NO:285 or a sequence substantially homologous thereto; and/or (preferably "and")

wherein said light chain variable region comprises:

(d) a variable light (VL) CDR1 that has the amino acid sequence of SEQ ID NO:286 or a sequence substantially homologous thereto, (e) a VL CDR2 that has the amino acid sequence of SEQ ID NO:287 or a sequence substantially homologous thereto, and (f) a VL CDR3 that has the amino acid sequence of SEQ ID NO:288 or a sequence substantially homologous thereto;

wherein said substantially homologous sequence is a sequence containing 1, 2 or 3 amino acid substitutions compared to the given CDR sequence, or wherein said substantially homologous sequence is a sequence containing conservative amino acid substitutions of the given CDR sequence.

Preferred embodiments of this aspect of the invention include antibodies comprising one or more of the antibody sequences (e.g. CDR sequences and/or VH domain and/or VL domain sequences) that are described elsewhere herein in connection with other aspects of the present invention. Thus, discussion of various features of the antibodies of other aspects of the invention and preferred embodiments apply mutatis mutandis to this aspect of the invention. In some preferred embodiments of this aspect of the invention, the invention provides an antibody comprising a VH domain that has the amino acid sequence of SEQ ID NO: 281 or a sequence substantially homologous thereto, and/or (preferably "and") a VL domain that has the amino acid sequence of SEQ ID NO: 282 or a sequence substantially homologous thereto. In some other preferred embodiments of this aspect of the invention, the invention provides an antibody comprising a VH domain that has the amino acid sequence of SEQ ID NO: 401 or a sequence substantially homologous thereto, and/or (preferably "and") a VL domain that has the amino acid sequence of SEQ ID NO: 402 or a sequence substantially homologous thereto.

In another aspect, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:303 or a sequence substantially homologous thereto, (b) a VH CDR2 that has the amino acid sequence of SEQ ID NO:304 or a sequence substantially homologous thereto, and (c) a VH CDR3 that has the amino acid sequence of SEQ ID NO:305 or a sequence substantially homologous thereto; and/or (preferably "and")

wherein said light chain variable region comprises:

(d) a variable light (VL) CDR1 that has the amino acid sequence of SEQ ID NO:306 or a sequence substantially homologous thereto, (e) a VL CDR2 that has the amino acid sequence of SEQ ID NO:307 or a sequence substantially homologous thereto, and (f) a VL CDR3 that has the amino acid sequence of SEQ ID NO:308 or a sequence substantially homologous thereto;

wherein said substantially homologous sequence is a sequence containing 1, 2 or 3 amino acid substitutions compared to the given CDR sequence, or wherein said substantially homologous sequence is a sequence containing conservative amino acid substitutions of the given CDR sequence.

Preferred embodiments of this aspect of the invention include antibodies comprising one or more of the antibody sequences (e.g. CDR sequences and/or VH domain and/or VL domain sequences) that are described elsewhere herein in connection with other aspects of the present invention. Thus, discussion of various features of the antibodies of other aspects of the invention and preferred embodiments apply mutatis mutandis to this aspect of the invention. In some preferred embodiments of this aspect of the invention, the invention provides an antibody comprising a VH domain that has the amino acid sequence of SEQ ID NO: 301 or a sequence substantially homologous thereto, and/or (preferably "and") a VL domain that has the amino acid sequence of SEQ ID NO: 302 or a sequence substantially homologous thereto.

In another aspect, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:323 or a sequence substantially homologous thereto, (b) a VH CDR2 that has the amino acid sequence of SEQ ID NO:324 or a sequence substantially homologous thereto, and (c) a VH CDR3 that has the amino acid sequence of SEQ ID NO:325 or a sequence substantially homologous thereto; and/or (preferably "and")

wherein said light chain variable region comprises:

(d) a variable light (VL) CDR1 that has the amino acid sequence of SEQ ID NO:326 or a sequence substantially homologous thereto, (e) a VL CDR2 that has the amino acid sequence of SEQ ID NO:327 or a sequence substantially homologous thereto, and (f) a VL CDR3 that has the amino acid sequence of SEQ ID NO:328 or a sequence substantially homologous thereto;

wherein said substantially homologous sequence is a sequence containing 1, 2 or 3 amino acid substitutions compared to the given CDR sequence, or wherein said substantially homologous sequence is a sequence containing conservative amino acid substitutions of the given CDR sequence.

Preferred embodiments of this aspect of the invention include antibodies comprising one or more of the antibody sequences (e.g. CDR sequences and/or VH domain and/or VL domain sequences) that are described elsewhere herein in connection with other aspects of the present invention. Thus, discussion of various features of the antibodies of other aspects of the invention and preferred embodiments apply mutatis mutandis to this aspect of the invention. In some preferred embodiments of this aspect of the invention, the invention provides an antibody comprising a VH domain that has the amino acid sequence of SEQ ID NO: 321 or a sequence substantially homologous thereto, and/or (preferably "and") a VL domain that has the amino acid sequence of SEQ ID NO: 322 or a sequence substantially homologous thereto.

In another aspect, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:343 or a sequence substantially homologous thereto, (b) a VH CDR2 that has the amino acid sequence of SEQ ID NO:344 or a sequence substantially homologous thereto, and (c) a VH CDR3 that has the amino acid sequence of SEQ ID NO:345 or a sequence substantially homologous thereto; and/or (preferably "and")

wherein said light chain variable region comprises:

(d) a variable light (VL) CDR1 that has the amino acid sequence of SEQ ID NO:346 or a sequence substantially homologous thereto, (e) a VL CDR2 that has the amino acid sequence of SEQ ID NO:347 or a sequence substantially homologous thereto, and (f) a VL CDR3 that has the amino acid sequence of SEQ ID NO:348 or a sequence substantially homologous thereto;

wherein said substantially homologous sequence is a sequence containing 1, 2 or 3 amino acid substitutions compared to the given CDR sequence, or wherein said substantially homologous sequence is a sequence containing conservative amino acid substitutions of the given CDR sequence.

Preferred embodiments of this aspect of the invention include antibodies comprising one or more of the antibody sequences (e.g. CDR sequences and/or VH domain and/or VL domain sequences) that are described elsewhere herein in connection with other aspects of the present invention. Thus, discussion of various features of the antibodies of other aspects of the invention and preferred embodiments apply mutatis mutandis to this aspect of the invention. In some preferred embodiments of this aspect of the invention, the invention provides an antibody comprising a VH domain that has the amino acid sequence of SEQ ID NO: 341 or a sequence substantially homologous thereto, and/or (preferably "and") a VL domain that has the amino acid sequence of SEQ ID NO: 342 or a sequence substantially homologous thereto.

In another aspect, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:363 or a sequence substantially homologous thereto, (b) a VH CDR2 that has the amino acid sequence of SEQ ID NO:364 or a sequence substantially homologous thereto, and (c) a VH CDR3 that has the amino acid sequence of SEQ ID NO:365 or a sequence substantially homologous thereto; and/or (preferably "and")

wherein said light chain variable region comprises:

(d) a variable light (VL) CDR1 that has the amino acid sequence of SEQ ID NO:366 or a sequence substantially homologous thereto, (e) a VL CDR2 that has the amino acid sequence of SEQ ID NO:367 or a sequence substantially homologous thereto, and (f) a VL CDR3 that has the amino acid sequence of SEQ ID NO:368 or a sequence substantially homologous thereto;

wherein said substantially homologous sequence is a sequence containing 1, 2 or 3 amino acid substitutions compared to the given CDR sequence, or wherein said substantially homologous sequence is a sequence containing conservative amino acid substitutions of the given CDR sequence.

Preferred embodiments of this aspect of the invention include antibodies comprising one or more of the antibody sequences (e.g. CDR sequences and/or VH domain and/or VL domain sequences) that are described elsewhere herein in connection with other aspects of the present invention. Thus, discussion of various features of the antibodies of other aspects of the invention and preferred embodiments apply mutatis mutandis to this aspect of the invention. In some preferred embodiments of this aspect of the invention, the invention provides an antibody comprising a VH domain that has the amino acid sequence of SEQ ID NO: 361 or a sequence substantially homologous thereto, and/or (preferably "and") a VL domain that has the amino acid sequence of SEQ ID NO: 362 or a sequence substantially homologous thereto. In some other preferred embodiments of this aspect of the invention, the invention provides an antibody comprising a VH domain that has the amino acid sequence of SEQ ID NO: 381 or a sequence substantially homologous thereto, and/or (preferably "and") a VL domain that has the amino acid sequence of SEQ ID NO: 382 or a sequence substantially homologous thereto.

In another aspect, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises:

(a) a variable heavy (VH) CDR1 that has the amino acid sequence of SEQ ID NO:423 or a sequence substantially homologous thereto, (b) a VH CDR2 that has the amino acid sequence of SEQ ID NO:424 or a sequence substantially homologous thereto, and (c) a VH CDR3 that has the amino acid sequence of SEQ ID NO:425 or a sequence substantially homologous thereto; and/or (preferably "and")

wherein said light chain variable region comprises:

(d) a variable light (VL) CDR1 that has the amino acid sequence of SEQ ID NO:426 or a sequence substantially homologous thereto, (e) a VL CDR2 that has the amino acid sequence of SEQ ID NO:427 or a sequence substantially homologous thereto, and (f) a VL CDR3 that has the amino acid sequence of SEQ ID NO:428 or a sequence substantially homologous thereto;

wherein said substantially homologous sequence is a sequence containing 1, 2 or 3 amino acid substitutions compared to the given CDR sequence, or wherein said substantially homologous sequence is a sequence containing conservative amino acid substitutions of the given CDR sequence.

Preferred embodiments of this aspect of the invention include antibodies comprising one or more of the antibody sequences (e.g. CDR sequences and/or VH domain and/or VL domain sequences) that are described elsewhere herein in connection with other aspects of the present invention. Thus, discussion of various features of the antibodies of other aspects of the invention and preferred embodiments apply mutatis mutandis to this aspect of the invention. In some preferred embodiments of this aspect of the invention, the invention provides an antibody comprising a VH domain that has the amino acid sequence of SEQ ID NO: 421 or a sequence substantially homologous thereto, and/or (preferably "and") a VL domain that has the amino acid sequence of SEQ ID NO: 422 or a sequence substantially homologous thereto.

In another aspect, the present invention provides an antibody, for example an isolated antibody, that binds to TRPV1 and that comprises at least one heavy chain variable region that comprises three CDRs and at least one light chain variable region that comprises three CDRs, wherein said heavy chain variable region comprises a VH CDR1, a VH CDR2 and VH CDR3 each having amino acid sequences as set elsewhere herein (e.g. in combination) in relation to other aspects of the invention, and wherein said light chain variable region comprises a VL CDR1, a VL CDR2 and VL CDR3 each having amino acid sequences as set elsewhere herein (e.g. in combination) in relation to other aspects of the invention.

The antibodies, peptides, binding proteins and nucleic acid molecules of the invention are generally "isolated" or "purified" molecules insofar as they are distinguished from any such components that may be present in situ within a human or animal body or a tissue sample derived from a human or animal body. The sequences may, however, correspond to or be substantially homologous to sequences as found in a human or animal body. Thus, the term "isolated" or "purified" as used herein in reference to nucleic acid molecules or sequences and proteins, peptides or polypeptides, e.g. antibodies, refers to such molecules when isolated from, purified from, or substantially free of their natural environment, e.g. isolated from or purified from the human or animal body (if indeed they occur naturally), or refers to such molecules when produced by a technical process, i.e. includes recombinant and synthetically produced molecules.

Thus, when used in connection with a protein or polypeptide molecule such as isolated peptides, light chain CDRs 1, 2 and 3, heavy chain CDRs 1, 2 and 3, light chain variable regions, heavy chain variable regions, and binding proteins or antibodies of the invention, including full length antibodies, the term "isolated" or "purified" typically refers to a protein substantially free of cellular material or other proteins from the source from which it is derived. In some embodiments, particularly where the protein is to be administered to humans or animals, such isolated or purified proteins are substantially free of culture medium when produced by recombinant techniques, or chemical precursors or other chemicals when chemically synthesized.

The term "fragment" as used herein refers to fragments of biological relevance, e.g. fragments that contribute to antigen binding, e.g. form part of the antigen binding site, and/or contribute to the functional properties of the TRPV1 antibody. Certain preferred fragments comprise a heavy chain variable region ($V_H$ domain) and/or a light chain variable region ($V_L$ domain) of the antibodies of the invention.

A person skilled in the art will appreciate that the antibodies, antibody fragments, and immunoconjugates of the invention may be prepared in any of several ways well known and described in the art. For example, polyclonal antibodies may be prepared by immunizing an animal (non-human animal e.g. a rabbit) with an isolated peptide or conjugate of the invention and isolating (and optionally purifying) antibodies to the isolated peptide or conjugate that have been generated by the animal. In other embodiments, antibodies, antibody fragments, and immunoconjugates of the invention may be prepared by recombinant methods.

Nucleic acid fragments encoding the light and heavy chain variable regions of the antibodies of the invention can be derived or produced by any appropriate method, e.g. by cloning or synthesis.

Once nucleic acid fragments encoding the light and heavy chain variable regions of the antibodies of the invention have been obtained, these fragments can be further manipulated by standard recombinant DNA techniques, for example to convert the variable region fragments into full length antibody molecules with appropriate constant region domains, or into particular formats of antibody fragment discussed elsewhere herein, e.g. Fab fragments, scFv fragments, etc. Typically, or as part of this further manipulation procedure, the nucleic acid fragments encoding antibody molecules of the invention are generally incorporated into one or more appropriate expression vectors in order to facilitate production of the antibodies of the invention.

Possible expression vectors include but are not limited to cosmids, plasmids, or modified viruses (e.g. replication defective retroviruses, adenoviruses and adeno-associated viruses), so long as the vector is compatible with the host cell used. The expression vectors are "suitable for transformation of a host cell", which means that the expression vectors contain a nucleic acid molecule of the invention and regulatory sequences selected on the basis of the host cells to be used for expression, which are operatively linked to the nucleic acid molecule. Operatively linked is intended to mean that the nucleic acid is linked to regulatory sequences in a manner that allows expression of the nucleic acid.

The invention therefore contemplates a recombinant expression vector containing a nucleic acid molecule of the invention, or a fragment thereof, and the necessary regulatory sequences for the transcription and translation of the protein sequence encoded by the nucleic acid molecule of the invention.

Suitable regulatory sequences may be derived from a variety of sources, including bacterial, fungal, viral, mammalian, or insect genes and are well known in the art. Selection of appropriate regulatory sequences is dependent on the host cell chosen as discussed below, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector.

The recombinant expression vectors of the invention may also contain a selectable marker gene that facilitates the selection of host cells transformed or transfected with a recombinant molecule of the invention.

The recombinant expression vectors may also contain genes that encode a fusion moiety that provides increased expression of the recombinant protein; increased solubility of the recombinant protein; and aid in the purification of the target recombinant protein by acting as a ligand in affinity purification (for example appropriate "tags" to enable purification and/or identification may be present, e.g., His tags or myc tags).

Recombinant expression vectors can be introduced into host cells to produce a transformed host cell. The terms "transformed with", "transfected with", "transformation" and "transfection" are intended to encompass introduction of nucleic acid (e.g., a vector) into a cell by one of many possible techniques known in the art. Suitable methods for transforming and transfecting host cells can be found in Sambrook et al., 1989 (Sambrook, Fritsch and Maniatis, *Molecular Cloning: A Laboratory Manual,* 2nd Ed., Cold Spring Harbor Press, Cold Spring Harbor, N Y, 1989) and other laboratory textbooks.

Suitable host cells include a wide variety of eukaryotic host cells and prokaryotic cells. For example, the proteins (e.g. antibodies) of the invention may be expressed in yeast cells or mammalian cells. In addition, the proteins of the invention may be expressed in prokaryotic cells, such as *Escherichia coli.*

Given the teachings provided herein, promoters, terminators, and methods for introducing expression vectors of an appropriate type into plant, avian, and insect cells may also be readily accomplished.

Alternatively, the proteins (e.g. antibodies) of the invention may also be expressed in non-human transgenic animals such as, rats, rabbits, sheep and pigs.

The proteins of the invention may also be prepared by chemical synthesis using techniques well known in the chemistry of proteins such as solid phase synthesis.

N-terminal or C-terminal fusion proteins comprising the antibodies and proteins (e.g. isolated peptides) of the invention conjugated to other molecules, such as proteins, may be prepared by fusing through recombinant techniques. The resultant fusion proteins contain an antibody or protein of the invention fused to the selected protein or marker protein, or tag protein as described herein. The antibodies and proteins of the invention may also be conjugated to other proteins by known techniques. For example, the proteins may be coupled using heterobifunctional thiol-containing linkers as described in WO 90/10457, N-succinimidyl-3-(2-pyridyldithio-proprionate) or N-succinimidyl-5 thioacetate.

A yet further aspect provides an expression construct or expression vector comprising one or more of the nucleic acid fragments or segments or molecules of the invention. Preferably the expression constructs or vectors are recombinant. Also provided is a set of expression vectors (or a set of expression constructs) which, together (collectively), encode an antibody of the invention. Such a set of expression vectors may be characterised in that when the set is expressed (i.e. expressed together) (e.g. in a host cell) an antibody (an entire antibody) of the present invention is expressed and preferably assembled.

Preferably said constructs or vectors further comprise the necessary regulatory sequences for the transcription and translation of the protein sequence encoded by the nucleic acid molecule of the invention.

A yet further aspect provides a host cell or virus comprising one or more expression constructs or expression vectors of the invention. Also provided are host cells or viruses comprising one or more of the nucleic acid molecules of the invention. A host cell (e.g. a mammalian host cell) or virus expressing an antibody of the invention forms a yet further aspect.

A yet further aspect of the invention provides a method of producing (or manufacturing or isolating or identifying or generating) an antibody of the present invention, said method employing an isolated peptide or conjugate of the invention Alternatively viewed, the present invention provides the use of an isolated peptide or conjugate of the invention for the identification (or isolation or generation or production) of an antibody of the invention.

A yet further aspect of the invention provides a method of producing (or manufacturing or isolating or identifying or generating) an antibody of the present invention comprising a step of immunizing an animal (non-human animal e.g. a rabbit) with an isolated peptide (or conjugate) of the invention. Preferred methods include a step of obtaining from said animal antibodies that have been generated (or raised) against the isolated peptide (or conjugate) of the invention, and optionally a step of purification of the antibody product and/or formulating the antibody or product into a composition including at least one additional component, such as a pharmaceutically acceptable carrier or excipient.

A yet further aspect of the invention provides a method of producing (or manufacturing or isolating or identifying or generating) an antibody of the present invention by employing an isolated peptide or conjugate of the invention in hybridoma technology (e.g. conventional hybridoma technology). Alternatively viewed, the present invention provides the use of an isolated peptide or conjugate of the invention for the identification (or isolation or generation or production) of an antibody of the invention using hybridoma technology. In some embodiments, a non-human animal (e.g. mouse) is immunized with an isolated peptide or conjugate of the invention, spleen cells are isolated from said immunized animal (e.g. mouse) and fused with myeloma cells (e.g. mouse myeloma cells) lacking HGPRT expression (such myeloma cells are unable to grow in HAT containing media) and hybrid (i.e. fused or hybridoma) cells are selected using hypoxanthine, aminopterin and thymine (HAT) containing media. Only fused cells grow in HAT containing media.

A yet further aspect of the invention provides a method of identifying (or isolating or generating) an antibody of the invention which employs phage display technology (with a phage display antibody library). Alternatively viewed, the present invention provides the use of an isolated peptide or conjugate of the invention for the identification (or isolation or generation or production) of an antibody of the invention using phage display technology (with a phage display antibody library). In some embodiments, an isolated peptide or conjugate of the invention (typically immobilised on a solid support such as a bead or microbead or plate or microtitre plate) is contacted with phage library (bacteriophage library typically a filamentous bacteriophage library such as an M13 of fd phage library) which displays (or presents or expresses) on the phage surface a library of antibodies or antibody fragments such as scFv or Fab fragments. Any suitable phage display antibody library may be used (e.g. a human phage-Fab library may be used (e.g. a human naïve phage-Fab library)) and the skilled person is familiar with these (and e.g. there are commercially available phage display antibody libraries). The bound phage is then eluted and the identity of the displayed antibody may be readily determined by isolating and sequencing the phage's nucleic acid (or at least the portion of the nucleic acid that encodes the displayed antibody). In some embodiments, after elution of the bound phage, one or more (e.g. 1, 2, 3, 4, 5 or more) additional rounds of contacting and eluting is performed prior to identifying the displayed antibody of the bound phage. Such additional rounds typically further enrich the library. In some typical embodiments, where the peptide or conjugate of the invention is immobilised on a solid support, the solid support is typically washed after the contacting step (and prior to the eluting step), with those phage displaying antibodies or antibody fragments that bind to the immobilised isolated peptide or conjugate remaining bound (and the others being washed away).

A yet further aspect of the invention provides a method of producing (or manufacturing) an antibody of the present invention comprising a step of culturing the host cells of the invention. Preferred methods comprise the steps of (i) culturing a host cell comprising one or more of the recombinant expression vectors (or a set of expression vectors) or one or more of the nucleic acid sequences (or a set of nucleic acid molecules) of the invention under conditions suitable for the expression of the encoded antibody; and optionally (ii) isolating or obtaining the antibody from the host cell or from the growth medium/supernatant.

In embodiments when the antibody or protein of the invention is made up of more than one polypeptide chain (e.g. certain fragments such as Fab fragments or whole antibodies), then all the polypeptides are preferably expressed in the host cell, either from the same or a different expression vector, so that the complete proteins, e.g. antibody proteins of the invention, can assemble in the host cell and be isolated or purified therefrom.

In some embodiments, methods of producing (or manufacturing or isolating or identifying or generating) an antibody in accordance with the invention may also comprise a step of purification of the antibody or protein product and/or formulating the antibody or product into a composition including at least one additional component, such as a pharmaceutically acceptable carrier or excipient.

In another aspect, the invention provides a method of binding TRPV1, comprising contacting a composition comprising TRPV1 with an antibody of the invention, or an immunoconjugate thereof.

In yet another aspect, the invention provides a method of detecting TRPV1, comprising contacting a composition suspected of containing TRPV1 with an antibody of the invention, or an immunoconjugate thereof, under conditions effective to allow the formation of TRPV1/antibody complexes and detecting the complexes so formed.

The antibodies of the invention may also be used to produce further antibodies that bind to TRPV1. Such uses involve for example the addition, deletion, substitution or insertion of one or more amino acids in the amino acid sequence of a parent antibody to form a new antibody, wherein said parent antibody is one of the antibodies of the invention as defined elsewhere herein, and testing the resulting new antibody to identify antibodies that bind to TRPV1 in accordance with the invention. Such methods can be used to form multiple new antibodies that can all be tested for their ability to bind TRPV1. Preferably said addition, deletion, substitution or insertion of one or more amino acids takes place in one or more of the CDR domains.

Such modification or mutation to a parent antibody can be carried out in any appropriate manner using techniques well known and documented in the art, for example by carrying out methods of random or directed mutagenesis. If directed mutagenesis is to be used then one strategy to identify appropriate residues for mutagenesis utilizes the resolution of the crystal structure of the binding protein-antigen complex, e.g., the Ab-Ag complex, to identify the key residues involved in the antigen binding. Alanine scanning mutagenesis is also a routine method which can be used to identify the key residues involved in the antigen binding. Subsequently, those residues can be mutated to enhance the interaction. Alternatively, one or more amino acid residues can simply be targeted for directed mutagenesis and the effect on binding to TRPV1 assessed.

Random mutagenesis can be carried out in any appropriate way, e.g., by error-prone PCR, chain shuffling or mutator *E. coli* strains.

Thus, one or more of the VH domains of the invention can be combined with a single VL domain or a repertoire of VL domains from any appropriate source and the resulting new antibodies tested to identify antibodies which bind to TRPV1. Conversely, one or more of the VL domains of the invention can be combined with a single VH domain or repertoire of VH domains from any appropriate source and the resulting new antibodies tested to identify antibodies that bind to TRPV1.

Similarly, one or more, or preferably all three CDRs of the VH and/or VL domains of the invention can be grafted into a single VH and/or VL domain or a repertoire of VH and/or VL domains, as appropriate, and the resulting new antibodies tested to identify antibodies that bind to TRPV1.

Methods of carrying out the above described manipulation of amino acids and protein domains are well known to a person skilled in the art. For example, said manipulations could conveniently be carried out by genetic engineering at the nucleic acid level wherein nucleic acid molecules encoding appropriate binding proteins and domains thereof are modified such that the amino acid sequence of the resulting expressed protein is in turn modified in the appropriate way.

Testing the ability of one or more antibodies to bind to TRPV1 can be carried out by any appropriate method, which are well known and described in the art. Suitable methods are also described in the Examples section.

The invention also provides a range of conjugated antibodies and fragments thereof in which the anti-TRPV1 antibody is operatively attached to at least one other therapeutic agent. The term "immunoconjugate" is broadly used to define the operative association of the antibody with another effective agent (e.g. therapeutic agent) and is not intended to refer solely to any type of operative association, and is particularly not limited to chemical "conjugation". Recombinant fusion proteins are particularly contemplated. So long as the delivery or targeting agent is able to bind to the target and the therapeutic or diagnostic agent is sufficiently functional upon delivery, the mode of attachment will be suitable.

In some embodiments, antibodies of the invention are used (e.g. used therapeutically) in their "naked" unconjugated form.

Compositions comprising at least a first antibody of the invention or an immunoconjugate thereof constitute a further aspect of the present invention. Formulations (compositions) comprising one or more antibodies of the invention in admixture with a suitable diluent, carrier or excipient constitute a preferred embodiment of the present invention. Such formulations may be for pharmaceutical use and thus compositions of the invention are preferably pharmaceutically acceptable. Suitable diluents, excipients and carriers are known to the skilled man.

The compositions according to the invention may be presented, for example, in a form suitable for oral, nasal, parenteral, intraperitoneal, intravenal, topical or rectal administration. In some embodiments, a form suitable for intravenal administration is preferred.

The active compounds defined herein may be presented in the conventional pharmacological forms of administration, such as tablets, coated tablets, nasal sprays, solutions, emulsions, liposomes, powders, capsules or sustained release forms. Conventional pharmaceutical excipients as well as the usual methods of production may be employed for the preparation of these forms.

Injection solutions may, for example, be produced in the conventional manner, such as by the addition of preservation agents, such as p-hydroxybenzoates, or stabilizers, such as EDTA. The solutions may then be filled into injection vials or ampoules.

Nasal sprays may be formulated similarly in aqueous solution and packed into spray containers, either with an aerosol propellant or provided with means for manual compression.

The pharmaceutical compositions (formulations) of the present invention are preferably administered parenterally. Intravenous administration is preferred in some embodiments. Parenteral administration may be performed by subcutaneous, intramuscular or intravenous injection by means of a syringe. Alternatively, parenteral administration can be performed by means of an infusion pump. A further option is a composition which may be a powder or a liquid for the administration of the antibody in the form of a nasal or pulmonal spray. As a still further option, the antibodies of the invention can also be administered transdermally, e.g. from a patch, optionally an iontophoretic patch, or transmucosally, e.g. bucally.

Suitable dosage units can be determined by a person skilled in the art.

The pharmaceutical compositions may additionally comprise further active ingredients in the context of co-administration regimens or combined regimens.

A further aspect of the present invention provides the anti-TRPV1 antibodies of the invention for use in therapy, in particular for use in pain therapy (or management of pain).

In some embodiments, the pain is acute pain. In some embodiments, the pain is chronic pain.

In some embodiments, the acute pain is acute postoperative pain or acute post-traumatic pain.

In some embodiments, the chronic pain is nociceptive pain, for example osteoarthritis associated pain, arthritis associated pain, low back pain or neck pain.

In some embodiments, the chronic pain is neuropathic pain, for example painful diabetic polyneuropathy, postherpetic neuralgia, post traumatic neuralgia or radiculopathy.

In some embodiments, the chronic pain is painful bladder syndrome, vulvodynia, chronic pancreatitis or visceral pain.

In some embodiments, the pain is itch (either acute or chronic itch).

In some embodiments, the pain is selected from the group consisting of inflammatory pain, idiopathic pain and neuropathic pain.

"Therapy" includes treatment and prophylaxis, i.e. in includes both treatment and preventative uses. "Pain therapy" thus includes the treatment of pain and the prevention of pain.

Thus, in some embodiments, the present invention provides the anti-TRPV1 antibodies of the invention for use in the treatment of pain. Thus, in some embodiments, the present invention provides the anti-TRPV1 antibodies of the invention for use in the prevention of pain.

In some embodiments, pain to be treated (or prevented) in accordance with the present invention is pain that is associated with (or caused by, or characterised by) activation of TPRV1 by a stimulus that has the same (or an analogous) mechanism of activating of TRPV1 as capsaicin (e.g. activation by structural and/or functional analogues of capsaicin). In some embodiments, pain to be treated (or prevented) in accordance with the present invention is pain that is associated with (or caused by, or characterised by) activation of TPRV1 by one or more endogenous ligands (or endogenous activators). Such endogenous ligands may be lipidic compounds, for example lipidic compounds produced during inflammation or tissue injury (e.g. anandamide, metabolites of lipoxygenase and lysophosphatidic acid (LPA)). In some embodiments, the endogenous ligand is a structural and/or functional analogue of capsaicin.

In some embodiments, pain to be treated (or prevented) in accordance with the present invention is pain that is inducible by capsaicin or by analogues of capsaicin.

A further aspect of the present invention provides the anti-TRPV1 antibodies of the invention for use in inhibiting activation of TRPV1, e.g. for use in inhibiting activation of TPRV1 by a stimulus that has the same (or analogous) mechanism of activating TRPV1 as capsaicin (e.g. activation by structural and/or functional analogues of capsaicin).

In another aspect, the present invention provides immunoconjugates of the invention for use in therapy, in particular for use in the treatment of pain.

The in vivo methods and uses as described herein are generally carried out in a mammal. Any mammal may be treated, for example humans and any livestock, domestic or laboratory animal. Specific examples include mice, rats, pigs, cats, dogs, sheep, rabbits, cows and monkey. Preferably, however, the mammal is a human.

Thus, the term "animal" or "patient" as used herein includes any mammal, for example humans and any livestock, domestic or laboratory animal. Specific examples include mice, rats, pigs, cats, dogs, sheep, rabbits, cows and monkey. Preferably, however, the animal or patient is a human subject. Thus, subjects or patients treated in accordance with the present invention will preferably be humans.

In some embodiments, subjects or patients will we those having pain (or suffering from or experiencing pain), or those at risk of having pain or at risk of developing pain.

In some embodiments, the subject to be treated has a tissue in which TRPV1 has been up-regulated. In such cases, the subject may have a high (or higher) pain awareness.

In some embodiments, the subject to be treated has a tissue in which TRPV1 has been sensitized such that the subject has a low (or lower) pain threshold.

Alternatively viewed, the present invention provides a method of treating pain which method comprises administering to a patient in need thereof a therapeutically effective amount of an antibody of the invention as defined herein. Embodiments of the therapeutic uses of the invention described herein apply, mutatis mutandis, to this aspect of the invention.

The present invention also provides a method of treating a disease that is characterized by activation of TPRV1, e.g. activation by a stimulus that has the same (or an analogous) mechanism of activating of TRPV1 as capsaicin (e.g. activation by structural and/or functional analogues of capsaicin), which method comprises administering to a patient in need thereof a therapeutically effective amount of an antibody of the invention as defined herein. Embodiments of the therapeutic uses of the invention described herein apply, mutatis mutandis, to this aspect of the invention.

A therapeutically effective amount will be determined based on the clinical assessment and can be readily monitored.

Further alternatively viewed, the present invention provides the use of an antibody of the invention as defined herein in the manufacture of a medicament for use in therapy. Preferred therapy is pain therapy as described elsewhere herein. Embodiments of the therapeutic uses of the invention described herein apply, mutatis mutandis, to this aspect of the invention.

Further alternatively viewed, the present invention provides the use of an antibody of the invention as defined herein for the treatment of a disease that is characterised by activation of TPRV1, e.g. activation by a stimulus that has the same (or analogous) mechanism of activating of TRPV1 as capsaicin (e.g. activation by structural and/or functional analogues of capsaicin). A preferred use is for the treatment of pain. Embodiments of the therapeutic uses of the invention described herein apply, mutatis mutandis, to this aspect of the invention.

The antibodies and compositions and methods and uses of the present invention may be used in combination with other therapeutics and diagnostics. In terms of biological agents, preferably diagnostic or therapeutic agents, for use "in combination" with an anti-TRPV1 antibody in accordance with the present invention, the term "in combination" is succinctly used to cover a range of embodiments. The "in combination" terminology, unless otherwise specifically stated or made clear from the scientific terminology, thus applies to various formats of combined compositions, pharmaceuticals, cocktails, kits, methods, and first and second medical uses.

The "combined" embodiments of the invention thus include, for example, where an anti-TRPV1 antibody of the invention is a naked antibody and is used in combination with an agent or therapeutic agent that is not operatively attached thereto. In other "combined" embodiments of the invention, an anti-TRPV1 antibody of the invention is an immunoconjugate wherein the antibody is itself operatively associated or combined with the agent or therapeutic agent. The operative attachment includes all forms of direct and indirect attachment as described herein and known in the art.

The "combined" uses, particularly in terms of an anti-TRPV1 antibody of the invention in combination with therapeutic agents, also include combined compositions, pharmaceuticals, cocktails, kits, methods, and first and second medical uses wherein the therapeutic agent is in the form of a prodrug. In such embodiments, the activating component able to convert the prodrug to the functional form of the drug may again be operatively associated with the anti-TRPV1 antibodies of the present invention.

Thus, where combined compositions, pharmaceuticals, cocktails, kits, methods, and first and second medical uses are described, preferably in terms of diagnostic agents, and more preferably therapeutic agents, the combinations include anti-TRPV1 antibodies that are naked antibodies and immunoconjugates, and wherein practice of the in vivo embodiments of the invention involves the prior, simultaneous or subsequent administration of the naked antibodies or immunoconjugate and the biological, diagnostic or therapeutic agent; so long as, in some conjugated or unconjugated form, the overall provision of some form of the antibody and some form of the biological, diagnostic or therapeutic agent is achieved.

The foregoing and other explanations of the effects of the present invention are made for simplicity to explain the combined mode of operation, type of attached agent(s) and such like. This descriptive approach should not be interpreted as either an understatement or an oversimplification of the beneficial properties of the anti-TRPV1 antibodies of the invention. It will therefore be understood that such antibodies themselves have anti-TRPV1 properties and that immunoconjugates of such antibodies will maintain these properties and combine them with the properties of the attached agent; and further, that the combined effect of the antibody and any attached agent will typically be enhanced and/or magnified.

The invention therefore provides compositions, pharmaceutical compositions, therapeutic kits and medicinal cocktails comprising, optionally in at least a first composition or container, a biologically effective amount of at least a first anti-TRPV1 antibody of the invention, or an antigen-binding fragment or immunoconjugate of such an anti-TRPV1 antibody; and a biologically effective amount of at least a second biological agent, component or system.

The "at least a second biological agent, component or system" will often be a therapeutic or diagnostic agent, component or system, but it need not be. For example, the at least a second biological agent, component or system may comprise components for modification of the antibody and/or for attaching other agents to the antibody.

Where therapeutic or diagnostic agents are included as the at least a second biological agent, component or system, such therapeutics and/or diagnostics will typically be those for use in connection with the treatment or diagnosis of one or more of the disorders defined above.

Thus, in certain embodiments "at least a second therapeutic agent" will be included in the therapeutic kit or cocktail. The term is chosen in reference to the anti-TRPV1 antibody of the invention being the first therapeutic agent.

In certain embodiments of the present invention, the second therapeutic agent may be a further pain therapy agent or an agent for the treatment of disease that is associated with (or characterised by or causes) pain.

In terms of compositions, kits and/or medicaments of the invention, the combined effective amounts of the therapeutic agents may be comprised within a single container or container means, or comprised within distinct containers or container means. The cocktails will generally be admixed together for combined use. Agents formulated for intravenous administration will often be preferred. Imaging components may also be included. The kits may also comprise instructions for using the at least a first antibody and the one or more other biological agents included.

Speaking generally, the at least a second therapeutic agent may be administered to the animal or patient substantially simultaneously with the anti-TRPV1 antibody of the invention; such as from a single pharmaceutical composition or from two pharmaceutical compositions administered closely together.

Alternatively, the at least a second therapeutic agent may be administered to the animal or patient at a time sequential to the administration of the anti-TRPV1 antibody of the invention. "At a time sequential", as used herein, means "staggered", such that the at least a second therapeutic agent is administered to the animal or patient at a time distinct to the administration of the anti-TRPV1 antibody of the invention. Generally, the two agents are administered at times effectively spaced apart to allow the two agents to exert their respective therapeutic effects, i.e., they are administered at "biologically effective time intervals". The at least a second therapeutic agent may be administered to the animal or patient at a biologically effective time prior to the anti-TRPV1 antibody of the invention, or at a biologically effective time subsequent to that therapeutic.

A yet further aspect is a method of imaging of a subject or sample comprising the administration of an appropriate amount of an antibody or other protein of the invention as defined herein to the subject or sample and detecting the presence and/or amount and/or the location of the antibody or other protein of the invention in the subject or sample.

For use in the imaging applications, the antibodies of the invention may be labeled with a detectable marker such as a radio-opaque or radioisotope, such as $^3H$, $^{14}C$, $^{32}P$, $^{35}S$, $^{123}I$, $^{125}I$, $^{131}I$; a radioactive emitter (e.g. $\alpha$, $\beta$ or $\gamma$ emitters); a fluorescent (fluorophore) or chemiluminescent (chromophore) compound, such as fluorescein isothiocyanate, rhodamine or luciferin; an enzyme, such as alkaline phosphatase, beta-galactosidase or horseradish peroxidase; an imaging agent; or a metal ion; or a chemical moiety such as biotin which may be detected by binding to a specific cognate detectable moiety, e.g. labelled avidin/streptavidin. Methods of attaching a label to a binding protein, such as an antibody or antibody fragment, are known in the art. Such detectable markers allow the presence, amount or location of binding protein-antigen complexes in the test sample to be examined.

The invention also includes imaging agents comprising an antibody of the invention attached to a label that produces a detectable signal, directly or indirectly. Appropriate labels are described elsewhere herein.

The invention further includes kits comprising one or more of the isolated peptides (isolated epitopes), antibodies, immunoconjugates or compositions of the invention or one or more of the nucleic acid molecules encoding the antibodies of the invention, or one or more recombinant expression vectors comprising the nucleic acid sequences of the invention, or one or more host cells or viruses comprising the recombinant expression vectors or nucleic acid sequences of the invention. Preferably said kits are for use in the methods and uses as described herein, e.g. the therapeutic, methods as described herein, or are for use in the in vitro assays or methods as described herein. The antibody in such kits may be a "naked" antibody or may be an antibody conjugate as described elsewhere herein, e.g. may be an immunoconjugate. Preferably said kits comprise instructions for use of the kit components. Preferably said kits are for treating diseases as described elsewhere herein, and optionally comprise instructions for use of the kit components to treat such diseases.

The antibodies of the invention as defined herein may also be used as molecular tools for in vitro or in vivo applications and assays. As the antibodies have an antigen binding site, these can function as members of specific binding pairs and these molecules can be used in any assay where the particular binding pair member is required.

Thus, yet further aspects of the invention provide a reagent that comprises an antibody of the invention as defined herein and the use of such antibodies as molecular tools, for example in in vitro or in vivo assays.

List and Tables of Nucleotide (nt) and Amino Acid (a.a.) Sequences Disclosed Herein and their Sequence Identifiers (SEQ ID NOs)

All nucleotide sequences are recited herein 5 to 3' in line with convention in this technical field.

Amino acid sequence of human TRPV1

(SEQ ID NO: 1)

MKKWSSTDLGAAADPLQKDTCPDPLDGDPNSRPPPAKPQLSTAKSRTRLFGKGDSEEAFP

VDCPHEEGELDSCPTITVSPVITIQRPGDGPTGARLLSQDSVAASTEKTLRLYDRRSIFEAVA

QNNCQDLESLLLFLQKSKKHLTDNEFKDPETGKTCLLKAMLNLHDGQNTTIPLLLEIARQTD

SLKELVNASYTDSYYKGQTALHIAIERRNMALVTLLVENGADVQAAAHGDFFKKTKGRPGF

YFGELPLSLAACTNQLGIVKFLLQNSWQTADISARDSVGNTVLHALVEVADNTADNTKFVTS

MYNEILMLGAKLHPTLKLEELTNKKGMTPLALAAGTGKIGVLAYILQREIQEPECRHLSRKFT

EWAYGPVHSSLYDLSCIDTCEKNSVLEVIAYSSSETPNRHDMLLVEPLNRLLQDKWDRFVK

RIFYFNFLVYCLYMIIFTMAAYYRPVDGLPPFKMEKTGDYFRVTGEILSVLGGVYFFFRGIQY

FLQRRPSMKTLFVDSYSEMLFFLQSLFMLATVVLYFSHLKEYVASMVFSLALGWTNMLYYT

RGFQQMGIYAVMIEKMILRDLCRFMFVYIVFLFGFSTAVVTLIEDGKNDSLPSESTSHRWRG

PACRPPDSSYNSLYSTCLELFKFTIGMGDLEFTENYDFKAVFIILLLAYVILTYILLLNMLIALM

GETVNKIAQESKNIWKLQRAITILDTEKSFLKCMRKAFRSGKLLQVGYTPDGKDDYRWCFR

VDEVNWTTWNTNVGIINEDPGNCEGVKRTLSFSLRSSRVSGRHWKNFALVPLLREASARD

RQSAQPEEVYLRQFSGSLKPEDAEVFKSPAASGEK

Amino acid sequence of isolated peptide OTV3, not including additional modifications
present for the purposes of antibody generation (SEQ ID NO: 2)

IEDGKNDSLPSESTSHRWRGPASRPPDSSYNS

Amino acid sequence of the isolated peptide OTV4, not including additional
modifications present for the purposes of antibody generation (SEQ ID NO: 3)

IEDGKNDSLPSESTSHRWRGPACRPPDSSYNS

Amino acid sequence of the isolated peptide OTV5, not including additional
modifications present for the purposes of antibody generation (SEQ ID NO: 4)

IEDGKNDSLPSESTSHRWRGPASRPPDSSYNS

Amino acid sequence of the isolated peptide OTV6, not including additional
modifications present for the purposes of antibody generation (SEQ ID NO: 5)

IEDGKNDS

Amino acid sequence of the isolated peptide OTV7, not including additional
modifications present for the purposes of antibody generation (SEQ ID NO: 6)

IEDGKNDSLPSESTSH

Amino acid sequence of the isolated peptide OTV8, not including additional
modifications present for the purposes of antibody generation (SEQ ID NO: 7)

IEDGKNDSLPSESTSHRWRGPASR

Amino acid sequence of the isolated peptide OTV9, not including additional
modifications present for the purposes of antibody generation (SEQ ID NO: 8)

LPSESTSHRWRGPASRPPDSSYNS

Amino acid sequence of the isolated peptide OTV10, not including additional
modifications present for the purposes of antibody generation (SEQ ID NO: 9)

RWRGPASRPPDSSYNS

Amino acid sequence of the isolated peptide OTV11, not including additional
modifications present for the purposes of antibody generation (SEQ ID NO: 10)

PPDSSYNS

Amino acid sequence of the isolated peptide OTV12, not including additional
modifications present for the purposes of antibody generation (SEQ ID NO: 11)

LYSTSLELFKFTI

-continued

```
Amino acid sequence of the isolated peptide OTV13, not including additional
modifications present for the purposes of antibody generation
                                                        (SEQ ID NO: 12)

GMGDLEFTENYDF

Amino acid sequence of the isolated peptide OTV14, not including additional
modifications present for the purposes of antibody generation
                                                        (SEQ ID NO: 13)

EPMNYDPDGSIEDAG

Amino acid sequence of the isolated peptide OTV15, not including additional
modifications present for the purposes of antibody generation
                                                        (SEQ ID NO: 14)

ESTSHRWRGPA

Amino acid sequence of isolated peptide OTV3, including additional modifications
present for the purposes of antibody generation
                                                        (SEQ ID NO: 16)

CIEDGKNDSLPSESTSHRWRGPASRPPDSSYNS
```

As compared to SEQ ID NO:2, this peptide has an additional cysteine residue at the N-terminus.

```
    Amino acid sequence of the isolated peptide
    OTV4, including additional modifications
    present for the purposes of antibody
    generation
                                    (SEQ ID NO: 17)
    CIEDGKNDSLPSESTSHRWRGPACRPPDSSYNS
```

As compared to SEQ ID NO:3, this peptide has an additional cysteine residue at the N-terminus.

```
Amino acid sequence of the isolated peptide
OTV5, including additional modifications
present for the purposes of antibody
generation
                                (SEQ ID NO: 18)
(Pra-)CIEDGKNDSLPSESTSHRWRGPASRPPDSSYNSC(CONH₂)
```

As compared to SEQ ID NO:4, this peptide has an additional cysteine residue at the N-terminus and at the C-terminus. The peptide is also amidated at the C-terminus and has a Propargyl group (Pra-) at the N-terminus. This peptide is cyclic, with the peptide being connected (cyclized) via the terminal cysteine residues. The Propargyl group provides a means for attaching the peptide to a peptide carrier (e.g. KLH).

```
    Amino acid sequence of the isolated
    peptide OTV6, including additional
    modifications present for the purposes
    of antibody generation
                                    (SEQ ID NO: 19)
    CIEDGKNDS
```

As compared to SEQ ID NO:5, this peptide has an additional cysteine residue at the N-terminus.

```
    Amino acid sequence of the isolated
    peptide OTV7, including additional
    modifications present for the purposes
    of antibody generation
                                    (SEQ ID NO: 20)
    CIEDGKNDSLPSESTSH
```

As compared to SEQ ID NO:6, this peptide has an additional cysteine residue at the N-terminus.

```
    Amino acid sequence of the isolated
    peptide OTV8, including additional
    modifications present for the purposes
    of antibody generation
                                    (SEQ ID NO: 21)
    CIEDGKNDSLPSESTSHRWRGPASR
```

As compared to SEQ ID NO:7, this peptide has an additional cysteine residue at the N-terminus.

```
Amino acid sequence of the isolated peptide
OTV9, including additional modifications
present for the purposes of antibody
generation
                                (SEQ ID NO: 22)
LPSESTSHRWRGPASRPPDSSYNSC
```

As compared to SEQ ID NO:8, this peptide has an additional cysteine residue at the C-terminus.

```
Amino acid sequence of the isolated peptide
OTV10, including additional modifications
present for the purposes of antibody
generation
                                (SEQ ID NO: 23)
RWRGPASRPPDSSYNSC
```

As compared to SEQ ID NO:9, this peptide has an additional cysteine residue at the C-terminus.

```
Amino acid sequence of the isolated peptide
OTV11, including additional modifications
present for the purposes of antibody
generation
                                (SEQ ID NO: 24)
PPDSSYNSC
```

As compared to SEQ ID NO:10, this peptide has an additional cysteine residue at the C-terminus.

```
Amino acid sequence of the isolated peptide
OTV12, including additional modifications
present for the purposes of antibody
generation
                                (SEQ ID NO: 25)
LYSTSLELFKFTIC
```

As compared to SEQ ID NO:11, this peptide has an additional cysteine residue at the C-terminus.

```
Amino acid sequence of the isolated peptide
OTV13, including additional modifications
present for the purposes of antibody
generation
                           (SEQ ID NO: 26)

CGMGDLEFTENYDF
```

As compared to SEQ ID NO:12, this peptide has an additional cysteine residue at the N-terminus.

```
Amino acid sequence of the isolated peptide
OTV14, including additional modifications
present for the purposes of antibody
generation
                           (SEQ ID NO: 27)
(Pra-)CEPMNYDPDGSIEDAGC(-CONH2)
```

As compared to SEQ ID NO:13, this peptide has an additional cysteine residue at the N-terminus and at the C-terminus. The peptide is also amidated at the C-terminus and has a Propargyl group (Pra-) at the N-terminus. This peptide is cyclic and represents a conformational epitope, with the peptide being connected (cyclized) via the terminal cysteine residues. The Propargyl group provides a means for attaching the peptide to a peptide carrier (e.g. KLH).

```
Amino acid sequence of the isolated peptide
OTV15, including additional modifications
present for the purposes of antibody
generation
                           (SEQ ID NO: 28)
(Pra-)CESTSHRWRGPAC(-CONH2)
```

As compared to SEQ ID NO:14, this peptide has an additional cysteine residue at the N-terminus and at the C-terminus. The peptide is also amidated at the C-terminus and has a Propargyl group (Pra-) at the N-terminus. This peptide is cyclic, with the peptide being connected (cyclized) via the terminal cysteine residues. The Propargyl group provides a means for attaching the peptide to a peptide carrier (e.g. KLH).

TABLE A

| SEQ ID NO: | Description | Sequence |
|---|---|---|
| | | Sequences of antibody OT-Ab3 |
| | | OT-Ab3 |
| 15 | VH domain (nt) | GAGGTGAACCTTCTCGAGTCTGGAGGTGGCC TGGTGCAGCCTGGAGGATCCCTGAAACTCTC CTGTGCAGCCTCAGGATTCGATTTTCGTAGAT ACTGGATGAGTTGGGTCCGGCAGGCTCCAGG GAAAGGGCTAGAATGGATTGGAGAAATTAATC CAGATAGTAGTACGATAAACTATACGCCATCT CTAAAGGATGAATTCATCATCTCCAGAGACAA CGCCAAAAATACGCTGTACCTGCAAATGAGCA AAGTGAGATCTGAGGACACAGTCCTTTATTAC TGTTCAAGAGGGGGGGACTACTGGGGTCAAG GAACCTCAGTCACCGTCTCCTCA |
| 29 | VL domain (nt) | GATGTTGTGATGACCCAGACTCCACTCACTTT GTCGGTTCCCATTGGACAACCAGCCTCCATCT CTTGCAAGTCAAGTCAGAGCCTCTTAGATAGT GCTGGAAAGACATATTTGAATTGGTTGTTACA GAGGCCAGGCCAGTCTCCAAAGCGCCTGATC TATCTGGTGTCTAAACTGGACTCTGGAGTCCC TGACAAGTTCACTGGCAGTGGATCAGGGACA GATTTCACACTGAAAATCAGCAGAGTGGAGG CTGAGGATTTGGGAATTTATTATTGCTGGCAA GGTACACATTTTCCATACACGTTCGGCTCGGG GACAAAATTGGAAATAAAA |
| 39 | VH domain (aa) | EVNLLESGGGLVQPGGSLKLSCAASGFDFRRY WMSWVRQAPGKGLEWIGEINPDSSTINYTPSLK DEFIISRDNAKNTLYLQMSKVRSEDTVLYYCSRG GDYWGQGTSVTVSS |
| 40 | VL domain (aa) | DVVMTQTPLTLSVPIGQPASISCKSSQSLLDSAG KTYLNWLLQRPGQSPKRLIYLVSKLDSGVPDKF TGSGSGTDFTLKISRVEAEDLGIYYCWQGTHFP YTFGSGTKLEIK |
| 41 | Heavy CDR1 | RYWMS |
| 42 | Heavy CDR2 | EINPDSSTINYTPSLKD |
| 43 | Heavy CDR3 | GGDY |
| 44 | Light CDR1 | KSSQSLLDSAGKTYLN |
| 45 | Light CDR2 | LVSKLDS |
| 46 | Light CDR3 | WQGTHFPYT |
| 47 | Heavy FR1 | EVNLLESGGGLVQPGGSLKLSCAASGFDFR |

TABLE A-continued

| | Sequences of antibody OT-Ab3 | |
|---|---|---|
| SEQ ID NO: | Description | Sequence |
| 48 | Heavy FR2 | WVRQAPGKGLEWIG |
| 49 | Heavy FR3 | EFIISRDNAKNTLYLQMSKVRSEDTVLYYCSR |
| 50 | Heavy FR4 | WGQGTSVTVSS |
| 51 | Light FR1 | DVVMTQTPLTLSVPIGQPASISC |
| 52 | Light FR2 | WLLQRPGQSPKRLIY |
| 53 | Light FR3 | GVPDKFTGSGSGTDFTLKISRVEAEDLGIYYC |
| 54 | Light FR4 | FGSGTKLEIK |
| 93 | VH Signal peptide | MDFGLIFFIVALLKGVQC |
| 94 | VL Signal peptide | MSPAQFLFLLVLWIRDTNG |

TABLE B

| | Sequences of antibody OT-Ab2 | |
|---|---|---|
| SEQ ID NO: | Description | Sequence |
| | OT-Ab2 | |
| 55 | VH domain (nt) | GAGGTGAAGCTTCTCGAGTCTGGAGGTGGCC TGGTGCAGCCTGGAGGATCCCTGAAACTCTC CTGTGCAGCCTCAGGATTCGATTTTCGTAGAT ACTGGATGAGTTGGGTCCGGCAGGCTCCAGG GAAAGGGCTAGAATGGATTGGAGAAATTAATC CAGATAGTAGTACGATAAACTATACGCCATCT CTAAAGGATGAATTCATCATCTCCAGAGACAA CGCCAAAAATACGCTGTACCTGCAAATGAGCA AAGTGAGATCTGAGGACACAGTCCTTTATTAC TGTTCAAGAGGGGGGGACTACTGGGGTCAAG GAACCTCAGTCACCGTCTCCTCA |
| 56 | VL domain (nt) | GATGTTGTGATGACCCAGACTCCACTCACTTT GTCGGTTCCCATTGGACAACCAGCCTCCATCT CTTGCAAGTCAAGTCAGAGCCTCTTAGATAGT GCTGGAAAGACATATTTGAATTGGTTGTTACA GAGGCCAGGCCAGTCTCCAAAGCGCCTAATC TATCTGGTGTCTAAACTGGACTCTGGAGTCCC TGACAAGTTCACTGGCAGTGGATCAGGGACA GATTTCACACTGAAAATCAGCAGAGTGGAGG CTGAGGATTTGGGAATTTATTATTGCTGGCAA GGTACACATTTTCCATACACGTTCGGCTCGGG GACAAAATTGGAAATAAAA |
| 57 | VH domain (aa) | EVKLLESGGGLVQPGGSLKLSCAASGFDFRRY WMSWVRQAPGKGLEWIGEINPDSSTINYTPSLK DEFIISRDNAKNTLYLQMSKVRSEDTVLYYCSRG GDYWGQGTSVTVSS |
| 58 or 40 | VL domain (aa) | DVVMTQTPLTLSVPIGQPASISCKSSQSLLDSAG KTYLNWLLQRPGQSPKRLIYLVSKLDSGVPDKF TGSGSGTDFTLKISRVEAEDLGIYYCWQGTHFP YTFGSGTKLEIK |
| 59 or 41 | Heavy CDR1 | RYWMS |
| 60 or 42 | Heavy CDR2 | EINPDSSTINYTPSLKD |
| 61 or 43 | Heavy CDR3 | GGDY |
| 62 or 44 | Light CDR1 | KSSQSLLDSAGKTYLN |
| 63 or 45 | Light CDR2 | LVSKLDS |

TABLE B-continued

Sequences of antibody OT-Ab2

| SEQ ID NO: | Description | Sequence |
|---|---|---|
| 64 or 46 | Light CDR3 | WQGTHFPYT |
| 65 | Heavy FR1 | EVKLLESGGGLVQPGGSLKLSCAASGFDFR |
| 66 | Heavy FR2 | WVRQAPGKGLEWIG |
| 67 | Heavy FR3 | EFIISRDNAKNTLYLQMSKVRSEDTVLYYCSR |
| 68 | Heavy FR4 | WGQGTSVTVSS |
| 69 | Light FR1 | DVVMTQTPLTLSVPIGQPASISC |
| 70 | Light FR2 | WLLQRPGQSPKRLIY |
| 71 | Light FR3 | GVPDKFTGSGSGTDFTLKISRVEAEDLGIYYC |
| 72 | Light FR4 | FGSGTKLEIK |
| 95 | VH Signal peptide | MDFGLIFFIVALLKGVQC |
| 96 | VL Signal peptide | MSPAQFLFLLVLWIRETNG |

TABLE C

Sequences of antibody OT-Ab1

| SEQ ID NO: | Description | Sequence |
|---|---|---|
| | | OT-Ab1 |
| 73 | VH domain (nt) | GAGGTTCAGCTGCAGCAGTCTGGGGCAGAGC<br>TTGTGAAGCCAGGGGCCTCAGTCAAATTGTC<br>CTGCACAGCTTCTGGCTTCAACATTAAAGACA<br>CCTATATACACTGGGTGAAGCAGAGGCCTGA<br>ACAGGGCCTGGAGTGGATTGGAAGGATTGAT<br>CCTGCGAATGGTAATACTAGATATGACCCGAA<br>ATTCCAGGGCAAGGCCACTATAACAGCAGAC<br>ACATCCTCCAACACAGCCTACCTGCAACTCAG<br>CAGCCTGACATCTGAGGACACTGCCGTCTATT<br>ACTGTGCTAAAGTCTCGGGGGATAGGAGGTT<br>TTACTGGTACTTCGATGTCTGGGGCGCAGGG<br>ACCACGGTCACCGTCTCCTCA |
| 74 | VL domain (nt) | GACATTGTGATGTCACAGTCTCCATCCTCCCT<br>AGCTGTGTCAGTTGGAGAGAAGGTTACTATGA<br>GCTGCAAGTCCAGTCAGAGCCTTTTATATAGT<br>AGCAATCAAAAGAACTGTTTGGCCTGGTACCA<br>GCAGAAACCAGGGCAGTCTCCTAAACTGCTG<br>ATTTACTGGGCATCCACTAGGGAATCTGGGGT<br>CCCTGATCGCTTCACAGGCAGTGGATCTGGG<br>ACAGATTTCACTCTCACCATCAGCAGTGTGAA<br>GGCTGAAGACCTGGCAGTTTATTACTGTCAGC<br>AATATTATAGCTATCCGACGTTCGGTGGAGGC<br>ACCAAGCTGGAAATCAAA |
| 75 | VH domain (aa) | EVQLQQSGAELVKPGASVKLSCTASGFNIKDTYI<br>HWVKQRPEQGLEWIGRIDPANGNTRYDPKFQG<br>KATITADTSSNTAYLQLSSLTSEDTAVYYCAKVS<br>GDRRFYWYFDVWGAGTTVTVSS |
| 76 | VL domain (aa) | DIVMSQSPSSLAVSVGEKVTMSCKSSQSLLYSS<br>NQKNCLAWYQQKPGQSPKLLIYWASTRESGVP<br>DRFTGSGSGTDFTLTISSVKAEDLAVYYCQQYY<br>SYPTFGGGTKLEIK |
| 77 | Heavy CDR1 | DTYIH |
| 78 | Heavy CDR2 | RIDPANGNTRYDPKFQG |
| 79 | Heavy CDR3 | VSGDRRFYWYFDV |

TABLE C-continued

Sequences of antibody OT-Ab1

| SEQ ID NO: | Description | Sequence |
|---|---|---|
| 80 | Light CDR1 | KSSQSLLYSSNQKNCLA |
| 81 | Light CDR2 | WASTRES |
| 82 | Light CDR3 | QQYYSYPT |
| 83 | Heavy FR1 | EVQLQQSGAELVKPGASVKLSCTASGFNIK |
| 84 | Heavy FR2 | WVKQRPEQGLEWIG |
| 85 | Heavy FR3 | KATITADTSSNTAYLQLSSLTSEDTAVYYCAK |
| 86 | Heavy FR4 | WGAGTTVTVSS |
| 87 | Light FR1 | DIVMSQSPSSLAVSVGEKVTMSC |
| 88 | Light FR2 | WYQQKPGQSPKLLIY |
| 89 | Light FR3 | GVPDRFTGSGSGTDFTLTISSVKAEDLAVYYC |
| 90 | Light FR4 | FGGGTKLEIK |
| 97 | VH Signal peptide | MKCSWVIFFLMAVVTGVNS |
| 98 | VL Signal peptide | MDSQAQVLMLLLLWVSGTCG |

TABLE D

Consensus amino acid sequences

| SEQ ID NO: | Description | Sequence |
|---|---|---|
| 91 | Light CDR1 | K S S Q S L L $X_8$ S $X_{10}$ $X_{11}$ $X_{12}$ $X_{13}$ $X_{14}$ $X_{15}$ $X_{16}$ $X_{17}$<br>wherein $X_8$, $X_{10}$, $X_{11}$, $X_{12}$, $X_{13}$, $X_{14}$, $X_{15}$ and $X_{16}$ are any amino acid, and $X_{17}$ is any amino acid or no amino acid. |
| 92 | Light CDR1 | K S S Q S L L $X_8$ S $X_{10}$ $X_{11}$ $X_{12}$ $X_{13}$ $X_{14}$ $X_{15}$ $X_{16}$ $X_{17}$ |

TABLE D-continued

Consensus amino acid sequences

| SEQ ID NO: | Description | Sequence |
|---|---|---|
| | | wherein $X_8$ is D or Y; $X_{10}$ is A or S; $X_{11}$ is G or N; $X_{12}$ is K or Q; $X_{13}$ is T or K; $X_{14}$ is Y or N; $X_{15}$ is L or C, $X_{16}$ is N or L; $X_{17}$ is A or is no amino acid. |

The VL (i.e. light) CDR1 amino acid sequences of the OT-Ab1, OT-Ab-2 and OT-Ab-3 antibodies of the invention fall within the consensus sequences of the above Table D.

TABLE E

Sequences of antibody 32C8-1

32C8-1

| SEQ ID NO: | Description | Sequence |
|---|---|---|
| 99 | VH domain (nt) | GATGTGCAGCTTCAGGAGTCGGGACCTGGCCTGGTGAA<br>ACCTTCTCAGTCTCTGTCCCTCACCTGCACTGTCACTGACT<br>ACTCATTCACCAGTGATTTTGCCTGGAACTGGATCCGGC<br>AGTTTCCAGGAAACAAACTGGAGTGGATGGGCTTCATA<br>ACCTACAGTGATCACACTAACTATAACCCATCTCTCATAA<br>GTCGAATCTCTATCACTCGAGACACATCCAAGAACCAGT<br>TCTTCCTGCAGTTGAATTCTGTGACTCCTGAAGACACAG<br>CCACATATTACTGTGCAAGATCTACTACCTATTTTGACTA<br>CTGGGGCCAAGGCACCACTCTCACAGTCTCCTCA |
| 100 | VL domain (nt) | GATGTTTTGATGACCCAAACTCCACTCTCCCTGCCTGTCA<br>GTCTTGGAGATCAAGCCTCCATCTCTTGCAGATCTAGTC<br>AGACCATTTTACATAGTGATGGAAACACCTATTTAGAAT<br>GGTACCTGCAGAAACCAGGCCAGTCTCCAAAGCTCCTGA<br>TCTACAAAGTTTCCAACCGATTTTCTGGGGTCCCAGACA<br>GGTTCAGTGGCAGTGGATCAGGGACAGATTTCACACTC<br>AAGATCAGCAGAGTGGAGGCTGAGGATCTGGGAGTTT<br>ATTATTGCTTTCAAGGTTCACATGTTCCTCCCACGTTCGG<br>AGGGGGGACCAAGCTGGAAATAAAA |

TABLE E-continued

| SEQ ID NO: | Description | Sequence |
|---|---|---|
| 101 | VH domain (aa) | DVQLQESGPGLVKPSQSLSLTCTVTDYSFTSDFAWNWIRQ FPGNKLEWMGFITYSDHTNYNPSLISRISITRDTSKNQFFLQ LNSVTPEDTATYYCARSTTYFDYWGQGTTLTVSS |
| 102 | VL domain (aa) | DVLMTQTPLSLPVSLGDQASISCRSSQTILHSDGNTYLEWY LQKPGQSPKLLIYKVSNRFSGVPDRFSGSGSGTDFTLKISRV EAEDLGVYYCFQGSHVPPTFGGGTKLEIK |
| 103 | Heavy CDR1 | SDFAWN |
| 104 | Heavy CDR2 | FITYSDHTNYNPSLIS |
| 105 | Heavy CDR3 | STTYFDY |
| 106 | Light CDR1 | RSSQTILHSDGNTYLE |
| 107 | Light CDR2 | KVSNRFS |
| 108 | Light CDR3 | FQGSHVPPT |
| 109 | Heavy FR1 | DVQLQESGPGLVKPSQSLSLTCTVTDYSFT |
| 110 | Heavy FR2 | WIRQFPGNKLEWMG |
| 111 | Heavy FR3 | RISITRDTSKNQFFLQLNSVTPEDTATYYCAR |
| 112 | Heavy FR4 | WGQGTTLTVSS |
| 113 | Light FR1 | DVLMTQTPLSLPVSLGDQASISC |
| 114 | Light FR2 | WYLQKPGQSPKLLIY |
| 115 | Light FR3 | GVPDRFSGSGSGTDFTLKISRVEAEDLGVYYC |
| 116 | Light FR4 | FGGGTKLEIK |
| 117 | VH Signal peptide | MRVLILLWLFTAFPGILS |
| 118 | VL Signal peptide | MKLPVRLLVLMFWIPASST |

TABLE F

Sequences of antibody 33C9-1

| SEQ ID NO: | Description | Sequence |
|---|---|---|
| | 33C9-1 | |
| 119 | VH domain (nt) | GATGTGCAGCTTCAGGAGTCGGGACCTGGCCTGGTGAAA CCTTCTCAGTCTCTGTCCCTCACCTGCACTGTCACTGACT ACTCACTCACCAGTGATTATGCCTGGAACTGGATCCGGC AGTTTCCAGGGAACAAACTGGAATGGATGGGCTACATA ACCTACAGTGGTTACACTAACTACAACCCATCTCTCAAA AGTCGAATCTCTATCACTCGAGACACATCCAAGAACCCAG TTCTTCCTGCAGTTGAGTTCTGTGACTACTGAGGACACA GCCACATATTACTGTGCGAGATCTACTACCTTCTTTGACT ACTGGGGCCAAGGCACCACTCTCACAGTCTCCTCA |
| 120 | VL domain (nt) | GATGTTTTGATGACCCAAACTCCACTCTCCCTGCCTGTCA GTCTTGGAGATCAAGCCTCCATCTCTTGCAGATCTAGTC AGAGCATTGTACATAGTGATGGAAACACCTATTTAGAAT GGTACCTGCAGAAACCAGGCCAGTCTCCAAAGCTCCTGA TCTACAAAGTTTCCAATCGATTTTCTGGGGTCCCAGACA GGTTCAGTGGCAGTGGATCAGGGACAGATTTCACACTC AAGATCAGTAGACTGGAGGATGAGGATCTGGGAGTCTAT TACTGCTTTCAAGGTTCACATGTTCCTCCCACGTTCGGA GGGGGGACCAAGCTGGAAATAAAA |
| 121 | VH domain (aa) | DVQLQESGPGLVKPSQSLSLTCTVTDYSLTSDYAWNWIRQ FPGNKLEWMGYITYSGYTNYNPSLKSRISITRDTSKTQFFL QLSSVTTEDTATYYCARSTTFFDYWGQGTTLTVSS |

TABLE F-continued

Sequences of antibody 33C9-1

| SEQ ID NO: | Description | Sequence |
|---|---|---|
| 122 | VL domain (aa) | DVLMTQTPLSLPVSLGDQASISCRSSQSIVHSDGNTYLEWY LQKPGQSPKLLIYKVSNRFSGVPDRFSGSGSGTDFTLKISR LEDEDLGVYYCFQGSHVPPTFGGGTKLEIK |
| 123 | Heavy CDR1 | SDYAWN |
| 124 | Heavy CDR2 | YITYSGYTNYNPSLKS |
| 125 | Heavy CDR3 | STTFFDY |
| 126 | Light CDR1 | RSSQSIVHSDGNTYLE |
| 127 or 107 | Light CDR2 | KVSNRFS |
| 128 | Light CDR3 | FQGSHVPPT |
| 129 | Heavy FR1 | DVQLQESGPGLVKPSQSLSLTCTVTDYSLT |
| 130 | Heavy FR2 | WIRQFPGNKLEWMG |
| 131 | Heavy FR3 | RISITRDTSKTQFFLQLSSVTTEDTATYYCAR |
| 132 | Heavy FR4 | WGQGTTLTVSS |
| 133 | Light FR1 | DVLMTQTPLSLPVSLGDQASISC |
| 134 | Light FR2 | WYLQKPGQSPKLLIY |
| 135 | Light FR3 | GVPDRFSGSGSGTDFTLKISRLEDEDLGVYYC |
| 136 | Light FR4 | FGGGTKLEIK |
| 137 | VH Signal peptide | MRVLILLWLFTAFPGILS |
| 138 | VL Signal peptide | MKLPVRLLVLMFWIPASSS |

TABLE G

Sequences of antibody 34C11-1

| SEQ ID NO: | Description | Sequence |
|---|---|---|
| | | 34C11-1 |
| 139 | VH domain (nt) | GATGTGCAGCTTCAGGAGTCGGGACCTGGCCTGGTGAA ACCTTCTCAGTCTCTGTCCCTCACCTGCACTGTCACTGACT ACTCATTCACCAGTGATTTTGCCTGGAACTGGATCCGGC AGTTTCCAGGAAACAAACTGGAGTGGATGGGCTTCATA ACCTACAGTGATCACACTAACTACAACCCATCTCTCATAA GTCGAATCTCTATCACTCGAGACACATCCAAGAACCAGT TCTTCCTGCTGTTGAATTCTGTGACTCCTGAAGACACAGC CACATATTACTGTGCAAGATCTACTACCTATTTTGACTAC TGGGGCCAAGGCACCACTCTCACAGTCTCCTCA |
| 140 | VL domain (nt) | GATGTTTTGATGACCCAAACTCCTCTCTCCCTGCCTGTCA GTCTTGGAGATCAAGCCTCCATCTCTTGTAGATCTAGTCA GAGCATTTTACATAGTGATGGAAACACCTATTTAGAATG GTACCTGCAGAAACCAGGCCAGTCTCCAAAGCTCCTGAT CTACAAAGTTTCCAACCGATTTTCTGGGGTCCCAGACAG GTTCAGTGGCAGTGGATCAGGGACAGATTTCACACTCA AGATCAGCAGAGTGGAAACCGAGGATCTGGGAGTTTAT TATTGCTTTCAAGGTTCACATGTTCCTCCCACGTTCGGAG GGGGGACCAAGTTGGAAATAAAA |
| 141 | VH domain (aa) | DVQLQESGPGLVKPSQSLSLTCTVTDYSFTSDFAWNWIRQ FPGNKLEWMGFITYSDHTNYNPSLISRISITRDTSKNQFF LLLNSVTPEDTATYYCARSTTYFDYWGQGTTLTVSS |

TABLE G-continued

| Sequences of antibody 34C11-1 | | |
| --- | --- | --- |
| SEQ ID NO: | Description | Sequence |
| 142 | VL domain (aa) | DVLMTQTPLSLPVSLGDQASISCRSSQSILHSDGNTYLEWY LQKPGQSPKLLIYKVSNRFSGVPDRFSGSGSGTDFTLKISR VETEDLGVYYCFQGSHVPPTFGGGTKLEIK |
| 143 | Heavy CDR1 | SDFAWN |
| 144 | Heavy CDR2 | FITYSDHTNYNPSLIS |
| 145 | Heavy CDR3 | STTYFDY |
| 146 | Light CDR1 | RSSQSILHSDGNTYLE |
| 147 or 107 | Light CDR2 | KVSNRFS |
| 148 | Light CDR3 | FQGSHVPPT |
| 149 | Heavy FR1 | DVQLQESGPGLVKPSQSLSLTCTVTDYSFT |
| 150 | Heavy FR2 | WIRQFPGNKLEWMG |
| 151 | Heavy FR3 | RISITRDTSKNQFFLLLNSVTPEDTATYYCAR |
| 152 | Heavy FR4 | WGQGTTLTVSS |
| 153 | Light FR1 | DVLMTQTPLSLPVSLGDQASISC |
| 154 | Light FR2 | WYLQKPGQSPKLLIY |
| 155 | Light FR3 | GVPDRFSGSGSGTDFTLKISRVETEDLGVYYC |
| 156 | Light FR4 | FGGGTKLEIK |
| 157 | VH Signal peptide | MRVLILLWLFTAFPGILS |
| 158 | VL Signal peptide | MKLPVRLLVLMFWIPASTT |

TABLE H

| Sequences of antibody 40B10-1 | | |
| --- | --- | --- |
| SEQ ID NO: | Description | Sequence |
| 40B10-1 | | |
| 159 | VH domain (nt) | GATGTGCAGCTTCAGGAGTCGGGACCTGGCCTGGTGAA ACCTTCTCAGTCTCTGTCCCTCACCTGCACTGTCACTGAC TACTCATTCACCAGTGATTTTGCCTGGAACTGGATCCGGC AGTTTCCAGGAAACAAACTGGAGTGGATGGGCTTCATA ACCTACAGTGATCACACTAACTACAACCCATCTCTCATAA GTCGAATCTCTATCACTCGAGACACATCCAAGAACCAGT TCTTCCTGCTGTTGAATTCTGTGACTCCTGAAGCACAGC CACATATTACTGTGCAAGATCTACTACCTATTTTGACTAC TGGGGCCAAGGCACCACTCTCACAGTCTCCTCA |
| 160 | VL domain (nt) | GATGTTTTGATGACCCAAACTCCTCTCTCCCTGCCTGTCA GTCTTGGAGATCAAGCCTCCATCTCTTGTAGATCTAGTCA GAGCATTTTACATAGTGATGGAAACACCTATTTAGAATG GTACCTGCAGAAACCAGGCCAGTCTCCAAAGCTCCTGAT CTACAAAGTTTCCAACCGATTTTCTGGGGTCCCAGACAG GTTCAGTGGCAGTGGATCAGGGACAGATTTCACACTCA AGATCAGCAGAGTGGAAACCGAGGATCTGGGAGTTTATT ATTGCTTTCAAGGTTCACATGTTCCTCCCACGTTCGGAG GGGGGACCAAGTTGGAAATAAAA |
| 161 | VH domain (aa) | DVQLQESGPGLVKPSQSLSLTCTVTDYSFTSDFAWNWIRQ FPGNKLEWMGFITYSDHTNYNPSLISRISITRDTSKNQFF LLLNSVTPEDTATYYCARSTTYFDYWGQGTTLTVSS |

TABLE H-continued

| Sequences of antibody 40B10-1 | | |
|---|---|---|
| SEQ ID NO: | Description | Sequence |
| 162 | VL domain (aa) | DVLMTQTPLSLPVSLGDQASISCRSSQSILHSDGNTYLEWY LQKPGQSPKLLIYKVSNRFSGVPDRFSGSGSGTDFTLKISR VETEDLGVYYCFQGSHVPPTFGGGTKLEIK |
| 163 or 143 | Heavy CDR1 | SDFAWN |
| 164 or 144 | Heavy CDR2 | FITYSDHTNYNPSLIS |
| 165 or 145 | Heavy CDR3 | STTYFDY |
| 166 or 146 | Light CDR1 | RSSQSILHSDGNTYLE |
| 167 or 147 or 107 | Light CDR2 | KVSNRFS |
| 168 or 148 | Light CDR3 | FQGSHVPPT |
| 169 | Heavy FR1 | DVQLQESGPGLVKPSQSLSLTCTVTDYSFT |
| 170 | Heavy FR2 | WIRQFPGNKLEWMG |
| 171 | Heavy FR3 | RISITRDTSKNQFFLLLNSVTPEDTATYYCAR |
| 172 | Heavy FR4 | WGQGTTLTVSS |
| 173 | Light FR1 | DVLMTQTPLSLPVSLGDQASISC |
| 174 | Light FR2 | WYLQKPGQSPKLLIY |
| 175 | Light FR3 | GVPDRFSGSGSGTDFTLKISRVETEDLGVYYC |
| 176 | Light FR4 | FGGGTKLEIK |
| 177 | VH Signal peptide | MRVLILLWLFTAFPGILS |
| 178 | VL Signal peptide | MKLPVRLLVLMFWIPASTT |

TABLE I

| Sequences of antibody 41B5-1 | | |
|---|---|---|
| SEQ ID NO: | Description | Sequence |
| 41B5-1 | | |
| 179 | VH domain (nt) | GATGTGCAGCTTCAGGAGTCGGGACCTGGCCTGGTGAAA CCTTCTCAGTCTCTGTCCCTCACCTGCACTGTCACTGAC TACTCACTCACCAGTGATTATGCCTGGAACTGGATCCGGC AGTTTCCAGGGAACAAACTGGAATGGATGGGCTACATAA CCTACAGTGGTTACACTAACTTCAACCCATCTCTCAGAA GTCGAATCTCTATCACTCGAGACACATCCAAGACCCAGT TCTTCCTGCAGTTGAATTCTGTGACTGCTGAGGACACAG CCACATATTACTGTGTGAGATCTACTACTTACTTTGACT ATTGGGGCCAAGGCACCACTCTCACAGTCTCCTCA |
| 180 | VL domain (nt) | GATGTTTTGATGACCCAAACTCCACTCTCCCTGCCTGTCA GTCTTGGAGATCAAGCCTCCATCTCTTGCAGATCTAGTC AGAGCATTGTACATAGTGATGGAAACACCTATTTAGAAT GGTACCTGCAGAAACCAGGCCAGTCTCCAAAGCTCCTGA |

TABLE I-continued

Sequences of antibody 41B5-1

| SEQ ID NO: | Description | Sequence |
|---|---|---|
| | | TCTACAAAGTTTCCAACCGATTTTCTGGGGTCCCAGACA GGTTCAGTGGCAGTGGATCAGGGACAGATTTCACACTC AAGATCAATAGAGTGGAGGCTGAGGATCTGGGAATTTA TTACTGCTTTCAAGGTTCACATGTTCCTCCCACGTTCG GAGGGGGGACCAAGCTGGAAATAAAA |
| 181 | VH domain (aa) | DVQLQESGPGLVKPSQSLSLTCTVTDYSLTSDYAWNWIRQ FPGNKLEWMGYITYSGYTNFNPSLRSRISITRDTSKTQFF LQLNSVTAEDTATYYCVRSTTYFDYWGQGTTLTVSS |
| 182 | VL domain (aa) | DVLMTQTPLSLPVSLGDQASISCRSSQSIVHSDGNTYLEWY LQKPGQSPKLLIYKVSNRFSGVPDRFSGSGSGTDFTLKINR VEAEDLGIYYCFQGSHVPPTFGGGTKLEIK |
| 183 | Heavy CDR1 | SDYAWN |
| 184 | Heavy CDR2 | YITYSGYTNFNPSLRS |
| 185 | Heavy CDR3 | STTYFDY |
| 186 | Light CDR1 | RSSQSIVHSDGNTYLE |
| 187 or 107 | Light CDR2 | KVSNRFS |
| 188 | Light CDR3 | FQGSHVPPT |
| 189 | Heavy FR1 | DVQLQESGPGLVKPSQSLSLTCTVTDYSLT |
| 190 | Heavy FR2 | WIRQFPGNKLEWMG |
| 191 | Heavy FR3 | RISITRDTSKTQFFLQLNSVTAEDTATYYCVR |
| 192 | Heavy FR4 | WGQGTTLTVSS |
| 193 | Light FR1 | DVLMTQTPLSLPVSLGDQASISC |
| 194 | Light FR2 | WYLQKPGQSPKLLIY |
| 195 | Light FR3 | GVPDRFSGSGSGTDFTLKINRVEAEDLGIYYC |
| 196 | Light FR4 | FGGGTKLEIK |
| 197 | VH Signal peptide | MRVLILLWLFTAFPGILS |
| 198 | VL Signal peptide | MKLPVRLLVLMFWIPASSS |

TABLE J

Table J - Sequences of antibody 43D6-1

| SEQ ID NO: | Description | Sequence |
|---|---|---|
| | | 43D6-1 |
| 199 | VH domain (nt) | GATGTGCAGCTTCAGGAGTCGGGACCTGGCCT GGTGAAACCTTCTCAGTCTCTGTCCCTCACCT GCACTGTCACTGACTACTCACTCACCAGTGAT TATGCCTGGAACTGGATCCGGCAGTTTCCAGG GAACAAACTGGAATGGATGGGCTACATAACCT ACAGTGGTTACACTAACTACAACCCATCTCTC AAAAGTCGAGTCTCTATCACTCGAGACACATC CAAGACCCAGTTCTTCCTGCAGTTGAATTCTG TGACTACTGAGGACACAGCCACATATTACTGT GCGAGATCTACTGCCTACTTTGACTACTGGGG CCAAGGCACCACTCTCACAGTCTCCTCA |

TABLE J-continued

Table J - Sequences of antibody 43D6-1

| SEQ ID NO: | Description | Sequence |
|---|---|---|
| 200 | VL domain (nt) | GATGTTTTGATGACCCAAACTCCACTCTCCCT GCCTGTCAGTCTTGGAGATCAAGCCTCCATCT CTTGCCGATCTAGTCAGAGCGTTATACATAGT GATGGAAACACCTATTTAGAATGGTACCTGCA GAAACCAGGCCAGTCTCCAAAGCTCCTGATCT ACAAAGTTTCCAACCGATTTTCTGGGGTCCCA GACAGGTTCAGTGGCAGTGGATCAGGGACAGA TTTCACACTCAAGATCAGTAGAGTGGAGGCTG AGGATCTGGGAGTTTATTACTGCTTTCAAGGT TCACATGTTCCTCCCACGTTCGGAGGGGGGAC CAAGCTGGAAATAAAA |
| 201 | VH domain (aa) | DVQLQESGPGLVKPSQSLSLTCTVTDYSLTSD YAWNWIRQFPGNKLEWMGYITYSGYTNYNPSL KSRVSITRDTSKTQFFLQLNSVTTEDTATYYC ARSTAYFDYWGQGTTLTVSS |

TABLE J-continued

| SEQ ID NO: | Description | Sequence |
|---|---|---|
| | Table J - Sequences of antibody 43D6-1 | |
| 202 | VL domain (aa) | DVLMTQTPLSLPVSLGDQASISCRSSQSVIHS DGNTYLEWYLQKPGQSPKLLIYKVSNRFSGVP DRFSGSGSGTDFTLKISRVEAEDLGVYYCFQG SHVPPTFGGGTKLEIK |
| 203 | Heavy CDR1 | SDYAWN |
| 204 | Heavy CDR2 | YITYSGYTNYNPSLKS |
| 205 | Heavy CDR3 | STAYFDY |
| 206 | Light CDR1 | RSSQSVIHSDGNTYLE |
| 207 or 107 | Light CDR2 | KVSNRFS |
| 208 | Light CDR3 | FQGSHVPPT |
| 209 | Heavy FR1 | DVQLQESGPGLVKPSQSLSLTCTVTDYSLT |
| 210 | Heavy FR2 | WIRQFPGNKLEWMG |
| 211 | Heavy FR3 | RVSITRDTSKTQFFLQLNSVTTEDTATYYCAR |
| 212 | Heavy FR4 | WGQGTTLTVSS |
| 213 | Light FR1 | DVLMTQTPLSLPVSLGDQASISC |
| 214 | Light FR2 | WYLQKPGQSPKLLIY |
| 215 | Light FR3 | GVPDRFSGSGSGTDFTLKISRVEAEDLGVYYC |
| 216 | Light FR4 | FGGGTKLEIK |
| 217 | VH Signal peptide | MRVLILLWLFTAFPGVLS |
| 218 | VL Signal peptide | MKLPVRLLVLMFWIPASSS |

TABLE K

| SEQ ID NO: | Description | Sequence |
|---|---|---|
| | Table K - Sequences of antibody 44E8-1 | |
| | 44E8-1 | |
| 219 | VH domain (nt) | GATGTGCAGCTTCAGGAGTCGGGACCTGGCCT GGTGAGACCTTCTCAGTCTCTGTCCCTCACAT GCACTGTCACTGGCTACTCAATCACCAGTGAT TATGCCTGGAACTGGATCCGACAGTTTCCAGG |

TABLE K-continued

| SEQ ID NO: | Description | Sequence |
|---|---|---|
| | Table K - Sequences of antibody 44E8-1 | |
| | | AAACAAACTGGAGTGGATGGGCTTCATAACCT ACAGTGGTAATACTAACTACAACCCATCTCTC AAAAGTCGAATCTCTATCACTCGAGACACATC CAAGAACCAGTTCTTCCTGCAGTTGAATTCTG TGACTACTGAGGAGACAGCCACATATTACTGT GCAAGTAGTGGAAACTACTTTGACTATTGGGG CCAAGGCACCACTCTCACAGTCTCCTCA |
| 220 | VL domain (nt) | GATGTTTTGATGACCCAAACTCCACTCTCCCT GCCTGTCAGTCTTGGAGATCAAGCCTCCATCT CTTGCAGATCTAGTCAGAGCATTGTACATAGT GATGGAAACACCTATTTAGAATGGTACCTGCA GAAACCAGGCCAGCCTCCAAAGCTCCTGATCT ACAAAGTTTCCAACCGATTTTCTGGGGTCCCA GACAGGTTCAGTGGCAGTGGATCAGGGACGGA TTTCACACTCAAAATCAGCAGAGTGGAGGCTG AGGATCTGGGATTTTATTACTGCTTTCAAGGT TCACATGTTCCTCCGACGTTCGGTGGAGGCAC CAAGCTGGAAATCAAA |
| 221 | VH domain (aa) | DVQLQESGPGLVRPSQSLSLTCTVTGYSITSD YAWNWIRQFPGNKLEWMGFITYSGNTNYNPSL KSRISITRDTSKNQFFLQLNSVTTEETATYYC ASSGNYFDYWGQGTTLTVSS |
| 222 | VL domain (aa) | DVLMTQTPLSLPVSLGDQASISCRSSQSIVHS DGNTYLEWYLQKPGQPPKLLIYKVSNRFSGVP DRFSGSGSGTDFTLKISRV EAEDLGFYYCFQGSHVPPTFGGGTKLEIK |
| 223 | Heavy CDR1 | SDYAWN |
| 224 | Heavy CDR2 | FITYSGNTNYNPSLKS |
| 225 | Heavy CDR3 | SGNYFDY |
| 226 | Light CDR1 | RSSQSIVHSDGNTYLE |
| 227 or 107 | Light CDR2 | KVSNRFS |
| 228 | Light CDR3 | FQGSHVPPT |
| 229 | Heavy FR1 | DVQLQESGPGLVRPSQSLSLTCTVTGYSIT |
| 230 | Heavy FR2 | WIRQFPGNKLEWMG |
| 231 | Heavy FR3 | RISITRDTSKNQFFLQLNSVTTEETATYYCAS |
| 232 | Heavy FR4 | WGQGTTLTVSS |
| 233 | Light FR1 | DVLMTQTPLSLPVSLGDQASISC |
| 234 | Light FR2 | WYLQKPGQPPKLLIY |
| 235 | Light FR3 | GVPDRFSGSGSGTDFTLKISRVEAEDLGFYYC |
| 236 | Light FR4 | FGGGTKLEIK |

TABLE K-continued

| SEQ ID NO: | Description | Sequence |
|---|---|---|
| | Table K - Sequences of antibody 44E8-1 | |
| 237 | VH Signal peptide | MRVLILLWLFTAFPGILS |
| 238 | VL Signal peptide | MKLPVRLLVLMFWIPASSS |

TABLE L

| SEQ ID NO: | Description | Sequence |
|---|---|---|
| | Table L - Sequences of antibody 46B7-1 | |
| | 46B7-1 | |
| 239 | VH domain (nt) | GATGTGCAGCTTCAGGAGTCGGGACCTGGCCT GGTGAAACCTTCTCAGTCTCTGTCCCTCACCT GCACTGTCACTGACTACTCACTCACCAGTGAT TATGCCTGGAACTGGATCCGGCAGTTTCCAGG GAACAAACTGGAATGGATGGGCTACATAACCT ACAGTGGTTACACTAACTACAACCCATCTCTC AAAAGTCGAGTCTCTATCACTCGAGACACATC CAAGACCCAGTTCTTCCTGCAGTTGAATTCTG TGACTACTGAGGACACAGCCACATATTACTGT GCGAGATCTACTGCCTACTTTGACTACTGGGG CCAAGGCACCACTCTCACAGTCTCCTCA |
| 240 | VL domain (nt) | GATGTTTTGATGACCCAAACTCCACTCTCCCT GCCTGTCAGTCTTGGAGATCAAGCCTCCATCT CTTGCCGATCTAGTCAGAGCGTTATACATAGT GATGGAAACACCTATTTAGAATGGTACCTGCA GAAACCAGGCCAGTCTCCAAAGCTCCTGATCT ACAAAGTTTCCAACCGATTTTCTGGGGTCCCA GACAGGTTCAGTGGCAGTGGATCAGGGACAGA TTTCACACTCAAGATCAGTAGAGTGGAGGCTG AGGATCTGGGAGTTTATTACTGCTTTCAAGGT TCACATGTTCCTCCCACGTTCGGAGGGGGGAC CAAGCTGGAAATAAAA |
| 241 | VH domain (aa) | DVQLQESGPGLVKPSQSLSLTCTVTDYSLTSD YAWNWIRQFPGNKLEWMGYITYSGYTNYNPSL KSRVSITRDTSKTQFFLQLNSVTTEDTATYYC ARSTAYFDYWGQGTTLTVSS |
| 242 | VL domain (aa) | DVLMTQTPLSLPVSLGDQASISCRSSQSVIHS DGNTYLEWYLQKPGQSPKLLIYKVSNRFSGVP DRFSGSGSGTDFTLKISRVEAEDLGVYYCFQG SHVPPTFGGGTKLEIK |
| 243 or 203 | Heavy CDR1 | SDYAWN |
| 244 or 204 | Heavy CDR2 | YITYSGYTNYNPSLKS |
| 245 or 205 | Heavy CDR3 | STAYFDY |
| 246 or 206 | Light CDR1 | RSSQSVIHSDGNTYLE |

TABLE L-continued

| SEQ ID NO: | Description | Sequence |
|---|---|---|
| | Table L - Sequences of antibody 46B7-1 | |
| 247 or 207 or 107 | Light CDR2 | KVSNRFS |
| 248 or 208 | Light CDR3 | FQGSHVPPT |
| 249 | Heavy FR1 | DVQLQESGPGLVKPSQSLSLTCTVTDYSLT |
| 250 | Heavy FR2 | WIRQFPGNKLEWMG |
| 251 | Heavy FR3 | RVSITRDTSKTQFFLQLNSVTTEDTATYYCAR |
| 252 | Heavy FR4 | WGQGTTLTVSS |
| 253 | Light FR1 | DVLMTQTPLSLPVSLGDQASISC |
| 254 | Light FR2 | WYLQKPGQSPKLLIY |
| 255 | Light FR3 | GVPDRFSGSGSGTDFTLKISRVEAEDLGVYYC |
| 256 | Light FR4 | FGGGTKLEIK |
| 257 | VH Signal peptide | MRVLILLWLFTAFPGVLS |
| 258 | VL Signal peptide | MKLPVRLLVLMFWIPASSS |

TABLE M

| SEQ ID NO: | Description | Sequence |
|---|---|---|
| | Table M - Sequences of antibody 46D9-1 | |
| | 46D9-1 | |
| 259 | VH domain (nt) | GATGTGCAGCTTCAGGAGTCGGGACCTGGCCT GGTGAAACCTTCTCAGTCTCTGTCCCTCACCT GCACTGTCACTGACTACTCATTCACCAGTGAT TTTGCCTGGAACTGGATCCGGCAGTTTCCAGG AAACAAACTGGAGTGGATGGGCTTCATAACCT ACAGTGATCACACTAACTACAACCCATCTCTC ATAAGTCGAATCTCTATCACTCGAGACACATC CAAGAACCAGTTCTTCCTGCAGTTGAATTCTG TGACTCCTGAAGACACAGCCACATATTACTGT GCAAGATCTACTACCTATTTTGACTACTGGGG CCAAGGCACCACTCTCACAGTCTCCTCA |
| 260 | VL domain (nt) | GATGTTTTGATGACCCAAACTCCACTCTCCCT GCCTGTCAGTCTTGGAGATCAAGCCTCCATCT CTTGCAGATCTAGTCAGAGCATTTTACATAGT GATGGAAACACCTATTTAGAATGGTACATGCA GAAACCAGGCCAGTCTCCAAAGCTCCTGATCT ACAAAGTTTCCAACCGATTTTCTGGGGTCCCA GACAGGTTCAGTGGCAGTGGATCAGGGACAGA |

TABLE M-continued

TABLE M-continued

| SEQ ID NO: | Description | Sequence |
|---|---|---|
| | | TTTCACACTCAAGATCAGCAGAGTGGAGGCTG AGGATCTGGGAGTTTATTATTGCTTTCAAGGT TCACATGTTCCTCCCACGTTCGGAGGGGGGAC CAAGCTGGAAATAAAA |
| 261 | VH domain (aa) | DVQLQESGPGLVKPSQSLSLTCTVTDYSFTSD FAWNWIRQFPGNKLEWMGFITYSDHTNYNPSL ISRISITRDTSKNQFFLQLNSVTPEDTATYYC ARSTTYFDYWGQGTTLTVSS |
| 262 | VL domain (aa) | DVLMTQTPLSLPVSLGDQASISCRSSQSILHS DGNTYLEWYMQKPGQSPKLLIYKVSNRFSGVP DRFSGSGSGTDFTLKISRVEAEDLGVYYCFQG SHVPPTFGGGTKLEIK |
| 263 or 143 or 163 | Heavy CDR1 | SDFAWN |
| 264 or 144 or 164 | Heavy CDR2 | FITYSDHTNYNPSLIS |
| 265 or 145 or 165 | Heavy CDR3 | STTYFDY |
| 266 or 146 or 166 | Light CDR1 | RSSQSILHSDGNTYLE |
| 267 or 147 or 167 or 107 | Light CDR2 | KVSNRFS |
| 268 or 148 or 168 | Light CDR3 | FQGSHVPPT |
| 269 | Heavy FR1 | DVQLQESGPGLVKPSQSLSLTCTVTDYSFT |
| 270 | Heavy FR2 | WIRQFPGNKLEWMG |
| 271 | Heavy FR3 | RISITRDTSKNQFFLQLNSVTPEDTATYYCAR |
| 272 | Heavy FR4 | WGQGTTLTVSS |
| 273 | Light FR1 | DVLMTQTPLSLPVSLGDQASISC |
| 274 | Light FR2 | WYMQKPGQSPKLLIY |
| 275 | Light FR3 | GVPDRFSGSGSGTDFTLKISRVEAEDLGVYYC |

TABLE M-continued

Table M - Sequences of antibody 46D9-1

| SEQ ID NO: | Description | Sequence |
|---|---|---|
| 276 | Light FR4 | FGGGTKLEIK |
| 277 | VH Signal peptide | MRVLILLWLFTAFPGILS |
| 278 | VL Signal peptide | MKLPVRLLVLMFWIPASST |

TABLE N

Table N - Sequences of antibody 12C9-1

| SEQ ID NO: | Description | Sequence |
|---|---|---|
| | | 12C9-1 |
| 279 | VH domain (nt) | GAGGTCCAGCTGCAACAATCTGGACCTGAGCT GGTGAAGCCTGGGACTTCAGTGAAGATATCCT GTAAGGCTTCTGGATACACGTTCACTGGCTAC TATATGAACTGGGTGAAACAGAGCCATGGAAA GAGCCTTGAGTGGATTGGAGATATTAATCCTA ACAATGGTGGTACTGACTACAACCGGAAGTTC AAGGGCAAGGCCACATTGACTGTAGACAAGTC ATCCAGCACAGCCTACATGGAGGTCCGCAGCC TGACATCTGAGGACTCTGCAGTCTATTACTGT GCAAAAGACTTCGCTGTCTGGGGCACAGGGAC CACGGTCACCGTCTCCTCA |
| 280 | VL domain (nt) | GATGTTGTGATGACCCAGACTCCACTCACTTT GTCGGTTACCATTGGACAACCAGCCTCCATCT CTTGCAAGTCAAGTCAGAGCCTCTTAGATAGT GATGGAAAGACATATTTGAATTGGTTGTTACA GAGGCCAGGCCAGTCTCCAAAGCGCCTAATCT ATCTGGTGTCTAAACTGGACTCTGGAGCCCCT GACAGGTTCACTGGCAGTGGATCAGGGACAGA TTTCACACTGAAAATCAACAGAGTGGAGGCTG AGGATTTGGGAGTTTATTATTGCTGGCAAGGT ACACATTTTCCCACGTTCGGAGGGGGGACCAA GCTGGAAATAAAA |
| 281 | VH domain (aa) | EVQLQQSGPELVKPGTSVKISCKASGYTFTGY YMNWVKQSHGKSLEWIGDINPNNGGTDYNRKF KGKATLTVDKSSSTAYMEVRSLTSEDSAVYYC AKDFAVWGTGTTVTVSS |
| 282 | VL domain (aa) | DVVMTQTPLTLSVTIGQPASISCKSSQSLLDS DGKTYLNWLLQRPGQSPKRLIYLVSKLDSGAP DRFTGSGSGTDFTLKINRVEAEDLGVYYCWQG THFPTFGGGTKLEIK |
| 283 | Heavy CDR1 | GYYMN |
| 284 | Heavy CDR2 | DINPNNGGTDYNRKFKG |
| 285 | Heavy CDR3 | DFAV |
| 286 | Light CDR1 | KSSQSLLDSDGKTYLN |
| 287 or 45 | Light CDR2 | LVSKLDS |

TABLE N-continued

| SEQ ID NO: | Description | Sequence |
|---|---|---|
| | Table N - Sequences of antibody 12C9-1 | |
| 288 | Light CDR3 | WQGTHFPT |
| 289 | Heavy FR1 | EVQLQQSGPELVKPGTSVKISCKASGYTFT |
| 290 | Heavy FR2 | WVKQSHGKSLEWIG |
| 291 | Heavy FR3 | KATLTVDKSSSTAYMEVRSLTSEDSAVYYCAK |
| 292 | Heavy FR4 | WGTGTTVTVSS |
| 293 | Light FR1 | DVVMTQTPLTLSVTIGQPASISC |
| 294 | Light FR2 | WLLQRPGQSPKRLIY |
| 295 | Light FR3 | GAPDRFTGSGSGTDFTLKINRVEAEDLGVYYC |
| 296 | Light FR4 | FGGGTKLEIK |
| 297 | VH Signal peptide | MGWSWIFLFLLSGTAGVLS |
| 298 | VL Signal peptide | MSPAQFLFLLVLWIREANG |

TABLE O

| SEQ ID NO: | Description | Sequence |
|---|---|---|
| | Table O - Sequences of antibody 12G6-1 | |
| | 12G6-1 | |
| 299 | VH domain (nt) | GAGGTGCAGCTGGTGGAGTCTGGGGGAGACTT AGTAAACCCTGGAGGGTCCCTGAAACTCTCCT GTGCAGCCTCTGGATTCACTATCAGTAACTAT GGCATGTCTTGGGTTCGCCAGACTCCAGACAA GAGGCTGGAATGGGTCGCTATCATTATTAGAG ATGGTGGTTATACCTACTATCCAGACAGTGTG AAGGGGCGATTCACCATCTCCAGAGACAGTGC CAAAAACACCCTGTACCTGCAAATGAGCAGTC TGAAGTCTGAAGACACAGCCATGTATTACTGT GCAAGACATGAGTATTACTTTGACTTCTGGGG CCAAGGCACCACTCTCACAGTCTCCTCA |
| 300 | VL domain (nt) | GATGTTTTGATGACCCAAACTCCACTCTCCCT GCCTGTCAGTCTTGGAGATCAAGCCTCCATCT CTTGCAGATCTAGTCAGACCATTTTACATAGT GATGGAAACACCTATTTAGAATGGTACCTGCA GAAACCAGGCCAGTCTCCAAAGCTCCTGATCT ACAAAGTTTCCAACCGATTTTCTGGGGTCCCA GACAGGTTCAGTGGCAGTGGATCAGGGACAGA TTTCACACTCAAGATCAGCAGAGTGGAGGCTG AGGATCTGGGAGTTTATTACTGCTCTCAAGGT TCACATTTTCCTCCGACGTTCGGTGGAGGCAC CAAGGTGGAAATCAAA |

TABLE O-continued

| SEQ ID NO: | Description | Sequence |
|---|---|---|
| | Table O - Sequences of antibody 12G6-1 | |
| 301 | VH domain (aa) | EVQLVESGGDLVNPGGSLKLSCAASGFTISNY GMSWVRQTPDKRLEWVAIIIRDGGYTYYPDSV KGRFTISRDSAKNTLYLQMSSLKSEDTAMYYC ARHEYYFDFWGQGTTLTVSS |
| 302 | VL domain (aa) | DVLMTQTPLSLPVSLGDQASISCRSSQTILHS DGNTYLEWYLQKPGQSPKLLIYKVSNRFSGVP DRFSGSGSGTDFTLKISRVEAEDLGVYYCSQG SHFPPTFGGGTKVEIK |
| 303 | Heavy CDR1 | NYGMS |
| 304 | Heavy CDR2 | IIIRDGGYTYYPDSVKG |
| 305 | Heavy CDR3 | HEYYFDF |
| 306 | Light CDR1 | RSSQTILHSDGNTYLE |
| 307 or 107 | Light CDR2 | KVSNRFS |
| 308 | Light CDR3 | SQGSHFPPT |
| 309 | Heavy FR1 | EVQLVESGGDLVNPGGSLKLSCAASGFTIS |
| 310 | Heavy FR2 | WVRQTPDKRLEWVA |
| 311 | Heavy FR3 | RFTISRDSAKNTLYLQMSSLKSEDTAMYYCAR |
| 312 | Heavy FR4 | WGQGTTLTVSS |
| 313 | Light FR1 | DVLMTQTPLSLPVSLGDQASISC |
| 314 | Light FR2 | WYLQKPGQSPKLLIY |
| 315 | Light FR3 | GVPDRFSGSGSGTDFTLKISRVEAEDLGVYYC |
| 316 | Light FR4 | FGGGTKVEIK |
| 317 | VH Signal peptide | MNFGLSLIFLALILKGVQC |
| 318 | VL Signal peptide | MKLPVRLLVLMFWIPESSS |

TABLE P

Table P - Sequences of antibody 15D8-1

| SEQ ID NO: | Description | Sequence |
|---|---|---|
| | | 15D8-1 |
| 319 | VH domain (nt) | GATGTGCAGCTGGTGGAGTCTGGGGGAGGCTT AGTGCAGCCTGGAGGGTCCCGGAAACTCTCCT GTGCAGCCTCTGGATTCACTTTCAGTAGCTTT GGAATGCACTGGGTTCGTCAGGCTCCAGAGAA GGGGCTGGAGTGGGTCGCATACATTAGTAGTG GCAGTAGTACCATCTACTATGCAGACACAGTG AAGGGCCGATTCACCATCTCCAGAGACAATCC CAAGAACACCCTGTTCCTGCAAATGACCAGTC TAAGGTCTGAGGACACGGCCATGTATTACTGT GCAAGACGGGGTAATGCTATGGACTACTGGGG TCAAGGAACCTCAGTCACCGTCTCCTCA |
| 320 | VL domain (nt) | AACATTATGATGACACAGTCGCCATCATCTCT GGCTGTGTCTGCAGGAGAAAAGGTCACTATGA GCTGTAAGTCCAGTCAAAGTGTTTTATACAGT TCAAATCAGAAGAACTACTTGGCCTGGTACCA GCAGAAACCAGGGCAGTCTCCTAAACTGCTGA TCTACTGGGCATCCACTAGGGAATCTGGTGTC CCTGATCGCTTCACAGGCAGTGGATCTGGGAC AGATTTTACTCTTACCATCAGCAGTGTACAAG CTGAAGACCTGGCAGTTTATTACTGTCATCAA TATTTCTCCTCGTGGACGTTCGGTGGAGGCAC CAAGCTGGAAATCAAA |
| 321 | VH domain (aa) | DVQLVESGGGLVQPGGSRKLSCAASGFTFSSF GMHWVRQAPEKGLEWVAYISSGSSTIYYADTV KGRFTISRDNPKNTLFLQMTSLRSEDTAMYYC ARRGNAMDYWGQGTSVTVSS |
| 322 | VL domain (aa) | NIMMTQSPSSLAVSAGEKVTMSCKSSQSVLYS SNQKNYLAWYQQKPGQSPKLLIYWASTRESGV PDRFTGSGSGTDFTLTISSVQAEDLAVYYCHQ YFSSWTFGGGTKLEIK |
| 323 | Heavy CDR1 | SFGMH |
| 324 | Heavy CDR2 | YISSGSSTIYYADTVKG |
| 325 | Heavy CDR3 | RGNAMDY |
| 326 | Light CDR1 | KSSQSVLYSSNQKNYLA |
| 327 or 81 | Light CDR2 | WASTRES |
| 328 | Light CDR3 | HQYFSSWT |
| 329 | Heavy FR1 | DVQLVESGGGLVQPGGSRKLSCAASGFTFS |
| 330 | Heavy FR2 | WVRQAPEKGLEWVA |
| 331 | Heavy FR3 | RFTISRDNPKNTLFLQMTSLRSEDTAMYYCAR |
| 332 | Heavy FR4 | WGQGTSVTVSS |
| 333 | Light FR1 | NIMMTQSPSSLAVSAGEKVTMSC |
| 334 | Light FR2 | WYQQKPGQSPKLLIY |

TABLE P-continued

Table P - Sequences of antibody 15D8-1

| SEQ ID NO: | Description | Sequence |
|---|---|---|
| 335 | Light FR3 | GVPDRFTGSGSGTDFTLTISSVQAEDLAVYYC |
| 336 | Light FR4 | FGGGTKLEIK |
| 337 | VH Signal peptide | MDSRLNLVFLVLILKGVQC |
| 338 | VL Signal peptide | MESQTQVFLSLLLWVSGTCG |

TABLE Q

Table Q - Sequences of antibody 16F1-1

| SEQ ID NO: | Description | Sequence |
|---|---|---|
| | | 16F1-1 |
| 339 | VH domain (nt) | GAGGTGCAGCTTGTTGAGTCTGGTGGAGGACT GGTGCAGCCTAAAGGATCATTGAAACTCTCAT GTGCCGCCTCTGGTTTCACCTTCAATACCTAT GCCATGCACTGGGTCCGCCAGGCTCCAGGAAA GGGTTTGGAATGGGTTGCTCGCATAAGAAGTA AAAGTAGTAATTATGCAACATATTATGCCGAT TCAGTGAAAGACAGATTCACCATCTCCAGAGA TGATTCACAAAGCATGGTCTATCTGCAGATGA ACAACCTGAAAACTGAGGACACAGCCATGTAT TACTGTGTGAGAAAGGGGGATGGTTACGACGG CTGGTTTGCTTACTGGGGCCAAGGGACTCTGG TCACTGTCTCTGCA |
| 340 | VL domain (nt) | GACATCCAGATGACTCAGTCTCCAGCCTCCCT ATCTGCATCTGTGGGAGAAACTGTCACCATCA CATGTCGACCAAGTGGGAATATTCACAATTAT TTAGTATGGTATCAGCAGAAACAGGGAAAATC TCCTCAGGTCCTGGTCTATAATTCAAAAACCT TAGCAGATGGTGTGCCATCACGGTTCAGTGGC AGTGGATCAGGAACACAGTATTCTCTCAAGAT CAACAGCCTGCAGCCTGAAGATTTTGGGACTT ATTACTGTCAACATTTTTGGAGTACTCCACTC ACGTTCGGTGCTGGGACCAAACTGGAGCTGAA A |
| 341 | VH domain (aa) | EVQLVESGGGLVQPKGSLKLSCAASGFTFNTY AMHWVRQAPGKGLEWVARIRSKSSNYATYYAD SVKDRFTISRDDSQSMVYLQMNNLKTEDTAMY YCVRKGDGYDGWFAYWGQGTLVTVSA |
| 342 | VL domain (aa) | DIQMTQSPASLSASVGETVTITCRPSGNIHNY GLVWYQQKQKSPQVLVYNSKTLADGVPSRFSG SGSGTQYSLKINSLQPEDFGTYYCQHFWSTPL TFGAGTKLELK |
| 343 | Heavy CDR1 | TYAMH |
| 344 | Heavy CDR2 | RIRSKSSNYATYYADSVKD |
| 345 | Heavy CDR3 | KGDGYDGWFAY |

TABLE Q-continued

Table Q – Sequences of antibody 16F1-1

| SEQ ID NO: | Description | Sequence |
|---|---|---|
| 346 | Light CDR1 | RPSGNIHNYLV |
| 347 | Light CDR2 | NSKTLAD |
| 348 | Light CDR3 | QHFWSTPLT |
| 349 | Heavy FR1 | EVQLVESGGGLVQPKGSLKLSCAASGFTFN |
| 350 | Heavy FR2 | WVRQAPGKGLEWVA |
| 351 | Heavy FR3 | RFTISRDDSQSMVYLQMNNLKTEDTAMYYCVR |
| 352 | Heavy FR4 | WGQGTLVTVSA |
| 353 | Light FR1 | DIQMTQSPASLSASVGETVTITC |
| 354 | Light FR2 | WYQQKQGKSPQVLVY |
| 355 | Light FR3 | GVPSRFSGSGSGTQYSLKINSLQPEDFGTYYC |
| 356 | Light FR4 | FGAGTKLELK |
| 357 | VH Signal peptide | MVLGLKWVFFVVLYQGVHC |
| 358 | VL Signal peptide | MSVLTQVLALLLLWLTGARC |

TABLE R

Table R – Sequences of antibody 17E11-1

| SEQ ID NO: | Description | Sequence |
|---|---|---|
| | | 17E11-1 |
| 359 | VH domain (nt) | GAGGTTCAACTGCTGCAGTCTGTGGCAGAGCT TGTGAGGCCAGGGGCCTCAGTCAAGTTGTCCT GCACAGCTTCTGGCTTCAACATTAAAAACACC TTTATACACTGGCTGAAGCAGAGGCCTGAGCA GGGCCTGGAGTGGATTGGAAAGATTGATCCTG CGAATGGTAATATTAGATGTGCCCCGAAGTTC CAGGGCAAGGCCACTATAACTGCAGACACATC CTCCAACACAGCCTACCTGCAGCTCAGCAGCC TGACATCTGGGGCACTGCCATCTATTACTGT GGTAGAGGTACTATGTTAGTAGGTCACTTCTA CTGGTACTTCGATGTCTGGGGCACAGGGACCA CGGTCACCGTCTCCTCA |
| 360 | VL domain (nt) | GACATTGTGATGTCACAGTCTCCATCCTCCCT CAGCTGTGTAGTTGGAGAGAAGATTACTATGA GCTGCAAGTCCAGTCAGAGCCTTTTATATAGT AGCAATCAAAAGAACTACTTGGCCTGGTACCA GCAGAAACCGGGGCAGTCTCCTAAACTGCTGA TTTACTGGGCATCCACTAGGGAATCTGGGGTC CCTGATCGCTTCTCAGGCAGTGGATCTGGAC |

TABLE R-continued

Table R – Sequences of antibody 17E11-1

| SEQ ID NO: | Description | Sequence |
|---|---|---|
| | | AGATTTCACTCTCACCATCAGCAGTGTGAAGA CTGAAGACCTGGCAATTTTTTACTGTCAGCAA TATTATTACTATCCTCCCACGTTCGGTGCTGG GACCAAGCTGGAGCTGAGA |
| 361 | VH domain (aa) | EVQLLQSVAELVRPGASVKLSCTASGFNIKNT FIHWLKQRPEQGLEWIGKIDPANGNIRCAPKF QGKATITADTSSNTAYLQLSSLTSGDTAIYYC GRGTMLVGHFYWYFDVWGTGTTVTVSS |
| 362 | VL domain (aa) | DIVMSQSPSSLAVSVGEKITMSCKSSQSLLYS SNQKNYLAWYQQKPGQSPKLLIYWASTRESGV PDRFSGSGSGTDFTLTISSVKTEDLAIFYCQQ YYYYPPTFGAGTKLELR |
| 363 | Heavy CDR1 | NTFIH |
| 364 | Heavy CDR2 | KIDPANGNIRCAPKFQG |
| 365 | Heavy CDR3 | GTMLVGHFYWYFDV |
| 366 | Light CDR1 | KSSQSLLYSSNQKNYLA |
| 367 or 81 | Light CDR2 | WASTRES |
| 368 | Light CDR3 | QQYYYYPPT |
| 369 | Heavy FR1 | EVQLLQSVAELVRPGASVKLSCTASGFNIK |
| 370 | Heavy FR2 | WLKQRPEQGLEWIG |
| 371 | Heavy FR3 | KATITADTSSNTAYLQLSSLTSGDTAIYYCGR |
| 372 | Heavy FR4 | WGTGTTVTVSS |
| 373 | Light FR1 | DIVMSQSPSSLAVSVGEKITMSC |
| 374 | Light FR2 | WYQQKPGQSPKLLIY |
| 375 | Light FR3 | GVPDRFSGSGSGTDFTLTISSVKTEDLAIFYC |
| 376 | Light FR4 | FGAGTKLELR |
| 377 | VH Signal peptide | MKFSWVIFFLMAVVTGVNS |
| 378 | VL Signal peptide | MDSQAQVLMLLLLWVSGTCG |

TABLE S

Table S - Sequences of antibody 17E9-1

| SEQ ID NO: | Description | Sequence |
|---|---|---|
| | | 17E9-1 |
| 379 | VH domain (nt) | GAGGTTCAACTGCTGCAGTCTGTGGCAGAGCT TGTGAGGCCAGGGGCCTCAGTCAAGTTGTCCT GCACAGCTTCTGGCTTCAACATTAAAAACACC TTTATACACTGGCTGAAGCAGAGGCCTGAGCA GGGCCTGGAGTGGATTGGAAAGATTGATCCTG CGAATGGTAATATTAGATGTGCCCCGAAGTTC CAGGGCAAGGCCACTATAACTGCAGACACATC CTCCAACACAGCCTACCTGCAGCTCAGCAGCC TGACATCTGGGGACACTGCCATCTATTACTGT GGTAGAGGTACTATGTTAGTAGGTCACTTCTA CTGGTACTTCGATGTCTGGGGCACAGGGACCA CGGTCACCGTCTCCTCA |
| 380 | VL domain (nt) | GACATTGTGATGTCACAGTCTCCATCCTCCCT AGCTGTGTCAGTTGGAGAGAAGATTACTATGA GCTGCAAGTCCAGTCAGAGCCTTTTATATAGT AGCAATCAAAAGAACTACTTGGCCTGGTACCA GCAGAAACCGGGGCAGTCTCCTAAACTGCTGA TTTACTGGGCATCCACTAGGGAATCTGGGGTC CCTGATCGCTTCTCAGGCAGTGGATCTGGGAC AGATTTCACTCTCACCATCAGCAGTGTGAAGA CTGAAGACCTGGCAATTTTTTACTGTCAGCAA TATTATTACTATCCTCCCACGTTCGGTGCTGG GACCAAGCTGGAGCTGAGA |
| 381 | VH domain (aa) | EVQLLQSVAELVRPGASVKLSCTASGFNIKNT FIHWLKQRPEQGLEWIGKIDPANGNIRCAPKF QGKATITADTSSNTAYLQLSSLTSGDTAIYYC GRGTMLVGHFYWYFDVWGTGTTVTVSS |
| 382 | VL domain (aa) | DIVMSQSPSSLAVSVGEKITMSCKSSQSLLYS SNQKNYLAWYQQKPGQSPKLLIYWASTRESGV PDRFSGSGSGTDFTLTISSVKTEDLAIFYCQQ YYYYPPTFGAGTKLELR |
| 383 or 363 | Heavy CDR1 | NTFIH |
| 384 or 364 | Heavy CDR2 | KIDPANGNIRCAPKFQG |
| 385 or 365 | Heavy CDR3 | GTMLVGHFYWYFDV |
| 386 or 366 | Light CDR1 | KSSQSLLYSSNQKNYLA |
| 387 or 367 or 81 | Light CDR2 | WASTRES |
| 388 or 368 | Light CDR3 | QQYYYYPPT |
| 389 | Heavy FR1 | EVQLLQSVAELVRPGASVKLSCTASGFNIK |
| 390 | Heavy FR2 | WLKQRPEQGLEWIG |
| 391 | Heavy FR3 | KATITADTSSNTAYLQLSSLTSGDTAIYYCGR |
| 392 | Heavy FR4 | WGTGTTVTVSS |

TABLE S-continued

Table S - Sequences of antibody 17E9-1

| SEQ ID NO: | Description | Sequence |
|---|---|---|
| 393 | Light FR1 | DIVMSQSPSSLAVSVGEKITMSC |
| 394 | Light FR2 | WYQQKPGQSPKLLIY |
| 395 | Light FR3 | GVPDRFSGSGSGTDFTLTISSVKTEDLAIFYC |
| 396 | Light FR4 | FGAGTKLELR |
| 397 | VH Signal peptide | MKFSWVIFFLMAVVTGVNS |
| 398 | VL Signal peptide | MDSQAQVLMLLLLWVSGTCG |

TABLE T

Table T - Sequences of antibody 18E10-1

| SEQ ID NO: | Description | Sequence |
|---|---|---|
| | | 18E10-1 |
| 399 | VH domain (nt) | GAGGTCCAGGTGCAACAATCTGGACCTGAGCT GGTGAAGCCTGGGGCTTCAGTGAAGATATCCT GTAAGGCTTCTGGATACACGTTCACTGGCTAC TACATGAACTGGGTGAAGCAGAGCCATGGAAA GAGCCTTGAGTGGATTGGAGATATTAATCCTA ACAATGGTGGCACTGACTACAATCGGAAGTTC AAGGGCAAGGCCACATTGACTGTAGACAAGTC CTCCAGCACAGCCTACATGGAGCTCCGCAGCC TGACATCTGAGGACTCTGCAGTCTATTACTGT AGCAAGGACTTCGCTGTCTGGGGCACAGGGAC CACGGTCACCGTCTCCTCA |
| 400 | VL domain (nt) | GATGTTGTGATGACCCAGACTCCACTCACTTT GTCGGTTACCATTGGACAACCAGCCTCCATCT CTTGCAAGTCAAGTCAGAGCCTCTTAGATAGT GATGGAAAGACATATTTGAATTGGTTGTTACA GAGGCCAGGCCAGTCTCCAAAGCGCCTAATCT ATCTGGTGTCTAAACTGGACTCTGGAGCCCCT GACAGGTTCACTGGCAGTGGATCAGGGACAGA TTTCACACTGAAAATCAGCAGAGTGGAGGCTG AGGATTTGGGAGTTTATTATTGCTGGCAAGGT ACACATTTTCCCACGTTCGGAGGGGGGACCAA GCTGGAAATAAAA |
| 401 | VH domain (aa) | EVQVQQSGPELVKPGASVKISCKASGYTFTGY YMNWVKQSHGKSLEWIGDINPNNGGTDYNRKF KGKATLTVDKSSSTAYMELRSLTSEDSAVYYC ARDFAVWGTGTTVTVSS |
| 402 | VL domain (aa) | DVVMTQTPLTLSVTIGQPASISCKSSQSLLDS DGKTYLNWLLQRPGQSPKRLIYLVSKLDSGAP DRFTGSGSGTDFTLKISRVEAEDLGVYYCWQG THFPTFGGGTKLEIK |
| 403 or 283 | Heavy CDR1 | GYYMN |

TABLE T-continued

| SEQ ID NO: | Description | Sequence |
|---|---|---|
| 404 or 284 | Heavy CDR2 | DINPNNGGTDYNRKFKG |
| 405 or 285 | Heavy CDR3 | DFAV |
| 406 or 286 | Light CDR1 | KSSQSLLDSDGKTYLN |
| 407 or 287 or 45 | Light CDR2 | LVSKLDS |
| 408 or 288 | Light CDR3 | WQGTHFPT |
| 409 | Heavy FR1 | EVQVQQSGPELVKPGASVKISCKASGYTFT |
| 410 | Heavy FR2 | WVKQSHGKSLEWIG |
| 411 | Heavy FR3 | KATLTVDKSSSTAYMELRSLTSEDSAVYYCAR |
| 412 | Heavy FR4 | WGTGTTVTVSS |
| 413 | Light FR1 | DVVMTQTPLTLSVTIGQPASISC |
| 414 | Light FR2 | WLLQRPGQSPKRLIY |
| 415 | Light FR3 | GAPDRFTGSGSGTDFTLKISRVEAEDLGVYYC |
| 416 | Light FR4 | FGGGTKLEIK |
| 417 | VH Signal peptide | MGWSWIFLFLLSGTAGVLS |
| 418 | VL Signal peptide | MSPAQFLFLLVLWIRETNG |

TABLE U

Table U - Sequences of antibody R4P1-C1

| SEQ ID NO: | Description | Sequence |
|---|---|---|
| | | R4P1-C1 |
| 419 | VH domain (nt) | CAGGTGCAGCTGCAGCAGTCCGGCCCCGGACT GGTGAAGCCTAGCCAGACACTGTCCCTGACCT GCGCCATCAGCGGCGATAGCGTGAGCTCCAAT TCCGCCGCCTGGAATTGGATCAGGCAGTCCCC TAGCAGAGGCCTGGAGTGGCTGGGCAGAACCT ACTACAGAAGCAAGTGGTACAATGATTACGCC GTGAGCGTGAAGTCCAGGATCACCATCAACCC |

TABLE U-continued

Table U - Sequences of antibody R4P1-C1

| SEQ ID NO: | Description | Sequence |
|---|---|---|
| | | CGACACCTCCAAGAACCAGTTCTCCCTGCAGC TGAATAGCGTGACACCTGAGGATACAGCCGTG TACTACTGTGCCAGAGACGATTACGACCCCGT GGGCATGTACGCCTTCGATATCTGGGGCCAGG GCACCCTGGTGACAGTGAGCAGC |
| 420 | VL domain (nt) | CTGCCTGTGCTGACCCAGCCCCCCTCTGCCAG CGGAACACCCGGACAGAGGGTGACCATCTCCT GCTCCGGCAGCAGCTCCAATATCGGCAGCAAT ACAGTGAACTGGTACCAGCAGCTGCCCGGCAC CGCCCCTAAGCTGCTGATCTACAGGAACACCC AGAGACCCTCCGGCGTGCCTGATAGATTTTCC GGCAGCAAGAGCGGCACCAGCGCCAGCCTGGC CATCTCCGGACTGCAGAGCGAGGACGAGGCCG ACTACTACTGTGAGGCCTGGGATGATTCCATG AGGGGCGCCGCCTTTGGCGGCGGAACCCAACT GACAGTGCTG |
| 421 | VH domain (aa) | QVQLQQSGPGLVKPSQTLSLTCAISGDSVSSN SAAWNWIRQSPSRGLEWLGRTYYRSKWYNDYA VSVKSRITINPDTSKNQFSLQLNSVTPEDTAV YYCARDDYDPVGMYAFDIWGQGTLVTVSS |
| 422 | VL domain (aa) | LPVLTQPPSASGTPGQRVTISCSGSSSNIGSN TVNWYQQLPGTAPKLLIYRNTQRPSGVPDRFS GSKSGTSASLAISGLQSEDEADYYCEAWDDSM RGAAFGGGTQLTVL |
| 423 | Heavy CDR1 | GDSVSSNSAA |
| 424 | Heavy CDR2 | TYYRSKWYN |
| 425 | Heavy CDR3 | ARDDYDPVGMYAFDI |
| 426 | Light CDR1 | SSNIGSNT |
| 427 | Light CDR2 | RNT |
| 428 | Light CDR3 | EAWDDSMRGAA |
| 429 | Heavy FR1 | QVQLQQSGPGLVKPSQTLSLTCAIS |
| 430 | Heavy FR2 | WNWIRQSPSRGLEWLGR |
| 431 | Heavy FR3 | DYAVSVKSRITINPDTSKNQFSLQLNSVTPED TAVYYC |
| 432 | Heavy FR4 | WGQGTLVTVSS |
| 433 | Light FR1 | LPVLTQPPSASGTPGQRVTISCSGS |
| 434 | Light FR2 | VNWYQQLPGTAPKLLIY |
| 435 | Light FR3 | QRPSGVPDRFSGSKSGTSASLAISGLQSEDEA DYYC |
| 436 | Light FR4 | FGGGTQLTVL |
| 437 | VH Signal peptide | MKHLWFFLLLVAAPRWVLS |

TABLE U-continued

Table U - Sequences of antibody R4P1-C1

| SEQ ID NO: | Description | Sequence |
|---|---|---|
| 438 | VL Signal peptide | MVLQTQVFISLLLWISGAYG |

TABLE V

Consensus amino acid sequences

| SEQ ID NO: | Description | Sequence |
|---|---|---|
| 440 | Heavy CDR1 | S D $X_3$ A W N<br>wherein $X_3$ is any amino acid. |
| 441 | Heavy CDR1 | S D $X_3$ A W N<br>wherein $X_3$ is F or Y. |
| 442 | Heavy CDR2 | $X_1$ I Y S $X_6$ $X_7$ T N $X_{10}$ N P S L $X_{15}$ S<br>wherein $X_1$, $X_6$, $X_7$, $X_{10}$ and $X_{15}$ are any amino acid |
| 443 | Heavy CDR2 | $X_1$ I T Y S $X_6$ $X_7$ T N $X_{10}$ N P S L $X_{15}$ S<br>wherein $X_1$ is Y or F, $X_6$ is G or D, $X_7$ is Y or H or N, $X_{10}$ is Y or F, and $X_{15}$ is K or I or R. |
| 444 | Heavy CDR3 | S $X_2$ $X_3$ $X_4$ F D Y<br>wherein $X_2$, $X_3$ and $X_4$ are any amino acid. |
| 445 | Heavy CDR3 | S $X_2$ $X_3$ $X_4$ F D Y<br>wherein $X_2$ is T or G, $X_3$ is T or A or N, and $X_4$ is Y or F. |
| 446 | Light CDR1 | R S S Q $X_5$ $X_6$ $X_7$ H S D G N T Y L E<br>wherein $X_5$, $X_6$ and $X_7$ are any amino acid. |
| 447 | Light CDR1 | R S S Q $X_5$ $X_6$ $X_7$ H S D G N T Y L E<br>wherein $X_5$ is S or T, $X_6$ is I or V, and $X_7$ is L or V or I. |

The VH (i.e. heavy) CDR1, CDR2 and CDR3 amino acid sequences and the VL (light) CDR 1 sequences of the 32C8-1, 33C9-1, 34C11-1, 40B10-1, 41B5-1, 43D6-1, 44E8-1, 46B7-1 and 46D9-1 antibodies of the invention each fall within the consensus sequences of the above Table V.

TABLE X

Consensus amino acid sequences

| SEQ ID NO: | Description | Sequence |
|---|---|---|
| 448 | Light CDR1 | $X_1$ S S Q $X_5$ $X_6$ $X_7$ $X_8$ S $X_{10}$ $X_{11}$ $X_{12}$ $X_{13}$ $X_{14}$ $X_{15}$ L $X_{17}$<br>wherein $X_1$, $X_5$, $X_6$, $X_7$, $X_8$, $X_{10}$, $X_{11}$, $X_{13}$, $X_{14}$, $X_{15}$ and $X_{17}$ are any amino acid, and $X_{12}$ is any amino acid or no amino acid. |
| 449 | Light CDR1 | $X_1$ S S Q $X_5$ $X_6$ $X_7$ $X_8$ S $X_{10}$ $X_{11}$ $X_{12}$ $X_{13}$ $X_{14}$ $X_{15}$ L $X_{17}$<br>wherein $X_1$ is K or R, $X_5$ is S or T, $X_6$ is L or V or I, $X_7$ is L or V or I, $X_8$ is H or D or Y, $X_{10}$ is S or A or D, $X_{11}$ is G or N, $X_{13}$ is K or N, $X_{14}$ is T or N, $X_{15}$ is Y or C and $X_{17}$ is A or N or E, and $X_{12}$ is Q or no amino acid. |

The VL (i.e. light) CDR1 amino acid sequences of the 32C8-1, 33C9-1, 34C11-1, 40B10-1, 41B5-1, 43D6-1, 44E8-1, 46B7-1, 46D9-1, 12G9-1, 12G6-1, 15D8-1, 17E11-1, 17E9-1, 18E10-1, OT-Ab1, OT-Ab2 and OT-Ab3 antibodies of the invention each fall within the consensus sequences of the above Table X.

TABLE Z

Consensus amino acid sequences

| SEQ ID NO: | Description | Sequence |
|---|---|---|
| 450 | Light CDR3 | $X_1$ Q G $X_4$ H $X_6$ P $X_8$ T<br>wherein $X_1$, $X_4$ and $X_6$ are any amino acid, and $X_8$ is any amino acid or no amino acid. |
| 451 | Light CDR3 | $X_1$ Q G $X_4$ H $X_6$ P $X_8$ T<br>wherein $X_1$ is W or For S; $X_4$ is T or S; $X_6$ is F or V; $X_8$ is P or Y or is no amino acid. |

The VL (i.e. light) CDR3 amino acid sequences of the 32C8-1, 33C9-1, 34C11-1, 40B10-1, 41B5-1, 43D6-1, 44E8-1, 46B7-1, 46D9-1, 12C9-1, 12G6-1, 18E10-1, OT-Ab2 and OT-Ab3 antibodies of the invention each fall within the consensus sequences of the above Table Z.

TABLE BB

Consensus amino acid sequences

| SEQ ID NO: | Description | Sequence |
|---|---|---|
| 452 | Light CDR3 | Q Q Y Y $X_5$ Y P $X_8$ $X_9$<br>wherein $X_5$ and $X_8$ are any amino acid, and $X_9$ is any amino acid or no amino acid. |
| 439 | Light CDR3 | Q Q Y Y $X_5$ Y P $X_8$ $X_9$<br>wherein $X_5$ is Y or S; $X_8$ is P or T; $X_9$ is T or is no amino acid. |

The VL (i.e. light) CDR3 amino acid sequences of the 17E11-1, 17E9-1 and OT-Ab1 antibodies of the invention each fall within the consensus sequences of the above Table BB.

The invention will now be further described in the following non-limiting Example with reference to the following drawings:

FIG. 1: Inhibition of heat activated or capsaicin activated TRPV1-activity after treatment with the OTV4 polyclonal antibody (cap n=6, heat n=6), the OTV5 polyclonal antibody (cap n=6, heat n=5), the OTV12 polyclonal antibody (cap n=7, heat n=5), AMG 517 (cap n=5, heat n=4), Mavatrep (cap n=3, heat n=3) or control antibody (cap n=4, heat n=7). The control antibody was Rabbit Gamma Globulin (RRID: AB_2532177—Thermofisher, catalogue number 31887). Mavatrep and AMG517 were evaluated at equal concentrations for analysing the inhibition of heat and capsaicin activation of TRPV1, whereas the inhibition of heat activation of TRPV1 with the antibodies was evaluated at 5× the concentration of the antibodies used for the evaluation of the inhibition of capsaicin activation of TRPV1. Inhibition of capsaicin activation was evaluated with patch-clamp experiments and inhibition of heat activation was evaluated with fluorescence intensity recordings of heat induced TRPV1-mediated calcium uptake.

Figure 2:
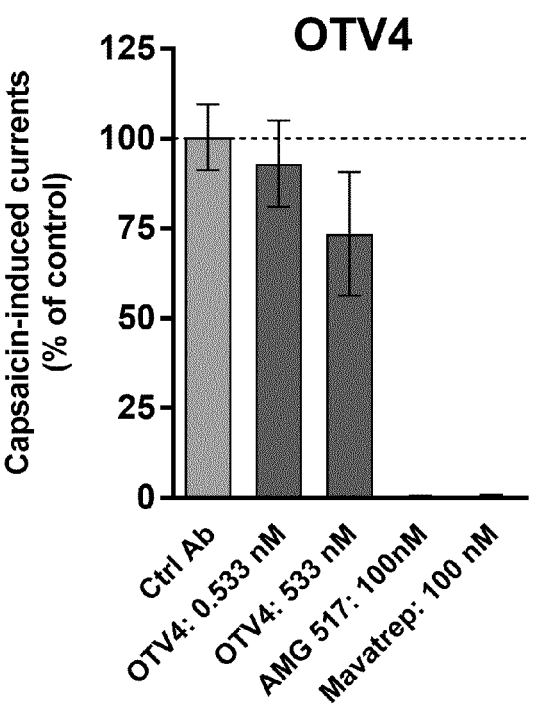
Figure 2:
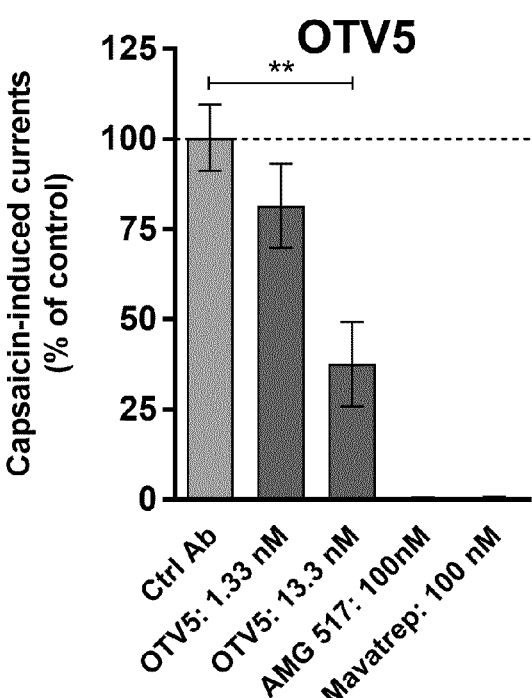
Figure 2:
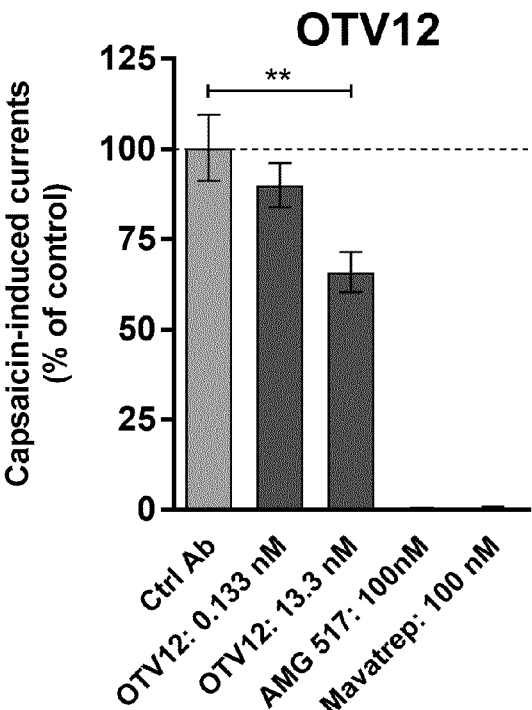

FIG. 2: Patch clamp recordings of capsaicin induced TRPV1-currents after treatment with the OTV4 polyclonal antibody, the OTV5 polyclonal antibody, the OTV12 polyclonal antibody, AMG 517, Mavatrep or control antibody. The control antibody was Rabbit Gamma Globulin (RRID: AB_2532177—Thermofisher, catalogue number 31887). The current amplitude for activation with capsaicin in the presence of antibody, calculated as a percentage of the amplitude for activation with capsaicin only, after treatment with either 0.533 nM OTV4 (n=6), 533 nM OTV4 (n=6), 1.33 nM OTV5 (n=8), 13.3 nM OTV5 (n=6), 0.133 nM OTV12 (n=6), 13.3 nM OTV12 (n=7), 100 nM Mavatrep (n=5), 100 nM AMG 517 (n=3) or 730 nM control antibody (n=4) is presented. Each data point (n) represents a single cell. Antibody treatments (OTV4, OTV5 & OTV12) were compared to treatment with control antibody. Statistical analysis was performed with one-way analysis of variance in combination with Dunnett's post-hoc test and p<0.05 was considered as statistically significant. Two asterisks=p value of less than 0.01. Data is presented as mean±SEM.

Figure 3:
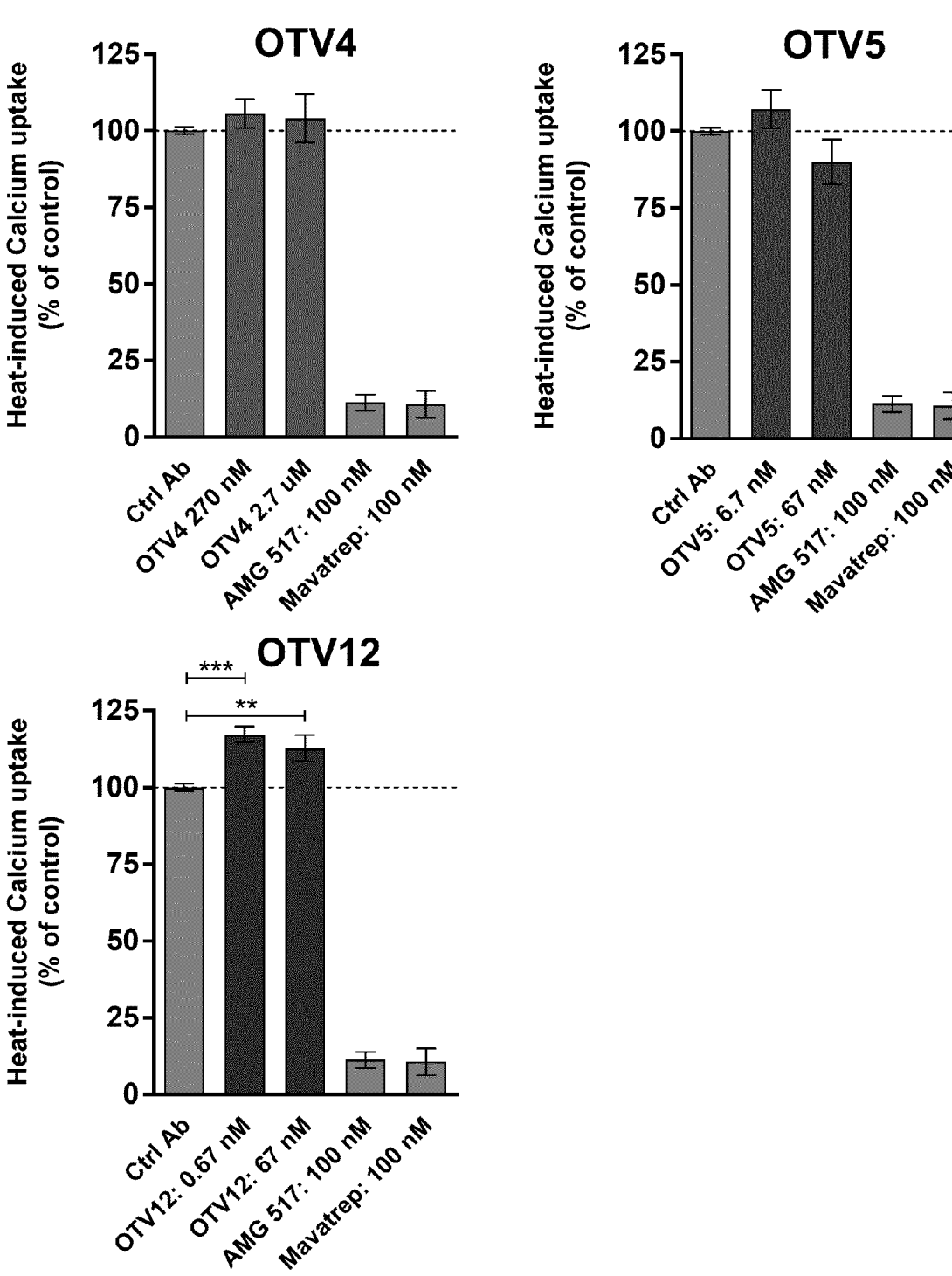

FIG. 3: Fluorescence intensity recordings of heat induced TRPV1-mediated calcium uptake after treatment with the OTV4 polyclonal antibody, the OTV5 polyclonal antibody, the OTV12 polyclonal antibody, AMG 517, Mavatrep or control antibody. The control antibody was Rabbit Gamma Globulin (RRID: AB_2532177—Thermofisher, catalogue number 31887). Antibody solutions was delivered using the Biopen® and heating to 42° C. was achieved using a heat-probe. Two pulses of heat were applied, the second in the presence of antibody. The fluorescence intensity for the second activation with heat in the presence of antibody, calculated as a percentage of the amplitude for the first activation with heat only, after treatment with either 270 nM OTV4 antibody (n=10), 2.7 µM OTV4 antibody (n=6), 6.7 nM OTV5 antibody (n=5), 67 nM OTV5 antibody (n=5), 0.67 nM OTV12 antibody (n=6), 67 nM OTV12 antibody (n=5), 100 nM Mavatrep (n=3), 100 nM AMG-517 (n=4) or 37 µM control antibody (n=7) is presented. Each data point (n) equals the number of experiments, each containing one or more cells. Antibody treatments (OTV4, OTV5 & OTV12) were compared to treatment with control antibody. Statistical analysis was performed with one-way analysis of variance in combination with Dunnett's post-hoc test and p<0.05 was considered as statistically significant. Two asterisks=p value of less than 0.01. Three asterisks=p value of less than 0.001. Data is presented as mean±SEM.

Figure 4:
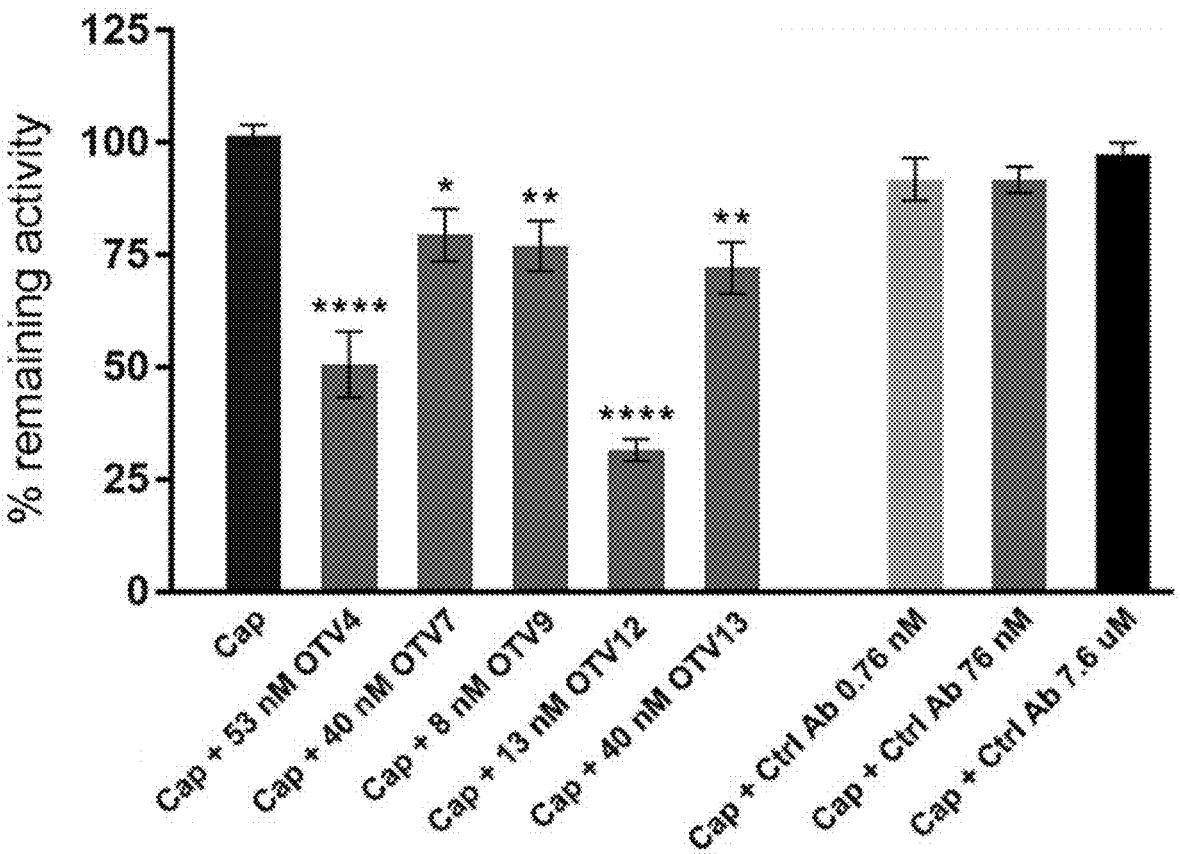

FIG. 4: Inhibition of capsaicin-induced calcium uptake for hTRPV1. CHO cells expressing hTRPV1 were incubated with the calcium indicator Fluo-3 AM for 30 min at 37° C. followed by antibody (OTV4 n=12, OTV7 n=12, OTV9 n=12, OTV12 n=11, OTV13 n=11, or control antibody n=12 (ThermoFischer #31887)) for 1 h, at room temperature. Calcium content within the cells was then monitored using a plate reader before and after application of 1 µM capsaicin and 150 µM Ca$^{2+}$ to the antibody solution covering the cells. The total calcium uptake for each antibody was normalized against the calcium uptake for capsaicin activation only (i.e. capsaicin+calcium; "Cap" in FIG. 4). % remaining activity means the amount of activity remaining as compared to the 1 µM capsaicin and 150 µM Ca$^{2+}$ reference (a control without antibody) which is labeled "Cap" on FIG. 4. Purely by way of an example, 30% remaining activity would mean that the activity is inhibited by 70%. Data is represented as mean±SEM. Statistical significance was determined using a Kruskal-Wallis test followed by Dunn's multiple comparison. One asterisk=p value of less than 0.05. Two asterisks=p value of less than 0.01. Four asterisks=p value of less than 0.0001.

Figure 5:
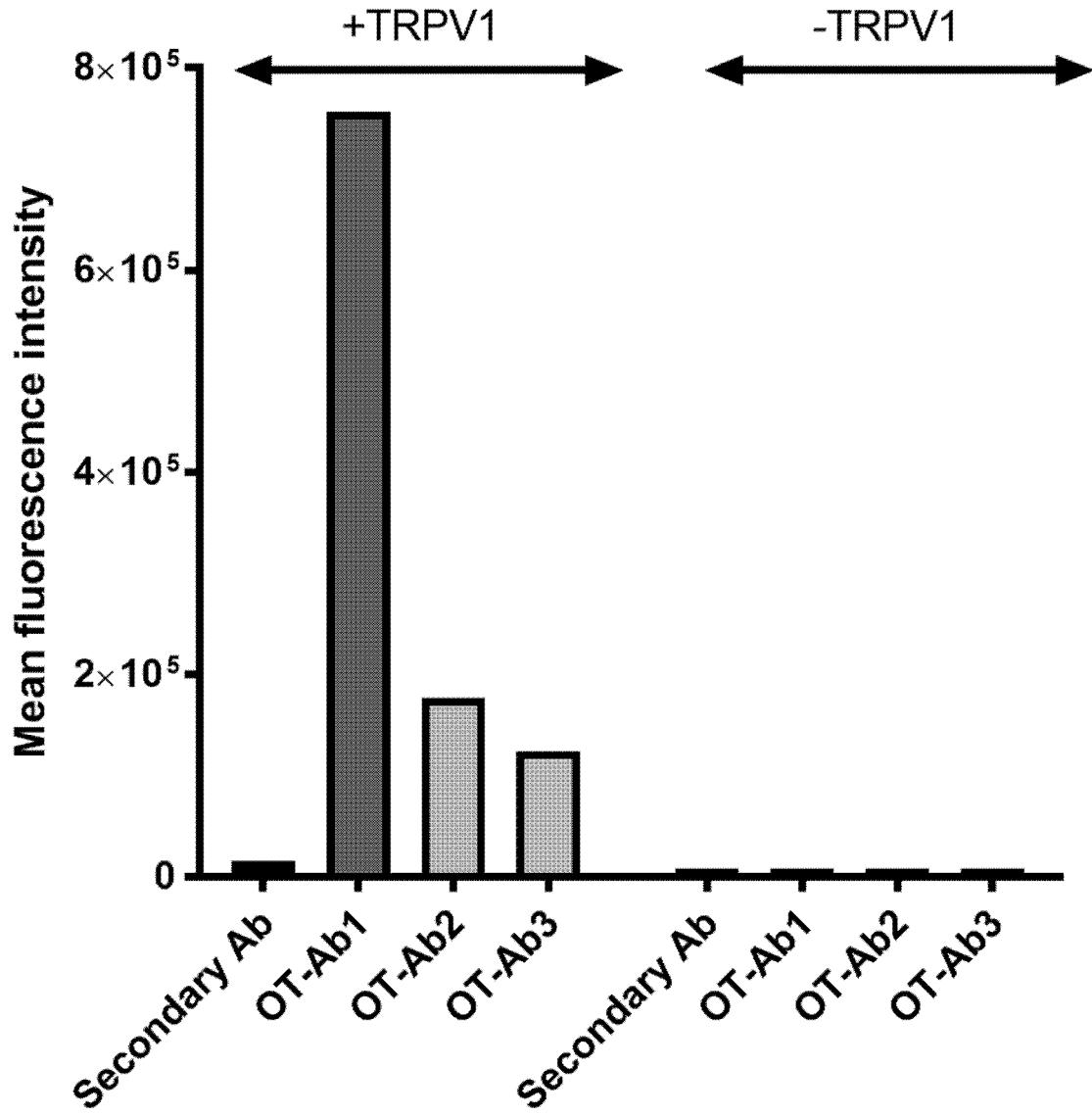

FIG. 5: Binding properties for TRPV1 antibodies was assessed using FACS and TRPV1-expressing CHO cells (+TRPV1). Live cells were incubated with candidate antibodies (10 µg/ml) and subsequent secondary antibody staining (anti-mouse IgG conjugated to fluorescent dye) and flow cytometry analysis was performed. The same antibodies were also screened against non-TRPV1-expressing CHO-cells (−TRPV1) to determine unspecific binding to cells. The secondary antibody was used as negative control also to detect unspecific binding.

Figure 6:
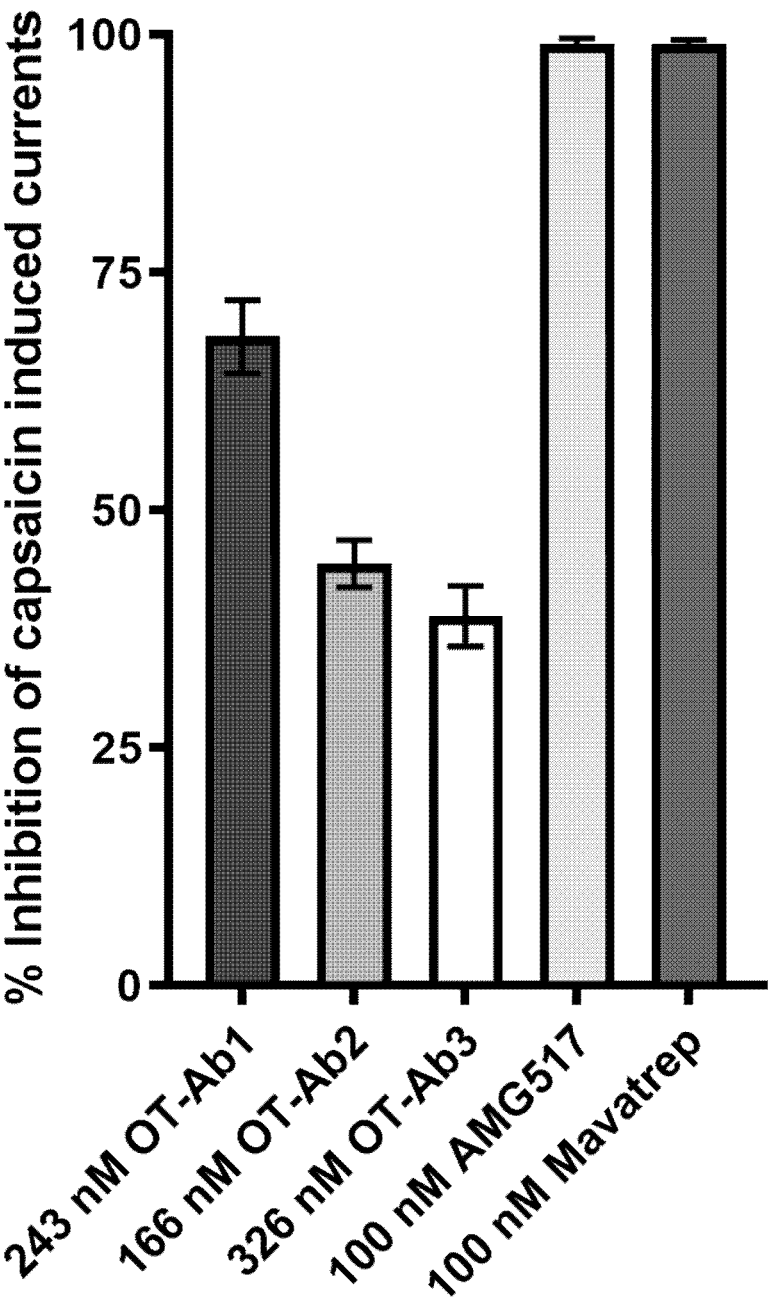

FIG. 6: The patch clamp method was used to measure the antibodies' inhibitory activity on hTRPV1 capsaicin (100 nM capsaicin) responses in TRPV1-expressing CHO cells. Small-molecule antagonists AMG517 and Mavatrep were included as positive controls that completely inhibit capsaicin-induced current. hTRPV1 was activated four subsequent times using 100 nM capsaicin. hTRPV1 expressing cells were pretreated with antibody or small molecule prior to the third activation and antibody or small molecule was added together with capsaicin during the third activation. The first, second and fourth activation was capsaicin only. The amplitude of the third current peak in the presence of antibody was compared to the mean of the amplitudes of current peaks two and four. (OT-Ab1 n=5, OT-Ab2 n=9, OT-Ab3 n=9, Mavatrep n=5, AMG517 n=3). % inhibition is (1−((peak 3)/((peak2+peak4)/2)))*100. Data is presented as mean±SEM.

Figure 7:
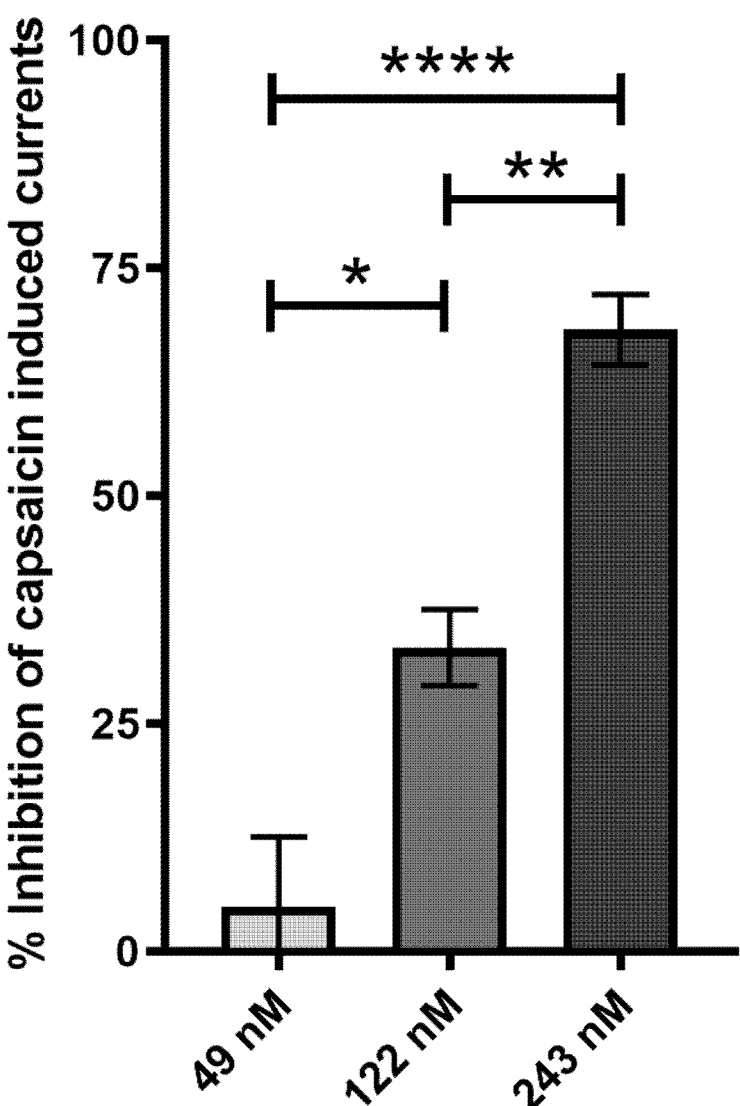

FIG. 7: Dose-dependent inhibition of TRPV1 capsaicin-induced currents by antibody OT-Ab1 was assessed at 100 nM capsaicin and three concentrations of OT-Ab1 (49 nM n=5, 122 nM n=4, 243 nM n=5). Whole cell recordings were performed using a microfluidic device for patch clamp recordings (Dynaflow, Cellectricon AB, Sweden) together with an Axopatch 200B (Molecular Devices, USA) patch clamp amplifier. The cells were clamped at −60 mV and the current signals were recorded with a sampling frequency of 10 kHz and low pass filtered at 2 kHz. The patch-clamp recordings were acquired using digital/analogue sampling (Axon Digidata 1550) and acquisition software (Clampex version 10.7, Molecular Devices). hTRPV1 was activated four subsequent times using 100 nM capsacin. hTRPV1 expressing cells were pretreated with antibody prior to the third activation and antibody was added together with capsaicin during the third activation. The first, second and fourth activation was capsaicin only. The amplitude of the third current peak in the presence of antibody was compared to the mean of the amplitudes of current peaks two and four. % inhibition is (1−((peak 3)/((peak2+peak4)/2)))*100. Statistical evaluation was done with a one-way ANOVA. Statistical significance is indicated as follows: *p<0.05, p<0.01, **p<0.0001. Data is presented as mean±SEM.

Figure 8:
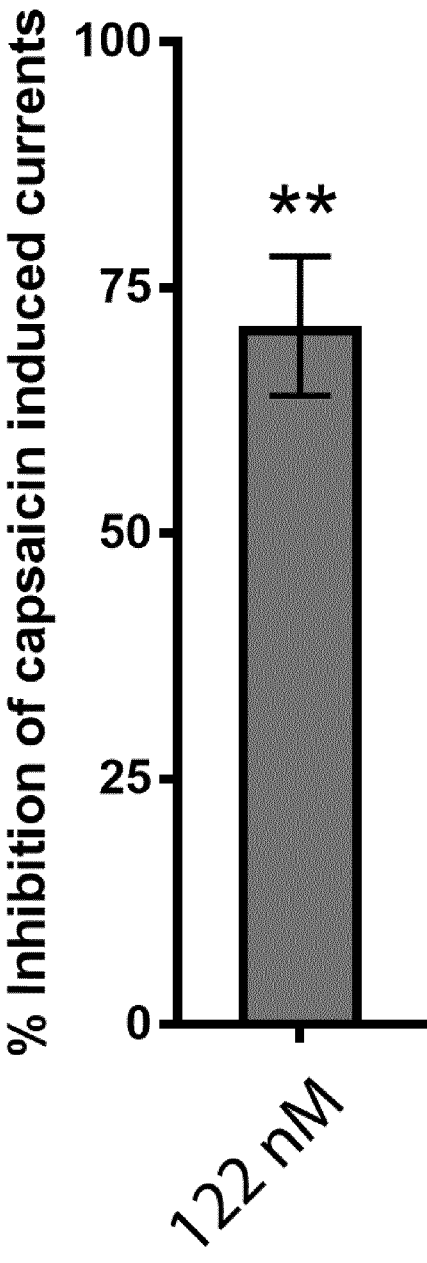

FIG. 8: Inhibition of TRPV1 capsaicin-induced currents by antibody OT-Ab1 was assessed at 300 nM capsaicin and one concentration of OT-Ab1 (122 nM). Whole cell recordings were performed using a microfluidic device for patch clamp recordings (Dynaflow, Cellectricon AB, Sweden). hTRPV1 was activated four subsequent times using 300 nM capsacin. hTRPV1 expressing cells were pretreated with antibody or vehicle prior to the third activation and antibody or vehicle was added together with capsaicin during the third activation. The first, second and fourth activation was capsaicin only. The ratio of the third current peak in the presence of antibody or vehicle to the second current peak was calculated. By comparing the ratios for antibody treated cells and vehicle treated cells, the percent of inhibition was calculated. % inhibition is (1−((Peak3$_{Ab}$/Peak2$_{Ab}$)/(peak3$_{veh}$/peak2$_{veh}$)))*100. Statistical evaluation was done with Students t-test. Statistical significance is indicated as follows: **p<0.01. n=3. Data is presented as mean±SEM.

Figure 9:
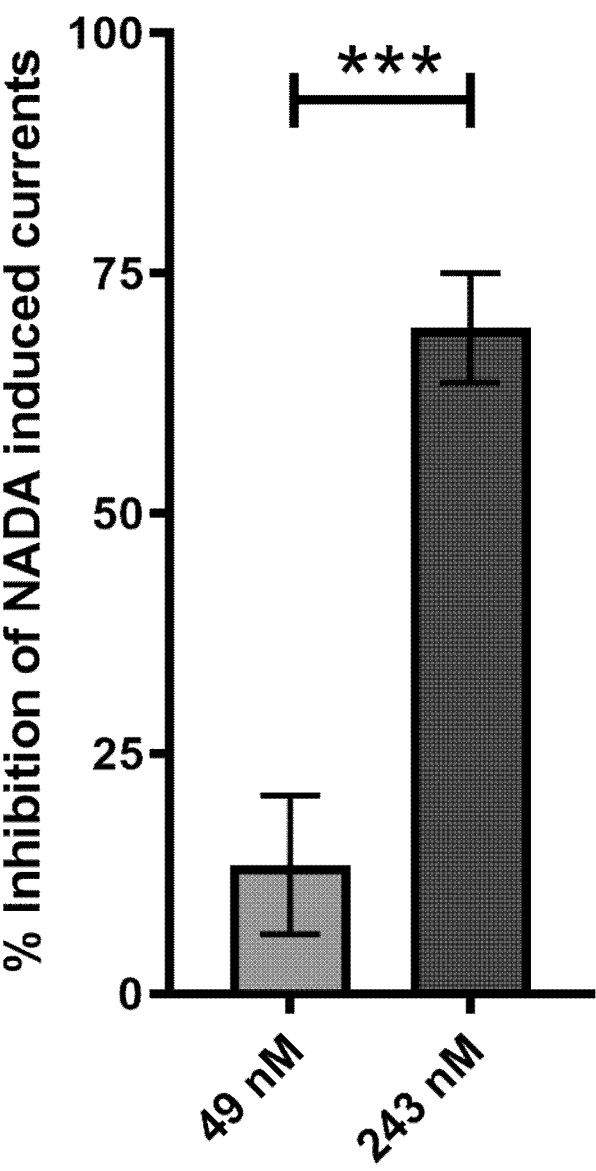

FIG. 9: Dose-dependent inhibition of TRPV1 NADA-induced currents by antibody OT-Ab1 was assessed at 1 µM NADA and two concentrations of OT-Ab1 (49 nM n=5, 243 nM n=4). Whole cell recordings were performed using a microfluidic device for patch clamp recordings (Dynaflow, Cellectricon AB, Sweden) together with an Axopatch 200B (Molecular Devices, USA) patch clamp amplifier. The cells were clamped at −60 mV and the current signals were recorded with a sampling frequency of 10 kHz and low pass filtered at 2 kHz. The patch-clamp recordings were acquired using digital/analogue sampling (Axon Digidata 1550) and acquisition software (Clampex version 10.7, Molecular Devices). hTRPV1 was activated four subsequent times using 1 uM NADA. hTRPV1 expressing cells were pre-treated with antibody prior to the third activation and antibody was added together with NADA during the third activation. The first, second and fourth activation was NADA only. The amplitude of the third current peak in the presence of antibody was compared to the mean of the amplitudes of current peaks two and four. % inhibition is $(1-((peak\ 3)/((peak2+peak4)/2)))*100$. Statistical evaluation was done with Students t-test. Statistical significance is indicated as follows: ***$p<0.001$. Data is presented as mean±SEM.

Figure 10:
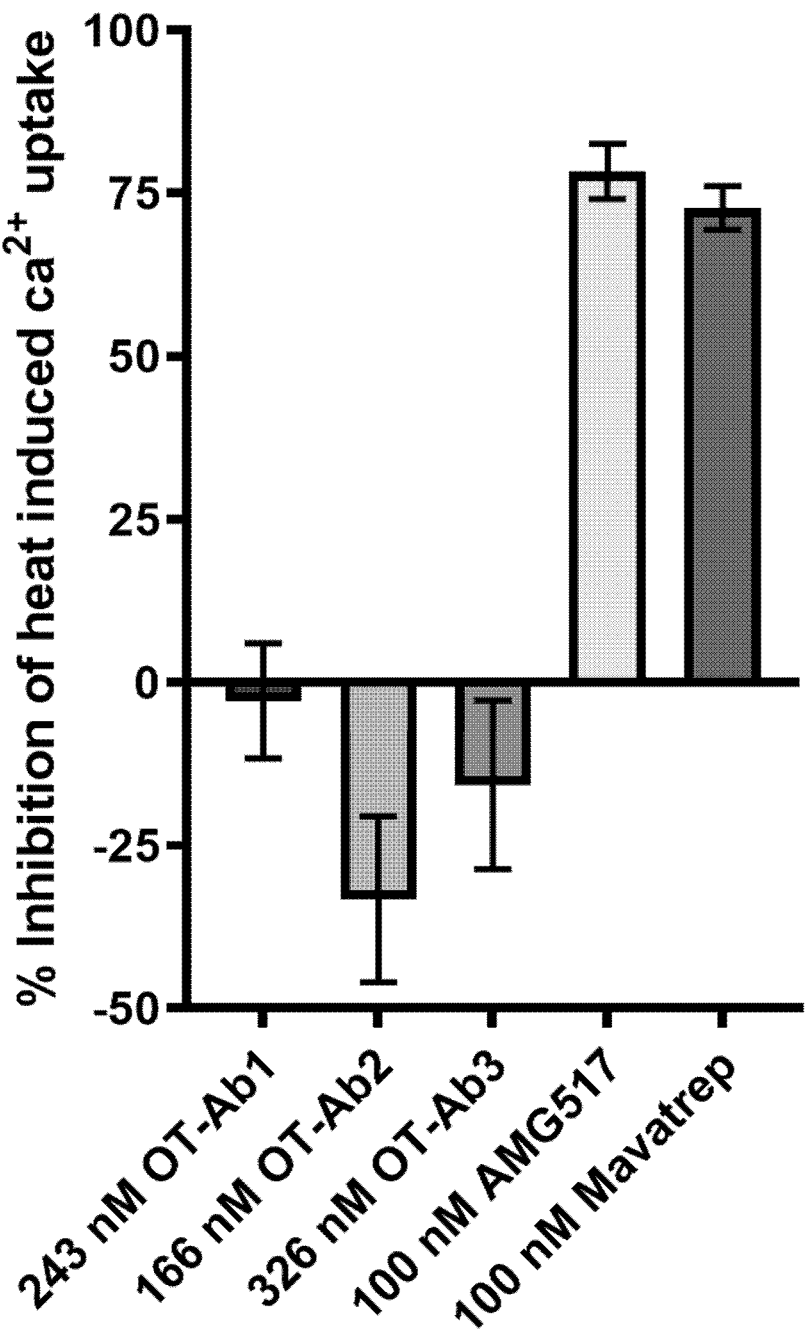

FIG. 10: $Ca^{2+}$-imaging was used to measure antibodies' inhibitory activity on hTRPV1 heat response (45° C.) in TRPV1-expressing CHO cells. An optical heating system was used to deliver heat pulses to cells which were observed with a microscope with fluorescence capability as described in FIG. 3. A commercial microfluidic device, Biopen®, was used to deliver the antibodies to the cells. Heat causes an influx of calcium ions through the TRPV1 channel into cells, and the influx is measured using a calcium indicator within the cells. Two pulses of heat were applied, the second in the presence of antibody (OT-Ab1, OT-Ab2, or OT-Ab3) or vehicle. The ratio of the second to first peak amplitude was calculated for both antibody and vehicle. The percent of inhibition was calculated by comparing the aforementioned ratio for the antibody to the ratio for the vehicle. % inhibition is $(1-((Peak2_{Ab}/Peak1_{Ab})/(peak2_{veh}/peak1_{veh})))*100$. The small-molecule antagonists AMG517 and Mavatrep were added directly to the bath solution and were not delivered using the microfluidic device. The cells treated with the small molecules were activated using the same protocol with heat pulses as for the antibodies and analysed the same way as the antibodies. Antibodies n=6, small molecules n=5. Data is presented as mean±SEM.

Figure 11:
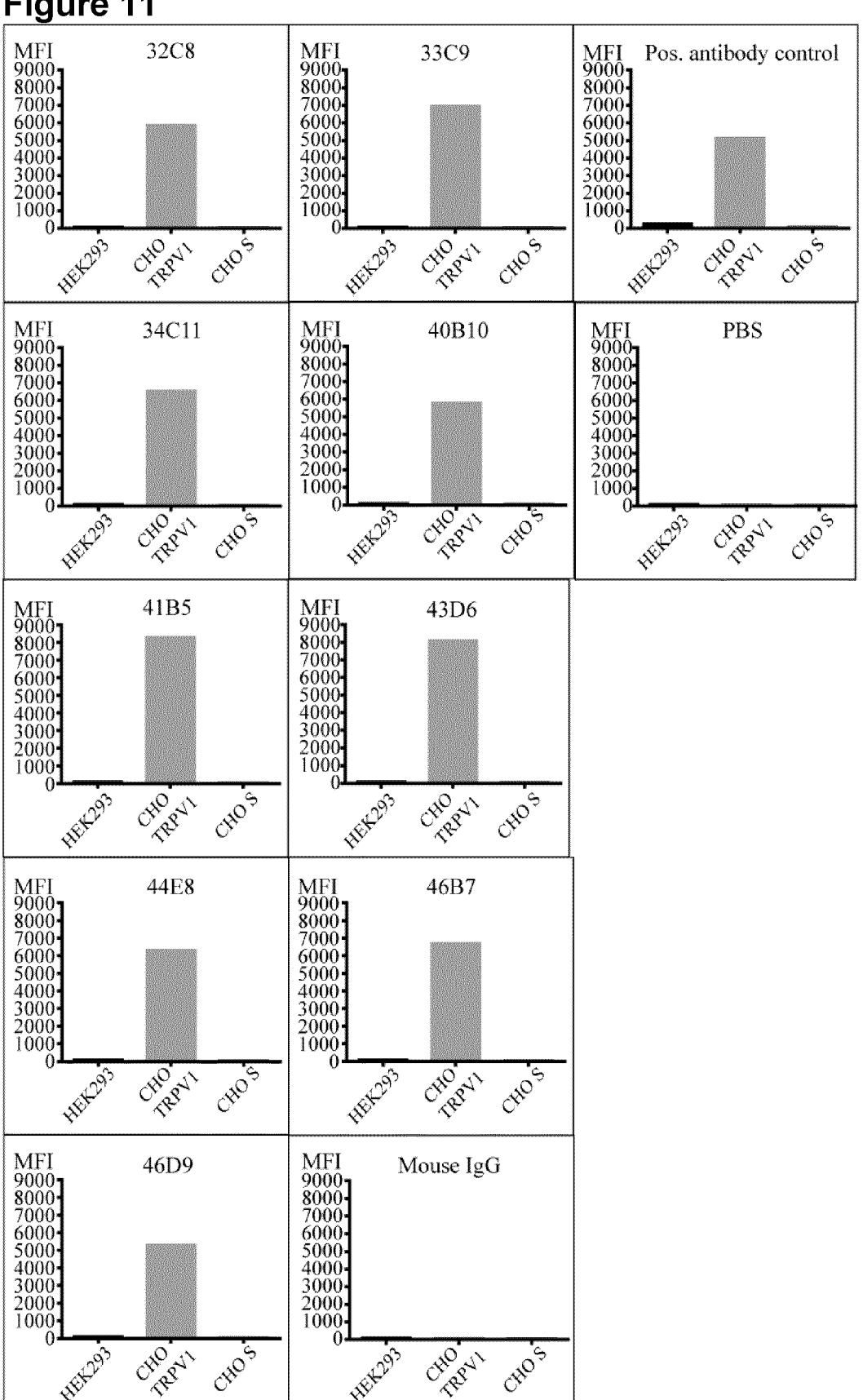

FIG. 11: FACS determination of binding of preparations of monoclonal antibodies in supernatant from parental mouse hybridoma clones to TRPV1-expressing cells (CHO TRPV1), and non-TRPV1-expressing cells (HEK293 and CHO S). Also shown is binding of Mouse IgG as a test for non-specific binding, a rabbit polyclonal positive control antibody (Pos. antibody control) with previously confirmed binding to TRPV1, and a test with pure PBS to measure background fluorescence. MFI=mean fluorescence intensity. N=1 per antibody.

Figure 12:
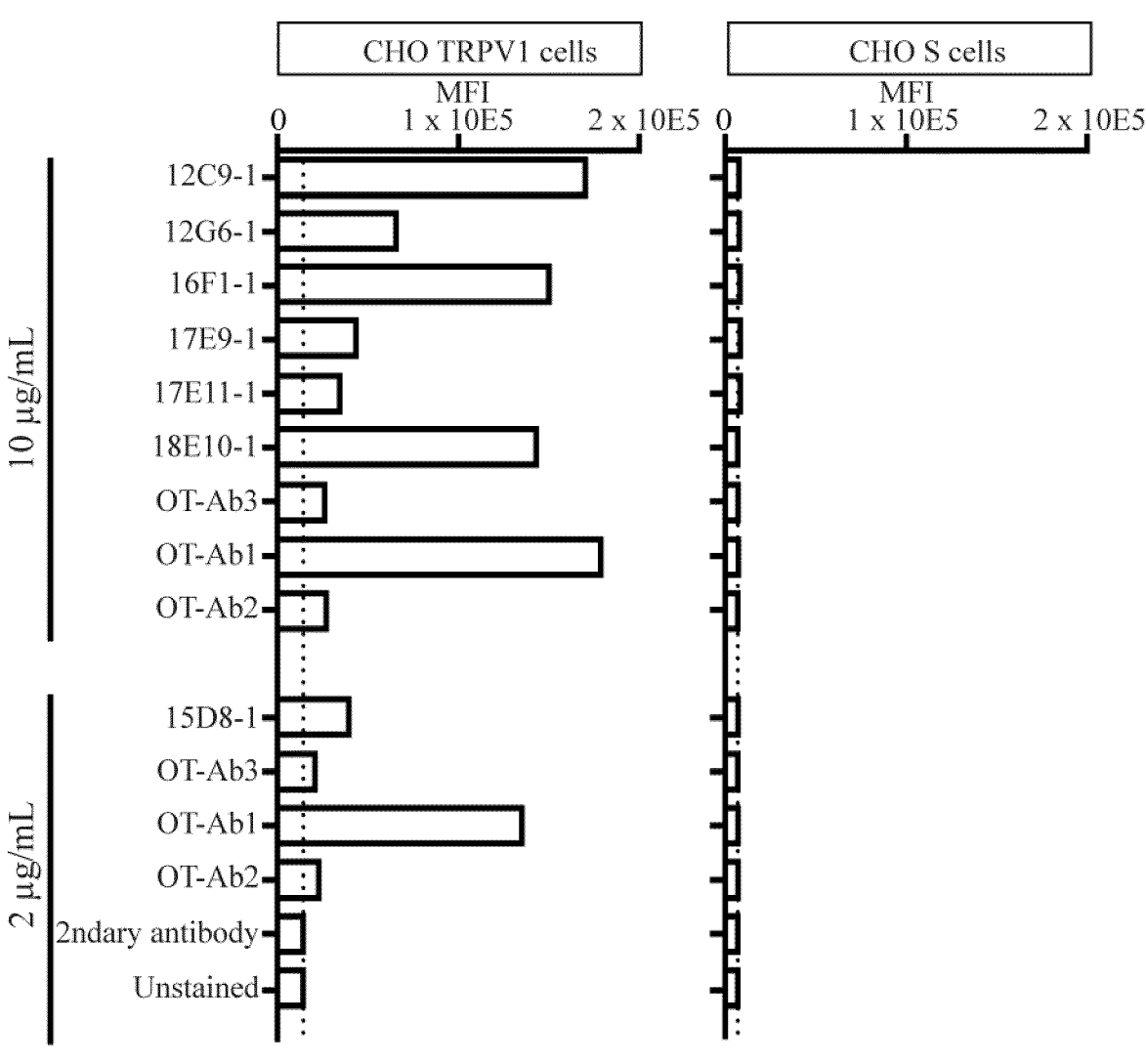

FIG. 12: FACS determination of binding of preparations of purified monoclonal antibodies to TRPV1-expressing cells (CHO TRPV1), and non-TRPV1-expressing cells (CHO S). Also shown is binding of anti-mouse secondary antibody IgG ("2ndary antibody") as a test for non-specific binding and a test with untreated cells ("Unstained") as a measure of cellular background fluorescence. MFI=mean fluorescence intensity. N=1 per antibody.

Figure 13:
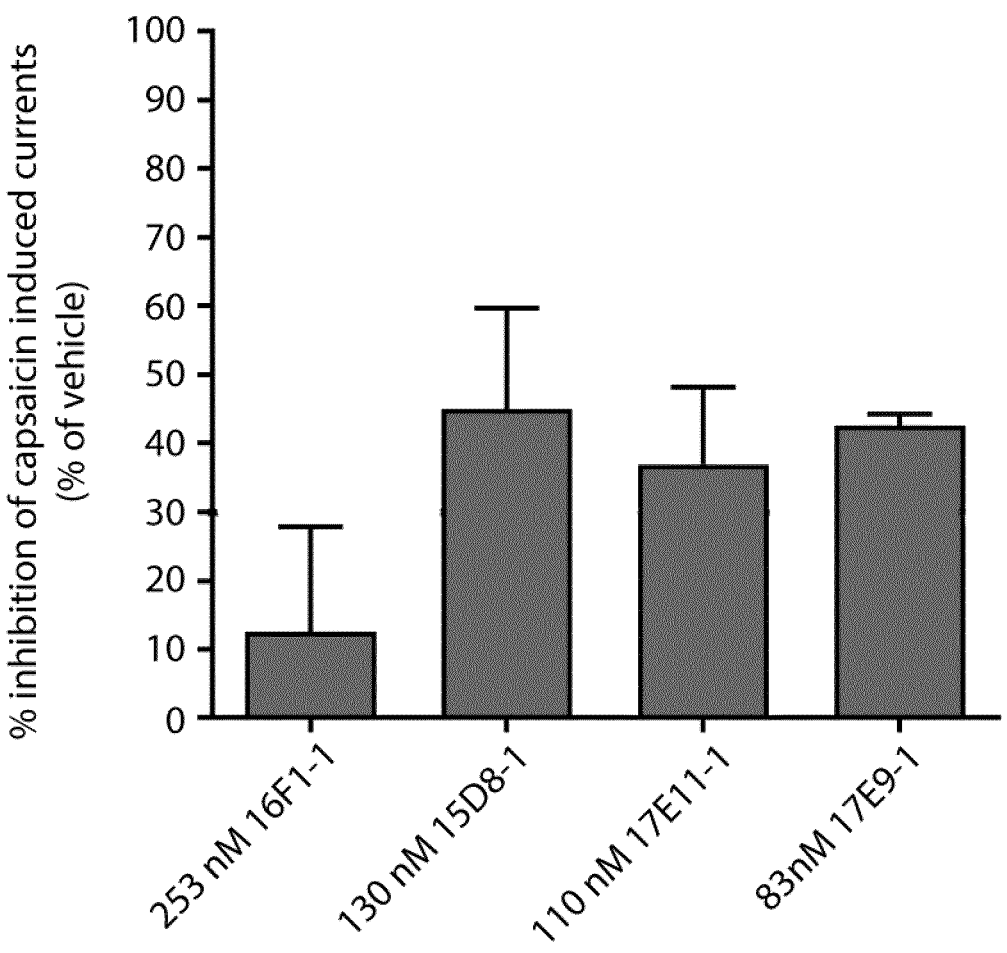

FIG. 13: Inhibition of TRPV1 capsaicin-induced currents by antibody was assessed by patch clamp, with antibodies 16F1-1 (253 nM), 15D8-1 (130 nM), 17E11-1 (110 nM) and 17E9-1 (83 nM). Whole cell recordings were performed using a microfluidic device for patch clamp recordings (Dynaflow, Cellectricon AB, Sweden). Current amplitudes were measured by exposing cells to 100 nM capsaicin, with and without antibody. The cells were exposed to 100 nM capsaicin in buffer, followed by buffer 60 s, antibody in buffer for 60 s and then 100 nM capsaicin together with antibody in buffer for 20 s. The amplitude of the peak during stimulation with antibody+capsaicin was divided by the amplitude of the peak during stimulation with capsaicin only. The obtained value was multiplied with 100 to obtain the cell response during antibody+capsaicin stimulation as a percentage of the control response (capsaicin only). Data is presented as mean±SEM. N=3 per antibody.

Figure 14:
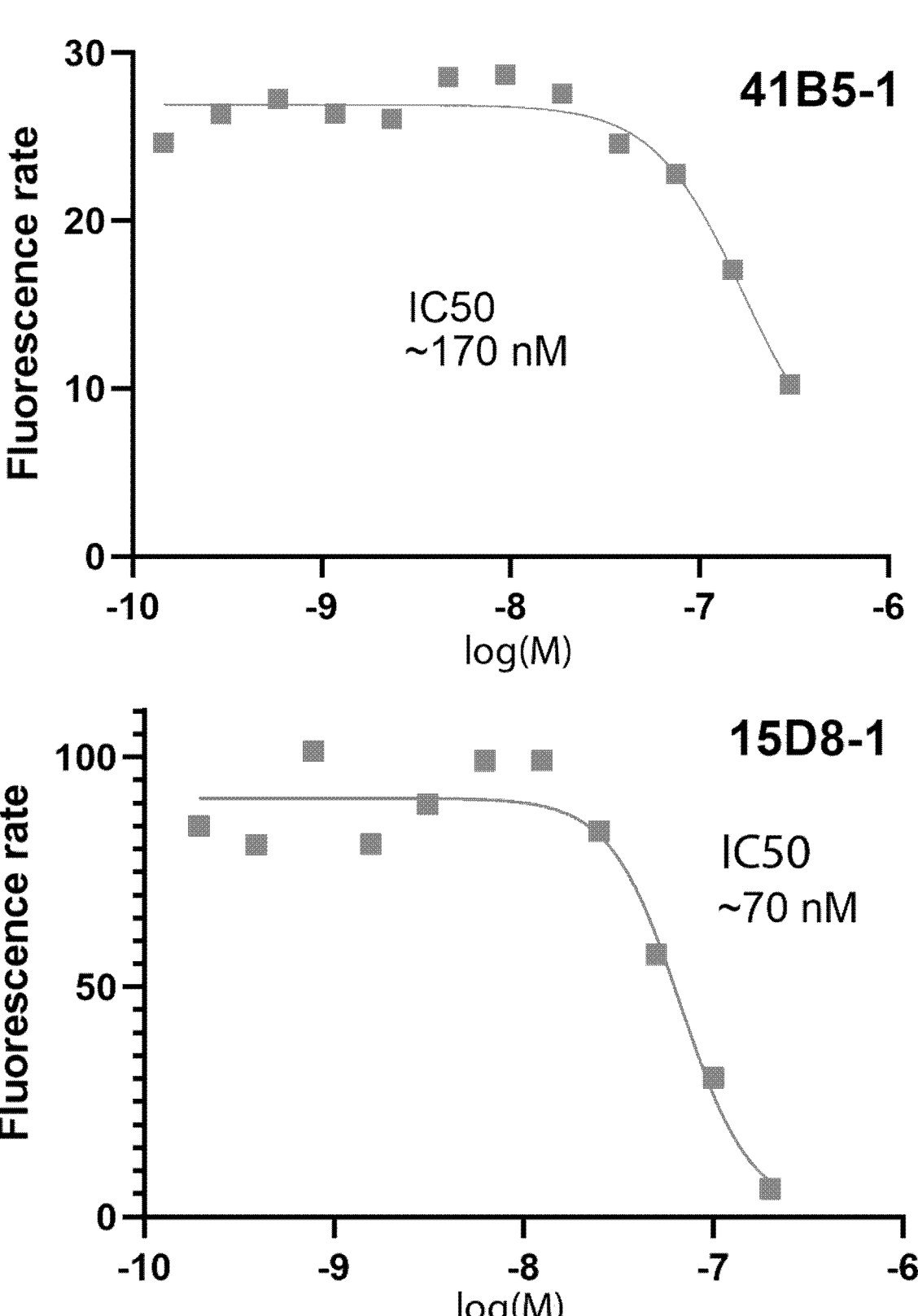
Figure 14:
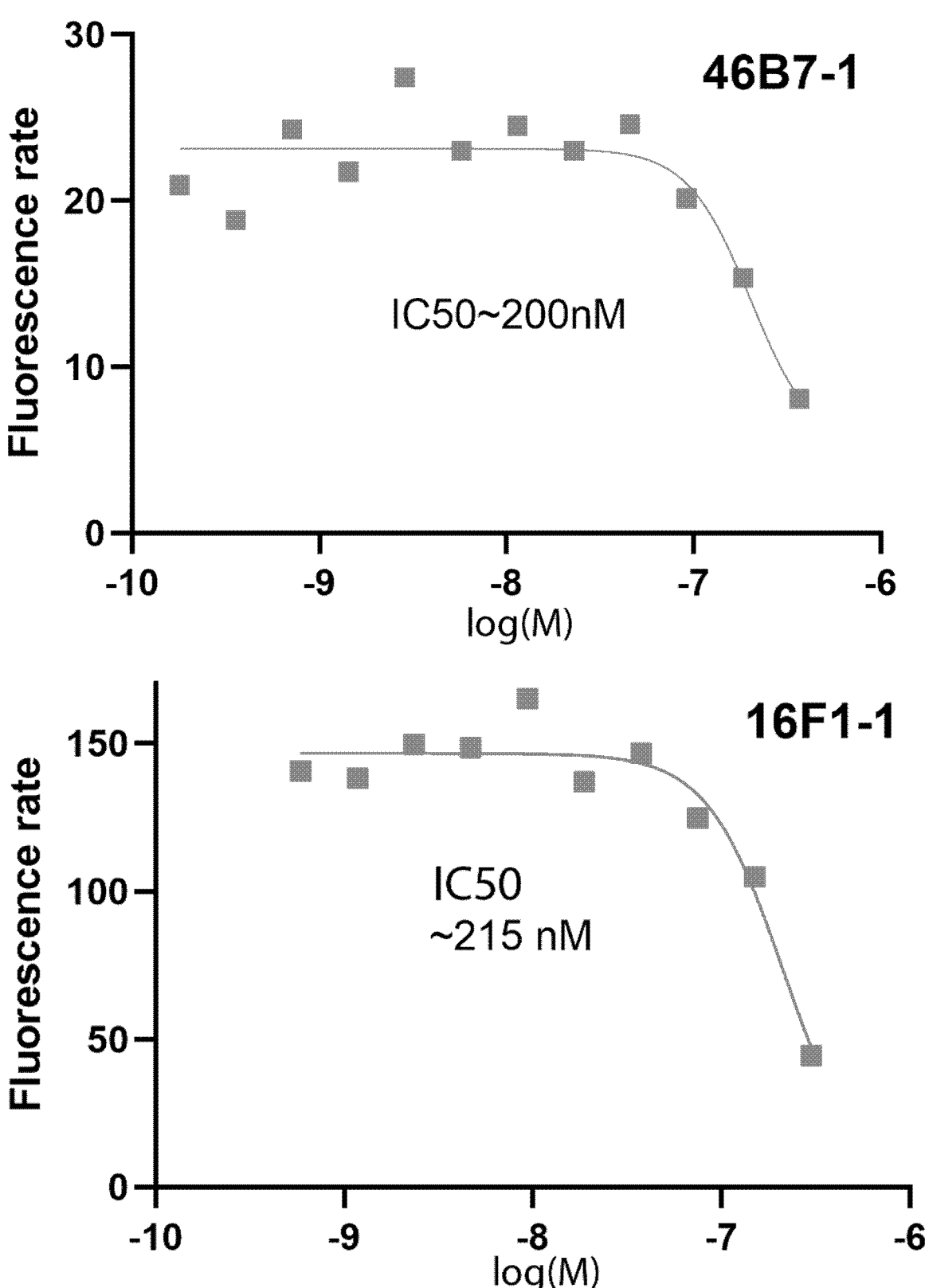
Figure 14:
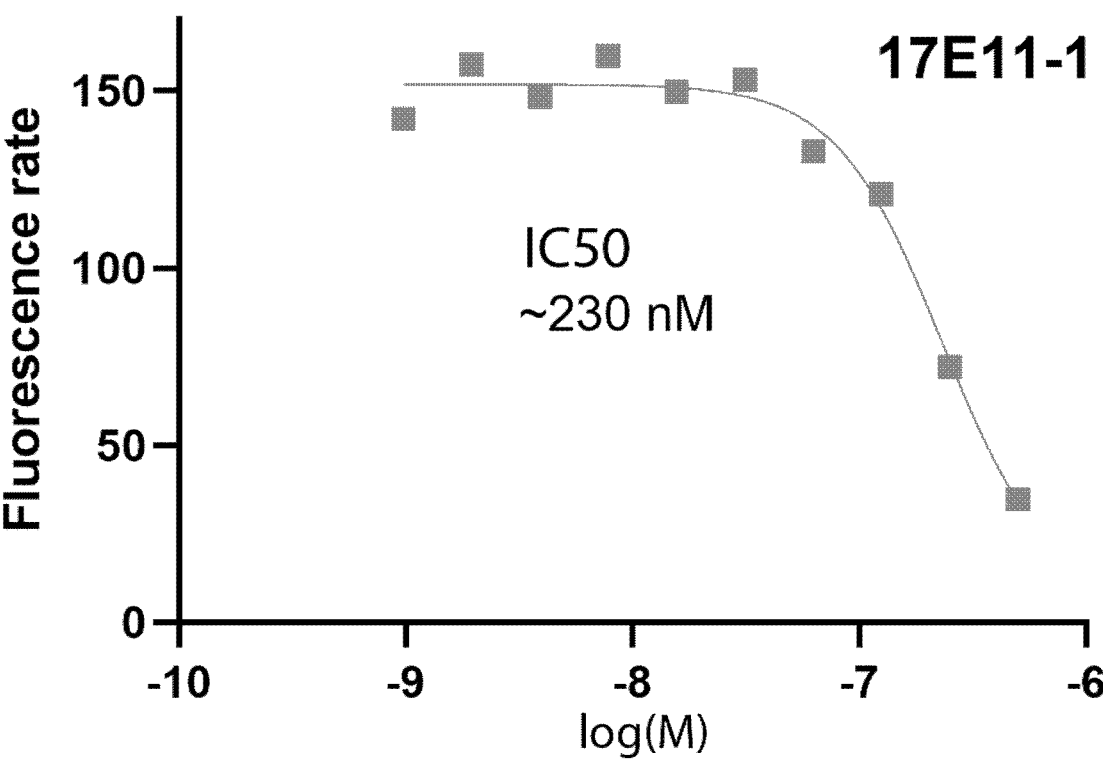
Figure 14:
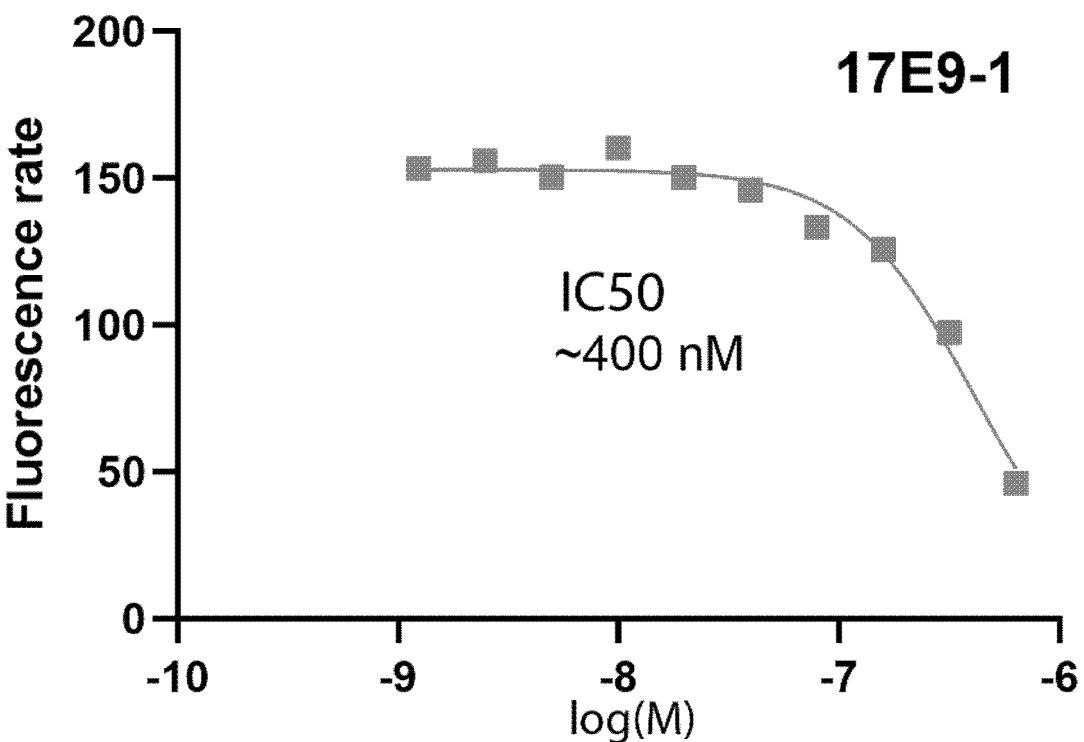

FIG. 14: FLIPR (Fluorescence imaging Plate Reader) determination of inhibition of TRPV1-mediated capsaicin-induced $Ca^{2+}$ uptake by antibodies 15D8-1, 16F1-1, 17E9-1, 17E11-1, 41B5-1, and 46B7-1. The x-axis shows antibody concentration (nM), and the y-axis shows Fluorescence rate ([fluorescence at a certain time after capsaicin addition]-[fluorescence before capsaicin addition]). N=1 per data point. Calculated IC50 values for each antibody are indicated in the graphs.

Figure 15:
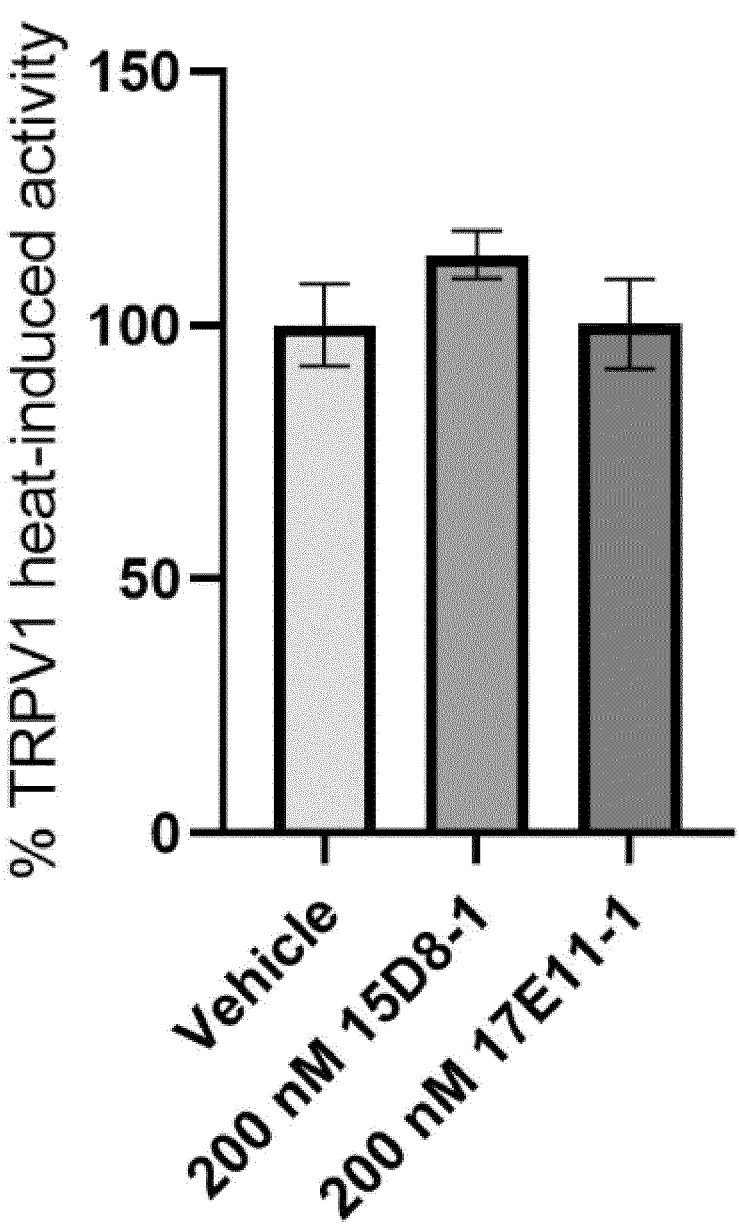

FIG. 15: $Ca^{2+}$-imaging was used to measure antibodies' inhibitory activity on hTRPV1 heat response (45° C.) in TRPV1-expressing CHO cells. An optical heating system was used to deliver heat pulses to cells which were observed with a microscope with fluorescence capability as described elsewhere. A commercial microfluidic device, Biopen, was used to deliver the antibodies to the cells. Heat causes an influx of calcium ions through the TRPV1 channel into cells, and the influx is measured using a calcium indicator within the cells. Two pulses of heat were applied, the second in the presence of antibody (15D8-1 or 17E11-1) or vehicle. The ratio of the second to first peak amplitude was calculated for both antibody and vehicle and compared between treatments. Statistical analysis was performed with one-way analysis of variance (ANOVA). Data is presented as mean±SEM. N=6, 6 and 10 for 15D8-1, 17E11-1 and vehicle respectively.

Figure 16:
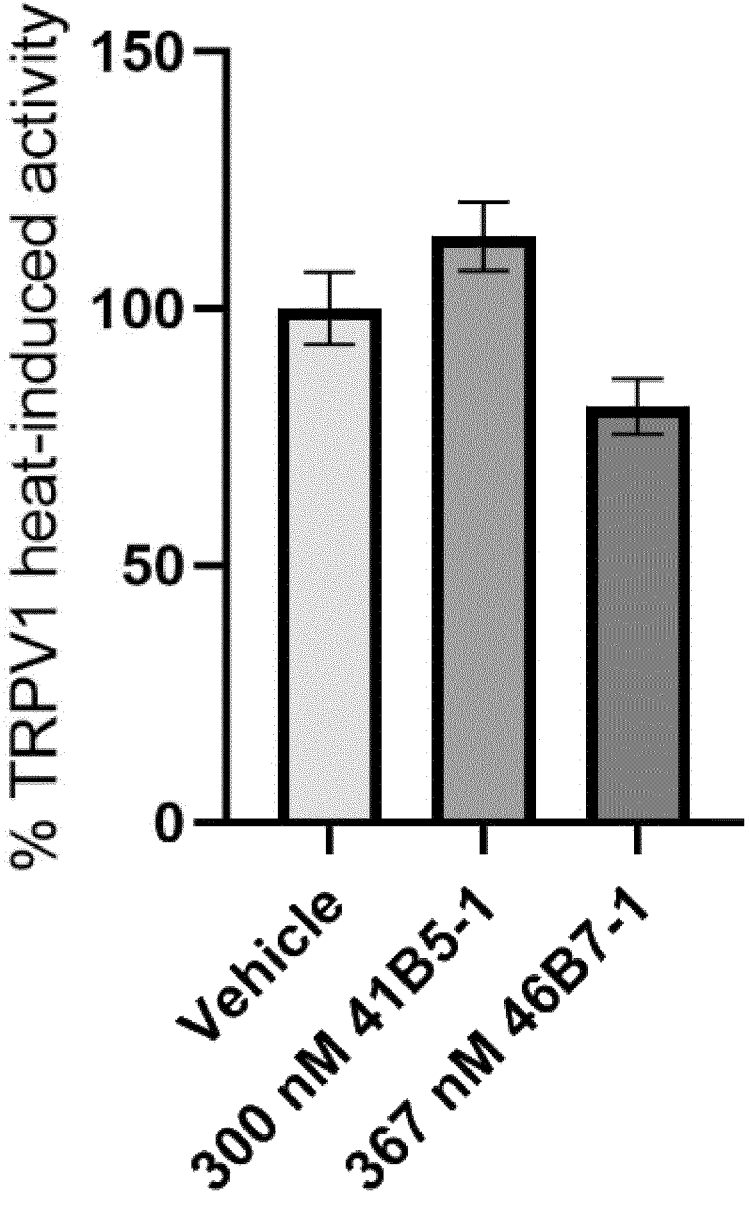

FIG. 16: $Ca^{2+}$-imaging was used to measure antibodies' inhibitory activity on hTRPV1 heat response (45° C.) in TRPV1-expressing CHO cells. An optical heating system was used to deliver heat pulses to cells which were observed with a microscope with fluorescence capability as described elsewhere. A commercial microfluidic device, Biopen, was used to deliver the antibodies to the cells. Heat causes an influx of calcium ions through the TRPV1 channel into cells, and the influx is measured using a calcium indicator within the cells. Two pulses of heat were applied, the second in the presence of antibody (41B5-1 or 46B7-1) or vehicle. The ratio of the second to first peak amplitude was calculated for both antibody and vehicle and compared between treatments. Statistical analysis was performed with one-way analysis of variance (ANOVA). Data is presented as mean±SEM. N=9, 7 and 10 for 41B5-1, 46B7-1 and vehicle respectively.

EXAMPLES

Example 1—Peptides and Antibody Generation and Testing

Materials and Methods

Chemicals

Cell culturing medium (DMEM/Ham's F12 with glutamine and Ham's F12), fetal bovine serum, and Accutase were purchased from PAA. Zeocin was purchased from Invitrogen.

The control antibody (Rabbit Gamma Globulin—RRID: AB_2532177—catalogue number 31887) was purchased from Thermo Fisher Scientific. Mavatrep and AMG517 were purchased from MedChemExpress. All other chemicals were purchased from Sigma. The following buffers were used; F: 140 mM NaCl, 5 mM KCl, 1 mM CaCl$_2$, 1 mM MgCl$_2$ 10 mM HEPES, 10 mM D-glucose, pH 7.4, G: 120 mM KCl, 2 mM MgCl$_2$, 10 mM HEPES, 10 mM EGTA, pH 7.2. H: 50 mM Tris, 100 mM NaCl, 10 mM MgCl$_2$, 1 mM EDTA, 0.01% Triton X-100 and 1 mM DTT.

Cell Culture

Adherent Chinese hamster ovary (CHO) cells with a tetracycline regulated expression system (T-REx) of hTRPV1 (human TRPV1) were cultivated in medium (DMEM/F12 with glutamine) supplemented with 10% fetal bovine serum (FBS), Zeocin (350 μg/ml), and Blasticidin (5 μg/ml). 18-24 hours before use, the cells were incubated in medium supplemented with 10% FBS and Doxycycline (1 μg/ml) in order to induce hTRPV1 expression.

Antibody Development

For each epitope (peptide) used for antibody generation, synthetic peptides including an additional cysteine(s) residue(s), were synthesized and purified. These synthetic peptide sequences are set forth as SEQ ID NO:16 (OTV3), SEQ ID NO:17 (OTV4), SEQ ID NO:18 (OTV5), SEQ ID NO:19 (OTV6), SEQ ID NO:20 (OTV7), SEQ ID NO:21 (OTV8), SEQ ID NO:22 (OTV9), SEQ ID NO:23 (OTV10), SEQ ID NO:24 (OTV11), SEQ ID NO:25 (OTV12), SEQ ID NO:26 (OTV13), SEQ ID NO:27 (OTV14) and SEQ ID NO:28 (OTV15).

For the linear epitopes (peptides) (SEQ ID NO:16 (OTV3), SEQ ID NO:17 (OTV4), SEQ ID NO:19 (OTV6), SEQ ID NO:20 (OTV7), SEQ ID NO:21 (OTV8), SEQ ID NO:22 (OTV9), SEQ ID NO:23 (OTV10), SEQ ID NO:24 (OTV11), SEQ ID NO:25 (OTV12), SEQ ID NO:26 (OTV13)), the peptides (epitopes) were linked by the terminal cysteine residue to keyhole limpet hemocyanin (KLH). For the cyclic epitopes (peptides) (SEQ ID NO: 18 (OTV5), SEQ ID NO:27 (OTV14) and SEQ ID NO:28 (OTV15)) the peptides (epitopes) were then linked to keyhole limpet hemocyanin (KLH) via the propargyl group. The KLH-linked epitopes (peptides) were used to produce polyclonal antibodies by immunization of specific pathogen-free (SPF) rabbits following injection of the KLH linked peptides.

The peptides were produced by solid phase peptide synthesis (SPPS) with capping step. Cyclization was done by oxidizing terminal cysteines, creating a disulphide bridge between peptide ends. Linear peptides were conjugated to KLH by coupling SH-group on cysteine to NH2-group on KLH. The cyclic peptides were conjugated by click chemistry using a propargyl group on the peptide and azide on KLH. Antibodies were purified using a Protein G column followed by affinity purification against the peptide.

The antibodies were affinity purified and subjected to an ELISA test. The ELISA test showed that the antibodies were able to bind to their respective peptides (i.e. the respective peptide used to immunize the rabbit to produce the relevant antibody) when the peptide was immobilized on a surface (data not shown).

Generation of both synthetic peptides and polyclonal antibodies were performed by Innovagen AB (Lund, Sweden).

Electrophysiology

Electrophysiological Patch Clamp Recordings—OTV4, OTV5 & OTV12

Whole cell recordings were performed using a microfluidic device for patch clamp recordings (Dynaflow, Cellectricon AB, Göteborg, Sweden) together with an Axopatch 200B (Molecular Devices, USA) patch clamp amplifier. The cells were adherent Chinese hamster ovary (CHO) cells, as described above. Bath and pipette (borosilicate glass capillaries, i.d. 0.86 mm; GC150F-7.5, Harvard Apparatus Ltd) solutions contained buffer F and G, respectively. The cells were clamped at −60 mV and the current signals were recorded with a sampling frequency of 10 kHz and low pass filtered at 2 kHz. The patch-clamp recordings were acquired using digital/analogue sampling (Axon Digidata 1550) and acquisition software (Clampex version 10.7, Molecular Devices). In experiments testing OTV4 antibody, OTV5 antibody, OTV12 antibody, AMG 517, Mavatrep and control antibody (ThermoFischer #31887), current amplitudes were measured by exposing cells to capsaicin, with and without antibody or small molecule (the small molecules are AMG 517 and Mavatrep). The cells were exposed to 100 nM capsaicin in buffer F for ~20 s, followed by buffer F for 60 s, antibody (or small molecule) in buffer F for 60 s and then 100 nM capsaicin together with antibody (or small molecule) in buffer F for ~20 s.

Measurements where the seal resistance shifted largely during treatment were excluded from analysis.

Electrophysiology Patch Clamp—Data Analysis—OTV4, OTV5 & OTV12

For all measurements, the recorded amplitude of the peak during stimulation with antibody+capsaicin was divided by the recorded amplitude of the peak during stimulation with capsaicin. Measurements were performed on cells from at least two different cell culture dishes. Each data point (n) represents a single cell. Statistical analysis was performed with one-way analysis of variance in combination with Dunnett's post-hoc test comparing each antibody to the control antibody. $p < 0.05$ was considered as statistically significant. Normality was assessed using the Shapiro-Wilk test. Data is presented as mean±SEM.

Calcium Imaging Method for Assessing Inhibition of Capsaicin-Induced Activation of TRPV1

CHO cells expressing hTRPV1 were incubated with 4.4 μM of the calcium indicator Fluo-3 AM for 30 min at 37° C. and thereafter washed and then incubated with various concentrations of antibodies dissolved in PBS (OTV4 n=12, OTV7 n=12, OTV9 n=12, OTV12 n=11, OTV13 n=11, or control antibody n=12 (ThermoFischer #31887)) for 1 h, at room temperature. Calcium content within the cells was then monitored by measuring fluorescence intensity using a plate reader (CLARIOstar, BMG Labtech) before and after application of 1 μM capsaicin and 150 μM Ca$^{2+}$ to the antibody solution covering the cells. The total calcium uptake caused by capsaicin in those samples that were prior incubated with antibodies was normalized against the calcium uptake caused by capsaicin activation (i.e. capsaicin+calcium) only (i.e. with no prior antibody incubation). Data is represented as mean±SEM. Statistical significance was determined using a Kruskal-Wallis test followed by Dunn's multiple comparison.

Imaging

Calcium Imaging of Heat Response

In order to measure the antibodies' effect on hTRPV1 heat response (42° C.) an optical heating system was used to deliver heat pulses to cells. The cells were adherent Chinese hamster ovary (CHO) cells, as described above. A commercial microfluidic device, the Biopen Prime (Fluicell AB), was used to deliver the antibodies to cells. Heat increases the open probability of hTRPV1 channels which causes an influx of calcium ions. This influx was measured using the calcium indicator Fluo-3. The experiments were performed in the same glass bottomed Petri dishes as the cells were grown in (50 mm uncoated, MatTek). All cell experiments including Fluo-3 AM incubation were performed using DMEM/F-12, HEPES cell culture medium without phenol red (Gibco). The "AM" ester is initially attached to the Fluo-3 indicator, which makes it cell permeable. Once added to the cell culture medium the Fluo-3 AM enters the cell and the "AM" ester part is cleaved off, leaving the Fluo-3 indicator inside the cell. The Fluo-3 indicator itself is non-cell permeable so it remains inside the cell.

Confocal Microscopy

Cells were imaged using a Bio-Rad MRC 1024 confocal unit fitted with a dual Calypso laser (Cobolt, Solna, Sweden) attached to a Nikon Diaphot 200 inverted microscope and a Nikon Plan Apo 20× dry objective (N.A. 0.75 Nikon, Tokyo, Japan). Excitation wavelengths used were 491 nm (Fluo-3) and the emitted light was collected through a 522 nM filter. Images were acquired for the full view of the 20× objective. The frame rate was one image per 7 sec and the pixel resolution 1024×1024.

Heat Probe

A laser heating system was used to locally increase the temperature to 42° C. around selected cells. The laser heating system was built in-house by Fluicell AB. This optical local heating system is based upon a CW 4W 1470-nm semiconductor diode laser (4PN-106, Seminex Corporation, USA) driven by a 20 A benchtop power source (ARO-4320, Arroyo Instruments). This delivers a localized beam to the sample (a group of cells in our case) through a 105 μm core, 0.22 NA, broadband optical fiber (M63L01, Thorlabs). The optical fiber is coupled to a 5 mm fiber optic cannula (CFMLC21L05, 105 μm, 0.22 NA, Thorlabs) so that it can be precisely positioned at any desired location in a Petri dish.

A narrow beam of 1470 nm radiation, exiting the tip of the optical fiber, induces local heating of the water within its path. The extent of heating is determined by the beam intensity which is modulated by the current setting of the laser, and the distance between the tip of the fiber and the sample. In this study, the current and distance are optimized to achieve a sample temperature of 42° C. The relationship between distance, applied current and temperature was calibrated using a previously described technique (Wegrzyn, I., et al. An optofluidic temperature probe. Sensors (Switzerland) (2013), 13(4), 4289-4302, doi:10.3390/s130404289), using a fluidic device (Biopen, Fluicell AB), probing the fluorescent responses.

Biopen

A Biopen Prime (Fluicell AB) was used to deliver antibodies to cells. The Biopen is a free-standing microfluidic device which can be readily positioned using micromanipulators such that the tip can be aligned adjacent to a selected group of cells in a Petri dish, to locally deliver a compound without contamination of the surrounding environment. The solutions to be delivered by the Biopen are loaded into wells on the Biopen to minimize compound consumption. The switching between solutions is controlled by dedicated software.

Calcium Imaging of Heat Response—Recording 30 min before imaging the cell medium was changed to medium containing 36 μM Fluo-3-AM (F1242, Thermo-Fisher) and the samples were incubated for 30 min at RT and then washed and provided with fresh growth medium which contains $Ca^{2+}$ (DMEM/F-12, HEPES cell culture medium without phenol red (Gibco)). The Biopen was positioned above a group of cells using a micromanipulator. The heat-probe was positioned 10 μm above the dish bottom and at approx. 100 μm distance from the Biopen outlet. To define which cells that are exposed to solution delivery from the Biopen, an initial pulse of Sulforhodamine B was delivered. After the Sulforhodamine B fluorescence declined the cells was optically heated for 7 s (42° C.) and the fluorescence response from Fluo-3 was measured (cell response, Peak #1). Subsequently, antibody solution (OTV4, OTV5, OTV12 antibody or control antibody (ThermoFischer #31887)) or small molecule solution (2 μM Mavatrep or 2 μM AMG-517) was delivered for 90 s and a second heat-pulse was applied during the last 7 s of application (cell response, Peak #2).

Data Analysis of Calcium Imaging of Heat Response

Data analyses were performed in Image J and GraphPad Prism software. The Sulforhodamine B pulse visualizes which cells that are reached by Biopen solution delivery and thereby defining which cell that will be included in the measurement. The fluorescence intensity of these cells was measured and averaged for each time point, to obtain an average curve for the cells stimulated in one experiment. The height of Peak #1 was measured to determine heat response without antibody present, and the height of Peak #2 was measured to determine heat response with antibody present. Peak #2 value was divided with Peak #1 to obtain a ratio. The ratio of the peaks for the OTV4, OTV5 and OTV12 antibodies was compared to the control antibody.

Statistical analysis was performed with one-way analysis of variance in combination with Dunnett's post-hoc test. $p < 0.05$ was considered as statistically significant. Normality was assessed using Shapiro-Wilk test. Data is presented as mean±SEM. n equals the number of experiments containing on average 5-10 cells.

Results and Discussion

Moduli selective antagonistic antibodies of TRPV1, named antibodies OTV4, OTV5 & OTV12 were developed as described above (i.e. by immunizing rabbits with the stated KLH-linked OTV4, OTV5 and OTV12). These moduli selective antibodies are capable of preferentially inhibiting capsaicin activation of TRPV1 as opposed to heat activation of TRPV1, thus reducing or avoiding the heat-related side-effects that have been observed with previous small molecule antagonists.

The moduli selective effect of the OTV4, OTV5 and OTV12 antibodies was determined by comparing the degree of inhibition of capsaicin and heat activation of TRPV1, respectively. The activity profiles were compared to those of the small molecule antagonists Mavatrep (Manitpisitkul P, et al. Scand. J. Pain (2018), 18(2):151-164) and AMG-517 (Gavva, N. R. et al. Pain (2008), 136 (1-2), 202-210) (FIG. 1). Inhibition of capsaicin-induced channel activity was evaluated using whole cell patch-clamp recordings and the effect on heat-induced activity was evaluated measuring intracellular $Ca^{2+}$ flux with fluorescence, where the antibody solution was delivered using the Biopen® (Fluicell AB) system.

During the patch-clamp experiments (which evaluated capsaicin-induced TRPV1 activation), cells were exposed to capsaicin followed by antibody (or small molecule) and finally capsaicin in the presence of antibody (or small molecule). During the fluorescence experiments (which evaluated heat-induced TRPV1 activation), cells were exposed to heat (42° C.) followed by antibody (or small molecule) and finally exposed to heat (42° C.) in the presence of antibody (or small molecule).

The level of heat and capsaicin inhibition by the antibodies can be found in FIG. 1, where the antibodies were used at a 5 times higher concentration for the evaluation of inhibition of heat-induced activation as compared to the antibody concentration used for the evaluation of inhibition of capsaicin-induced activation of TRPV1, whereas Mavatrep and AMG517 were evaluated at equal concentrations.

The OTV4 antibody elicited a 26.5% inhibition of capsaicin-induced TRPV1 activation at 533 nM and a −4.1% inhibition of temperature (heat)-induced TRPV1 activation at 2.7 μM (FIG. 1).

The OTV5 antibody elicited a 62.4% inhibition of capsaicin-induced TRPV1 activation at 13.3 nM and a 10.0% inhibition of temperature (heat)-induced TRPV1 activation at 67 nM (FIG. 1).

The OTV12 antibody elicited a 34.1% inhibition of capsaicin-induced TRPV1 activation at 13.3 nM and a −12.8% inhibition of temperature (heat)-induced TRPV1 activation at 67 nM (FIG. 1).

Mavatrep elicited a 100% inhibition of capsaicin-induced TRPV1 activation at 100 nM and a 89.3% inhibition of temperature (heat)-induced TRPV1 activation at 100 nM (FIG. 1).

AMG517 elicited a capsaicin inhibition of 100% inhibition of capsaicin-induced TRPV1 activation at 100 nM and a 88.8% inhibition of temperature (heat)-induced TRPV1 activation at 100 nM (FIG. 1).

The control antibody elicited no inhibition of either capsaicin- or temperature-induced activation of TRPV1 (FIG. 1).

All antibody concentrations evaluated can be seen in FIG. 2 (in connection with the inhibition of capsaicin-induced TRPV1 activation) and in FIG. 3 (in connection with the inhibition of temperature (heat)-induced TRPV1 activation).

In summary, all three antibodies (OTV4, OTV5 and OTV12 antibodies) demonstrated a moduli-selective activity profile by eliciting a higher inhibition of capsaicin activation compared to heat-activation even though evaluation of heat activation was performed at 5 times higher antibody concentration, with OTV5 having the highest difference. In contrast, both Mavatrep and AMG517 inhibited capsaicin and heat activation at close to equal levels at 100 nM. This clearly demonstrates that the OTV4, OTV5 and OTV12 antibodies are more than simple TRPV1 antagonists; they selectivity inhibit capsaicin induced activation of TRPV1 as opposed to heat-induced activation of TRPV1. The OTV4 and OTV12 antibodies, and especially the OTV5 antibody, are promising new candidates for TRPV1-targeted pain therapy and are currently pursued as drug candidates. These would not only be the first therapeutic anti-TRPV1 antibodies, they would also be the first therapeutic antibodies ever developed for an ion channel. The present data also establishes that epitopes on TRPV1 that correspond to (or correspond essentially to) the epitope (peptide) amino acid sequences used to generate the OTV4, OTV5 and OTV12 antibodies are useful epitopes to target (i.e. to generate antibodies against) in order to identify moduli selective antibodies as described herein.

In addition to containing data for the OTV4 and OTV12 polyclonal antibodies, FIG. 4 additionally shows that the OTV7, OTV9 and OTV13 polyclonal antibodies are able to significantly inhibit capsaicin induced activation of TRPV1. For the FIG. 4 experiments, rather than assessing capsaicin induced TRPV1 activation by the patch-clamp method, calcium imaging was utilized and FIG. 4 shows that these OTV antibodies are able to inhibit capsaicin-induced calcium uptake. Cells expressing hTRPV1 were incubated with 4.4 μM Fluo-3 AM for 30 min. Cells were thereafter washed and incubated for 1 h with antibodies dissolved in PBS, at varying concentrations. Fluorescence intensity was measured before and after application of 1 μM capsaicin and 150 μM $Ca^{2+}$ using a CLARIOstar (BMG Labtech) micro plate reader.

It is believed that the OTV7, OTV9 and OTV13 polyclonal antibodies preferentially inhibit capsaicin induced activation of TRPV1 as opposed to heat-induced activation of TRPV1. As described above, the inventors have also generated polyclonal antibodies OTV3, OTV6, OTV8, OTV10, OTV11, OTV13, OTV14 and OTV15. It is believed that these antibodies also preferentially inhibit capsaicin induced activation of TRPV1 as opposed to heat-induced activation of TRPV1.

It is evident from the above that the inventors have identified certain peptide sequences (epitope sequences) that correspond to (or correspond essentially to) epitopes on TRPV1 that are very useful to target with antibodies in order to achieve inhibition of TRPV1. In particular, the inventors have identified epitopes on TRPV1 that are very useful to target with antibodies in order to achieve preferential inhibition of capsaicin-induced activation of TRPV1 as opposed to heat-induced activation of TRPV1. Antibodies with such selectivity for inhibition of the capsaicin axis of TRPV1 will be therapeutically advantageous as avoiding (or reducing) concomitant inhibition of the heat axis of TRPV1 would avoid (or reduce) adverse effects such as hyperthermia or loss of heat sensation that are observed with other TRPV1 inhibitors (as discussed elsewhere herein).

Example 2—Generation and Testing of Monoclonal Antibodies (Antibodies Named OT-Ab1, OT-Ab2 and OT-Ab-3)

Materials and Methods

Production of Monoclonal Antibodies (Mouse IgG) Using the Hybridoma Technology

Mice were immunized with the cyclic peptide of SEQ ID NO:18 (OTV5) linked to keyhole limpet hemocyanin (KLH) (the KLH linked peptide is as described above in Example 1). Immune responses were evaluated with ELISA. After the immunization process mice were selected based on ELISA and/or FACS screening of serum, and spleen cells from mouse were extracted and fused with myeloma cells to produce hybridoma cells. Hybridomas were screened by ELISA and/or FACS to obtain positive clones (i.e. that produce antibody that binds to the target). After this screening, sub cloning of the selected hybridomas was performed and a further round of screening was performed using ELISA and/or FACS. Subcloned hybridomas were then used to produce monoclonal antibodies and the antibodies were purified. The binding properties of purified antibodies were tested using ELISA and/or FACS. Three monoclonal antibodies were identified, OT-Ab1, OT-Ab2 and OT-Ab3.

Cloning and Sequencing of Mouse Hybridoma IgG

From mouse hybridomas, RNA was prepared from which cDNA was synthesized. Variable Light (VL) and Variable Heavy (VH) regions of cDNA were amplified and cloned into standard cloning vector separately. Identification of positive clones was done by colony PCR followed by gel electrophoresis. VL and VH DNA and amino acid sequences were obtained from positive clones.

Sequences of the antibodies OT-Ab1, OT-Ab2 and OT-Ab3 are set out in Tables C, B and A herein.

The IgG type of OT-Ab1 is IgG2b/kappa, OT-Ab2 is IgG1/kappa and OT-Ab3 is IgG1/kappa.

Determination of Binding of Antibodies to TRPV1-Expressing CHO Cells Using Fluorescence-Activated Cell Sorting (FACS)

For monoclonal antibody preparations, CHO-TRPV1 cells were incubated with 50 μl antibody preparation (serum, hybridoma supernatant or purified monoclonal antibody) for 30 min at 4° C., followed by 30 min incubation at 4° C. with 50 µl secondary antibody (anti-mouse IgG, conjugated to fluorescent probe). The negative control was secondary antibody only (anti-mouse IgG at 10 mg/mL in the 50 µL sample). Binding was assessed by measurement of fluorescence signal from cells and reported as mean fluorescence intensity (MFI). CHO-TRPV1 cells are adherent Chinese hamster ovary (CHO) cells with a tetracycline regulated expression system (T-REx) of hTRPV1 (human TRPV1) as described elsewhere. Doxycycline was used to induce expression of TRPV1 (denoted +TRPV1). Non-induced cells are denoted –TRPV1.

Measurement of Capsaicin-Induced Currents or NADA-Induced Currents by Patch Clamp Whole cell recordings were performed using a microfluidic device for patch clamp recordings (Dynaflow, Cellectricon AB, Sweden) together with an Axopatch 200B (Molecular Devices, USA) patch clamp amplifier. The cells (in 140 mM NaCl, 5 mM KCl, 1 mM CaCl2, 1 mM MgCl2, 10 mM HEPES, 10 mM D-glucose, pH 7.4) were clamped, using pipettes (i.d. 0.86 mm; GC150F-7.5, Harvard Apparatus Ltd; filled with 120 mM KCl, 2 mM MgCl2, 10 mM HEPES, 10 mM EGTA, pH 7.2, tip resistance 3-6 MOhm), at –60 mV and the current signals were recorded with a sampling frequency of 10 kHz and low pass filtered at 2 kHz. The patch-clamp recordings were acquired using digital/analogue sampling (Axon Digidata 1550) and acquisition software (Clampex version 10.7, Molecular Devices). Current amplitudes were measured by exposing cells to 100 nM capsaicin, 300 nM capsaicin or 1 µM NADA, with and without antibody. For experiments testing the effect of 100 nM capsaicin or 1 µM NADA, cells were first treated twice with capsaicin (or NADA) alone giving peak 1 and 2, then treated with antibody and then antibody together with capsaicin (or NADA) giving peak 3, followed by capsaicin (or NADA) alone giving peak 4. The effect is then calculated as $(1-((peak\ 3)/((peak\ 2+peak\ 4)/2)))*100$. This method of calculating effect has been described in the literature (Nikolaev, M. V. et al. TRPV1 activation power can switch an action mode for its polypeptide ligands. *PLoS One* 12, 1-16, 2017). For experiments testing the effect of 300 nM capsaicin cells were first treated twice with capsaicin alone giving peak 1 and 2, then treated with antibody or vehicle and then antibody or vehicle together with capsaicin giving peak 3, followed by capsaicin alone giving peak 4. The effect is then calculated as $(1-((Peak3_{Ab}/Peak2_{Ab})/(peak3_{veh}/peak2_{veh})))*100$.

Measurement of Heat-Induced Currents Using Ca$^{2+}$-Imaging

In order to measure the antibodies' effect on hTRPV1 heat response an optical heating system was used to deliver heat pulses to cells (45° C.). A commercial microfluidic device, the Biopen Prime (Fluicell AB, Sweden), was used to deliver the antibodies to cells. Heat increases the open probability of hTRPV1 channels which causes an influx of calcium ions. This influx was measured using the calcium indicator Fluo-3. The experiments were performed in the same glass bottomed Petri dishes as the cells were cultured in (50 mm uncoated, MatTek). The cells were adherent TRPV1 expressing Chinese hamster ovary (CHO) cells, as described above. All cell experiments including Fluo-3 AM incubation were performed using buffer 140 mM NaCl, 5 mM KCl, 1 mM CaCl2, 1 mM MgCl2, 10 mM HEPES, 10 mM D-glucose, pH 7.4. Cells were imaged using a Bio-Rad MRC 1024 confocal unit fitted with a dual Calypso laser (Cobolt, Solna, Sweden) attached to a Nikon Diaphot 200 inverted microscope and a Nikon Plan Apo 20× dry objective (N.A. 0.75 Nikon, Tokyo, Japan). In this example, the effect of the antibody was determined as follows: cells were first pulsed with heat, followed by cooldown, followed by administration of antibody or small molecule and a heat pulse in combination, followed by a cooldown. The small molecules Mavatrep or AG517 were applied directly to the bath solution using the same protocol as for the antibodies. The effect of the antibodies (or the small molecule inhibitors AMG517 or Mavatrep) on heat-induced activation of TRPV1 was assessed by determining the effect of the antibodies (or the small molecule inhibitors AMG517 or Mavatrep) on heat-induced influx of calcium ions into the cells.

The peak amplitudes represent the influx of calcium into the cells measured using the calcium indicator Fluo-3.

The ratio of the second to first peak amplitude was calculated for both antibody and vehicle. The percent of inhibition was calculated by comparing the aforementioned ratio for the antibody to the ratio for the vehicle. % inhibition is $(1-((Peak2_{Ab}/Peak1_{Ab})/(peak2_{veh}/peak1_{veh})))*100$.

Microscopy-Aided Determination of Antibody Binding to Live Cells

To demonstrate binding of OT-Ab1 to live cells by microscopy, live TRPV1-expressing CHO-cells were incubated for 1 hour with OT-Ab1, subsequently fixed in formaldehyde solution, stained with fluorescent secondary antibody and counterstained with Hoechst to visualize nuclei. Cells were observed with confocal microscopy equipped with fluorescence capability. Binding was assessed as fluorescence signal located at the cell membranes.

Results and Discussion

TRPV1 is an ion channel that is a member of the TRP-family that is considered to be very difficult to approach with antibodies due to its small extracellular region. Despite their irrefutable importance as drug targets, ion channels are significantly underexploited as antibody targets. In the present study, three modality-selective monoclonal antibodies (mAbs) were developed, that aside from being the first inhibitory mAbs developed against TRPV1, to our knowledge these are the most functionally complex antibodies developed against an ion channel. These antibodies preferentially inhibit capsaicin-induced activation of TRPV1 as opposed to heat-induced activation of TRPV1.

Three examples of mouse monoclonal antibodies against human TRPV1, OT-Ab1, OT-Ab2 and OT-Ab3, were produced using the hybridoma technology. Specificity of binding to hTRPV1 was determined using FACS, employing a CHO cell line with inducible hTRPV1 expression. OT-Ab1, OT-Ab2 and OT-Ab3 bound to hTRPV1-expressing cells but not to non-hTRPV1-expressing cells indicating strongly specific binding to hTRPV1 (FIG. 5).

OT-Ab1, OT-Ab2 and OT-Ab3 were evaluated for effect on hTRPV1 activation in several different ways. The patch clamp method was used to measure the antibodies' inhibitory activity on hTRPV1 capsaicin responses in hTRPV1-expressing CHO cells. One aspect tested was the propensity to inhibit capsaicin-induced currents at capsaicin concentrations of 100 nM or 300 nM. OT-Ab1, OT-Ab2 and OT-Ab3 inhibited capsaicin-induced currents (FIG. 6). The hTRPV1 antagonists AMG517 and Mavatrep (positive controls) inhibited capsaicin-induced currents completely (FIG. 6). Inhibition of capsaicin-induced currents (100 nM capsaicin) by OT-Ab1 was dose-dependent, where increasing inhibition was observed for increasing concentration of OT-Ab1. The relationship between dose and effect was statistically significant (FIG. 7). Inhibition of capsaicin-induced currents by 122 nM OT-Ab1 was also confirmed at 300 nM capsaicin (FIG. 8).

The patch clamp method was also used to measure OT-Ab1 inhibitory activity on hTRPV1 NADA responses in hTRPV1-expressing CHO cells. Dose-dependent inhibition of hTRPV1 NADA-induced currents by antibody OT-Ab1 was observed at 1 μM NADA and two concentrations of OT-Ab1, and the relationship between dose and effect was statistically significant (FIG. 9). NADA (N-arachidonoyl dopamine) has been described as a potent natural TRPV1 agonist in the scientific literature. It belongs to the family of endocannabinoids. It is suggested that NADA plays an important role in nociception and inflammation in the central and peripheral nervous system.

$Ca^{2+}$-imaging was used to measure the inhibitory activity of OT-Ab1, OT-Ab2 and OT-Ab3 on hTRPV1 heat response in hTRPV1-expressing CHO cells. Small-molecule antagonists AMG517 and Mavatrep inhibited heat-induced $Ca^{2+}$ uptake by around 75% in this example, whereas OT-Ab1, OT-Ab2 and OT-Ab3 did not inhibit heat-induced $Ca^{2+}$ uptake (FIG. 10).

The ability of OT-Ab1 to bind to TRPV1 on live cells was also assessed by fluorescence microscopy, and OT-Ab1 was found to bind to live TRPV1 expressing cells, binding at the cell membranes (data not shown)

The ability to inhibit activation of hTRPV1 by either capsaicin or NADA but not inhibit activation of hTRPV1 by heat indicates that these antibodies show modality-selective pharmacology, which is a highly desired property for a clinically acceptable and useful therapeutic agent.

In the present study, modality-selective monoclonal antibodies targeting hTRPV1, a clinically important target that has failed using small molecule approaches, have been developed. These antibodies are promising new candidates for TRPV1-targeted pain therapy and are currently pursued as drug candidates.

Example 3—Generation and Testing of Monoclonal Antibodies (Antibodies Named 32C8-1, 33C9-1, 34C11-1, 40B10-1, 41B5-1, 43D6-1, 44E8-1, 46B7-1, 46D9-1, 12C9-1, 12G6-1, 15D8-1, 16F1-1, 17E11-1, 17E9-1 and 18E10-1)

Materials and Methods

Production of Monoclonal Antibodies (Mouse IgG) Using the Hybridoma Technology

Mice were immunized with the linear peptide of SEQ ID NO:16 (Peptide OTV3) linked to keyhole limpet hemocyanin or were immunized with the linear peptide of SEQ ID NO:17 (Peptide OTV4) linked to keyhole limpet hemocyanin (KLH) (the KLH linked peptide is as described above in Example 1). Immune responses were evaluated with ELISA. After the immunization process mice were selected based on ELISA and/or FACS screening of serum, and spleen cells from mouse were extracted and fused with myeloma cells to produce hybridoma cells. Hybridomas were screened by ELISA and/or FACS to obtain positive clones (i.e. that produce antibody that binds to the target). After this screening, sub cloning of the selected hybridomas was performed and a further round of screening was performed using ELISA and/or FACS. Subcloned hybridomas were then used to produce monoclonal antibodies and the antibodies were purified. The binding properties of purified antibodies were tested using ELISA and/or FACS. 16 monoclonal antibodies were identified, 32C8-1, 33C9-1, 34C11-1, 40B10-1, 41B5-

1, 43D6-1, 44E8-1, 46B7-1, 46D9-1, 12C9-1, 12G6-1, 15D8-1, 16F1-1, 17E11-1, 17E9-1 and 18E10-1. The peptide (immunogen) used to generate the 32C8-1, 33C9-1, 34C11-1, 40B10-1, 41B5-1, 43D6-1, 44E8-1, 46B7-1 and 46D9-1 antibodies was the peptide of SEQ ID NO:16 (OTV3), and as mentioned above this was linked to keyhole limpet hemocyanin. The peptide (immunogen) used to generate the 12C9-1, 12G6-1, 15D8-1, 16F1-1, 17E11-1, 17E9-1 and 18E10-1 antibodies was the peptide of SEQ ID NO:17 (OTV4), and as mentioned above this was linked to keyhole limpet hemocyanin. The suffix "–1" in each of the antibody names is merely indicative that each of these antibodies is a daughter clone of from a respective parental hybridoma (the parental hybridomas have the same names without the "–1" suffix, for example 32C8 is the parental hybridoma of the 32C8-1 antibody (daughter clone)).

For OTV4-based and OTV5-based purified antibodies the storage buffer was PBS (2.7 mM KCl, 1.5 mM $KH_2PO_4$, 137 mM NaCl, 8 mM $Na_2HPO_4$, pH 7.2).

For OTV3-based purified antibodies the storage buffer was PBS-Tween (0.02% Tween 80, 2.7 mM KCl, 1.5 mM $KH_2PO_4$, 137 mM NaCl, 8 mM $Na_2HPO_4$, pH 7.2).

Cloning and Sequencing of Mouse Hybridoma IgG

From mouse hybridomas, RNA was prepared from which cDNA was synthesized. Variable Light (VL) and Variable Heavy (VH) regions of cDNA were amplified and cloned into standard cloning vector separately. Identification of positive clones was done by colony PCR followed by gel electrophoresis. VL and VH DNA and amino acid sequences were obtained from positive clones.

Sequences of the antibodies 32C8-1, 33C9-1, 34C11-1, 40B10-1, 41B5-1, 43D6-1, 44E8-1, 46B7-1, 46D9-1, 12C9-1, 12G6-1, 15D8-1, 16F1-1, 17E11-1, 17E9-1 and 18E10-1 are set out in Tables E-T herein.

The IgG type of 15D8-1, 17E11-1, and 12G6-1 is IgG1/kappa. The IgG type of 16F1-1 is IgG2a/kappa. The IgG type of 17E9-1 and 12C9-1 is type IgG2b/kappa. The IgG type of 18E10-1 is IgG2c/kappa.

Cell Culture

Adherent Chinese hamster ovary (CHO) cells with a tetracycline regulated expression system (T-REx) of hTRPV1 (human TRPV1) were cultivated in medium (DMEM/F12 with glutamine) supplemented with 10% fetal bovine serum (FBS), Zeocin (350 μg/ml), and Blasticidin (5 μg/ml). 18-24 hours before use, the cells were incubated in medium supplemented with 10% FBS and Doxycycline (1 μg/ml) in order to induce hTRPV1 expression.

HEK293 cells and CHO S cells were grown under standard cell culture conditions.

Determination of Binding of Antibodies to TRPV1-Expressing CHO Cells Using Fluorescence-Activated Cell Sorting (FACS)

For monoclonal antibody preparations for FACS analysis, CHO TRPV1 cells, HEK 293 cells or CHO S cells were incubated with 50 μl antibody preparation (serum, hybridoma supernatant or purified monoclonal antibody or control) for 40 min at room temperature, followed by 30 min incubation at room temperature with 100 μl secondary antibody (anti-mouse IgG, conjugated to fluorescent probe). Binding was assessed by measurement of fluorescence signal from cells and reported as mean fluorescence intensity (MFI). CHO TRPV1 cells are adherent Chinese hamster ovary (CHO) cells with a tetracycline regulated expression system (T-REx) of hTRPV1 (human TRPV1) as described elsewhere. Doxycycline was used to induce expression of TRPV1. CHO S cells and HEK 293 cells were used as negative control cells. CHO S cells are a high-density suspension-adapted cell type used as a tool for high level expression of recombinant protein, with little or no basal expression of TRPV1. HEK 293 cells are human embryonic kidney 293 cells widely used in cell biology which have little or no basal expression of TRPV1.

A negative control was secondary antibody only (anti-mouse IgG at 10 mg/mL in the 50 μL sample). Another negative control, of non-specific binding, was mouse IgG. Another control was unstained CHO TRPV1 cells, which are cells not treated with anything and thus provide a measure of background fluorescence.

Measurement of Capsaicin-Induced Currents by Patch Clamp

Whole cell recordings were performed using a microfluidic device for patch clamp recordings (Dynaflow, Cellectricon AB, Sweden) together with an Axopatch 200B (Molecular Devices, USA) patch clamp amplifier. The cells (in Buffer A: 140 mM NaCl, 5 mM KCl, 1 mM CaCl2, 1 mM MgCl2, 10 mM HEPES, 10 mM D-glucose, pH 7.4) were clamped, using pipettes (filled with Buffer B: 120 mM KCl, 2 mM MgCl2, 10 mM HEPES, 10 mM EGTA, pH 7.2), at −60 mV and the current signals were recorded with a sampling frequency of 10 kHz and low pass filtered at 2 kHz. The patch-clamp recordings were acquired using digital/analogue sampling (Axon Digidata 1550) and acquisition software (Clampex version 10.7, Molecular Devices).

Current amplitudes were measured by exposing cells to 100 nM capsaicin, with and without antibody. The cells were exposed to 100 nM capsaicin in buffer A for 20 s, followed by buffer A for 60 s, antibody in buffer A for 60 s and then 100 nM capsaicin together with antibody in buffer A for 20 s.

Data was analysed as follows: for all measurements, the amplitude of the peak during stimulation with antibody+capsaicin was divided by the amplitude of the peak during stimulation with capsaicin only. The obtained value was multiplied with 100 to obtain the cell response during antibody+capsaicin stimulation as a percentage of the control response (capsaicin only).

Measurement of Heat-Induced Currents Using $Ca^{2+}$-Imaging

In order to measure the antibodies' effect on hTRPV1 heat response an optical heating system was used to deliver heat pulses to cells (45° C.). A commercial microfluidic device, the Biopen Prime (Fluicell AB, Sweden), was used to deliver the antibodies to cells. Heat increases the open probability of hTRPV1 channels which causes an influx of calcium ions. This influx was measured using the calcium indicator Fluo-3. The experiments were performed in the same glass bottomed Petri dishes as the cells were cultured in (50 mm uncoated, MatTek). The cells were adherent TRPV1 expressing Chinese hamster ovary (CHO) cells, as described above. All cell experiments including Fluo-3 AM incubation were performed using HEPES buffer (140 mM NaCl, 5 mM KCl, 1 mM CaCl2, 1 mM MgCl2, 10 mM HEPES, 10 mM D-glucose, pH 7.4). Cells were imaged using a Bio-Rad MRC 1024 confocal unit fitted with a dual Calypso laser (Cobolt, Solna, Sweden) attached to a Nikon Diaphot 200 inverted microscope and a Nikon Plan Apo 20× dry objective (N.A. 0.75 Nikon, Tokyo, Japan). In this example, the effect of the antibody was determined as follows: cells were first pulsed with heat, followed by cooldown, followed by administration of antibody or small molecule and a heat pulse in combination, followed by a cooldown. The effect of the antibodies on heat-induced activation of TRPV1 was assessed by determining the effect of the antibodies on heat-induced influx of calcium ions into the cells.

The peak amplitudes represent the influx of calcium into the cells measured using the calcium indicator Fluo-3.

The ratio of the second to first peak amplitude was calculated for both antibody and vehicle. The percent of inhibition was calculated by comparing the aforementioned ratio for the antibody to the ratio for the vehicle. % inhibition is $(1-((Peak2_{Ab}/Peak1_{Ab})/(peak2_{veh}/peak1_{veh})))*100$.

Measurement of Capsaicin-Induced Activity Using Fluorescence Imaging Plate Reader (FLIPR)

CHO cells with inducible TRPV1 expression were cultured in black, clear bottom 96-well microplates (Corning ltd.) and TRPV1 expression was induced. Cells were loaded with Fluo-3 AM Calcium indicator (Thermo Fisher, cat. no. F1242) by incubating the cells with 4 μM Fluo-3 in HEPES buffer (140 nM NaCl, 5 mM KCl, 1 mM CaCl2, 1 mM MgCl2, 10 mM HEPES, 10 mM D-glucose, pH 7.4) for 30 minutes at room temperature. After subsequent washing of cells with HEPES buffer to remove extracellular Fluo-3, serially diluted antibody was added to wells. Cells were incubated in the presence of antibody for 4 minutes at room temperature. Fluorescence measurements were made using a ClarioSTAR microplate reader (BMG Labtech) with excitation at 483 nm (bandwidth 14 nm) and emission at 530 (bandwidth 30 nm). Baseline fluorescence intensity was first measured, then a fixed amount of capsaicin (in HEPES buffer) was added to each well (to give a concentration of capsaicin that had been previously established as representing the EC50 value of capsaicin for the batch of cells under study, typically such a concentration was in the lower nM range e.g. 10 nM) and a second fluorescence intensity measurement was performed after a certain time (within minutes). EC50 is the concentration of a substance that gives half-maximal response of a biological process, in this case TRPV1-mediated $Ca^{2+}$ entry into cells. Data is presented as the Fluorescence rate, which is calculated as fluorescence at a certain time after addition of capsaicin minus the fluorescence measured before capsaicin addition. The IC50 values for the tested antibodies was calculated. The IC50 value is the half maximal inhibitory concentration of a substance for a biological process under study, in this case capsaicin-induced cellular TRPV1-mediated $Ca^{2+}$ influx.

Results and Discussion

In the study described in the present example, 16 mouse monoclonal antibodies against human TRPV1, 32C8-1, 33C9-1, 34C11-1, 40B10-1, 41B5-1, 43D6-1, 44E8-1, 46B7-1, 46D9-1, 12C9-1, 12G6-1, 15D8-1, 16F1-1, 17E11-1, 17E9-1, 18E10-1, were produced using the hybridoma technology. Specificity of binding to hTRPV1 was determined using FACS, employing a CHO cell line with inducible hTRPV1 expression. Hybridoma supernatant preparations from parental hybridomas from which the 32C8-1, 33C9-1, 34C11-1, 40B10-1, 41B5-1, 43D6-1, 44E8-1, 46B7-1 and 46D9-1 antibodies were derived bound to hTRPV1-expressing cells but not to non-hTRPV1-expressing cells indicating strongly specific binding to hTRPV1 (FIG. 11). Preparations of purified antibody 12C9-1, 12G6-1, 15D8-1, 16F1-1, 17E11-1, 17E9-1 and 18E10-1 bound to hTRPV1-expressing cells but not to non-hTRPV1-expressing cells indicating strongly specific binding to hTRPV1 (FIG. 12).

Further testing of certain of the antibodies is described below.

15D8-1, 16F1-1, 17E9-1 and 17E11-1 were evaluated for their effect on hTRPV1 activation in several different ways. The patch clamp method was used to measure the antibodies' inhibitory activity on hTRPV1 capsaicin responses in hTRPV1-expressing CHO cells. One aspect tested was the propensity to inhibit capsaicin-induced currents at capsaicin concentrations of 100 nM. Antibodies 15D8-1 (at 130 nM), 16F1-1 (at 253 nM), 17E9-1 (at 83 nM), and 17E11-1 (at 110 nM) inhibited capsaicin-induced currents at 100 nM capsaicin and therefore are antagonists of the capsaicin axis of TRPV1 (FIG. 13).

We used FLIPR to determine the capacity to inhibit TRPV1-mediated capsaicin-induced Ca2+ uptake in hTRPV1-expressing CHO cells by antibodies 15D8-1, 16F1-1, 17E9-1, 17E11-1, 41B5-1, and 46B7-1. Efficacy of inhibition can be expressed by the IC50 value, which is the half maximal inhibitory concentration of a substance for the biological process under study, in this case cellular TRPV1-mediated Ca2+ influx. All these antibodies were inhibitory in this regard. From the data we calculated approximate IC50 values of 70 nM for 15D8-1, 170 nM for 41B5-1, 200 nM for 46B7-1, 215 nM for 16F1-1, 230 nM for 17E11-1, and 400 nM for 17E9-1 (FIG. 14).

The antibodies 44E8-1, 40B10-1, 43D6-1 were also tested for their ability to inhibit the capsaicin axis of TRPV1, and each of these antibodies showed an inhibitory effect on the capsaicin axis (data not shown), i.e. showed inhibition of capsaicin-induced activation of TRPV1.

$Ca^{2+}$-imaging was used to measure the inhibitory activity of 15D8-1, 17E11-1, 41B5-1 and 46B7-1 on hTRPV1 heat response in hTRPV1-expressing CHO cells (FIG. 15 and FIG. 16).

When compared to a vehicle control 15D8-1, 17E11-1 and 41B5-1 did not inhibit heat-induced $Ca^{2+}$ uptake in a statistically significant manner. In other words, TRPV1 heat-induced activity remained at approximately 100% (where 100% is that of the vehicle) after antibody treatment (FIG. 15 and FIG. 16). 15D8-1, 17E11-1 and 41B5-1 are therefore not antagonists of the heat axis of TRPV1. The data in this Example shows that antibodies 15D8-1, 17E11-1 and 41E5-1 preferentially inhibit capsaicin-induced activation of TRPV1 as opposed to heat-induced activation of TRPV1.

The data described in this Example also shows that the antibody 46B7-1 preferentially inhibits capsaicin-induced activation of TRPV1 as opposed to heat-induced activation of TRPV1.

The ability to preferentially inhibit activation of hTRPV1 by capsaicin as opposed to activation of hTRPV1 by heat indicates a modality-selective pharmacology, which is a highly desired property for a clinically acceptable and useful therapeutic agent.

In the present study, modality-selective monoclonal antibodies targeting hTRPV1, a clinically important target that has failed using small molecule approaches, have been developed. These antibodies are promising new candidates for TRPV1-targeted pain therapy and are currently pursued as drug candidates.

Example 4—Generation of a Monoclonal Antibody (Antibody Named R4P1-C1)

Materials and Methods

Production of a Monoclonal Antibody (IgG) Using the Phage Display Technology

The antigen mixture for phage display consisted of 3 different peptides (OTV3, OTV4, OTV5) each synthesized and conjugated to 3 different carriers via N-terminal Cys (BSA, OVA+KLH). Thus there were nine different conjugates in total (i.e. OTV3+BSA, OTV3+OVA, OTV3+KLH, OTV4+BSA, OTV4+OVA, OTV4+KLH, OTV5+BSA, OTV5+OVA and OTV5+KLH). BSA is an abbreviation for bovine serum albumin. OVA is an abbreviation for ovalbumin. KLH is an abbreviation for keyhole limpet hemocyanin.

The peptide sequences were as follows:

```
OTV3:
                                        (SEQ ID NO: 16)
CIEDGKNDSLPSESTSHRWRGPASRPPDSSYNS

OTV4:
                                        (SEQ ID NO: 17)
CIEDGKNDSLPSESTSHRWRGPACRPPDSSYNS

OTV5:
                                        (SEQ ID NO: 18)
(Pra-)CIEDGKNDSLPSESTSHRWRGPASRPPDSSYNSC(-CONH2)
```

The OTV3 and OTV4 peptides used are linear peptides. The OTV5 peptide used is a cyclic peptide.

Biopanning

Tubes were coated with antigen mixture, then washed, blocked, and washed again. A phage library depleted by exposure to carriers (BSA, OVA+KLH) was then added followed by incubation. The tubes were then washed again and phage binders were eluted with Glycine HCl followed by neutralization. Eluted phages were added to *E. Coli* culture for amplification, and the amplified phage was collected for a further round of biopanning. After the last biopanning, the polyclonal phage was tested by ELISA.

Polyclonal Phage ELISA

ELISA plates were coated with antigens conjugated to carriers or carriers alone (control), followed by washing, blocking, washing and addition of amplified eluted phages from the biopanning step. After additional washing, bound phage was detected using anti-phage-HRP antibody.

Monoclonal Phage ELISA

Single *E. coli* clones were picked randomly selected during the biopanning step and cultured. Supernatants containing phage were prepared and purified. ELISA plates were coated with antigens conjugated to carriers or carriers alone (control), followed by washing, blocking, washing and addition of purified phage. After additional washing, bound phage was detected using anti-phage-HRP antibody.

Gene Synthesis & Sub-Cloning

A vector construction (plasmid) was prepared as follows. The cDNA of the variable heavy (VH) and the variable light (VL) sequence from phage clone R4P1-C1 that was identified via phage display were chemically synthesized with optimization for mammalian expression in CHO cells, then sub-cloned into a mammalian cell expression vector in order to obtain the full-length sequences of the heavy (HC) and light (LC) chains of human IgG1.

Sequences of the antibody R4P1-C1 are set out in Table U herein.

The IgG type of the R4P1-C1 antibody made in this example is IgG1/kappa.

Expression & Purification of Monoclonal Antibody

Plasmid DNA was transiently co-transfected into CHO cells. Culture medium was collected after 14 days and recombinant antibodies were then purified on a Protein A/G column into PBS buffer (pH 7.5). Purity was assessed by both reduced and non-reduced SDS-PAGE with Coomassie blue staining.

Results and Discussion

This example describes the production of a monoclonal antibody by phage display. The phage library used in this case was a commercially available human naïve LiAb-Fab library (high diversity of 2×10E$^{10}$ variants). After 4 rounds of biopanning and ELISA tests, 80 clones were selected and 5 different sequences were identified within this group of phage clones, represented by R4P1-C1, #1, #2, #3, and #4. Each of these phage clones were tested by ELISA for binding to each of the individual peptides OTV3, OTV4, and OTV5 each coupled to either BSA, OVA or KLH (a total of 9 peptide-conjugates). This is an important confirmation step to ensure clone specificity because due to their nature phages can sometimes bind unspecifically. In the ELISA tests (monoclonal phage ELISA tests) one phage Fab clone, R4P1-C1, bound specifically and strongly to all three of the peptides (all nine of the peptide-carrier conjugates), whereas the other phage Fab clones appeared to be non-specific binders (see Table GG below, all phages were tested at the same concentration).

TABLE GG

|  | #1 | | #2 | | R4P1-C1 | | #3 | | #4 | |
|---|---|---|---|---|---|---|---|---|---|---|
|  | 1 | 2 | 1 | 2 | 1 | 2 | 1 | 2 | 1 | 2 |
| OTV3-KLH | 0.41 | 0.55 | 0.41 | 0.56 | 3.13 | 2.94 | 1.02 | 1.15 | 1.65 | 1.61 |
| OTV4-KLH | 0.60 | 0.68 | 0.38 | 0.40 | 2.81 | 2.51 | 0.78 | 0.88 | 1.06 | 0.91 |
| OTV5-KLH | 0.94 | 0.46 | 0.65 | 0.58 | 2.74 | 2.58 | 1.51 | 1.41 | 1.07 | 1.08 |
| OTV3-OVA | 0.80 | 0.89 | 1.03 | 1.16 | 2.85 | 2.72 | 1.70 | 1.66 | 2.19 | 2.09 |
| OTV4-OVA | 0.86 | 0.85 | 0.77 | 0.94 | 2.84 | 2.78 | 1.06 | 0.91 | 2.22 | 1.98 |
| OTV5-OVA | 0.62 | 0.73 | 0.66 | 0.61 | 2.61 | 2.49 | 2.06 | 1.99 | 2.22 | 1.80 |
| OTV3-BSA | 0.68 | 0.62 | 0.47 | 0.49 | 2.87 | 2.65 | 2.04 | 2.21 | 1.89 | 2.10 |
| OTV4-BSA | 0.56 | 0.52 | 0.67 | 0.82 | 2.95 | 2.80 | 2.32 | 2.11 | 1.52 | 1.34 |
| OTV5-BSA | 0.53 | 0.50 | 0.68 | 0.81 | 2.63 | 2.56 | 2.25 | 2.12 | 1.83 | 1.45 |
| NC1 | 0.70 | 0.64 | 0.82 | 1.07 | 0.06 | 0.06 | 2.17 | 1.91 | 2.21 | 2.00 |
| NC2 | 0.79 | 0.84 | 0.39 | 0.34 | 0.05 | 0.04 | 1.66 | 2.19 | 1.84 | 2.00 |

NC1, Negative control = coating with mix of 3 carriers alone (BSA + OVA + KLH)
NC2, Negative control = coating with buffer only

The invention claimed is:

1. An antibody which binds to TRPV1, wherein said antibody binds to TRPV1 in the extracellular region of TRPV1 wherein the antibody comprises a heavy chain variable region comprising three complementarity determining regions (CDRs) and a light chain variable region comprising three CDRs, wherein the heavy chain variable region comprises a variable heavy (VH) CDR1 comprising the amino acid sequence of SEQ ID NO: 363, a VH CDR2 comprising the amino acid sequence of SEQ ID NO: 364, and a VH CDR3 comprising the amino acid sequence of SEQ ID NO: 365, and wherein the light chain variable region comprises a variable light (VL) CDR1 comprising the amino acid sequence of SEQ ID NO: 366, a VL CDR2 comprising the amino acid sequence of SEQ ID NO: 367, and a VL CDR3 comprising the amino acid sequence of SEQ ID NO: 368.

2. The antibody of claim 1, wherein said antibody comprises a heavy chain variable region that comprises three CDRs and a light chain variable region that comprises three CDRs, wherein the light chain variable region comprises the amino acid sequence of SEQ ID NO:362, or a sequence comprising at least 80% sequence identity of SEQ ID NO:362 and/or wherein the heavy chain variable region comprises the amino acid sequence of SEQ ID NO:361, or a sequence comprising at least 80% sequence identity of SEQ ID NO:361; or the light chain variable region comprises the amino acid sequence of SEQ ID NO:382, or a sequence having at least 80% sequence identity of SEQ ID NO:382 and/or wherein the heavy chain variable region comprises the amino acid sequence of SEQ ID NO:381, or a sequence having at least 80% sequence identity of SEQ ID NO:381.

3. The antibody of claim 1, wherein said antibody is a polyclonal antibody or a monoclonal antibody.

4. The antibody of claim 1, wherein said antibody is a whole antibody comprising an antibody constant region.

5. The antibody of claim 1, wherein said antibody is an IgG antibody.

6. The antibody of claim 1, wherein said antibody is an antigen binding fragment of an antibody.

7. A composition comprising the antibody of claim 1 and a diluent, carrier or excipient.

8. A nucleic acid molecule comprising a nucleotide sequence that encodes the antibody of claim 1, or a set of nucleic acid molecules each comprising a nucleotide sequence, wherein said set of nucleic acid molecules together encode the antibody of claim 1.

9. A method of producing the antibody of claim 1, comprising the steps of:

(i) culturing a host cell comprising one or more nucleic acid molecules encoding an antibody according to claim 1 or a set of nucleic acid molecules each comprising a nucleotide sequence, wherein said set of nucleic acid molecules together encode an antibody of claim 1, or one or more recombinant expression vectors comprising one or more of said nucleic acid molecules, under conditions suitable for the expression of the encoded antibody; and (ii) isolating the antibody from the host cell or from the growth medium or supernatant.

10. The composition of claim 7, wherein the diluent, carrier, or excipient is a pharmaceutically acceptable diluent, carrier, or excipient.

\* \* \* \* \*

SEQUENCE LISTING

<160> NUMBER OF SEQ ID NOS: 452

<210> SEQ ID NO 1
<211> LENGTH: 839
<212> TYPE: PRT
<213> ORGANISM: Homo sapiens

<400> SEQUENCE: 1

```
Met Lys Lys Trp Ser Ser Thr Asp Leu Gly Ala Ala Ala Asp Pro Leu
1               5                   10                  15

Gln Lys Asp Thr Cys Pro Asp Pro Leu Asp Gly Asp Pro Asn Ser Arg
            20                  25                  30

Pro Pro Pro Ala Lys Pro Gln Leu Ser Thr Ala Lys Ser Arg Thr Arg
            35                  40                  45

Leu Phe Gly Lys Gly Asp Ser Glu Glu Ala Phe Pro Val Asp Cys Pro
    50                  55                  60

His Glu Glu Gly Glu Leu Asp Ser Cys Pro Thr Ile Thr Val Ser Pro
65                  70                  75                  80

Val Ile Thr Ile Gln Arg Pro Gly Asp Gly Pro Thr Gly Ala Arg Leu
                85                  90                  95

Leu Ser Gln Asp Ser Val Ala Ala Ser Thr Glu Lys Thr Leu Arg Leu
                100                 105                 110

Tyr Asp Arg Arg Ser Ile Phe Glu Ala Val Ala Gln Asn Asn Cys Gln
            115                 120                 125

Asp Leu Glu Ser Leu Leu Leu Phe Leu Gln Lys Ser Lys Lys His Leu
    130                 135                 140

Thr Asp Asn Glu Phe Lys Asp Pro Glu Thr Gly Lys Thr Cys Leu Leu
145                 150                 155                 160

Lys Ala Met Leu Asn Leu His Asp Gly Gln Asn Thr Thr Ile Pro Leu
                165                 170                 175

Leu Leu Glu Ile Ala Arg Gln Thr Asp Ser Leu Lys Glu Leu Val Asn
                180                 185                 190
```

```
Ala Ser Tyr Thr Asp Ser Tyr Tyr Lys Gly Gln Thr Ala Leu His Ile
        195                 200                 205

Ala Ile Glu Arg Arg Asn Met Ala Leu Val Thr Leu Leu Val Glu Asn
        210                 215                 220

Gly Ala Asp Val Gln Ala Ala Ala His Gly Asp Phe Phe Lys Lys Thr
225                 230                 235                 240

Lys Gly Arg Pro Gly Phe Tyr Phe Gly Glu Leu Pro Leu Ser Leu Ala
                245                 250                 255

Ala Cys Thr Asn Gln Leu Gly Ile Val Lys Phe Leu Leu Gln Asn Ser
                260                 265                 270

Trp Gln Thr Ala Asp Ile Ser Ala Arg Asp Ser Val Gly Asn Thr Val
        275                 280                 285

Leu His Ala Leu Val Glu Val Ala Asp Asn Thr Ala Asp Asn Thr Lys
        290                 295                 300

Phe Val Thr Ser Met Tyr Asn Glu Ile Leu Met Leu Gly Ala Lys Leu
305                 310                 315                 320

His Pro Thr Leu Lys Leu Glu Glu Leu Thr Asn Lys Lys Gly Met Thr
                325                 330                 335

Pro Leu Ala Leu Ala Ala Gly Thr Gly Lys Ile Gly Val Leu Ala Tyr
                340                 345                 350

Ile Leu Gln Arg Glu Ile Gln Glu Pro Glu Cys Arg His Leu Ser Arg
        355                 360                 365

Lys Phe Thr Glu Trp Ala Tyr Gly Pro Val His Ser Ser Leu Tyr Asp
        370                 375                 380

Leu Ser Cys Ile Asp Thr Cys Glu Lys Asn Ser Val Leu Glu Val Ile
385                 390                 395                 400

Ala Tyr Ser Ser Ser Glu Thr Pro Asn Arg His Asp Met Leu Leu Val
                405                 410                 415

Glu Pro Leu Asn Arg Leu Leu Gln Asp Lys Trp Asp Arg Phe Val Lys
                420                 425                 430

Arg Ile Phe Tyr Phe Asn Phe Leu Val Tyr Cys Leu Tyr Met Ile Ile
        435                 440                 445

Phe Thr Met Ala Ala Tyr Tyr Arg Pro Val Asp Gly Leu Pro Pro Phe
        450                 455                 460

Lys Met Glu Lys Thr Gly Asp Tyr Phe Arg Val Thr Gly Glu Ile Leu
465                 470                 475                 480

Ser Val Leu Gly Gly Val Tyr Phe Phe Phe Arg Gly Ile Gln Tyr Phe
                485                 490                 495

Leu Gln Arg Arg Pro Ser Met Lys Thr Leu Phe Val Asp Ser Tyr Ser
                500                 505                 510

Glu Met Leu Phe Phe Leu Gln Ser Leu Phe Met Leu Ala Thr Val Val
        515                 520                 525

Leu Tyr Phe Ser His Leu Lys Glu Tyr Val Ala Ser Met Val Phe Ser
        530                 535                 540

Leu Ala Leu Gly Trp Thr Asn Met Leu Tyr Tyr Thr Arg Gly Phe Gln
545                 550                 555                 560

Gln Met Gly Ile Tyr Ala Val Met Ile Glu Lys Met Ile Leu Arg Asp
                565                 570                 575

Leu Cys Arg Phe Met Phe Val Tyr Ile Val Phe Leu Phe Gly Phe Ser
                580                 585                 590

Thr Ala Val Val Thr Leu Ile Glu Asp Gly Lys Asn Asp Ser Leu Pro
        595                 600                 605

Ser Glu Ser Thr Ser His Arg Trp Arg Gly Pro Ala Cys Arg Pro Pro
```

-continued

```
           610              615              620

Asp Ser Ser Tyr Asn Ser Leu Tyr Ser Thr Cys Leu Glu Leu Phe Lys
625              630              635              640

Phe Thr Ile Gly Met Gly Asp Leu Glu Phe Thr Glu Asn Tyr Asp Phe
             645              650              655

Lys Ala Val Phe Ile Ile Leu Leu Leu Ala Tyr Val Ile Leu Thr Tyr
             660              665              670

Ile Leu Leu Leu Asn Met Leu Ile Ala Leu Met Gly Glu Thr Val Asn
             675              680              685

Lys Ile Ala Gln Glu Ser Lys Asn Ile Trp Lys Leu Gln Arg Ala Ile
             690              695              700

Thr Ile Leu Asp Thr Glu Lys Ser Phe Leu Lys Cys Met Arg Lys Ala
705              710              715              720

Phe Arg Ser Gly Lys Leu Leu Gln Val Gly Tyr Thr Pro Asp Gly Lys
             725              730              735

Asp Asp Tyr Arg Trp Cys Phe Arg Val Asp Glu Val Asn Trp Thr Thr
             740              745              750

Trp Asn Thr Asn Val Gly Ile Ile Asn Glu Asp Pro Gly Asn Cys Glu
             755              760              765

Gly Val Lys Arg Thr Leu Ser Phe Ser Leu Arg Ser Ser Arg Val Ser
770              775              780

Gly Arg His Trp Lys Asn Phe Ala Leu Val Pro Leu Leu Arg Glu Ala
785              790              795              800

Ser Ala Arg Asp Arg Gln Ser Ala Gln Pro Glu Glu Val Tyr Leu Arg
             805              810              815

Gln Phe Ser Gly Ser Leu Lys Pro Glu Asp Ala Glu Val Phe Lys Ser
             820              825              830

Pro Ala Ala Ser Gly Glu Lys
             835
```

<210> SEQ ID NO 2
<211> LENGTH: 32
<212> TYPE: PRT
<213> ORGANISM: Artificial Sequence
<220> FEATURE:
<223> OTHER INFORMATION: Isolated peptide (OTV3)

<400> SEQUENCE: 2

```
Ile Glu Asp Gly Lys Asn Asp Ser Leu Pro Ser Glu Ser Thr Ser His
1               5               10              15

Arg Trp Arg Gly Pro Ala Ser Arg Pro Pro Asp Ser Ser Tyr Asn Ser
             20              25              30
```

<210> SEQ ID NO 3
<211> LENGTH: 32
<212> TYPE: PRT
<213> ORGANISM: Artificial Sequence
<220> FEATURE:
<223> OTHER INFORMATION: Isolated peptide (OTV4)

<400> SEQUENCE: 3

```
Ile Glu Asp Gly Lys Asn Asp Ser Leu Pro Ser Glu Ser Thr Ser His
1               5               10              15

Arg Trp Arg Gly Pro Ala Cys Arg Pro Pro Asp Ser Ser Tyr Asn Ser
             20              25              30
```

<210> SEQ ID NO 4
<211> LENGTH: 32

<212> TYPE: PRT
<213> ORGANISM: Artificial Sequence
<220> FEATURE:
<223> OTHER INFORMATION: Isolated peptide (OTV5)

<400> SEQUENCE: 4

Ile Glu Asp Gly Lys Asn Asp Ser Leu Pro Ser Glu Ser Thr Ser His
1               5                   10                  15

Arg Trp Arg Gly Pro Ala Ser Arg Pro Pro Asp Ser Ser Tyr Asn Ser
            20                  25                  30

<210> SEQ ID NO 5
<211> LENGTH: 8
<212> TYPE: PRT
<213> ORGANISM: Artificial Sequence
<220> FEATURE:
<223> OTHER INFORMATION: Isolated peptide (OTV6)

<400> SEQUENCE: 5

Ile Glu Asp Gly Lys Asn Asp Ser
1               5

<210> SEQ ID NO 6
<211> LENGTH: 16
<212> TYPE: PRT
<213> ORGANISM: Artificial Sequence
<220> FEATURE:
<223> OTHER INFORMATION: Isolated peptide (OTV7)

<400> SEQUENCE: 6

Ile Glu Asp Gly Lys Asn Asp Ser Leu Pro Ser Glu Ser Thr Ser His
1               5                   10                  15

<210> SEQ ID NO 7
<211> LENGTH: 24
<212> TYPE: PRT
<213> ORGANISM: Artificial Sequence
<220> FEATURE:
<223> OTHER INFORMATION: Isolated peptide (OTV8)

<400> SEQUENCE: 7

Ile Glu Asp Gly Lys Asn Asp Ser Leu Pro Ser Glu Ser Thr Ser His
1               5                   10                  15

Arg Trp Arg Gly Pro Ala Ser Arg
            20

<210> SEQ ID NO 8
<211> LENGTH: 24
<212> TYPE: PRT
<213> ORGANISM: Artificial Sequence
<220> FEATURE:
<223> OTHER INFORMATION: Isolated peptide (OTV9)

<400> SEQUENCE: 8

Leu Pro Ser Glu Ser Thr Ser His Arg Trp Arg Gly Pro Ala Ser Arg
1               5                   10                  15

Pro Pro Asp Ser Ser Tyr Asn Ser
            20

<210> SEQ ID NO 9
<211> LENGTH: 16
<212> TYPE: PRT
<213> ORGANISM: Artificial Sequence
<220> FEATURE:
<223> OTHER INFORMATION: Isolated peptide (OTV10)

```
<400> SEQUENCE: 9

Arg Trp Arg Gly Pro Ala Ser Arg Pro Pro Asp Ser Ser Tyr Asn Ser
1               5                   10                  15

<210> SEQ ID NO 10
<211> LENGTH: 8
<212> TYPE: PRT
<213> ORGANISM: Artificial Sequence
<220> FEATURE:
<223> OTHER INFORMATION: Isolated peptide (OTV11)

<400> SEQUENCE: 10

Pro Pro Asp Ser Ser Tyr Asn Ser
1               5

<210> SEQ ID NO 11
<211> LENGTH: 13
<212> TYPE: PRT
<213> ORGANISM: Artificial Sequence
<220> FEATURE:
<223> OTHER INFORMATION: Isolated peptide (OTV12)

<400> SEQUENCE: 11

Leu Tyr Ser Thr Ser Leu Glu Leu Phe Lys Phe Thr Ile
1               5                   10

<210> SEQ ID NO 12
<211> LENGTH: 13
<212> TYPE: PRT
<213> ORGANISM: Artificial Sequence
<220> FEATURE:
<223> OTHER INFORMATION: Isolated peptide (OTV13)

<400> SEQUENCE: 12

Gly Met Gly Asp Leu Glu Phe Thr Glu Asn Tyr Asp Phe
1               5                   10

<210> SEQ ID NO 13
<211> LENGTH: 15
<212> TYPE: PRT
<213> ORGANISM: Artificial Sequence
<220> FEATURE:
<223> OTHER INFORMATION: Isolated peptide (OTV14)

<400> SEQUENCE: 13

Glu Pro Met Asn Tyr Asp Pro Asp Gly Ser Ile Glu Asp Ala Gly
1               5                   10                  15

<210> SEQ ID NO 14
<211> LENGTH: 11
<212> TYPE: PRT
<213> ORGANISM: Artificial Sequence
<220> FEATURE:
<223> OTHER INFORMATION: Isolated peptide (OTV15)

<400> SEQUENCE: 14

Glu Ser Thr Ser His Arg Trp Arg Gly Pro Ala
1               5                   10

<210> SEQ ID NO 15
<211> LENGTH: 339
<212> TYPE: DNA
<213> ORGANISM: Mus musculus

<400> SEQUENCE: 15
gaggtgaacc ttctcgagtc tggaggtggc ctggtgcagc ctggaggatc cctgaaactc    60
```

-continued

```
tcctgtgcag cctcaggatt cgattttcgt agatactgga tgagttgggt ccggcaggct    120
ccagggaaag ggctagaatg gattggagaa attaatccag atagtagtac gataaactat    180
acgccatctc taaaggatga attcatcatc tccagagaca acgccaaaaa tacgctgtac    240
ctgcaaatga gcaaagtgag atctgaggac acagtccttt attactgttc aagaggggg     300 gactactggg gtcaaggaac ctcagtcacc gtctcctca                           339
```

```
<210> SEQ ID NO 16
<211> LENGTH: 33
<212> TYPE: PRT
<213> ORGANISM: Artificial Sequence
<220> FEATURE:
<223> OTHER INFORMATION: Isolated peptide (OTV3)

<400> SEQUENCE: 16

Cys Ile Glu Asp Gly Lys Asn Asp Ser Leu Pro Ser Glu Ser Thr Ser
1               5                   10                  15

His Arg Trp Arg Gly Pro Ala Ser Arg Pro Pro Asp Ser Ser Tyr Asn
            20                  25                  30

Ser
```

```
<210> SEQ ID NO 17
<211> LENGTH: 33
<212> TYPE: PRT
<213> ORGANISM: Artificial Sequence
<220> FEATURE:
<223> OTHER INFORMATION: Isolated peptide (OTV4)

<400> SEQUENCE: 17

Cys Ile Glu Asp Gly Lys Asn Asp Ser Leu Pro Ser Glu Ser Thr Ser
1               5                   10                  15

His Arg Trp Arg Gly Pro Ala Cys Arg Pro Pro Asp Ser Ser Tyr Asn
            20                  25                  30

Ser
```

```
<210> SEQ ID NO 18
<211> LENGTH: 34
<212> TYPE: PRT
<213> ORGANISM: Artificial Sequence
<220> FEATURE:
<223> OTHER INFORMATION: Isolated peptide (OTV5)
<220> FEATURE:
<221> NAME/KEY: MISC_FEATURE
<222> LOCATION: (1)..(34)
<223> OTHER INFORMATION: The peptide is amidated at the C-terminus and
      has a Propargyl group (Pra-) at the N-terminus and is cyclized via
      residues 1 and 34

<400> SEQUENCE: 18

Cys Ile Glu Asp Gly Lys Asn Asp Ser Leu Pro Ser Glu Ser Thr Ser
1               5                   10                  15

His Arg Trp Arg Gly Pro Ala Ser Arg Pro Pro Asp Ser Ser Tyr Asn
            20                  25                  30

Ser Cys
```

```
<210> SEQ ID NO 19
<211> LENGTH: 9
<212> TYPE: PRT
<213> ORGANISM: Artificial Sequence
<220> FEATURE:
<223> OTHER INFORMATION: Isolated peptide (OTV6)
```

```
<400> SEQUENCE: 19

Cys Ile Glu Asp Gly Lys Asn Asp Ser
1               5

<210> SEQ ID NO 20
<211> LENGTH: 17
<212> TYPE: PRT
<213> ORGANISM: Artificial Sequence
<220> FEATURE:
<223> OTHER INFORMATION: Isolated peptide (OTV7)

<400> SEQUENCE: 20

Cys Ile Glu Asp Gly Lys Asn Asp Ser Leu Pro Ser Glu Ser Thr Ser
1               5                   10                  15

His

<210> SEQ ID NO 21
<211> LENGTH: 25
<212> TYPE: PRT
<213> ORGANISM: Artificial Sequence
<220> FEATURE:
<223> OTHER INFORMATION: Isolated peptide (OTV8)

<400> SEQUENCE: 21

Cys Ile Glu Asp Gly Lys Asn Asp Ser Leu Pro Ser Glu Ser Thr Ser
1               5                   10                  15

His Arg Trp Arg Gly Pro Ala Ser Arg
            20                  25

<210> SEQ ID NO 22
<211> LENGTH: 25
<212> TYPE: PRT
<213> ORGANISM: Artificial Sequence
<220> FEATURE:
<223> OTHER INFORMATION: Isolated peptide (OTV9)

<400> SEQUENCE: 22

Leu Pro Ser Glu Ser Thr Ser His Arg Trp Arg Gly Pro Ala Ser Arg
1               5                   10                  15

Pro Pro Asp Ser Ser Tyr Asn Ser Cys
            20                  25

<210> SEQ ID NO 23
<211> LENGTH: 17
<212> TYPE: PRT
<213> ORGANISM: Artificial Sequence
<220> FEATURE:
<223> OTHER INFORMATION: Isolated peptide (OTV10)

<400> SEQUENCE: 23

Arg Trp Arg Gly Pro Ala Ser Arg Pro Pro Asp Ser Ser Tyr Asn Ser
1               5                   10                  15

Cys

<210> SEQ ID NO 24
<211> LENGTH: 9
<212> TYPE: PRT
<213> ORGANISM: Artificial Sequence
<220> FEATURE:
<223> OTHER INFORMATION: Isolated peptide (OTV11)

<400> SEQUENCE: 24

Pro Pro Asp Ser Ser Tyr Asn Ser Cys
1               5
```

<210> SEQ ID NO 25
<211> LENGTH: 14
<212> TYPE: PRT
<213> ORGANISM: Artificial Sequence
<220> FEATURE:
<223> OTHER INFORMATION: Isolated peptide (OTV12)

<400> SEQUENCE: 25

Leu Tyr Ser Thr Ser Leu Glu Leu Phe Lys Phe Thr Ile Cys
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Isolated peptide (OTV13)

<400> SEQUENCE: 26

Cys Gly Met Gly Asp Leu Glu Phe Thr Glu Asn Tyr Asp Phe
1               5                   10

<210> SEQ ID NO 27
<211> LENGTH: 17
<212> TYPE: PRT
<213> ORGANISM: Artificial Sequence
<220> FEATURE:
<223> OTHER INFORMATION: Isolated peptide (OTV14)
<220> FEATURE:
<221> NAME/KEY: MISC_FEATURE
<222> LOCATION: (1)..(17)
<223> OTHER INFORMATION: The peptide is amidated at the C-terminus and
      has a Propargyl group (Pra-) at the N-terminus and is cyclized via
      residues 1 and 17

<400> SEQUENCE: 27

Cys Glu Pro Met Asn Tyr Asp Pro Asp Gly Ser Ile Glu Asp Ala Gly
1               5                   10                  15

Cys

<210> SEQ ID NO 28
<211> LENGTH: 13
<212> TYPE: PRT
<213> ORGANISM: Artificial Sequence
<220> FEATURE:
<223> OTHER INFORMATION: Isolated peptide (OTV15)
<220> FEATURE:
<221> NAME/KEY: MISC_FEATURE
<222> LOCATION: (1)..(13)
<223> OTHER INFORMATION: The peptide is amidated at the C-terminus and
      has a Propargyl group (Pra-) at the N-terminus and is cyclized via
      residues 1 and 13

<400> SEQUENCE: 28

Cys Glu Ser Thr Ser His Arg Trp Arg Gly Pro Ala Cys
1               5                   10

<210> SEQ ID NO 29
<211> LENGTH: 336
<212> TYPE: DNA
<213> ORGANISM: Mus musculus

<400> SEQUENCE: 29
gatgttgtga tgacccagac tccactcact ttgtcggttc ccattggaca accagcctcc      60
atctcttgca agtcaagtca gagcctctta gatagtgctg gaaagacata tttgaattgg     120

-continued

```
ttgttacaga ggccaggcca gtctccaaag cgcctgatct atctggtgtc taaactggac        180
tctggagtcc ctgacaagtt cactggcagt ggatcaggga cagatttcac actgaaaatc        240
agcagagtgg aggctgagga tttgggaatt tattattgct ggcaaggtac acattttcca        300
tacacgttcg gctcgggggac aaaattggaa ataaaa                                 336
```

```
<210> SEQ ID NO 30
<211> LENGTH: 24
<212> TYPE: PRT
<213> ORGANISM: Artificial Sequence
<220> FEATURE:
<223> OTHER INFORMATION: Description of sequence: sequence motif

<400> SEQUENCE: 30

Glu Asp Gly Lys Asn Asn Ser Leu Pro Met Glu Ser Thr Pro His Lys
1               5                   10                  15

Cys Arg Gly Ser Ala Cys Lys Pro
            20
```

```
<210> SEQ ID NO 31
<211> LENGTH: 39
<212> TYPE: PRT
<213> ORGANISM: Artificial Sequence
<220> FEATURE:
<223> OTHER INFORMATION: Description of sequence: sequence motif

<400> SEQUENCE: 31

Thr Leu Ile Glu Asp Gly Lys Asn Asp Ser Leu Pro Ser Glu Ser Thr
1               5                   10                  15

Ser His Arg Trp Arg Gly Pro Ala Cys Arg Pro Pro Asp Ser Ser Tyr
            20                  25                  30

Asn Ser Leu Tyr Ser Thr Cys
        35
```

```
<210> SEQ ID NO 32
<211> LENGTH: 9
<212> TYPE: PRT
<213> ORGANISM: Artificial Sequence
<220> FEATURE:
<223> OTHER INFORMATION: Description of sequence: sequence motif

<400> SEQUENCE: 32

Ser Leu Pro Ser Glu Ser Thr Ser His
1               5
```

```
<210> SEQ ID NO 33
<211> LENGTH: 6
<212> TYPE: PRT
<213> ORGANISM: Artificial Sequence
<220> FEATURE:
<223> OTHER INFORMATION: Description of sequence: Region of TRPV1

<400> SEQUENCE: 33

Ile Glu Asp Gly Lys Asn
1               5
```

```
<210> SEQ ID NO 34
<211> LENGTH: 6
<212> TYPE: PRT
<213> ORGANISM: Artificial Sequence
<220> FEATURE:
<223> OTHER INFORMATION: Description of sequence: Region of TRPV1

<400> SEQUENCE: 34
```

```
Leu Pro Ser Glu Ser Thr
1               5

<210> SEQ ID NO 35
<211> LENGTH: 8
<212> TYPE: PRT
<213> ORGANISM: Artificial Sequence
<220> FEATURE:
<223> OTHER INFORMATION: Description of sequence: Region of TRPV1

<400> SEQUENCE: 35

Pro Pro Asp Ser Ser Tyr Asn Ser
1               5

<210> SEQ ID NO 36
<211> LENGTH: 6
<212> TYPE: PRT
<213> ORGANISM: Artificial Sequence
<220> FEATURE:
<223> OTHER INFORMATION: Description of sequence: Region of TRPV1

<400> SEQUENCE: 36

Arg Trp Arg Gly Pro Ala
1               5

<210> SEQ ID NO 37
<211> LENGTH: 6
<212> TYPE: PRT
<213> ORGANISM: Artificial Sequence
<220> FEATURE:
<223> OTHER INFORMATION: Description of sequence: Region of TRPV1

<400> SEQUENCE: 37

Arg Gly Pro Ala Ser Arg
1               5

<210> SEQ ID NO 38
<211> LENGTH: 4
<212> TYPE: PRT
<213> ORGANISM: Artificial Sequence
<220> FEATURE:
<223> OTHER INFORMATION: Peptide spacer between motifs

<400> SEQUENCE: 38

Pro Asp Gly Ser
1

<210> SEQ ID NO 39
<211> LENGTH: 113
<212> TYPE: PRT
<213> ORGANISM: Mus musculus

<400> SEQUENCE: 39

Glu Val Asn Leu Leu Glu Ser Gly Gly Gly Leu Val Gln Pro Gly Gly
1               5                   10                  15

Ser Leu Lys Leu Ser Cys Ala Ala Ser Gly Phe Asp Phe Arg Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Glu Phe Ile Ile Ser Arg Asp Asn Ala Lys Asn Thr Leu Tyr
65                  70                  75                  80

Leu Gln Met Ser Lys Val Arg Ser Glu Asp Thr Val Leu Tyr Tyr Cys
```

-continued

```
                 85              90              95

Ser Arg Gly Gly Asp Tyr Trp Gly Gln Gly Thr Ser Val Thr Val Ser
            100             105             110

Ser

<210> SEQ ID NO 40
<211> LENGTH: 112
<212> TYPE: PRT
<213> ORGANISM: Mus musculus

<400> SEQUENCE: 40

Asp Val Val Met Thr Gln Thr Pro Leu Thr Leu Ser Val Pro Ile Gly
1               5              10              15

Gln Pro Ala Ser Ile Ser Cys Lys Ser Ser Gln Ser Leu Leu Asp Ser
            20              25              30

Ala Gly Lys Thr Tyr Leu Asn Trp Leu Leu Gln Arg Pro Gly Gln Ser
        35              40              45

Pro Lys Arg Leu Ile Tyr Leu Val Ser Lys Leu Asp Ser Gly Val Pro
    50              55              60

Asp Lys Phe Thr Gly Ser Gly Ser Gly Thr Asp Phe Thr Leu Lys Ile
65              70              75              80

Ser Arg Val Glu Ala Glu Asp Leu Gly Ile Tyr Tyr Cys Trp Gln Gly
            85              90              95

Thr His Phe Pro Tyr Thr Phe Gly Ser Gly Thr Lys Leu Glu Ile Lys
            100             105             110

<210> SEQ ID NO 41
<211> LENGTH: 5
<212> TYPE: PRT
<213> ORGANISM: Mus musculus

<400> SEQUENCE: 41

Arg Tyr Trp Met Ser
1               5

<210> SEQ ID NO 42
<211> LENGTH: 17
<212> TYPE: PRT
<213> ORGANISM: Mus musculus

<400> SEQUENCE: 42

Glu Ile Asn Pro Asp Ser Ser Thr Ile Asn Tyr Thr Pro Ser Leu Lys
1               5              10              15

Asp

<210> SEQ ID NO 43
<211> LENGTH: 4
<212> TYPE: PRT
<213> ORGANISM: Mus musculus

<400> SEQUENCE: 43

Gly Gly Asp Tyr
1

<210> SEQ ID NO 44
<211> LENGTH: 16
<212> TYPE: PRT
<213> ORGANISM: Mus musculus

<400> SEQUENCE: 44
```

-continued

```
Lys Ser Ser Gln Ser Leu Leu Asp Ser Ala Gly Lys Thr Tyr Leu Asn
1               5                   10                  15

<210> SEQ ID NO 45
<211> LENGTH: 7
<212> TYPE: PRT
<213> ORGANISM: Mus musculus

<400> SEQUENCE: 45

Leu Val Ser Lys Leu Asp Ser
1               5

<210> SEQ ID NO 46
<211> LENGTH: 9
<212> TYPE: PRT
<213> ORGANISM: Mus musculus

<400> SEQUENCE: 46

Trp Gln Gly Thr His Phe Pro Tyr Thr
1               5

<210> SEQ ID NO 47
<211> LENGTH: 30
<212> TYPE: PRT
<213> ORGANISM: Mus musculus

<400> SEQUENCE: 47

Glu Val Asn Leu Leu Glu Ser Gly Gly Gly Leu Val Gln Pro Gly Gly
1               5                   10                  15

Ser Leu Lys Leu Ser Cys Ala Ala Ser Gly Phe Asp Phe Arg
            20                  25                  30

<210> SEQ ID NO 48
<211> LENGTH: 14
<212> TYPE: PRT
<213> ORGANISM: Mus musculus

<400> SEQUENCE: 48

Trp Val Arg Gln Ala Pro Gly Lys Gly Leu Glu Trp Ile Gly
1               5                   10

<210> SEQ ID NO 49
<211> LENGTH: 32
<212> TYPE: PRT
<213> ORGANISM: Mus musculus

<400> SEQUENCE: 49

Glu Phe Ile Ile Ser Arg Asp Asn Ala Lys Asn Thr Leu Tyr Leu Gln
1               5                   10                  15

Met Ser Lys Val Arg Ser Glu Asp Thr Val Leu Tyr Tyr Cys Ser Arg
            20                  25                  30

<210> SEQ ID NO 50
<211> LENGTH: 11
<212> TYPE: PRT
<213> ORGANISM: Mus musculus

<400> SEQUENCE: 50

Trp Gly Gln Gly Thr Ser Val Thr Val Ser Ser
1               5                   10

<210> SEQ ID NO 51
<211> LENGTH: 23
<212> TYPE: PRT
```

<213> ORGANISM: Mus musculus

<400> SEQUENCE: 51

Asp Val Val Met Thr Gln Thr Pro Leu Thr Leu Ser Val Pro Ile Gly
1               5                   10                  15

Gln Pro Ala Ser Ile Ser Cys
            20

<210> SEQ ID NO 52
<211> LENGTH: 15
<212> TYPE: PRT
<213> ORGANISM: Mus musculus

<400> SEQUENCE: 52

Trp Leu Leu Gln Arg Pro Gly Gln Ser Pro Lys Arg Leu Ile Tyr
1               5                   10                  15

<210> SEQ ID NO 53
<211> LENGTH: 32
<212> TYPE: PRT
<213> ORGANISM: Mus musculus

<400> SEQUENCE: 53

Gly Val Pro Asp Lys Phe Thr Gly Ser Gly Ser Gly Thr Asp Phe Thr
1               5                   10                  15

Leu Lys Ile Ser Arg Val Glu Ala Glu Asp Leu Gly Ile Tyr Tyr Cys
            20                  25                  30

<210> SEQ ID NO 54
<211> LENGTH: 10
<212> TYPE: PRT
<213> ORGANISM: Mus musculus

<400> SEQUENCE: 54

Phe Gly Ser Gly Thr Lys Leu Glu Ile Lys
1               5                   10

<210> SEQ ID NO 55
<211> LENGTH: 339
<212> TYPE: DNA
<213> ORGANISM: Mus musculus

<400> SEQUENCE: 55
gaggtgaagc ttctcgagtc tggaggtggc ctggtgcagc ctggaggatc cctgaaactc      60
tcctgtgcag cctcaggatt cgattttcgt agatactgga tgagttgggt ccggcaggct     120
ccagggaaag ggctagaatg gattggagaa attaatccag atagtagtac gataaactat     180
acgccatctc taaaggatga attcatcatc tccagagaca cgccaaaaa tacgctgtac       240 ctgcaaatga gcaaagtgag atctgaggac acagtccttt attactgttc aagaggggggg    300 gactactggg gtcaaggaac ctcagtcacc gtctcctca                            339

<210> SEQ ID NO 56
<211> LENGTH: 336
<212> TYPE: DNA
<213> ORGANISM: Mus musculus

<400> SEQUENCE: 56
gatgttgtga tgacccagac tccactcact ttgtcggttc ccattggaca accagcctcc      60
atctcttgca gtcaagtca gagcctctta gatagtgctg aaagacata tttgaattgg       120 ttgttacaga ggccaggcca gtctccaaag cgcctaatct atctggtgtc taaactggac     180

-continued

```
tctggagtcc ctgacaagtt cactggcagt ggatcaggga cagatttcac actgaaaatc      240
agcagagtgg aggctgagga tttgggaatt tattattgct ggcaaggtac acattttcca      300
tacacgttcg gctcggggac aaaattggaa ataaaa                                336
```

<210> SEQ ID NO 57
<211> LENGTH: 113
<212> TYPE: PRT
<213> ORGANISM: Mus musculus

<400> SEQUENCE: 57

```
Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Arg Arg Tyr
            20                  25                  30

Trp Met Ser Trp Val Arg Gln Ala Pro Gly Lys Gly Leu Glu Trp Ile
        35                  40                  45

Gly Glu Ile Asn Pro Asp Ser Ser Thr Ile Asn Tyr Thr Pro Ser Leu
    50                  55                  60

Lys Asp Glu Phe Ile Ile Ser Arg Asp Asn Ala Lys Asn Thr Leu Tyr
65                  70                  75                  80

Leu Gln Met Ser Lys Val Arg Ser Glu Asp Thr Val Leu Tyr Tyr Cys
                85                  90                  95

Ser Arg Gly Gly Asp Tyr Trp Gly Gln Gly Thr Ser Val Thr Val Ser
            100                 105                 110

Ser
```

<210> SEQ ID NO 58
<211> LENGTH: 112
<212> TYPE: PRT
<213> ORGANISM: Mus musculus

<400> SEQUENCE: 58

```
Asp Val Val Met Thr Gln Thr Pro Leu Thr Leu Ser Val Pro Ile Gly
1               5                   10                  15

Gln Pro Ala Ser Ile Ser Cys Lys Ser Ser Gln Ser Leu Leu Asp Ser
            20                  25                  30

Ala Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Lys Phe Thr Gly Ser Gly Ser Gly Thr Asp Phe Thr Leu Lys Ile
65                  70                  75                  80

Ser Arg Val Glu Ala Glu Asp Leu Gly Ile Tyr Tyr Cys Trp Gln Gly
                85                  90                  95

Thr His Phe Pro Tyr Thr Phe Gly Ser Gly Thr Lys Leu Glu Ile Lys
            100                 105                 110
```

<210> SEQ ID NO 59
<211> LENGTH: 5
<212> TYPE: PRT
<213> ORGANISM: Mus musculus

<400> SEQUENCE: 59

```
Arg Tyr Trp Met Ser
1               5
```

-continued

```
<210> SEQ ID NO 60
<211> LENGTH: 17
<212> TYPE: PRT
<213> ORGANISM: Mus musculus

<400> SEQUENCE: 60

Glu Ile Asn Pro Asp Ser Ser Thr Ile Asn Tyr Thr Pro Ser Leu Lys
1               5                   10                  15

Asp

<210> SEQ ID NO 61
<211> LENGTH: 4
<212> TYPE: PRT
<213> ORGANISM: Mus musculus

<400> SEQUENCE: 61

Gly Gly Asp Tyr
1

<210> SEQ ID NO 62
<211> LENGTH: 16
<212> TYPE: PRT
<213> ORGANISM: Mus musculus

<400> SEQUENCE: 62

Lys Ser Ser Gln Ser Leu Leu Asp Ser Ala Gly Lys Thr Tyr Leu Asn
1               5                   10                  15

<210> SEQ ID NO 63
<211> LENGTH: 7
<212> TYPE: PRT
<213> ORGANISM: Mus musculus

<400> SEQUENCE: 63

Leu Val Ser Lys Leu Asp Ser
1               5

<210> SEQ ID NO 64
<211> LENGTH: 9
<212> TYPE: PRT
<213> ORGANISM: Mus musculus

<400> SEQUENCE: 64

Trp Gln Gly Thr His Phe Pro Tyr Thr
1               5

<210> SEQ ID NO 65
<211> LENGTH: 30
<212> TYPE: PRT
<213> ORGANISM: Mus musculus

<400> SEQUENCE: 65

Glu Val Lys Leu Leu Glu Ser Gly Gly Gly Leu Val Gln Pro Gly Gly
1               5                   10                  15

Ser Leu Lys Leu Ser Cys Ala Ala Ser Gly Phe Asp Phe Arg
            20                  25                  30

<210> SEQ ID NO 66
<211> LENGTH: 14
<212> TYPE: PRT
<213> ORGANISM: Mus musculus

<400> SEQUENCE: 66

Trp Val Arg Gln Ala Pro Gly Lys Gly Leu Glu Trp Ile Gly
```

-continued

```
1               5                   10

<210> SEQ ID NO 67
<211> LENGTH: 32
<212> TYPE: PRT
<213> ORGANISM: Mus musculus

<400> SEQUENCE: 67

Glu Phe Ile Ile Ser Arg Asp Asn Ala Lys Asn Thr Leu Tyr Leu Gln
1               5                   10                  15

Met Ser Lys Val Arg Ser Glu Asp Thr Val Leu Tyr Tyr Cys Ser Arg
                20                  25                  30

<210> SEQ ID NO 68
<211> LENGTH: 11
<212> TYPE: PRT
<213> ORGANISM: Mus musculus

<400> SEQUENCE: 68

Trp Gly Gln Gly Thr Ser Val Thr Val Ser Ser
1               5                   10

<210> SEQ ID NO 69
<211> LENGTH: 23
<212> TYPE: PRT
<213> ORGANISM: Mus musculus

<400> SEQUENCE: 69

Asp Val Val Met Thr Gln Thr Pro Leu Thr Leu Ser Val Pro Ile Gly
1               5                   10                  15

Gln Pro Ala Ser Ile Ser Cys
                20

<210> SEQ ID NO 70
<211> LENGTH: 15
<212> TYPE: PRT
<213> ORGANISM: Mus musculus

<400> SEQUENCE: 70

Trp Leu Leu Gln Arg Pro Gly Gln Ser Pro Lys Arg Leu Ile Tyr
1               5                   10                  15

<210> SEQ ID NO 71
<211> LENGTH: 32
<212> TYPE: PRT
<213> ORGANISM: Mus musculus

<400> SEQUENCE: 71

Gly Val Pro Asp Lys Phe Thr Gly Ser Gly Ser Gly Thr Asp Phe Thr
1               5                   10                  15

Leu Lys Ile Ser Arg Val Glu Ala Glu Asp Leu Gly Ile Tyr Tyr Cys
                20                  25                  30

<210> SEQ ID NO 72
<211> LENGTH: 10
<212> TYPE: PRT
<213> ORGANISM: Mus musculus

<400> SEQUENCE: 72

Phe Gly Ser Gly Thr Lys Leu Glu Ile Lys
1               5                   10

<210> SEQ ID NO 73
```

<211> LENGTH: 366
<212> TYPE: DNA
<213> ORGANISM: Mus musculus

<400> SEQUENCE: 73
gaggttcagc tgcagcagtc tgggggcagag cttgtgaagc cagggggcctc agtcaaattg      60 tcctgcacag cttctggctt caacattaaa gacacctata tacactgggt gaagcagagg     120
cctgaacagg gcctggagtg gattggaagg attgatcctg cgaatggtaa tactagatat     180
gacccgaaat tccagggcaa ggccactata acagcagaca catcctccaa cacagcctac     240
ctgcaactca gcagcctgac atctgaggac actgccgtct attactgtgc taaagtctcg     300
ggggatagga ggttttactg gtacttcgat gtctggggcg cagggaccac ggtcaccgtc     360
tcctca                                                                366

<210> SEQ ID NO 74
<211> LENGTH: 336
<212> TYPE: DNA
<213> ORGANISM: Mus musculus

<400> SEQUENCE: 74
gacattgtga tgtcacagtc tccatcctcc ctagctgtgt cagttggaga gaaggttact      60
atgagctgca agtccagtca gagccttttta tatagtagca atcaaaagaa ctgtttggcc     120
tggtaccagc agaaaccagg gcagtctcct aaactgctga tttactgggc atccactagg     180
gaatctgggg tccctgatcg cttcacaggc agtggatctg ggacagattt cactctcacc     240
atcagcagtg tgaaggctga agacctggca gtttattact gtcagcaata ttatagctat     300
ccgacgttcg gtggaggcac caagctggaa atcaaa                               336

<210> SEQ ID NO 75
<211> LENGTH: 122
<212> TYPE: PRT
<213> ORGANISM: Mus musculus

<400> SEQUENCE: 75

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Asp Pro Ala Asn Gly Asn Thr Arg Tyr Asp Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Lys Val Ser Gly Asp Arg Arg Phe Tyr Trp Tyr Phe Asp Val Trp
            100                 105                 110

Gly Ala Gly Thr Thr Val Thr Val Ser Ser
        115                 120

<210> SEQ ID NO 76
<211> LENGTH: 112
<212> TYPE: PRT
<213> ORGANISM: Mus musculus

<400> SEQUENCE: 76

-continued

```
Asp Ile Val Met Ser Gln Ser Pro Ser Ser Leu Ala Val Ser Val Gly
1               5                   10                  15

Glu Lys Val Thr Met Ser Cys Lys Ser Ser Gln Ser Leu Leu Tyr Ser
            20                  25                  30

Ser Asn Gln Lys Asn Cys Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
                85                  90                  95

Tyr Tyr Ser Tyr Pro Thr Phe Gly Gly Gly Thr Lys Leu Glu Ile Lys
            100                 105                 110
```

```
<210> SEQ ID NO 77
<211> LENGTH: 5
<212> TYPE: PRT
<213> ORGANISM: Mus musculus

<400> SEQUENCE: 77

Asp Thr Tyr Ile His
1               5
```

```
<210> SEQ ID NO 78
<211> LENGTH: 17
<212> TYPE: PRT
<213> ORGANISM: Mus musculus

<400> SEQUENCE: 78

Arg Ile Asp Pro Ala Asn Gly Asn Thr Arg Tyr Asp Pro Lys Phe Gln
1               5                   10                  15

Gly
```

```
<210> SEQ ID NO 79
<211> LENGTH: 13
<212> TYPE: PRT
<213> ORGANISM: Mus musculus

<400> SEQUENCE: 79

Val Ser Gly Asp Arg Arg Phe Tyr Trp Tyr Phe Asp Val
1               5                   10
```

```
<210> SEQ ID NO 80
<211> LENGTH: 17
<212> TYPE: PRT
<213> ORGANISM: Mus musculus

<400> SEQUENCE: 80

Lys Ser Ser Gln Ser Leu Leu Tyr Ser Ser Asn Gln Lys Asn Cys Leu
1               5                   10                  15

Ala
```

```
<210> SEQ ID NO 81
<211> LENGTH: 7
<212> TYPE: PRT
<213> ORGANISM: Mus musculus

<400> SEQUENCE: 81

Trp Ala Ser Thr Arg Glu Ser
```

-continued

```
1               5

<210> SEQ ID NO 82
<211> LENGTH: 8
<212> TYPE: PRT
<213> ORGANISM: Mus musculus

<400> SEQUENCE: 82

Gln Gln Tyr Tyr Ser Tyr Pro Thr
1               5

<210> SEQ ID NO 83
<211> LENGTH: 30
<212> TYPE: PRT
<213> ORGANISM: Mus musculus

<400> SEQUENCE: 83

Glu Val Gln Leu Gln Gln Ser Gly Ala Glu Leu Val Lys Pro Gly Ala
1               5                   10                  15

Ser Val Lys Leu Ser Cys Thr Ala Ser Gly Phe Asn Ile Lys
            20                  25                  30

<210> SEQ ID NO 84
<211> LENGTH: 14
<212> TYPE: PRT
<213> ORGANISM: Mus musculus

<400> SEQUENCE: 84

Trp Val Lys Gln Arg Pro Glu Gln Gly Leu Glu Trp Ile Gly
1               5                   10

<210> SEQ ID NO 85
<211> LENGTH: 32
<212> TYPE: PRT
<213> ORGANISM: Mus musculus

<400> SEQUENCE: 85

Lys Ala Thr Ile Thr Ala Asp Thr Ser Ser Asn Thr Ala Tyr Leu Gln
1               5                   10                  15

Leu Ser Ser Leu Thr Ser Glu Asp Thr Ala Val Tyr Tyr Cys Ala Lys
            20                  25                  30

<210> SEQ ID NO 86
<211> LENGTH: 11
<212> TYPE: PRT
<213> ORGANISM: Mus musculus

<400> SEQUENCE: 86

Trp Gly Ala Gly Thr Thr Val Thr Val Ser Ser
1               5                   10

<210> SEQ ID NO 87
<211> LENGTH: 23
<212> TYPE: PRT
<213> ORGANISM: Mus musculus

<400> SEQUENCE: 87

Asp Ile Val Met Ser Gln Ser Pro Ser Ser Leu Ala Val Ser Val Gly
1               5                   10                  15

Glu Lys Val Thr Met Ser Cys
            20

<210> SEQ ID NO 88
```

```
<211> LENGTH: 15
<212> TYPE: PRT
<213> ORGANISM: Mus musculus

<400> SEQUENCE: 88

Trp Tyr Gln Gln Lys Pro Gly Gln Ser Pro Lys Leu Leu Ile Tyr
1               5                   10                  15

<210> SEQ ID NO 89
<211> LENGTH: 32
<212> TYPE: PRT
<213> ORGANISM: Mus musculus

<400> SEQUENCE: 89

Gly Val Pro Asp Arg Phe Thr Gly Ser Gly Ser Gly Thr Asp Phe Thr
1               5                   10                  15

Leu Thr Ile Ser Ser Val Lys Ala Glu Asp Leu Ala Val Tyr Tyr Cys
            20                  25                  30

<210> SEQ ID NO 90
<211> LENGTH: 10
<212> TYPE: PRT
<213> ORGANISM: Mus musculus

<400> SEQUENCE: 90

Phe Gly Gly Gly Thr Lys Leu Glu Ile Lys
1               5                   10

<210> SEQ ID NO 91
<211> LENGTH: 17
<212> TYPE: PRT
<213> ORGANISM: Artificial Sequence
<220> FEATURE:
<223> OTHER INFORMATION: VL CDR1 consensus sequence
<220> FEATURE:
<221> NAME/KEY: MISC_FEATURE
<222> LOCATION: (8)..(8)
<223> OTHER INFORMATION: any amino acid
<220> FEATURE:
<221> NAME/KEY: MISC_FEATURE
<222> LOCATION: (10)..(10)
<223> OTHER INFORMATION: any amino acid
<220> FEATURE:
<221> NAME/KEY: MISC_FEATURE
<222> LOCATION: (11)..(11)
<223> OTHER INFORMATION: any amino acid
<220> FEATURE:
<221> NAME/KEY: MISC_FEATURE
<222> LOCATION: (12)..(12)
<223> OTHER INFORMATION: any amino acid
<220> FEATURE:
<221> NAME/KEY: MISC_FEATURE
<222> LOCATION: (13)..(13)
<223> OTHER INFORMATION: any amino acid
<220> FEATURE:
<221> NAME/KEY: MISC_FEATURE
<222> LOCATION: (14)..(14)
<223> OTHER INFORMATION: any amino acid
<220> FEATURE:
<221> NAME/KEY: MISC_FEATURE
<222> LOCATION: (15)..(15)
<223> OTHER INFORMATION: any amino acid
<220> FEATURE:
<221> NAME/KEY: MISC_FEATURE
<222> LOCATION: (16)..(16)
<223> OTHER INFORMATION: any amino acid
<220> FEATURE:
<221> NAME/KEY: MISC_FEATURE
<222> LOCATION: (17)..(17)
<223> OTHER INFORMATION: any amino acid or no amino acid

<400> SEQUENCE: 91
```

-continued

Lys Ser Ser Gln Ser Leu Leu Xaa Ser Xaa Xaa Xaa Xaa Xaa Xaa Xaa
1               5                   10                  15

Xaa

<210> SEQ ID NO 92
<211> LENGTH: 17
<212> TYPE: PRT
<213> ORGANISM: Artificial Sequence
<220> FEATURE:
<223> OTHER INFORMATION: VL CDR1 consensus sequence
<220> FEATURE:
<221> NAME/KEY: MISC_FEATURE
<222> LOCATION: (8)..(8)
<223> OTHER INFORMATION: Asp or Tyr
<220> FEATURE:
<221> NAME/KEY: MISC_FEATURE
<222> LOCATION: (10)..(10)
<223> OTHER INFORMATION: Ala or Ser
<220> FEATURE:
<221> NAME/KEY: MISC_FEATURE
<222> LOCATION: (11)..(11)
<223> OTHER INFORMATION: Gly or Asn
<220> FEATURE:
<221> NAME/KEY: MISC_FEATURE
<222> LOCATION: (12)..(12)
<223> OTHER INFORMATION: Lys or Gln
<220> FEATURE:
<221> NAME/KEY: MISC_FEATURE
<222> LOCATION: (13)..(13)
<223> OTHER INFORMATION: Thr or Lys
<220> FEATURE:
<221> NAME/KEY: MISC_FEATURE
<222> LOCATION: (14)..(14)
<223> OTHER INFORMATION: Tyr or Asn
<220> FEATURE:
<221> NAME/KEY: MISC_FEATURE
<222> LOCATION: (15)..(15)
<223> OTHER INFORMATION: Leu or Cys
<220> FEATURE:
<221> NAME/KEY: MISC_FEATURE
<222> LOCATION: (16)..(16)
<223> OTHER INFORMATION: Asn or Leu
<220> FEATURE:
<221> NAME/KEY: MISC_FEATURE
<222> LOCATION: (17)..(17)
<223> OTHER INFORMATION: Ala or no amino acid

<400> SEQUENCE: 92

Lys Ser Ser Gln Ser Leu Leu Xaa Ser Xaa Xaa Xaa Xaa Xaa Xaa Xaa
1               5                   10                  15

Xaa

<210> SEQ ID NO 93
<211> LENGTH: 18
<212> TYPE: PRT
<213> ORGANISM: Mus musculus

<400> SEQUENCE: 93

Met Asp Phe Gly Leu Ile Phe Phe Ile Val Ala Leu Leu Lys Gly Val
1               5                   10                  15

Gln Cys

<210> SEQ ID NO 94
<211> LENGTH: 19
<212> TYPE: PRT
<213> ORGANISM: Mus musculus

<400> SEQUENCE: 94

Met Ser Pro Ala Gln Phe Leu Phe Leu Leu Val Leu Trp Ile Arg Asp

```
1               5               10              15

Thr Asn Gly

<210> SEQ ID NO 95
<211> LENGTH: 18
<212> TYPE: PRT
<213> ORGANISM: Mus musculus

<400> SEQUENCE: 95

Met Asp Phe Gly Leu Ile Phe Phe Ile Val Ala Leu Leu Lys Gly Val
1               5               10              15

Gln Cys

<210> SEQ ID NO 96
<211> LENGTH: 19
<212> TYPE: PRT
<213> ORGANISM: Mus musculus

<400> SEQUENCE: 96

Met Ser Pro Ala Gln Phe Leu Phe Leu Leu Val Leu Trp Ile Arg Glu
1               5               10              15

Thr Asn Gly

<210> SEQ ID NO 97
<211> LENGTH: 19
<212> TYPE: PRT
<213> ORGANISM: Mus musculus

<400> SEQUENCE: 97

Met Lys Cys Ser Trp Val Ile Phe Phe Leu Met Ala Val Val Thr Gly
1               5               10              15

Val Asn Ser

<210> SEQ ID NO 98
<211> LENGTH: 20
<212> TYPE: PRT
<213> ORGANISM: Mus musculus

<400> SEQUENCE: 98

Met Asp Ser Gln Ala Gln Val Leu Met Leu Leu Leu Leu Trp Val Ser
1               5               10              15

Gly Thr Cys Gly
            20

<210> SEQ ID NO 99
<211> LENGTH: 348
<212> TYPE: DNA
<213> ORGANISM: Mus musculus

<400> SEQUENCE: 99
gatgtgcagc ttcaggagtc gggacctggc ctggtgaaac cttctcagtc tctgtccctc      60
acctgcactg tcactgacta ctcattcacc agtgattttg cctggaactg gatccggcag     120
tttccaggaa acaaactgga gtggatgggc ttcataacct acagtgatca cactaactat     180
aacccatctc tcataagtcg aatctctatc actcgagaca catccaagaa ccagttcttc     240
ctgcagttga attctgtgac tcctgaagac acagccacat attactgtgc aagatctact     300
acctattttg actactgggg ccaaggcacc actctcacag tctcctca                  348

<210> SEQ ID NO 100
```

<211> LENGTH: 336
<212> TYPE: DNA
<213> ORGANISM: Mus musculus

<400> SEQUENCE: 100
gatgttttga tgacccaaac tccactctcc ctgcctgtca gtcttggaga tcaagcctcc        60
atctcttgca gatctagtca gaccatttta catagtgatg gaaacaccta tttagaatgg       120
tacctgcaga aaccaggcca gtctccaaag ctcctgatct acaaagtttc caaccgattt       180
tctggggtcc cagacaggtt cagtggcagt ggatcaggga cagatttcac actcaagatc       240
agcagagtgg aggctgagga tctgggagtt tattattgct ttcaaggttc acatgttcct       300
cccacgttcg gagggggggac caagctggaa ataaaa                                336

<210> SEQ ID NO 101
<211> LENGTH: 116
<212> TYPE: PRT
<213> ORGANISM: Mus musculus

<400> SEQUENCE: 101

Asp Val Gln Leu Gln Glu Ser Gly Pro Gly Leu Val Lys Pro Ser Gln
1               5                   10                  15

Ser Leu Ser Leu Thr Cys Thr Val Thr Asp Tyr Ser Phe Thr Ser Asp
                20                  25                  30

Phe Ala Trp Asn Trp Ile Arg Gln Phe Pro Gly Asn Lys Leu Glu Trp
            35                  40                  45

Met Gly Phe Ile Thr Tyr Ser Asp His Thr Asn Tyr Asn Pro Ser Leu
        50                  55                  60

Ile Ser Arg Ile Ser Ile Thr Arg Asp Thr Ser Lys Asn Gln Phe Phe
65                  70                  75                  80

Leu Gln Leu Asn Ser Val Thr Pro Glu Asp Thr Ala Thr Tyr Tyr Cys
                85                  90                  95

Ala Arg Ser Thr Thr Tyr Phe Asp Tyr Trp Gly Gln Gly Thr Thr Leu
            100                 105                 110

Thr Val Ser Ser
        115

<210> SEQ ID NO 102
<211> LENGTH: 112
<212> TYPE: PRT
<213> ORGANISM: Mus musculus

<400> SEQUENCE: 102

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Leu His Ser
                20                  25                  30

Asp Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 103
<211> LENGTH: 6
<212> TYPE: PRT
<213> ORGANISM: Mus musculus

<400> SEQUENCE: 103

Ser Asp Phe Ala Trp Asn
1               5

<210> SEQ ID NO 104
<211> LENGTH: 16
<212> TYPE: PRT
<213> ORGANISM: Mus musculus

<400> SEQUENCE: 104

Phe Ile Thr Tyr Ser Asp His Thr Asn Tyr Asn Pro Ser Leu Ile Ser
1               5                   10                  15

<210> SEQ ID NO 105
<211> LENGTH: 7
<212> TYPE: PRT
<213> ORGANISM: Mus musculus

<400> SEQUENCE: 105

Ser Thr Thr Tyr Phe Asp Tyr
1               5

<210> SEQ ID NO 106
<211> LENGTH: 16
<212> TYPE: PRT
<213> ORGANISM: Mus musculus

<400> SEQUENCE: 106

Arg Ser Ser Gln Thr Ile Leu His Ser Asp Gly Asn Thr Tyr Leu Glu
1               5                   10                  15

<210> SEQ ID NO 107
<211> LENGTH: 7
<212> TYPE: PRT
<213> ORGANISM: Mus musculus

<400> SEQUENCE: 107

Lys Val Ser Asn Arg Phe Ser
1               5

<210> SEQ ID NO 108
<211> LENGTH: 9
<212> TYPE: PRT
<213> ORGANISM: Mus musculus

<400> SEQUENCE: 108

Phe Gln Gly Ser His Val Pro Pro Thr
1               5

<210> SEQ ID NO 109
<211> LENGTH: 30
<212> TYPE: PRT
<213> ORGANISM: Mus musculus

<400> SEQUENCE: 109

Asp Val Gln Leu Gln Glu Ser Gly Pro Gly Leu Val Lys Pro Ser Gln
1               5                   10                  15

Ser Leu Ser Leu Thr Cys Thr Val Thr Asp Tyr Ser Phe Thr
            20                  25                  30

<210> SEQ ID NO 110
<211> LENGTH: 14
<212> TYPE: PRT
<213> ORGANISM: Mus musculus

<400> SEQUENCE: 110

Trp Ile Arg Gln Phe Pro Gly Asn Lys Leu Glu Trp Met Gly
1               5                   10

<210> SEQ ID NO 111
<211> LENGTH: 32
<212> TYPE: PRT
<213> ORGANISM: Mus musculus

<400> SEQUENCE: 111

Arg Ile Ser Ile Thr Arg Asp Thr Ser Lys Asn Gln Phe Phe Leu Gln
1               5                   10                  15

Leu Asn Ser Val Thr Pro Glu Asp Thr Ala Thr Tyr Tyr Cys Ala Arg
            20                  25                  30

<210> SEQ ID NO 112
<211> LENGTH: 11
<212> TYPE: PRT
<213> ORGANISM: Mus musculus

<400> SEQUENCE: 112

Trp Gly Gln Gly Thr Thr Leu Thr Val Ser Ser
1               5                   10

<210> SEQ ID NO 113
<211> LENGTH: 23
<212> TYPE: PRT
<213> ORGANISM: Mus musculus

<400> SEQUENCE: 113

Asp Val Leu Met Thr Gln Thr Pro Leu Ser Leu Pro Val Ser Leu Gly
1               5                   10                  15

Asp Gln Ala Ser Ile Ser Cys
            20

<210> SEQ ID NO 114
<211> LENGTH: 15
<212> TYPE: PRT
<213> ORGANISM: Mus musculus

<400> SEQUENCE: 114

Trp Tyr Leu Gln Lys Pro Gly Gln Ser Pro Lys Leu Leu Ile Tyr
1               5                   10                  15

<210> SEQ ID NO 115
<211> LENGTH: 32
<212> TYPE: PRT
<213> ORGANISM: Mus musculus

<400> SEQUENCE: 115

Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Val Tyr Tyr Cys
            20                  25                  30

<210> SEQ ID NO 116
<211> LENGTH: 10

```
<212> TYPE: PRT
<213> ORGANISM: Mus musculus

<400> SEQUENCE: 116

Phe Gly Gly Gly Thr Lys Leu Glu Ile Lys
1               5                   10

<210> SEQ ID NO 117
<211> LENGTH: 18
<212> TYPE: PRT
<213> ORGANISM: Mus musculus

<400> SEQUENCE: 117

Met Arg Val Leu Ile Leu Leu Trp Leu Phe Thr Ala Phe Pro Gly Ile
1               5                   10                  15

Leu Ser

<210> SEQ ID NO 118
<211> LENGTH: 19
<212> TYPE: PRT
<213> ORGANISM: Mus musculus

<400> SEQUENCE: 118

Met Lys Leu Pro Val Arg Leu Leu Val Leu Met Phe Trp Ile Pro Ala
1               5                   10                  15

Ser Ser Thr

<210> SEQ ID NO 119
<211> LENGTH: 348
<212> TYPE: DNA
<213> ORGANISM: Mus musculus

<400> SEQUENCE: 119
gatgtgcagc ttcaggagtc gggacctggc ctggtgaaac cttctcagtc tctgtccctc     60
acctgcactg tcactgacta ctcactcacc agtgattatg cctggaactg gatccggcag    120
tttccaggga acaaactgga atggatgggc tacataacct acagtggtta cactaactac    180
aacccatctc tcaaaagtcg aatctctatc actcgagaca catccaagac ccagttcttc    240
ctgcagttga gttctgtgac tactgaggac acagccacat attactgtgc gagatctact    300
accttctttg actactgggg ccaaggcacc actctcacag tctcctca                 348

<210> SEQ ID NO 120
<211> LENGTH: 336
<212> TYPE: DNA
<213> ORGANISM: Mus musculus

<400> SEQUENCE: 120
gatgttttga tgacccaaac tccactctcc ctgcctgtca gtcttggaga tcaagcctcc     60
atctcttgca gatctagtca gagcattgta catagtgatg aaacacccta tttagaatgg    120
tacctgcaga aaccaggcca gtctccaaag ctcctgatct acaaagtttc caatcgattt    180
tctggggtcc cagacaggtt cagtggcagt ggatcaggga cagatttcac actcaagatc    240
agtagactgg aggatgagga tctgggagtc tattactgct ttcaaggttc acatgttcct    300
cccacgttcg gaggggggac caagctggaa ataaaa                              336

<210> SEQ ID NO 121
<211> LENGTH: 116
<212> TYPE: PRT
<213> ORGANISM: Mus musculus
```

<400> SEQUENCE: 121

Asp Val Gln Leu Gln Glu Ser Gly Pro Gly Leu Val Lys Pro Ser Gln
1               5                   10                  15

Ser Leu Ser Leu Thr Cys Thr Val Thr Asp Tyr Ser Leu Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Thr Tyr Ser Gly Tyr Thr Asn Tyr Asn Pro Ser Leu
        50                  55                  60

Lys Ser Arg Ile Ser Ile Thr Arg Asp Thr Ser Lys Thr Gln Phe Phe
65                  70                  75                  80

Leu Gln Leu Ser Ser Val Thr Thr Glu Asp Thr Ala Thr Tyr Tyr Cys
                85                  90                  95

Ala Arg Ser Thr Thr Phe Phe Asp Tyr Trp Gly Gln Gly Thr Thr Leu
                100                 105                 110

Thr Val Ser Ser
        115

<210> SEQ ID NO 122
<211> LENGTH: 112
<212> TYPE: PRT
<213> ORGANISM: Mus musculus

<400> SEQUENCE: 122

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Leu Glu Asp Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
                100                 105                 110

<210> SEQ ID NO 123
<211> LENGTH: 6
<212> TYPE: PRT
<213> ORGANISM: Mus musculus

<400> SEQUENCE: 123

Ser Asp Tyr Ala Trp Asn
1               5

<210> SEQ ID NO 124
<211> LENGTH: 16
<212> TYPE: PRT
<213> ORGANISM: Mus musculus

<400> SEQUENCE: 124

Tyr Ile Thr Tyr Ser Gly Tyr Thr Asn Tyr Asn Pro Ser Leu Lys Ser
1               5                   10                  15

```
<210> SEQ ID NO 125
<211> LENGTH: 7
<212> TYPE: PRT
<213> ORGANISM: Mus musculus

<400> SEQUENCE: 125

Ser Thr Thr Phe Phe Asp Tyr
1               5

<210> SEQ ID NO 126
<211> LENGTH: 16
<212> TYPE: PRT
<213> ORGANISM: Mus musculus

<400> SEQUENCE: 126

Arg Ser Ser Gln Ser Ile Val His Ser Asp Gly Asn Thr Tyr Leu Glu
1               5               10              15

<210> SEQ ID NO 127
<211> LENGTH: 7
<212> TYPE: PRT
<213> ORGANISM: Mus musculus

<400> SEQUENCE: 127

Lys Val Ser Asn Arg Phe Ser
1               5

<210> SEQ ID NO 128
<211> LENGTH: 9
<212> TYPE: PRT
<213> ORGANISM: Mus musculus

<400> SEQUENCE: 128

Phe Gln Gly Ser His Val Pro Pro Thr
1               5

<210> SEQ ID NO 129
<211> LENGTH: 30
<212> TYPE: PRT
<213> ORGANISM: Mus musculus

<400> SEQUENCE: 129

Asp Val Gln Leu Gln Glu Ser Gly Pro Gly Leu Val Lys Pro Ser Gln
1               5               10              15

Ser Leu Ser Leu Thr Cys Thr Val Thr Asp Tyr Ser Leu Thr
            20              25              30

<210> SEQ ID NO 130
<211> LENGTH: 14
<212> TYPE: PRT
<213> ORGANISM: Mus musculus

<400> SEQUENCE: 130

Trp Ile Arg Gln Phe Pro Gly Asn Lys Leu Glu Trp Met Gly
1               5               10

<210> SEQ ID NO 131
<211> LENGTH: 32
<212> TYPE: PRT
<213> ORGANISM: Mus musculus

<400> SEQUENCE: 131

Arg Ile Ser Ile Thr Arg Asp Thr Ser Lys Thr Gln Phe Phe Leu Gln
1               5               10              15
```

-continued

```
Leu Ser Ser Val Thr Thr Glu Asp Thr Ala Thr Tyr Tyr Cys Ala Arg
            20              25              30

<210> SEQ ID NO 132
<211> LENGTH: 11
<212> TYPE: PRT
<213> ORGANISM: Mus musculus

<400> SEQUENCE: 132

Trp Gly Gln Gly Thr Thr Leu Thr Val Ser Ser
1               5               10

<210> SEQ ID NO 133
<211> LENGTH: 23
<212> TYPE: PRT
<213> ORGANISM: Mus musculus

<400> SEQUENCE: 133

Asp Val Leu Met Thr Gln Thr Pro Leu Ser Leu Pro Val Ser Leu Gly
1               5               10              15

Asp Gln Ala Ser Ile Ser Cys
            20

<210> SEQ ID NO 134
<211> LENGTH: 15
<212> TYPE: PRT
<213> ORGANISM: Mus musculus

<400> SEQUENCE: 134

Trp Tyr Leu Gln Lys Pro Gly Gln Ser Pro Lys Leu Leu Ile Tyr
1               5               10              15

<210> SEQ ID NO 135
<211> LENGTH: 32
<212> TYPE: PRT
<213> ORGANISM: Mus musculus

<400> SEQUENCE: 135

Gly Val Pro Asp Arg Phe Ser Gly Ser Gly Ser Gly Thr Asp Phe Thr
1               5               10              15

Leu Lys Ile Ser Arg Leu Glu Asp Glu Asp Leu Gly Val Tyr Tyr Cys
            20              25              30

<210> SEQ ID NO 136
<211> LENGTH: 10
<212> TYPE: PRT
<213> ORGANISM: Mus musculus

<400> SEQUENCE: 136

Phe Gly Gly Gly Thr Lys Leu Glu Ile Lys
1               5               10

<210> SEQ ID NO 137
<211> LENGTH: 18
<212> TYPE: PRT
<213> ORGANISM: Mus musculus

<400> SEQUENCE: 137

Met Arg Val Leu Ile Leu Leu Trp Leu Phe Thr Ala Phe Pro Gly Ile
1               5               10              15

Leu Ser

<210> SEQ ID NO 138
```

-continued

<211> LENGTH: 19
<212> TYPE: PRT
<213> ORGANISM: Mus musculus

<400> SEQUENCE: 138

Met Lys Leu Pro Val Arg Leu Leu Val Leu Met Phe Trp Ile Pro Ala
1               5                   10                  15

Ser Ser Ser

<210> SEQ ID NO 139
<211> LENGTH: 348
<212> TYPE: DNA
<213> ORGANISM: Mus musculus

<400> SEQUENCE: 139
gatgtgcagc ttcaggagtc gggacctggc ctggtgaaac cttctcagtc tctgtccctc      60
acctgcactg tcactgacta ctcattcacc agtgattttg cctggaactg gatccggcag     120
tttccaggaa acaaactgga gtggatgggc ttcataacct acagtgatca cactaactac     180
aacccatctc tcataagtcg aatctctatc actcgagaca catccaagaa ccagttcttc     240
ctgctgttga attctgtgac tcctgaagac acagccacat attactgtgc aagatctact     300
acctattttg actactgggg ccaaggcacc actctcacag tctcctca                  348

<210> SEQ ID NO 140
<211> LENGTH: 336
<212> TYPE: DNA
<213> ORGANISM: Mus musculus

<400> SEQUENCE: 140
gatgttttga tgacccaaac tcctctctcc ctgcctgtca gtcttggaga tcaagcctcc      60
atctcttgta gatctagtca gagcatttta catagtgatg gaaacaccta tttagaatgg     120
tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aaaccgagga tctgggagtt tattattgct ttcaaggttc acatgttcct     300
cccacgttcg gaggggggac caagttggaa ataaaa                               336

<210> SEQ ID NO 141
<211> LENGTH: 116
<212> TYPE: PRT
<213> ORGANISM: Mus musculus

<400> SEQUENCE: 141

Asp Val Gln Leu Gln Glu Ser Gly Pro Gly Leu Val Lys Pro Ser Gln
1               5                   10                  15

Ser Leu Ser Leu Thr Cys Thr Val Thr Asp Tyr Ser Phe Thr Ser Asp
                20                  25                  30

Phe Ala Trp Asn Trp Ile Arg Gln Phe Pro Gly Asn Lys Leu Glu Trp
            35                  40                  45

Met Gly Phe Ile Thr Tyr Ser Asp His Thr Asn Tyr Asn Pro Ser Leu
        50                  55                  60

Ile Ser Arg Ile Ser Ile Thr Arg Asp Thr Ser Lys Asn Gln Phe Phe
65                  70                  75                  80

Leu Leu Leu Asn Ser Val Thr Pro Glu Asp Thr Ala Thr Tyr Tyr Cys
                85                  90                  95

Ala Arg Ser Thr Thr Tyr Phe Asp Tyr Trp Gly Gln Gly Thr Thr Leu
            100                 105                 110

-continued

```
Thr Val Ser Ser
        115

<210> SEQ ID NO 142
<211> LENGTH: 112
<212> TYPE: PRT
<213> ORGANISM: Mus musculus

<400> SEQUENCE: 142

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Leu His Ser
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Thr Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 143
<211> LENGTH: 6
<212> TYPE: PRT
<213> ORGANISM: Mus musculus

<400> SEQUENCE: 143

Ser Asp Phe Ala Trp Asn
1               5

<210> SEQ ID NO 144
<211> LENGTH: 16
<212> TYPE: PRT
<213> ORGANISM: Mus musculus

<400> SEQUENCE: 144

Phe Ile Thr Tyr Ser Asp His Thr Asn Tyr Asn Pro Ser Leu Ile Ser
1               5                   10                  15

<210> SEQ ID NO 145
<211> LENGTH: 7
<212> TYPE: PRT
<213> ORGANISM: Mus musculus

<400> SEQUENCE: 145

Ser Thr Thr Tyr Phe Asp Tyr
1               5

<210> SEQ ID NO 146
<211> LENGTH: 16
<212> TYPE: PRT
<213> ORGANISM: Mus musculus

<400> SEQUENCE: 146

Arg Ser Ser Gln Ser Ile Leu His Ser Asp Gly Asn Thr Tyr Leu Glu
1               5                   10                  15

<210> SEQ ID NO 147
```

```
<211> LENGTH: 7
<212> TYPE: PRT
<213> ORGANISM: Mus musculus

<400> SEQUENCE: 147

Lys Val Ser Asn Arg Phe Ser
1               5

<210> SEQ ID NO 148
<211> LENGTH: 9
<212> TYPE: PRT
<213> ORGANISM: Mus musculus

<400> SEQUENCE: 148

Phe Gln Gly Ser His Val Pro Pro Thr
1               5

<210> SEQ ID NO 149
<211> LENGTH: 30
<212> TYPE: PRT
<213> ORGANISM: Mus musculus

<400> SEQUENCE: 149

Asp Val Gln Leu Gln Glu Ser Gly Pro Gly Leu Val Lys Pro Ser Gln
1               5                   10                  15

Ser Leu Ser Leu Thr Cys Thr Val Thr Asp Tyr Ser Phe Thr
            20                  25                  30

<210> SEQ ID NO 150
<211> LENGTH: 14
<212> TYPE: PRT
<213> ORGANISM: Mus musculus

<400> SEQUENCE: 150

Trp Ile Arg Gln Phe Pro Gly Asn Lys Leu Glu Trp Met Gly
1               5                   10

<210> SEQ ID NO 151
<211> LENGTH: 32
<212> TYPE: PRT
<213> ORGANISM: Mus musculus

<400> SEQUENCE: 151

Arg Ile Ser Ile Thr Arg Asp Thr Ser Lys Asn Gln Phe Phe Leu Leu
1               5                   10                  15

Leu Asn Ser Val Thr Pro Glu Asp Thr Ala Thr Tyr Tyr Cys Ala Arg
            20                  25                  30

<210> SEQ ID NO 152
<211> LENGTH: 11
<212> TYPE: PRT
<213> ORGANISM: Mus musculus

<400> SEQUENCE: 152

Trp Gly Gln Gly Thr Thr Leu Thr Val Ser Ser
1               5                   10

<210> SEQ ID NO 153
<211> LENGTH: 23
<212> TYPE: PRT
<213> ORGANISM: Mus musculus

<400> SEQUENCE: 153

Asp Val Leu Met Thr Gln Thr Pro Leu Ser Leu Pro Val Ser Leu Gly
```

-continued

```
1               5                   10                  15

Asp Gln Ala Ser Ile Ser Cys
            20

<210> SEQ ID NO 154
<211> LENGTH: 15
<212> TYPE: PRT
<213> ORGANISM: Mus musculus

<400> SEQUENCE: 154

Trp Tyr Leu Gln Lys Pro Gly Gln Ser Pro Lys Leu Leu Ile Tyr
1               5                   10                  15

<210> SEQ ID NO 155
<211> LENGTH: 32
<212> TYPE: PRT
<213> ORGANISM: Mus musculus

<400> SEQUENCE: 155

Gly Val Pro Asp Arg Phe Ser Gly Ser Gly Ser Gly Thr Asp Phe Thr
1               5                   10                  15

Leu Lys Ile Ser Arg Val Glu Thr Glu Asp Leu Gly Val Tyr Tyr Cys
            20                  25                  30

<210> SEQ ID NO 156
<211> LENGTH: 10
<212> TYPE: PRT
<213> ORGANISM: Mus musculus

<400> SEQUENCE: 156

Phe Gly Gly Gly Thr Lys Leu Glu Ile Lys
1               5                   10

<210> SEQ ID NO 157
<211> LENGTH: 18
<212> TYPE: PRT
<213> ORGANISM: Mus musculus

<400> SEQUENCE: 157

Met Arg Val Leu Ile Leu Leu Trp Leu Phe Thr Ala Phe Pro Gly Ile
1               5                   10                  15

Leu Ser

<210> SEQ ID NO 158
<211> LENGTH: 19
<212> TYPE: PRT
<213> ORGANISM: Mus musculus

<400> SEQUENCE: 158

Met Lys Leu Pro Val Arg Leu Leu Val Leu Met Phe Trp Ile Pro Ala
1               5                   10                  15

Ser Thr Thr

<210> SEQ ID NO 159
<211> LENGTH: 348
<212> TYPE: DNA
<213> ORGANISM: Mus musculus

<400> SEQUENCE: 159
gatgtgcagc ttcaggagtc gggacctggc ctggtgaaac cttctcagtc tctgtccctc      60
acctgcactg tcactgacta ctcattcacc agtgattttg cctggaactg gatccggcag     120
```

-continued

```
tttccaggaa acaaactgga gtggatgggc ttcataacct acagtgatca cactaactac      180
aacccatctc tcataagtcg aatctctatc actcgagaca catccaagaa ccagttcttc      240
ctgctgttga attctgtgac tcctgaagac acagccacat attactgtgc aagatctact      300
acctattttg actactgggg ccaaggcacc actctcacag tctcctca      348

<210> SEQ ID NO 160
<211> LENGTH: 336
<212> TYPE: DNA
<213> ORGANISM: Mus musculus

<400> SEQUENCE: 160
gatgttttga tgacccaaac tcctctctcc ctgcctgtca gtcttggaga tcaagcctcc       60
atctcttgta gatctagtca gagcatttta catagtgatg gaaacaccta tttagaatgg      120
tacctgcaga aaccaggcca gtctccaaag ctcctgatct acaaagtttc caaccgattt      180
tctggggtcc cagacaggtt cagtggcagt ggatcaggga cagatttcac actcaagatc      240
agcagagtgg aaaccgagga tctgggagtt tattattgct ttcaaggttc acatgttcct      300
cccacgttcg gagggggac caagttggaa ataaaa      336

<210> SEQ ID NO 161
<211> LENGTH: 116
<212> TYPE: PRT
<213> ORGANISM: Mus musculus

<400> SEQUENCE: 161

Asp Val Gln Leu Gln Glu Ser Gly Pro Gly Leu Val Lys Pro Ser Gln
1               5                   10                  15

Ser Leu Ser Leu Thr Cys Thr Val Thr Asp Tyr Ser Phe Thr Ser Asp
            20                  25                  30

Phe Ala Trp Asn Trp Ile Arg Gln Phe Pro Gly Asn Lys Leu Glu Trp
        35                  40                  45

Met Gly Phe Ile Thr Tyr Ser Asp His Thr Asn Tyr Asn Pro Ser Leu
    50                  55                  60

Ile Ser Arg Ile Ser Ile Thr Arg Asp Thr Ser Lys Asn Gln Phe Phe
65                  70                  75                  80

Leu Leu Leu Asn Ser Val Thr Pro Glu Asp Thr Ala Thr Tyr Tyr Cys
                85                  90                  95

Ala Arg Ser Thr Thr Tyr Phe Asp Tyr Trp Gly Gln Gly Thr Thr Leu
            100                 105                 110

Thr Val Ser Ser
        115

<210> SEQ ID NO 162
<211> LENGTH: 112
<212> TYPE: PRT
<213> ORGANISM: Mus musculus

<400> SEQUENCE: 162

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Leu His Ser
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60
```

-continued

```
Asp Arg Phe Ser Gly Ser Gly Ser Gly Thr Asp Phe Thr Leu Lys Ile
65                  70                  75                  80

Ser Arg Val Glu Thr Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 163
<211> LENGTH: 6
<212> TYPE: PRT
<213> ORGANISM: Mus musculus

<400> SEQUENCE: 163

Ser Asp Phe Ala Trp Asn
1               5

<210> SEQ ID NO 164
<211> LENGTH: 16
<212> TYPE: PRT
<213> ORGANISM: Mus musculus

<400> SEQUENCE: 164

Phe Ile Thr Tyr Ser Asp His Thr Asn Tyr Asn Pro Ser Leu Ile Ser
1               5                   10                  15

<210> SEQ ID NO 165
<211> LENGTH: 7
<212> TYPE: PRT
<213> ORGANISM: Mus musculus

<400> SEQUENCE: 165

Ser Thr Thr Tyr Phe Asp Tyr
1               5

<210> SEQ ID NO 166
<211> LENGTH: 16
<212> TYPE: PRT
<213> ORGANISM: Mus musculus

<400> SEQUENCE: 166

Arg Ser Ser Gln Ser Ile Leu His Ser Asp Gly Asn Thr Tyr Leu Glu
1               5                   10                  15

<210> SEQ ID NO 167
<211> LENGTH: 7
<212> TYPE: PRT
<213> ORGANISM: Mus musculus

<400> SEQUENCE: 167

Lys Val Ser Asn Arg Phe Ser
1               5

<210> SEQ ID NO 168
<211> LENGTH: 9
<212> TYPE: PRT
<213> ORGANISM: Mus musculus

<400> SEQUENCE: 168

Phe Gln Gly Ser His Val Pro Pro Thr
1               5

<210> SEQ ID NO 169
<211> LENGTH: 30
```

-continued

```
<212> TYPE: PRT
<213> ORGANISM: Mus musculus

<400> SEQUENCE: 169

Asp Val Gln Leu Gln Glu Ser Gly Pro Gly Leu Val Lys Pro Ser Gln
1               5                   10                  15

Ser Leu Ser Leu Thr Cys Thr Val Thr Asp Tyr Ser Phe Thr
            20                  25                  30

<210> SEQ ID NO 170
<211> LENGTH: 14
<212> TYPE: PRT
<213> ORGANISM: Mus musculus

<400> SEQUENCE: 170

Trp Ile Arg Gln Phe Pro Gly Asn Lys Leu Glu Trp Met Gly
1               5                   10

<210> SEQ ID NO 171
<211> LENGTH: 32
<212> TYPE: PRT
<213> ORGANISM: Mus musculus

<400> SEQUENCE: 171

Arg Ile Ser Ile Thr Arg Asp Thr Ser Lys Asn Gln Phe Phe Leu Leu
1               5                   10                  15

Leu Asn Ser Val Thr Pro Glu Asp Thr Ala Thr Tyr Tyr Cys Ala Arg
            20                  25                  30

<210> SEQ ID NO 172
<211> LENGTH: 11
<212> TYPE: PRT
<213> ORGANISM: Mus musculus

<400> SEQUENCE: 172

Trp Gly Gln Gly Thr Thr Leu Thr Val Ser Ser
1               5                   10

<210> SEQ ID NO 173
<211> LENGTH: 23
<212> TYPE: PRT
<213> ORGANISM: Mus musculus

<400> SEQUENCE: 173

Asp Val Leu Met Thr Gln Thr Pro Leu Ser Leu Pro Val Ser Leu Gly
1               5                   10                  15

Asp Gln Ala Ser Ile Ser Cys
            20

<210> SEQ ID NO 174
<211> LENGTH: 15
<212> TYPE: PRT
<213> ORGANISM: Mus musculus

<400> SEQUENCE: 174

Trp Tyr Leu Gln Lys Pro Gly Gln Ser Pro Lys Leu Leu Ile Tyr
1               5                   10                  15

<210> SEQ ID NO 175
<211> LENGTH: 32
<212> TYPE: PRT
<213> ORGANISM: Mus musculus

<400> SEQUENCE: 175
```

-continued

Gly Val Pro Asp Arg Phe Ser Gly Ser Gly Ser Gly Thr Asp Phe Thr
1               5                   10                  15

Leu Lys Ile Ser Arg Val Glu Thr Glu Asp Leu Gly Val Tyr Tyr Cys
            20                  25                  30

<210> SEQ ID NO 176
<211> LENGTH: 10
<212> TYPE: PRT
<213> ORGANISM: Mus musculus

<400> SEQUENCE: 176

Phe Gly Gly Gly Thr Lys Leu Glu Ile Lys
1               5                   10

<210> SEQ ID NO 177
<211> LENGTH: 18
<212> TYPE: PRT
<213> ORGANISM: Mus musculus

<400> SEQUENCE: 177

Met Arg Val Leu Ile Leu Leu Trp Leu Phe Thr Ala Phe Pro Gly Ile
1               5                   10                  15

Leu Ser

<210> SEQ ID NO 178
<211> LENGTH: 19
<212> TYPE: PRT
<213> ORGANISM: Mus musculus

<400> SEQUENCE: 178

Met Lys Leu Pro Val Arg Leu Leu Val Leu Met Phe Trp Ile Pro Ala
1               5                   10                  15

Ser Thr Thr

<210> SEQ ID NO 179
<211> LENGTH: 348
<212> TYPE: DNA
<213> ORGANISM: Mus musculus

<400> SEQUENCE: 179
gatgtgcagc ttcaggagtc gggacctggc ctggtgaaac cttctcagtc tctgtccctc        60
acctgcactg tcactgacta ctcactcacc agtgattatg cctggaactg gatccggcag       120
tttccaggga acaaactgga atggatgggc tacataacct acagtggtta cactaacttc       180
aacccatctc tcagaagtcg aatctctatc actcgagaca catccaagac ccagttcttc       240
ctgcagttga attctgtgac tgctgaggac acagccacat attactgtgt gagatctact       300
acttactttg actattgggg ccaaggcacc actctcacag tctcctca                   348

<210> SEQ ID NO 180
<211> LENGTH: 336
<212> TYPE: DNA
<213> ORGANISM: Mus musculus

<400> SEQUENCE: 180
gatgttttga tgacccaaac tccactctcc ctgcctgtca gtcttggaga tcaagcctcc        60
atctcttgca gatctagtca gagcattgta catagtgatg gaaacaccta tttagaatgg       120
tacctgcaga aaccaggcca gtctccaaag ctcctgatct acaaagtttc caaccgattt       180
tctggggtcc cagacaggtt cagtggcagt ggatcaggga cagatttcac actcaagatc       240
aatagagtgg aggctgagga tctgggaatt tattactgct ttcaaggttc acatgttcct        300
cccacgttcg gagggggggac caagctggaa ataaaa                                  336

<210> SEQ ID NO 181
<211> LENGTH: 116
<212> TYPE: PRT
<213> ORGANISM: Mus musculus

<400> SEQUENCE: 181

Asp Val Gln Leu Gln Glu Ser Gly Pro Gly Leu Val Lys Pro Ser Gln
1               5                   10                  15

Ser Leu Ser Leu Thr Cys Thr Val Thr Asp Tyr Ser Leu Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Thr Tyr Ser Gly Tyr Thr Asn Phe Asn Pro Ser Leu
    50                  55                  60

Arg Ser Arg Ile Ser Ile Thr Arg Asp Thr Ser Lys Thr Gln Phe Phe
65                  70                  75                  80

Leu Gln Leu Asn Ser Val Thr Ala Glu Asp Thr Ala Thr Tyr Tyr Cys
                85                  90                  95

Val Arg Ser Thr Thr Tyr Phe Asp Tyr Trp Gly Gln Gly Thr Thr Leu
            100                 105                 110

Thr Val Ser Ser
        115

<210> SEQ ID NO 182
<211> LENGTH: 112
<212> TYPE: PRT
<213> ORGANISM: Mus musculus

<400> SEQUENCE: 182

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Asn Arg Val Glu Ala Glu Asp Leu Gly Ile Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 183
<211> LENGTH: 6
<212> TYPE: PRT
<213> ORGANISM: Mus musculus

<400> SEQUENCE: 183

Ser Asp Tyr Ala Trp Asn
1               5

<210> SEQ ID NO 184

-continued

```
<211> LENGTH: 16
<212> TYPE: PRT
<213> ORGANISM: Mus musculus

<400> SEQUENCE: 184

Tyr Ile Thr Tyr Ser Gly Tyr Thr Asn Phe Asn Pro Ser Leu Arg Ser
1               5                   10                  15

<210> SEQ ID NO 185
<211> LENGTH: 7
<212> TYPE: PRT
<213> ORGANISM: Mus musculus

<400> SEQUENCE: 185

Ser Thr Thr Tyr Phe Asp Tyr
1               5

<210> SEQ ID NO 186
<211> LENGTH: 16
<212> TYPE: PRT
<213> ORGANISM: Mus musculus

<400> SEQUENCE: 186

Arg Ser Ser Gln Ser Ile Val His Ser Asp Gly Asn Thr Tyr Leu Glu
1               5                   10                  15

<210> SEQ ID NO 187
<211> LENGTH: 7
<212> TYPE: PRT
<213> ORGANISM: Mus musculus

<400> SEQUENCE: 187

Lys Val Ser Asn Arg Phe Ser
1               5

<210> SEQ ID NO 188
<211> LENGTH: 9
<212> TYPE: PRT
<213> ORGANISM: Mus musculus

<400> SEQUENCE: 188

Phe Gln Gly Ser His Val Pro Pro Thr
1               5

<210> SEQ ID NO 189
<211> LENGTH: 30
<212> TYPE: PRT
<213> ORGANISM: Mus musculus

<400> SEQUENCE: 189

Asp Val Gln Leu Gln Glu Ser Gly Pro Gly Leu Val Lys Pro Ser Gln
1               5                   10                  15

Ser Leu Ser Leu Thr Cys Thr Val Thr Asp Tyr Ser Leu Thr
            20                  25                  30

<210> SEQ ID NO 190
<211> LENGTH: 14
<212> TYPE: PRT
<213> ORGANISM: Mus musculus

<400> SEQUENCE: 190

Trp Ile Arg Gln Phe Pro Gly Asn Lys Leu Glu Trp Met Gly
1               5                   10
```

```
<210> SEQ ID NO 191
<211> LENGTH: 32
<212> TYPE: PRT
<213> ORGANISM: Mus musculus

<400> SEQUENCE: 191

Arg Ile Ser Ile Thr Arg Asp Thr Ser Lys Thr Gln Phe Phe Leu Gln
1               5                   10                  15

Leu Asn Ser Val Thr Ala Glu Asp Thr Ala Thr Tyr Tyr Cys Val Arg
            20                  25                  30

<210> SEQ ID NO 192
<211> LENGTH: 11
<212> TYPE: PRT
<213> ORGANISM: Mus musculus

<400> SEQUENCE: 192

Trp Gly Gln Gly Thr Thr Leu Thr Val Ser Ser
1               5                   10

<210> SEQ ID NO 193
<211> LENGTH: 23
<212> TYPE: PRT
<213> ORGANISM: Mus musculus

<400> SEQUENCE: 193

Asp Val Leu Met Thr Gln Thr Pro Leu Ser Leu Pro Val Ser Leu Gly
1               5                   10                  15

Asp Gln Ala Ser Ile Ser Cys
            20

<210> SEQ ID NO 194
<211> LENGTH: 15
<212> TYPE: PRT
<213> ORGANISM: Mus musculus

<400> SEQUENCE: 194

Trp Tyr Leu Gln Lys Pro Gly Gln Ser Pro Lys Leu Leu Ile Tyr
1               5                   10                  15

<210> SEQ ID NO 195
<211> LENGTH: 32
<212> TYPE: PRT
<213> ORGANISM: Mus musculus

<400> SEQUENCE: 195

Gly Val Pro Asp Arg Phe Ser Gly Ser Gly Ser Gly Thr Asp Phe Thr
1               5                   10                  15

Leu Lys Ile Asn Arg Val Glu Ala Glu Asp Leu Gly Ile Tyr Tyr Cys
            20                  25                  30

<210> SEQ ID NO 196
<211> LENGTH: 10
<212> TYPE: PRT
<213> ORGANISM: Mus musculus

<400> SEQUENCE: 196

Phe Gly Gly Gly Thr Lys Leu Glu Ile Lys
1               5                   10

<210> SEQ ID NO 197
<211> LENGTH: 18
<212> TYPE: PRT
<213> ORGANISM: Mus musculus
```

<400> SEQUENCE: 197

Met Arg Val Leu Ile Leu Leu Trp Leu Phe Thr Ala Phe Pro Gly Ile
1               5                   10                  15

Leu Ser

<210> SEQ ID NO 198
<211> LENGTH: 19
<212> TYPE: PRT
<213> ORGANISM: Mus musculus

<400> SEQUENCE: 198

Met Lys Leu Pro Val Arg Leu Leu Val Leu Met Phe Trp Ile Pro Ala
1               5                   10                  15

Ser Ser Ser

<210> SEQ ID NO 199
<211> LENGTH: 348
<212> TYPE: DNA
<213> ORGANISM: Mus musculus

<400> SEQUENCE: 199
gatgtgcagc ttcaggagtc gggacctggc ctggtgaaac cttctcagtc tctgtccctc     60
acctgcactg tcactgacta ctcactcacc agtgattatg cctggaactg gatccggcag    120
tttccaggga acaaactgga atggatgggc tacataacct acagtggtta cactaactac    180
aacccatctc tcaaaagtcg agtctctatc actcgagaca catccaagac ccagttcttc    240
ctgcagttga attctgtgac tactgaggac acagccacat attactgtgc gagatctact    300
gcctactttg actactgggg ccaaggcacc actctcacag tctcctca                 348

<210> SEQ ID NO 200
<211> LENGTH: 336
<212> TYPE: DNA
<213> ORGANISM: Mus musculus

<400> SEQUENCE: 200
gatgttttga tgacccaaac tccactctcc ctgcctgtca gtcttggaga tcaagcctcc     60
atctcttgcc gatctagtca gagcgttata catagtgatg gaaacaccta tttagaatgg    120
tacctgcaga aaccaggcca gtctccaaag ctcctgatct acaaagtttc caaccgattt    180
tctggggtcc cagacaggtt cagtggcagt ggatcaggga cagatttcac actcaagatc    240
agtagagtgg aggctgagga tctgggagtt tattactgct ttcaaggttc acatgttcct    300
cccacgttcg gagggggggac caagctggaa ataaaa                              336

<210> SEQ ID NO 201
<211> LENGTH: 116
<212> TYPE: PRT
<213> ORGANISM: Mus musculus

<400> SEQUENCE: 201

Asp Val Gln Leu Gln Glu Ser Gly Pro Gly Leu Val Lys Pro Ser Gln
1               5                   10                  15

Ser Leu Ser Leu Thr Cys Thr Val Thr Asp Tyr Ser Leu Thr Ser Asp
                20                  25                  30

Tyr Ala Trp Asn Trp Ile Arg Gln Phe Pro Gly Asn Lys Leu Glu Trp
            35                  40                  45

Met Gly Tyr Ile Thr Tyr Ser Gly Tyr Thr Asn Tyr Asn Pro Ser Leu

-continued

```
                50                  55                  60

Lys Ser Arg Val Ser Ile Thr Arg Asp Thr Ser Lys Thr Gln Phe Phe
65                  70                  75                  80

Leu Gln Leu Asn Ser Val Thr Thr Glu Asp Thr Ala Thr Tyr Tyr Cys
                    85                  90                  95

Ala Arg Ser Thr Ala Tyr Phe Asp Tyr Trp Gly Gln Gly Thr Thr Leu
                100                 105                 110

Thr Val Ser Ser
        115

<210> SEQ ID NO 202
<211> LENGTH: 112
<212> TYPE: PRT
<213> ORGANISM: Mus musculus

<400> SEQUENCE: 202

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Val Ile His Ser
                20                  25                  30

Asp Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                    85                  90                  95

Ser His Val Pro Pro Thr Phe Gly Gly Gly Thr Lys Leu Glu Ile Lys
                100                 105                 110

<210> SEQ ID NO 203
<211> LENGTH: 6
<212> TYPE: PRT
<213> ORGANISM: Mus musculus

<400> SEQUENCE: 203

Ser Asp Tyr Ala Trp Asn
1               5

<210> SEQ ID NO 204
<211> LENGTH: 16
<212> TYPE: PRT
<213> ORGANISM: Mus musculus

<400> SEQUENCE: 204

Tyr Ile Thr Tyr Ser Gly Tyr Thr Asn Tyr Asn Pro Ser Leu Lys Ser
1               5                   10                  15

<210> SEQ ID NO 205
<211> LENGTH: 7
<212> TYPE: PRT
<213> ORGANISM: Mus musculus

<400> SEQUENCE: 205

Ser Thr Ala Tyr Phe Asp Tyr
1               5

<210> SEQ ID NO 206
<211> LENGTH: 16
```

<212> TYPE: PRT
<213> ORGANISM: Mus musculus

<400> SEQUENCE: 206

Arg Ser Ser Gln Ser Val Ile His Ser Asp Gly Asn Thr Tyr Leu Glu
1               5                   10                  15

<210> SEQ ID NO 207
<211> LENGTH: 7
<212> TYPE: PRT
<213> ORGANISM: Mus musculus

<400> SEQUENCE: 207

Lys Val Ser Asn Arg Phe Ser
1               5

<210> SEQ ID NO 208
<211> LENGTH: 9
<212> TYPE: PRT
<213> ORGANISM: Mus musculus

<400> SEQUENCE: 208

Phe Gln Gly Ser His Val Pro Pro Thr
1               5

<210> SEQ ID NO 209
<211> LENGTH: 30
<212> TYPE: PRT
<213> ORGANISM: Mus musculus

<400> SEQUENCE: 209

Asp Val Gln Leu Gln Glu Ser Gly Pro Gly Leu Val Lys Pro Ser Gln
1               5                   10                  15

Ser Leu Ser Leu Thr Cys Thr Val Thr Asp Tyr Ser Leu Thr
            20                  25                  30

<210> SEQ ID NO 210
<211> LENGTH: 14
<212> TYPE: PRT
<213> ORGANISM: Mus musculus

<400> SEQUENCE: 210

Trp Ile Arg Gln Phe Pro Gly Asn Lys Leu Glu Trp Met Gly
1               5                   10

<210> SEQ ID NO 211
<211> LENGTH: 32
<212> TYPE: PRT
<213> ORGANISM: Mus musculus

<400> SEQUENCE: 211

Arg Val Ser Ile Thr Arg Asp Thr Ser Lys Thr Gln Phe Phe Leu Gln
1               5                   10                  15

Leu Asn Ser Val Thr Thr Glu Asp Thr Ala Thr Tyr Tyr Cys Ala Arg
            20                  25                  30

<210> SEQ ID NO 212
<211> LENGTH: 11
<212> TYPE: PRT
<213> ORGANISM: Mus musculus

<400> SEQUENCE: 212

Trp Gly Gln Gly Thr Thr Leu Thr Val Ser Ser
1               5                   10

-continued

```
<210> SEQ ID NO 213
<211> LENGTH: 23
<212> TYPE: PRT
<213> ORGANISM: Mus musculus

<400> SEQUENCE: 213

Asp Val Leu Met Thr Gln Thr Pro Leu Ser Leu Pro Val Ser Leu Gly
1               5                   10                  15

Asp Gln Ala Ser Ile Ser Cys
            20

<210> SEQ ID NO 214
<211> LENGTH: 15
<212> TYPE: PRT
<213> ORGANISM: Mus musculus

<400> SEQUENCE: 214

Trp Tyr Leu Gln Lys Pro Gly Gln Ser Pro Lys Leu Leu Ile Tyr
1               5                   10                  15

<210> SEQ ID NO 215
<211> LENGTH: 32
<212> TYPE: PRT
<213> ORGANISM: Mus musculus

<400> SEQUENCE: 215

Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Val Tyr Tyr Cys
            20                  25                  30

<210> SEQ ID NO 216
<211> LENGTH: 10
<212> TYPE: PRT
<213> ORGANISM: Mus musculus

<400> SEQUENCE: 216

Phe Gly Gly Gly Thr Lys Leu Glu Ile Lys
1               5                   10

<210> SEQ ID NO 217
<211> LENGTH: 18
<212> TYPE: PRT
<213> ORGANISM: Mus musculus

<400> SEQUENCE: 217

Met Arg Val Leu Ile Leu Leu Trp Leu Phe Thr Ala Phe Pro Gly Val
1               5                   10                  15

Leu Ser

<210> SEQ ID NO 218
<211> LENGTH: 19
<212> TYPE: PRT
<213> ORGANISM: Mus musculus

<400> SEQUENCE: 218

Met Lys Leu Pro Val Arg Leu Leu Val Leu Met Phe Trp Ile Pro Ala
1               5                   10                  15

Ser Ser Ser

<210> SEQ ID NO 219
```

```
<211> LENGTH: 348
<212> TYPE: DNA
<213> ORGANISM: Mus musculus

<400> SEQUENCE: 219
gatgtgcagc ttcaggagtc gggacctggc ctggtgagac cttctcagtc tctgtccctc     60
acatgcactg tcactggcta ctcaatcacc agtgattatg cctggaactg gatccgacag    120
tttccaggaa acaaactgga gtggatgggc ttcataacct acagtggtaa tactaactac    180
aacccatctc tcaaaagtcg aatctctatc actcgagaca catccaagaa ccagttcttc    240
ctgcagttga attctgtgac tactgaggag acagccacat attactgtgc aagtagtgga    300
aactactttg actattgggg ccaaggcacc actctcacag tctcctca                 348

<210> SEQ ID NO 220
<211> LENGTH: 336
<212> TYPE: DNA
<213> ORGANISM: Mus musculus

<400> SEQUENCE: 220
gatgttttga tgacccaaac tccactctcc ctgcctgtca gtcttggaga tcaagcctcc     60
atctcttgca gatctagtca gagcattgta catagtgatg gaaacaccta tttagaatgg    120
tacctgcaga aaccaggcca gcctccaaag ctcctgatct acaaagtttc caaccgattt    180
tctggggtcc cagacaggtt cagtggcagt ggatcaggga cggatttcac actcaaaatc    240
agcagagtgg aggctgagga tctgggattt tattactgct ttcaaggttc acatgttcct    300
ccgacgttcg gtggaggcac caagctggaa atcaaa                              336

<210> SEQ ID NO 221
<211> LENGTH: 116
<212> TYPE: PRT
<213> ORGANISM: Mus musculus

<400> SEQUENCE: 221

Asp Val Gln Leu Gln Glu Ser Gly Pro Gly Leu Val Arg Pro Ser Gln
1               5                   10                  15

Ser Leu Ser Leu Thr Cys Thr Val Thr Gly Tyr Ser Ile Thr Ser Asp
            20                  25                  30

Tyr Ala Trp Asn Trp Ile Arg Gln Phe Pro Gly Asn Lys Leu Glu Trp
        35                  40                  45

Met Gly Phe Ile Thr Tyr Ser Gly Asn Thr Asn Tyr Asn Pro Ser Leu
    50                  55                  60

Lys Ser Arg Ile Ser Ile Thr Arg Asp Thr Ser Lys Asn Gln Phe Phe
65                  70                  75                  80

Leu Gln Leu Asn Ser Val Thr Thr Glu Glu Thr Ala Thr Tyr Tyr Cys
                85                  90                  95

Ala Ser Ser Gly Asn Tyr Phe Asp Tyr Trp Gly Gln Gly Thr Thr Leu
            100                 105                 110

Thr Val Ser Ser
        115

<210> SEQ ID NO 222
<211> LENGTH: 112
<212> TYPE: PRT
<213> ORGANISM: Mus musculus

<400> SEQUENCE: 222

Asp Val Leu Met Thr Gln Thr Pro Leu Ser Leu Pro Val Ser Leu Gly
```

-continued

```
1              5              10             15

Asp Gln Ala Ser Ile Ser Cys Arg Ser Ser Gln Ser Ile Val His Ser
        20              25              30

Asp Gly Asn Thr Tyr Leu Glu Trp Tyr Leu Gln Lys Pro Gly Gln Pro
        35              40              45

Pro Lys Leu Leu Ile Tyr Lys Val Ser Asn Arg Phe Ser Gly Val Pro
        50              55              60

Asp Arg Phe Ser Gly Ser Gly Ser Gly Thr Asp Phe Thr Leu Lys Ile
65              70              75              80

Ser Arg Val Glu Ala Glu Asp Leu Gly Phe Tyr Tyr Cys Phe Gln Gly
                85              90              95

Ser His Val Pro Pro Thr Phe Gly Gly Gly Thr Lys Leu Glu Ile Lys
        100             105             110
```

<210> SEQ ID NO 223
<211> LENGTH: 6
<212> TYPE: PRT
<213> ORGANISM: Mus musculus

<400> SEQUENCE: 223

```
Ser Asp Tyr Ala Trp Asn
1               5
```

<210> SEQ ID NO 224
<211> LENGTH: 16
<212> TYPE: PRT
<213> ORGANISM: Mus musculus

<400> SEQUENCE: 224

```
Phe Ile Thr Tyr Ser Gly Asn Thr Asn Tyr Asn Pro Ser Leu Lys Ser
1               5               10              15
```

<210> SEQ ID NO 225
<211> LENGTH: 7
<212> TYPE: PRT
<213> ORGANISM: Mus musculus

<400> SEQUENCE: 225

```
Ser Gly Asn Tyr Phe Asp Tyr
1               5
```

<210> SEQ ID NO 226
<211> LENGTH: 16
<212> TYPE: PRT
<213> ORGANISM: Mus musculus

<400> SEQUENCE: 226

```
Arg Ser Ser Gln Ser Ile Val His Ser Asp Gly Asn Thr Tyr Leu Glu
1               5               10              15
```

<210> SEQ ID NO 227
<211> LENGTH: 7
<212> TYPE: PRT
<213> ORGANISM: Mus musculus

<400> SEQUENCE: 227

```
Lys Val Ser Asn Arg Phe Ser
1               5
```

<210> SEQ ID NO 228
<211> LENGTH: 9
<212> TYPE: PRT

```
<213> ORGANISM: Mus musculus

<400> SEQUENCE: 228

Phe Gln Gly Ser His Val Pro Pro Thr
1               5

<210> SEQ ID NO 229
<211> LENGTH: 30
<212> TYPE: PRT
<213> ORGANISM: Mus musculus

<400> SEQUENCE: 229

Asp Val Gln Leu Gln Glu Ser Gly Pro Gly Leu Val Arg Pro Ser Gln
1               5                   10                  15

Ser Leu Ser Leu Thr Cys Thr Val Thr Gly Tyr Ser Ile Thr
                20                  25                  30

<210> SEQ ID NO 230
<211> LENGTH: 14
<212> TYPE: PRT
<213> ORGANISM: Mus musculus

<400> SEQUENCE: 230

Trp Ile Arg Gln Phe Pro Gly Asn Lys Leu Glu Trp Met Gly
1               5                   10

<210> SEQ ID NO 231
<211> LENGTH: 32
<212> TYPE: PRT
<213> ORGANISM: Mus musculus

<400> SEQUENCE: 231

Arg Ile Ser Ile Thr Arg Asp Thr Ser Lys Asn Gln Phe Phe Leu Gln
1               5                   10                  15

Leu Asn Ser Val Thr Thr Glu Glu Thr Ala Thr Tyr Tyr Cys Ala Ser
                20                  25                  30

<210> SEQ ID NO 232
<211> LENGTH: 11
<212> TYPE: PRT
<213> ORGANISM: Mus musculus

<400> SEQUENCE: 232

Trp Gly Gln Gly Thr Thr Leu Thr Val Ser Ser
1               5                   10

<210> SEQ ID NO 233
<211> LENGTH: 23
<212> TYPE: PRT
<213> ORGANISM: Mus musculus

<400> SEQUENCE: 233

Asp Val Leu Met Thr Gln Thr Pro Leu Ser Leu Pro Val Ser Leu Gly
1               5                   10                  15

Asp Gln Ala Ser Ile Ser Cys
                20

<210> SEQ ID NO 234
<211> LENGTH: 15
<212> TYPE: PRT
<213> ORGANISM: Mus musculus

<400> SEQUENCE: 234
```

-continued

```
Trp Tyr Leu Gln Lys Pro Gly Gln Pro Pro Lys Leu Leu Ile Tyr
1               5                   10                  15

<210> SEQ ID NO 235
<211> LENGTH: 32
<212> TYPE: PRT
<213> ORGANISM: Mus musculus

<400> SEQUENCE: 235

Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Phe Tyr Tyr Cys
            20                  25                  30

<210> SEQ ID NO 236
<211> LENGTH: 10
<212> TYPE: PRT
<213> ORGANISM: Mus musculus

<400> SEQUENCE: 236

Phe Gly Gly Gly Thr Lys Leu Glu Ile Lys
1               5                   10

<210> SEQ ID NO 237
<211> LENGTH: 18
<212> TYPE: PRT
<213> ORGANISM: Mus musculus

<400> SEQUENCE: 237

Met Arg Val Leu Ile Leu Leu Trp Leu Phe Thr Ala Phe Pro Gly Ile
1               5                   10                  15

Leu Ser

<210> SEQ ID NO 238
<211> LENGTH: 19
<212> TYPE: PRT
<213> ORGANISM: Mus musculus

<400> SEQUENCE: 238

Met Lys Leu Pro Val Arg Leu Leu Val Leu Met Phe Trp Ile Pro Ala
1               5                   10                  15

Ser Ser Ser

<210> SEQ ID NO 239
<211> LENGTH: 348
<212> TYPE: DNA
<213> ORGANISM: Mus musculus

<400> SEQUENCE: 239
gatgtgcagc ttcaggagtc gggacctggc ctggtgaaac cttctcagtc tctgtccctc      60
acctgcactg tcactgacta ctcactcacc agtgattatg cctggaactg gatccggcag     120
tttccaggga caaactgga atggatgggc tacataacct acagtggtta cactaactac      180
aacccatctc tcaaaagtcg agtctctatc actcgagaca catccaagac ccagttcttc     240
ctgcagttga attctgtgac tactgaggac acagccacat attactgtgc gagatctact     300
gcctactttg actactgggg ccaaggcacc actctcacag tctcctca                  348

<210> SEQ ID NO 240
<211> LENGTH: 336
<212> TYPE: DNA
<213> ORGANISM: Mus musculus
```

<400> SEQUENCE: 240
gatgttttga tgacccaaac tccactctcc ctgcctgtca gtcttggaga tcaagcctcc          60
atctcttgcc gatctagtca gagcgttata catagtgatg gaaacaccta tttagaatgg         120
tacctgcaga aaccaggcca gtctccaaag ctcctgatct acaaagtttc caaccgattt         180
tctggggtcc cagacaggtt cagtggcagt ggatcaggga cagatttcac actcaagatc         240
agtagagtgg aggctgagga tctgggagtt tattactgct ttcaaggttc acatgttcct         300
cccacgttcg aggggggac caagctggaa ataaaa                                    336

<210> SEQ ID NO 241
<211> LENGTH: 116
<212> TYPE: PRT
<213> ORGANISM: Mus musculus

<400> SEQUENCE: 241

Asp Val Gln Leu Gln Glu Ser Gly Pro Gly Leu Val Lys Pro Ser Gln
1               5                   10                  15

Ser Leu Ser Leu Thr Cys Thr Val Thr Asp Tyr Ser Leu Thr Ser Asp
            20                  25                  30

Tyr Ala Trp Asn Trp Ile Arg Gln Phe Pro Gly Asn Lys Leu Glu Trp
        35                  40                  45

Met Gly Tyr Ile Thr Tyr Ser Gly Tyr Thr Asn Tyr Asn Pro Ser Leu
    50                  55                  60

Lys Ser Arg Val Ser Ile Thr Arg Asp Thr Ser Lys Thr Gln Phe Phe
65                  70                  75                  80

Leu Gln Leu Asn Ser Val Thr Thr Glu Asp Thr Ala Thr Tyr Tyr Cys
                85                  90                  95

Ala Arg Ser Thr Ala Tyr Phe Asp Tyr Trp Gly Gln Gly Thr Thr Leu
            100                 105                 110

Thr Val Ser Ser
        115

<210> SEQ ID NO 242
<211> LENGTH: 112
<212> TYPE: PRT
<213> ORGANISM: Mus musculus

<400> SEQUENCE: 242

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Val Ile His Ser
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 243
<211> LENGTH: 6

```
<212> TYPE: PRT
<213> ORGANISM: Mus musculus

<400> SEQUENCE: 243

Ser Asp Tyr Ala Trp Asn
1               5

<210> SEQ ID NO 244
<211> LENGTH: 16
<212> TYPE: PRT
<213> ORGANISM: Mus musculus

<400> SEQUENCE: 244

Tyr Ile Thr Tyr Ser Gly Tyr Thr Asn Tyr Asn Pro Ser Leu Lys Ser
1               5               10                  15

<210> SEQ ID NO 245
<211> LENGTH: 7
<212> TYPE: PRT
<213> ORGANISM: Mus musculus

<400> SEQUENCE: 245

Ser Thr Ala Tyr Phe Asp Tyr
1               5

<210> SEQ ID NO 246
<211> LENGTH: 16
<212> TYPE: PRT
<213> ORGANISM: Mus musculus

<400> SEQUENCE: 246

Arg Ser Ser Gln Ser Val Ile His Ser Asp Gly Asn Thr Tyr Leu Glu
1               5               10                  15

<210> SEQ ID NO 247
<211> LENGTH: 7
<212> TYPE: PRT
<213> ORGANISM: Mus musculus

<400> SEQUENCE: 247

Lys Val Ser Asn Arg Phe Ser
1               5

<210> SEQ ID NO 248
<211> LENGTH: 9
<212> TYPE: PRT
<213> ORGANISM: Mus musculus

<400> SEQUENCE: 248

Phe Gln Gly Ser His Val Pro Pro Thr
1               5

<210> SEQ ID NO 249
<211> LENGTH: 30
<212> TYPE: PRT
<213> ORGANISM: Mus musculus

<400> SEQUENCE: 249

Asp Val Gln Leu Gln Glu Ser Gly Pro Gly Leu Val Lys Pro Ser Gln
1               5               10                  15

Ser Leu Ser Leu Thr Cys Thr Val Thr Asp Tyr Ser Leu Thr
            20              25                  30

<210> SEQ ID NO 250
```

```
<211> LENGTH: 14
<212> TYPE: PRT
<213> ORGANISM: Mus musculus

<400> SEQUENCE: 250

Trp Ile Arg Gln Phe Pro Gly Asn Lys Leu Glu Trp Met Gly
1               5                   10

<210> SEQ ID NO 251
<211> LENGTH: 32
<212> TYPE: PRT
<213> ORGANISM: Mus musculus

<400> SEQUENCE: 251

Arg Val Ser Ile Thr Arg Asp Thr Ser Lys Thr Gln Phe Phe Leu Gln
1               5                   10                  15

Leu Asn Ser Val Thr Thr Glu Asp Thr Ala Thr Tyr Tyr Cys Ala Arg
            20                  25                  30

<210> SEQ ID NO 252
<211> LENGTH: 11
<212> TYPE: PRT
<213> ORGANISM: Mus musculus

<400> SEQUENCE: 252

Trp Gly Gln Gly Thr Thr Leu Thr Val Ser Ser
1               5                   10

<210> SEQ ID NO 253
<211> LENGTH: 23
<212> TYPE: PRT
<213> ORGANISM: Mus musculus

<400> SEQUENCE: 253

Asp Val Leu Met Thr Gln Thr Pro Leu Ser Leu Pro Val Ser Leu Gly
1               5                   10                  15

Asp Gln Ala Ser Ile Ser Cys
            20

<210> SEQ ID NO 254
<211> LENGTH: 15
<212> TYPE: PRT
<213> ORGANISM: Mus musculus

<400> SEQUENCE: 254

Trp Tyr Leu Gln Lys Pro Gly Gln Ser Pro Lys Leu Leu Ile Tyr
1               5                   10                  15

<210> SEQ ID NO 255
<211> LENGTH: 32
<212> TYPE: PRT
<213> ORGANISM: Mus musculus

<400> SEQUENCE: 255

Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Val Tyr Tyr Cys
            20                  25                  30

<210> SEQ ID NO 256
<211> LENGTH: 10
<212> TYPE: PRT
<213> ORGANISM: Mus musculus
```

<400> SEQUENCE: 256

Phe Gly Gly Gly Thr Lys Leu Glu Ile Lys
1               5               10

<210> SEQ ID NO 257
<211> LENGTH: 18
<212> TYPE: PRT
<213> ORGANISM: Mus musculus

<400> SEQUENCE: 257

Met Arg Val Leu Ile Leu Leu Trp Leu Phe Thr Ala Phe Pro Gly Val
1               5               10              15

Leu Ser

<210> SEQ ID NO 258
<211> LENGTH: 19
<212> TYPE: PRT
<213> ORGANISM: Mus musculus

<400> SEQUENCE: 258

Met Lys Leu Pro Val Arg Leu Leu Val Leu Met Phe Trp Ile Pro Ala
1               5               10              15

Ser Ser Ser

<210> SEQ ID NO 259
<211> LENGTH: 348
<212> TYPE: DNA
<213> ORGANISM: Mus musculus

<400> SEQUENCE: 259
gatgtgcagc ttcaggagtc gggacctggc ctggtgaaac cttctcagtc tctgtccctc      60
acctgcactg tcactgacta ctcattcacc agtgattttg cctggaactg gatccggcag     120
tttccaggaa acaaactgga gtggatgggc ttcataacct acagtgatca cactaactac     180
aacccatctc tcataagtcg aatctctatc actcgagaca catccaagaa ccagttcttc     240
ctgcagttga attctgtgac tcctgaagac acagccacat attactgtgc aagatctact     300
acctattttg actactgggg ccaaggcacc actctcacag tctcctca                  348

<210> SEQ ID NO 260
<211> LENGTH: 336
<212> TYPE: DNA
<213> ORGANISM: Mus musculus

<400> SEQUENCE: 260
gatgttttga tgacccaaac tccactctcc ctgcctgtca gtcttggaga tcaagcctcc      60
atctcttgca gatctagtca gagcatttta catagtgatg aaacaccta tttagaatgg      120 tacatgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattattgct ttcaaggttc acatgttcct     300
cccacgttcg gagggggggac caagctggaa ataaaa                              336

<210> SEQ ID NO 261
<211> LENGTH: 116
<212> TYPE: PRT
<213> ORGANISM: Mus musculus

<400> SEQUENCE: 261

-continued

```
Asp Val Gln Leu Gln Glu Ser Gly Pro Gly Leu Val Lys Pro Ser Gln
1               5                   10                  15

Ser Leu Ser Leu Thr Cys Thr Val Thr Asp Tyr Ser Phe Thr Ser Asp
            20                  25                  30

Phe Ala Trp Asn Trp Ile Arg Gln Phe Pro Gly Asn Lys Leu Glu Trp
        35                  40                  45

Met Gly Phe Ile Thr Tyr Ser Asp His Thr Asn Tyr Asn Pro Ser Leu
    50                  55                  60

Ile Ser Arg Ile Ser Ile Thr Arg Asp Thr Ser Lys Asn Gln Phe Phe
65                  70                  75                  80

Leu Gln Leu Asn Ser Val Thr Pro Glu Asp Thr Ala Thr Tyr Tyr Cys
                85                  90                  95

Ala Arg Ser Thr Thr Tyr Phe Asp Tyr Trp Gly Gln Gly Thr Thr Leu
            100                 105                 110

Thr Val Ser Ser
        115

<210> SEQ ID NO 262
<211> LENGTH: 112
<212> TYPE: PRT
<213> ORGANISM: Mus musculus

<400> SEQUENCE: 262

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Leu His Ser
            20                  25                  30

Asp Gly Asn Thr Tyr Leu Glu Trp Tyr Met Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Pro Thr Phe Gly Gly Gly Thr Lys Leu Glu Ile Lys
            100                 105                 110

<210> SEQ ID NO 263
<211> LENGTH: 6
<212> TYPE: PRT
<213> ORGANISM: Mus musculus

<400> SEQUENCE: 263

Ser Asp Phe Ala Trp Asn
1               5

<210> SEQ ID NO 264
<211> LENGTH: 16
<212> TYPE: PRT
<213> ORGANISM: Mus musculus

<400> SEQUENCE: 264

Phe Ile Thr Tyr Ser Asp His Thr Asn Tyr Asn Pro Ser Leu Ile Ser
1               5                   10                  15

<210> SEQ ID NO 265
<211> LENGTH: 7
<212> TYPE: PRT
```

<213> ORGANISM: Mus musculus

<400> SEQUENCE: 265

Ser Thr Thr Tyr Phe Asp Tyr
1               5

<210> SEQ ID NO 266
<211> LENGTH: 16
<212> TYPE: PRT
<213> ORGANISM: Mus musculus

<400> SEQUENCE: 266

Arg Ser Ser Gln Ser Ile Leu His Ser Asp Gly Asn Thr Tyr Leu Glu
1               5                   10                  15

<210> SEQ ID NO 267
<211> LENGTH: 7
<212> TYPE: PRT
<213> ORGANISM: Mus musculus

<400> SEQUENCE: 267

Lys Val Ser Asn Arg Phe Ser
1               5

<210> SEQ ID NO 268
<211> LENGTH: 9
<212> TYPE: PRT
<213> ORGANISM: Mus musculus

<400> SEQUENCE: 268

Phe Gln Gly Ser His Val Pro Pro Thr
1               5

<210> SEQ ID NO 269
<211> LENGTH: 30
<212> TYPE: PRT
<213> ORGANISM: Mus musculus

<400> SEQUENCE: 269

Asp Val Gln Leu Gln Glu Ser Gly Pro Gly Leu Val Lys Pro Ser Gln
1               5                   10                  15

Ser Leu Ser Leu Thr Cys Thr Val Thr Asp Tyr Ser Phe Thr
            20                  25                  30

<210> SEQ ID NO 270
<211> LENGTH: 14
<212> TYPE: PRT
<213> ORGANISM: Mus musculus

<400> SEQUENCE: 270

Trp Ile Arg Gln Phe Pro Gly Asn Lys Leu Glu Trp Met Gly
1               5                   10

<210> SEQ ID NO 271
<211> LENGTH: 32
<212> TYPE: PRT
<213> ORGANISM: Mus musculus

<400> SEQUENCE: 271

Arg Ile Ser Ile Thr Arg Asp Thr Ser Lys Asn Gln Phe Phe Leu Gln
1               5                   10                  15

Leu Asn Ser Val Thr Pro Glu Asp Thr Ala Thr Tyr Tyr Cys Ala Arg
            20                  25                  30

-continued

<210> SEQ ID NO 272
<211> LENGTH: 11
<212> TYPE: PRT
<213> ORGANISM: Mus musculus

<400> SEQUENCE: 272

Trp Gly Gln Gly Thr Thr Leu Thr Val Ser Ser
1               5                   10

<210> SEQ ID NO 273
<211> LENGTH: 23
<212> TYPE: PRT
<213> ORGANISM: Mus musculus

<400> SEQUENCE: 273

Asp Val Leu Met Thr Gln Thr Pro Leu Ser Leu Pro Val Ser Leu Gly
1               5                   10                  15

Asp Gln Ala Ser Ile Ser Cys
            20

<210> SEQ ID NO 274
<211> LENGTH: 15
<212> TYPE: PRT
<213> ORGANISM: Mus musculus

<400> SEQUENCE: 274

Trp Tyr Met Gln Lys Pro Gly Gln Ser Pro Lys Leu Leu Ile Tyr
1               5                   10                  15

<210> SEQ ID NO 275
<211> LENGTH: 32
<212> TYPE: PRT
<213> ORGANISM: Mus musculus

<400> SEQUENCE: 275

Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Val Tyr Tyr Cys
            20                  25                  30

<210> SEQ ID NO 276
<211> LENGTH: 10
<212> TYPE: PRT
<213> ORGANISM: Mus musculus

<400> SEQUENCE: 276

Phe Gly Gly Gly Thr Lys Leu Glu Ile Lys
1               5                   10

<210> SEQ ID NO 277
<211> LENGTH: 18
<212> TYPE: PRT
<213> ORGANISM: Mus musculus

<400> SEQUENCE: 277

Met Arg Val Leu Ile Leu Leu Trp Leu Phe Thr Ala Phe Pro Gly Ile
1               5                   10                  15

Leu Ser

<210> SEQ ID NO 278
<211> LENGTH: 19
<212> TYPE: PRT
<213> ORGANISM: Mus musculus

<400> SEQUENCE: 278

Met Lys Leu Pro Val Arg Leu Leu Val Leu Met Phe Trp Ile Pro Ala
1               5                   10                  15

Ser Ser Thr

<210> SEQ ID NO 279
<211> LENGTH: 339
<212> TYPE: DNA
<213> ORGANISM: Mus musculus

<400> SEQUENCE: 279
gaggtccagc tgcaacaatc tggacctgag ctggtgaagc ctgggacttc agtgaagata        60
tcctgtaagg cttctggata cacgttcact ggctactata tgaactgggt gaaacagagc       120
catggaaaga gccttgagtg gattggagat attaatccta caatggtgg tactgactac        180 aaccggaagt tcaagggcaa ggccacattg actgtagaca gtcatccag cacagcctac        240 atggaggtcc gcagcctgac atctgaggac tctgcagtct attactgtgc aaaagacttc       300
gctgtctggg gcacagggac cacggtcacc gtctcctca                              339

<210> SEQ ID NO 280
<211> LENGTH: 333
<212> TYPE: DNA
<213> ORGANISM: Mus musculus

<400> SEQUENCE: 280
gatgttgtga tgacccagac tccactcact ttgtcggtta ccattggaca accagcctcc        60
atctcttgca agtcaagtca gagcctctta gatagtgatg gaaagacata tttgaattgg       120
ttgttacaga ggccaggcca gtctccaaag cgcctaatct atctggtgtc taaactggac       180
tctggagccc ctgacaggtt cactggcagt ggatcaggga cagatttcac actgaaaatc       240
aacagagtgg aggctgagga tttgggagtt tattattgct ggcaaggtac acattttccc       300
acgttcggag gggggaccaa gctggaaata aaa                                   333

<210> SEQ ID NO 281
<211> LENGTH: 113
<212> TYPE: PRT
<213> ORGANISM: Mus musculus

<400> SEQUENCE: 281

Glu Val Gln Leu Gln Gln Ser Gly Pro Glu Leu Val Lys Pro Gly Thr
1               5                   10                  15

Ser Val Lys Ile Ser Cys Lys Ala Ser Gly Tyr Thr Phe Thr Gly Tyr
                20                  25                  30

Tyr Met Asn Trp Val Lys Gln Ser His Gly Lys Ser Leu Glu Trp Ile
            35                  40                  45

Gly Asp Ile Asn Pro Asn Asn Gly Gly Thr Asp Tyr Asn Arg Lys Phe
        50                  55                  60

Lys Gly Lys Ala Thr Leu Thr Val Asp Lys Ser Ser Ser Thr Ala Tyr
65                  70                  75                  80

Met Glu Val Arg Ser Leu Thr Ser Glu Asp Ser Ala Val Tyr Tyr Cys
                85                  90                  95

Ala Lys Asp Phe Ala Val Trp Gly Thr Gly Thr Thr Val Thr Val Ser
            100                 105                 110

Ser

```
<210> SEQ ID NO 282
<211> LENGTH: 111
<212> TYPE: PRT
<213> ORGANISM: Mus musculus

<400> SEQUENCE: 282

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Ala Pro
    50                  55                  60

Asp Arg Phe Thr Gly Ser Gly Ser Gly Thr Asp Phe Thr Leu Lys Ile
65                  70                  75                  80

Asn Arg Val Glu Ala Glu Asp Leu Gly Val Tyr Tyr Cys Trp Gln Gly
                85                  90                  95

Thr His Phe Pro Thr Phe Gly Gly Gly Thr Lys Leu Glu Ile Lys
            100                 105                 110

<210> SEQ ID NO 283
<211> LENGTH: 5
<212> TYPE: PRT
<213> ORGANISM: Mus musculus

<400> SEQUENCE: 283

Gly Tyr Tyr Met Asn
1               5

<210> SEQ ID NO 284
<211> LENGTH: 17
<212> TYPE: PRT
<213> ORGANISM: Mus musculus

<400> SEQUENCE: 284

Asp Ile Asn Pro Asn Asn Gly Gly Thr Asp Tyr Asn Arg Lys Phe Lys
1               5                   10                  15

Gly

<210> SEQ ID NO 285
<211> LENGTH: 4
<212> TYPE: PRT
<213> ORGANISM: Mus musculus

<400> SEQUENCE: 285

Asp Phe Ala Val
1

<210> SEQ ID NO 286
<211> LENGTH: 16
<212> TYPE: PRT
<213> ORGANISM: Mus musculus

<400> SEQUENCE: 286

Lys Ser Ser Gln Ser Leu Leu Asp Ser Asp Gly Lys Thr Tyr Leu Asn
1               5                   10                  15

<210> SEQ ID NO 287
<211> LENGTH: 7
<212> TYPE: PRT
```

-continued

<213> ORGANISM: Mus musculus

<400> SEQUENCE: 287

Leu Val Ser Lys Leu Asp Ser
1               5

<210> SEQ ID NO 288
<211> LENGTH: 8
<212> TYPE: PRT
<213> ORGANISM: Mus musculus

<400> SEQUENCE: 288

Trp Gln Gly Thr His Phe Pro Thr
1               5

<210> SEQ ID NO 289
<211> LENGTH: 30
<212> TYPE: PRT
<213> ORGANISM: Mus musculus

<400> SEQUENCE: 289

Glu Val Gln Leu Gln Gln Ser Gly Pro Glu Leu Val Lys Pro Gly Thr
1               5                   10                  15

Ser Val Lys Ile Ser Cys Lys Ala Ser Gly Tyr Thr Phe Thr
            20                  25                  30

<210> SEQ ID NO 290
<211> LENGTH: 14
<212> TYPE: PRT
<213> ORGANISM: Mus musculus

<400> SEQUENCE: 290

Trp Val Lys Gln Ser His Gly Lys Ser Leu Glu Trp Ile Gly
1               5                   10

<210> SEQ ID NO 291
<211> LENGTH: 32
<212> TYPE: PRT
<213> ORGANISM: Mus musculus

<400> SEQUENCE: 291

Lys Ala Thr Leu Thr Val Asp Lys Ser Ser Ser Thr Ala Tyr Met Glu
1               5                   10                  15

Val Arg Ser Leu Thr Ser Glu Asp Ser Ala Val Tyr Tyr Cys Ala Lys
            20                  25                  30

<210> SEQ ID NO 292
<211> LENGTH: 11
<212> TYPE: PRT
<213> ORGANISM: Mus musculus

<400> SEQUENCE: 292

Trp Gly Thr Gly Thr Thr Val Thr Val Ser Ser
1               5                   10

<210> SEQ ID NO 293
<211> LENGTH: 23
<212> TYPE: PRT
<213> ORGANISM: Mus musculus

<400> SEQUENCE: 293

Asp Val Val Met Thr Gln Thr Pro Leu Thr Leu Ser Val Thr Ile Gly
1               5                   10                  15

```
Gln Pro Ala Ser Ile Ser Cys
            20

<210> SEQ ID NO 294
<211> LENGTH: 15
<212> TYPE: PRT
<213> ORGANISM: Mus musculus

<400> SEQUENCE: 294

Trp Leu Leu Gln Arg Pro Gly Gln Ser Pro Lys Arg Leu Ile Tyr
1               5                   10                  15

<210> SEQ ID NO 295
<211> LENGTH: 32
<212> TYPE: PRT
<213> ORGANISM: Mus musculus

<400> SEQUENCE: 295

Gly Ala Pro Asp Arg Phe Thr Gly Ser Gly Ser Gly Thr Asp Phe Thr
1               5                   10                  15

Leu Lys Ile Asn Arg Val Glu Ala Glu Asp Leu Gly Val Tyr Tyr Cys
            20                  25                  30

<210> SEQ ID NO 296
<211> LENGTH: 10
<212> TYPE: PRT
<213> ORGANISM: Mus musculus

<400> SEQUENCE: 296

Phe Gly Gly Gly Thr Lys Leu Glu Ile Lys
1               5                   10

<210> SEQ ID NO 297
<211> LENGTH: 19
<212> TYPE: PRT
<213> ORGANISM: Mus musculus

<400> SEQUENCE: 297

Met Gly Trp Ser Trp Ile Phe Leu Phe Leu Leu Ser Gly Thr Ala Gly
1               5                   10                  15

Val Leu Ser

<210> SEQ ID NO 298
<211> LENGTH: 19
<212> TYPE: PRT
<213> ORGANISM: Mus musculus

<400> SEQUENCE: 298

Met Ser Pro Ala Gln Phe Leu Phe Leu Leu Val Leu Trp Ile Arg Glu
1               5                   10                  15

Ala Asn Gly

<210> SEQ ID NO 299
<211> LENGTH: 348
<212> TYPE: DNA
<213> ORGANISM: Mus musculus

<400> SEQUENCE: 299
gaggtgcagc tggtggagtc tgggggagac ttagtaaacc ctggagggtc cctgaaactc       60
tcctgtgcag cctctggatt cactatcagt aactatggca tgtcttgggt tcgccagact      120
ccagacaaga ggctggaatg ggtcgctatc attattagag atggtggtta tacctactat      180
```

```
ccagacagtg tgaaggggcg attcaccatc tccagagaca gtgccaaaaa caccctgtac      240
ctgcaaatga gcagtctgaa gtctgaagac acagccatgt attactgtgc aagacatgag      300
tattactttg acttctgggg ccaaggcacc actctcacag tctcctca                   348

<210> SEQ ID NO 300
<211> LENGTH: 336
<212> TYPE: DNA
<213> ORGANISM: Mus musculus

<400> SEQUENCE: 300
gatgttttga tgacccaaac tccactctcc ctgcctgtca gtcttggaga tcaagcctcc       60
atctcttgca gatctagtca gaccatttta catagtgatg gaaacaccta tttagaatgg      120
tacctgcaga aaccaggcca gtctccaaag ctcctgatct acaaagtttc caaccgattt      180
tctggggtcc cagacaggtt cagtggcagt ggatcaggga cagatttcac actcaagatc      240
agcagagtgg aggctgagga tctgggagtt tattactgct ctcaaggttc acattttcct      300
ccgacgttcg gtggaggcac caaggtggaa atcaaa                                336

<210> SEQ ID NO 301
<211> LENGTH: 116
<212> TYPE: PRT
<213> ORGANISM: Mus musculus

<400> SEQUENCE: 301

Glu Val Gln Leu Val Glu Ser Gly Gly Asp Leu Val Asn Pro Gly Gly
1               5                   10                  15

Ser Leu Lys Leu Ser Cys Ala Ala Ser Gly Phe Thr Ile Ser Asn Tyr
            20                  25                  30

Gly Met Ser Trp Val Arg Gln Thr Pro Asp Lys Arg Leu Glu Trp Val
        35                  40                  45

Ala Ile Ile Ile Arg Asp Gly Gly Tyr Thr Tyr Tyr Pro Asp Ser Val
    50                  55                  60

Lys Gly Arg Phe Thr Ile Ser Arg Asp Ser Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Glu Tyr Tyr Phe Asp Phe Trp Gly Gln Gly Thr Thr Leu
            100                 105                 110

Thr Val Ser Ser
        115

<210> SEQ ID NO 302
<211> LENGTH: 112
<212> TYPE: PRT
<213> ORGANISM: Mus musculus

<400> SEQUENCE: 302

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Thr Ile Leu His Ser
            20                  25                  30

Asp Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
```

-continued

```
65                    70              75                    80

Ser Arg Val Glu Ala Glu Asp Leu Gly Val Tyr Tyr Cys Ser Gln Gly
                85                    90                    95

Ser His Phe Pro Pro Thr Phe Gly Gly Gly Thr Lys Val Glu Ile Lys
            100                   105                   110

<210> SEQ ID NO 303
<211> LENGTH: 5
<212> TYPE: PRT
<213> ORGANISM: Mus musculus

<400> SEQUENCE: 303

Asn Tyr Gly Met Ser
1               5

<210> SEQ ID NO 304
<211> LENGTH: 17
<212> TYPE: PRT
<213> ORGANISM: Mus musculus

<400> SEQUENCE: 304

Ile Ile Ile Arg Asp Gly Gly Tyr Thr Tyr Tyr Pro Asp Ser Val Lys
1               5                   10                  15

Gly

<210> SEQ ID NO 305
<211> LENGTH: 7
<212> TYPE: PRT
<213> ORGANISM: Mus musculus

<400> SEQUENCE: 305

His Glu Tyr Tyr Phe Asp Phe
1               5

<210> SEQ ID NO 306
<211> LENGTH: 16
<212> TYPE: PRT
<213> ORGANISM: Mus musculus

<400> SEQUENCE: 306

Arg Ser Ser Gln Thr Ile Leu His Ser Asp Gly Asn Thr Tyr Leu Glu
1               5                   10                  15

<210> SEQ ID NO 307
<211> LENGTH: 7
<212> TYPE: PRT
<213> ORGANISM: Mus musculus

<400> SEQUENCE: 307

Lys Val Ser Asn Arg Phe Ser
1               5

<210> SEQ ID NO 308
<211> LENGTH: 9
<212> TYPE: PRT
<213> ORGANISM: Mus musculus

<400> SEQUENCE: 308

Ser Gln Gly Ser His Phe Pro Pro Thr
1               5

<210> SEQ ID NO 309
<211> LENGTH: 30
```

-continued

<212> TYPE: PRT
<213> ORGANISM: Mus musculus

<400> SEQUENCE: 309

Glu Val Gln Leu Val Glu Ser Gly Gly Asp Leu Val Asn Pro Gly Gly
1               5                   10                  15

Ser Leu Lys Leu Ser Cys Ala Ala Ser Gly Phe Thr Ile Ser
            20                  25                  30

<210> SEQ ID NO 310
<211> LENGTH: 14
<212> TYPE: PRT
<213> ORGANISM: Mus musculus

<400> SEQUENCE: 310

Trp Val Arg Gln Thr Pro Asp Lys Arg Leu Glu Trp Val Ala
1               5                   10

<210> SEQ ID NO 311
<211> LENGTH: 32
<212> TYPE: PRT
<213> ORGANISM: Mus musculus

<400> SEQUENCE: 311

Arg Phe Thr Ile Ser Arg Asp Ser Ala Lys Asn Thr Leu Tyr Leu Gln
1               5                   10                  15

Met Ser Ser Leu Lys Ser Glu Asp Thr Ala Met Tyr Tyr Cys Ala Arg
            20                  25                  30

<210> SEQ ID NO 312
<211> LENGTH: 11
<212> TYPE: PRT
<213> ORGANISM: Mus musculus

<400> SEQUENCE: 312

Trp Gly Gln Gly Thr Thr Leu Thr Val Ser Ser
1               5                   10

<210> SEQ ID NO 313
<211> LENGTH: 23
<212> TYPE: PRT
<213> ORGANISM: Mus musculus

<400> SEQUENCE: 313

Asp Val Leu Met Thr Gln Thr Pro Leu Ser Leu Pro Val Ser Leu Gly
1               5                   10                  15

Asp Gln Ala Ser Ile Ser Cys
            20

<210> SEQ ID NO 314
<211> LENGTH: 15
<212> TYPE: PRT
<213> ORGANISM: Mus musculus

<400> SEQUENCE: 314

Trp Tyr Leu Gln Lys Pro Gly Gln Ser Pro Lys Leu Leu Ile Tyr
1               5                   10                  15

<210> SEQ ID NO 315
<211> LENGTH: 32
<212> TYPE: PRT
<213> ORGANISM: Mus musculus

<400> SEQUENCE: 315

```
Gly Val Pro Asp Arg Phe Ser Gly Ser Gly Ser Gly Thr Asp Phe Thr
1               5                   10                  15

Leu Lys Ile Ser Arg Val Glu Ala Glu Asp Leu Gly Val Tyr Tyr Cys
            20                  25                  30

<210> SEQ ID NO 316
<211> LENGTH: 10
<212> TYPE: PRT
<213> ORGANISM: Mus musculus

<400> SEQUENCE: 316

Phe Gly Gly Gly Thr Lys Val Glu Ile Lys
1               5                   10

<210> SEQ ID NO 317
<211> LENGTH: 19
<212> TYPE: PRT
<213> ORGANISM: Mus musculus

<400> SEQUENCE: 317

Met Asn Phe Gly Leu Ser Leu Ile Phe Leu Ala Leu Ile Leu Lys Gly
1               5                   10                  15

Val Gln Cys

<210> SEQ ID NO 318
<211> LENGTH: 19
<212> TYPE: PRT
<213> ORGANISM: Mus musculus

<400> SEQUENCE: 318

Met Lys Leu Pro Val Arg Leu Leu Val Leu Met Phe Trp Ile Pro Glu
1               5                   10                  15

Ser Ser Ser

<210> SEQ ID NO 319
<211> LENGTH: 348
<212> TYPE: DNA
<213> ORGANISM: Mus musculus

<400> SEQUENCE: 319
gatgtgcagc tggtggagtc tgggggaggc ttagtgcagc ctggagggtc ccggaaactc      60
tcctgtgcag cctctggatt cactttcagt agctttggaa tgcactgggt tcgtcaggct     120
ccagagaagg ggctggagtg ggtcgcatac attagtagtg gcagtagtac catctactat     180
gcagacacag tgaagggccg attcaccatc tccagagaca atcccaagaa caccctgttc     240
ctgcaaatga ccagtctaag gtctgaggac acggccatgt attactgtgc aagacggggt     300
aatgctatgg actactgggg tcaaggaacc tcagtcaccg tctcctca                  348

<210> SEQ ID NO 320
<211> LENGTH: 336
<212> TYPE: DNA
<213> ORGANISM: Mus musculus

<400> SEQUENCE: 320
aacattatga tgacacagtc gccatcatct ctggctgtgt ctgcaggaga aaaggtcact      60
atgagctgta agtccagtca aagtgtttta tacagttcaa atcagaagaa ctacttggcc     120
tggtaccagc agaaaccagg gcagtctcct aaactgctga tctactgggc atccactagg     180
gaatctggtg tccctgatcg cttcacaggc agtggatctg ggacagattt tactcttacc     240
```

```
atcagcagtg tacaagctga agacctggca gtttattact gtcatcaata tttctcctcg      300
tggacgttcg gtggaggcac caagctggaa atcaaa                                 336
```

```
<210> SEQ ID NO 321
<211> LENGTH: 116
<212> TYPE: PRT
<213> ORGANISM: Mus musculus

<400> SEQUENCE: 321

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser Ser Phe
            20                  25                  30

Gly Met His Trp Val Arg Gln Ala Pro Glu Lys Gly Leu Glu Trp Val
        35                  40                  45

Ala Tyr Ile Ser Ser Gly Ser Ser Thr Ile Tyr Tyr Ala Asp Thr Val
    50                  55                  60

Lys Gly Arg Phe Thr Ile Ser Arg Asp Asn Pro Lys Asn Thr Leu Phe
65                  70                  75                  80

Leu Gln Met Thr Ser Leu Arg Ser Glu Asp Thr Ala Met Tyr Tyr Cys
                85                  90                  95

Ala Arg Arg Gly Asn Ala Met Asp Tyr Trp Gly Gln Gly Thr Ser Val
            100                 105                 110

Thr Val Ser Ser
        115
```

```
<210> SEQ ID NO 322
<211> LENGTH: 112
<212> TYPE: PRT
<213> ORGANISM: Mus musculus

<400> SEQUENCE: 322

Asn Ile Met Met Thr Gln Ser Pro Ser Ser Leu Ala Val Ser Ala Gly
1               5                   10                  15

Glu Lys Val Thr Met Ser Cys Lys Ser Ser Gln Ser Val Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Gln Ala Glu Asp Leu Ala Val Tyr Tyr Cys His Gln
                85                  90                  95

Tyr Phe Ser Ser Trp Thr Phe Gly Gly Gly Thr Lys Leu Glu Ile Lys
            100                 105                 110
```

```
<210> SEQ ID NO 323
<211> LENGTH: 5
<212> TYPE: PRT
<213> ORGANISM: Mus musculus

<400> SEQUENCE: 323

Ser Phe Gly Met His
1               5
```

```
<210> SEQ ID NO 324
```

-continued

```
<211> LENGTH: 17
<212> TYPE: PRT
<213> ORGANISM: Mus musculus

<400> SEQUENCE: 324

Tyr Ile Ser Ser Gly Ser Ser Thr Ile Tyr Tyr Ala Asp Thr Val Lys
1               5                   10                  15

Gly

<210> SEQ ID NO 325
<211> LENGTH: 7
<212> TYPE: PRT
<213> ORGANISM: Mus musculus

<400> SEQUENCE: 325

Arg Gly Asn Ala Met Asp Tyr
1               5

<210> SEQ ID NO 326
<211> LENGTH: 17
<212> TYPE: PRT
<213> ORGANISM: Mus musculus

<400> SEQUENCE: 326

Lys Ser Ser Gln Ser Val Leu Tyr Ser Asn Gln Lys Asn Tyr Leu
1               5                   10                  15

Ala

<210> SEQ ID NO 327
<211> LENGTH: 7
<212> TYPE: PRT
<213> ORGANISM: Mus musculus

<400> SEQUENCE: 327

Trp Ala Ser Thr Arg Glu Ser
1               5

<210> SEQ ID NO 328
<211> LENGTH: 8
<212> TYPE: PRT
<213> ORGANISM: Mus musculus

<400> SEQUENCE: 328

His Gln Tyr Phe Ser Ser Trp Thr
1               5

<210> SEQ ID NO 329
<211> LENGTH: 30
<212> TYPE: PRT
<213> ORGANISM: Mus musculus

<400> SEQUENCE: 329

Asp Val Gln Leu Val Glu Ser Gly Gly Gly Leu Val Gln Pro Gly Gly
1               5                   10                  15

Ser Arg Lys Leu Ser Cys Ala Ala Ser Gly Phe Thr Phe Ser
                20                  25                  30

<210> SEQ ID NO 330
<211> LENGTH: 14
<212> TYPE: PRT
<213> ORGANISM: Mus musculus

<400> SEQUENCE: 330
```

-continued

```
Trp Val Arg Gln Ala Pro Glu Lys Gly Leu Glu Trp Val Ala
1               5                   10

<210> SEQ ID NO 331
<211> LENGTH: 32
<212> TYPE: PRT
<213> ORGANISM: Mus musculus

<400> SEQUENCE: 331

Arg Phe Thr Ile Ser Arg Asp Asn Pro Lys Asn Thr Leu Phe Leu Gln
1               5                   10                  15

Met Thr Ser Leu Arg Ser Glu Asp Thr Ala Met Tyr Tyr Cys Ala Arg
            20                  25                  30

<210> SEQ ID NO 332
<211> LENGTH: 11
<212> TYPE: PRT
<213> ORGANISM: Mus musculus

<400> SEQUENCE: 332

Trp Gly Gln Gly Thr Ser Val Thr Val Ser Ser
1               5                   10

<210> SEQ ID NO 333
<211> LENGTH: 23
<212> TYPE: PRT
<213> ORGANISM: Mus musculus

<400> SEQUENCE: 333

Asn Ile Met Met Thr Gln Ser Pro Ser Ser Leu Ala Val Ser Ala Gly
1               5                   10                  15

Glu Lys Val Thr Met Ser Cys
            20

<210> SEQ ID NO 334
<211> LENGTH: 15
<212> TYPE: PRT
<213> ORGANISM: Mus musculus

<400> SEQUENCE: 334

Trp Tyr Gln Gln Lys Pro Gly Gln Ser Pro Lys Leu Leu Ile Tyr
1               5                   10                  15

<210> SEQ ID NO 335
<211> LENGTH: 32
<212> TYPE: PRT
<213> ORGANISM: Mus musculus

<400> SEQUENCE: 335

Gly Val Pro Asp Arg Phe Thr Gly Ser Gly Ser Gly Thr Asp Phe Thr
1               5                   10                  15

Leu Thr Ile Ser Ser Val Gln Ala Glu Asp Leu Ala Val Tyr Tyr Cys
            20                  25                  30

<210> SEQ ID NO 336
<211> LENGTH: 10
<212> TYPE: PRT
<213> ORGANISM: Mus musculus

<400> SEQUENCE: 336

Phe Gly Gly Gly Thr Lys Leu Glu Ile Lys
1               5                   10
```

<210> SEQ ID NO 337
<211> LENGTH: 19
<212> TYPE: PRT
<213> ORGANISM: Mus musculus

<400> SEQUENCE: 337

Met Asp Ser Arg Leu Asn Leu Val Phe Leu Val Leu Ile Leu Lys Gly
1               5                   10                  15

Val Gln Cys

<210> SEQ ID NO 338
<211> LENGTH: 20
<212> TYPE: PRT
<213> ORGANISM: Mus musculus

<400> SEQUENCE: 338

Met Glu Ser Gln Thr Gln Val Phe Leu Ser Leu Leu Leu Trp Val Ser
1               5                   10                  15

Gly Thr Cys Gly
            20

<210> SEQ ID NO 339
<211> LENGTH: 366
<212> TYPE: DNA
<213> ORGANISM: Mus musculus

<400> SEQUENCE: 339
gaggtgcagc ttgttgagtc tggtggagga ctggtgcagc ctaaaggatc attgaaactc        60
tcatgtgccg cctctggttt caccttcaat acctatgcca tgcactgggt ccgccaggct       120
ccaggaaagg gtttggaatg ggttgctcgc ataagaagta aaagtagtaa ttatgcaaca       180
tattatgccg attcagtgaa agacagattc accatctcca gagatgattc acaaagcatg       240
gtctatctgc agatgaacaa cctgaaaact gaggacacag ccatgtatta ctgtgtgaga       300 aaggggatg gttacgacgg ctggtttgct tactggggcc aagggactct ggtcactgtc       360
tctgca                                                                  366

<210> SEQ ID NO 340
<211> LENGTH: 321
<212> TYPE: DNA
<213> ORGANISM: Mus musculus

<400> SEQUENCE: 340
gacatccaga tgactcagtc tccagcctcc ctatctgcat ctgtgggaga aactgtcacc        60
atcacatgtc gaccaagtgg gaatattcac aattatttag tatggtatca gcagaaacag       120 ggaaatctc ctcaggtcct ggtctataat tcaaaaacct tagcagatgg tgtgccatca       180
cggttcagtg gcagtggatc aggaacacag tattctctca agatcaacag cctgcagcct       240
gaagattttg ggacttatta ctgtcaacat ttttggagta ctccactcac gttcggtgct       300
gggaccaaac tggagctgaa a                                                 321

<210> SEQ ID NO 341
<211> LENGTH: 122
<212> TYPE: PRT
<213> ORGANISM: Mus musculus

<400> SEQUENCE: 341

Glu Val Gln Leu Val Glu Ser Gly Gly Gly Leu Val Gln Pro Lys Gly
1               5                   10                  15

```
Ser Leu Lys Leu Ser Cys Ala Ala Ser Gly Phe Thr Phe Asn Thr Tyr
            20                  25                  30

Ala Met His Trp Val Arg Gln Ala Pro Gly Lys Gly Leu Glu Trp Val
            35                  40                  45

Ala Arg Ile Arg Ser Lys Ser Ser Asn Tyr Ala Thr Tyr Tyr Ala Asp
    50                  55                  60

Ser Val Lys Asp Arg Phe Thr Ile Ser Arg Asp Asp Ser Gln Ser Met
65                  70                  75                  80

Val Tyr Leu Gln Met Asn Asn Leu Lys Thr Glu Asp Thr Ala Met Tyr
                85                  90                  95

Tyr Cys Val Arg Lys Gly Asp Gly Tyr Asp Gly Trp Phe Ala Tyr Trp
            100                 105                 110

Gly Gln Gly Thr Leu Val Thr Val Ser Ala
            115                 120
```

```
<210> SEQ ID NO 342
<211> LENGTH: 107
<212> TYPE: PRT
<213> ORGANISM: Mus musculus

<400> SEQUENCE: 342

Asp Ile Gln Met Thr Gln Ser Pro Ala Ser Leu Ser Ala Ser Val Gly
1               5                   10                  15

Glu Thr Val Thr Ile Thr Cys Arg Pro Ser Gly Asn Ile His Asn Tyr
            20                  25                  30

Leu Val Trp Tyr Gln Gln Lys Gln Gly Lys Ser Pro Gln Val Leu Val
            35                  40                  45

Tyr Asn Ser Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Thr Tyr Tyr Cys Gln His Phe Trp Ser Thr Pro Leu
                85                  90                  95

Thr Phe Gly Ala Gly Thr Lys Leu Glu Leu Lys
            100                 105
```

```
<210> SEQ ID NO 343
<211> LENGTH: 5
<212> TYPE: PRT
<213> ORGANISM: Mus musculus

<400> SEQUENCE: 343

Thr Tyr Ala Met His
1               5
```

```
<210> SEQ ID NO 344
<211> LENGTH: 19
<212> TYPE: PRT
<213> ORGANISM: Mus musculus

<400> SEQUENCE: 344

Arg Ile Arg Ser Lys Ser Ser Asn Tyr Ala Thr Tyr Tyr Ala Asp Ser
1               5                   10                  15

Val Lys Asp
```

```
<210> SEQ ID NO 345
<211> LENGTH: 11
<212> TYPE: PRT
<213> ORGANISM: Mus musculus
```

<400> SEQUENCE: 345

Lys Gly Asp Gly Tyr Asp Gly Trp Phe Ala Tyr
1               5                   10

<210> SEQ ID NO 346
<211> LENGTH: 11
<212> TYPE: PRT
<213> ORGANISM: Mus musculus

<400> SEQUENCE: 346

Arg Pro Ser Gly Asn Ile His Asn Tyr Leu Val
1               5                   10

<210> SEQ ID NO 347
<211> LENGTH: 7
<212> TYPE: PRT
<213> ORGANISM: Mus musculus

<400> SEQUENCE: 347

Asn Ser Lys Thr Leu Ala Asp
1               5

<210> SEQ ID NO 348
<211> LENGTH: 9
<212> TYPE: PRT
<213> ORGANISM: Mus musculus

<400> SEQUENCE: 348

Gln His Phe Trp Ser Thr Pro Leu Thr
1               5

<210> SEQ ID NO 349
<211> LENGTH: 30
<212> TYPE: PRT
<213> ORGANISM: Mus musculus

<400> SEQUENCE: 349

Glu Val Gln Leu Val Glu Ser Gly Gly Gly Leu Val Gln Pro Lys Gly
1               5                   10                  15

Ser Leu Lys Leu Ser Cys Ala Ala Ser Gly Phe Thr Phe Asn
            20                  25                  30

<210> SEQ ID NO 350
<211> LENGTH: 14
<212> TYPE: PRT
<213> ORGANISM: Mus musculus

<400> SEQUENCE: 350

Trp Val Arg Gln Ala Pro Gly Lys Gly Leu Glu Trp Val Ala
1               5                   10

<210> SEQ ID NO 351
<211> LENGTH: 32
<212> TYPE: PRT
<213> ORGANISM: Mus musculus

<400> SEQUENCE: 351

Arg Phe Thr Ile Ser Arg Asp Asp Ser Gln Ser Met Val Tyr Leu Gln
1               5                   10                  15

Met Asn Asn Leu Lys Thr Glu Asp Thr Ala Met Tyr Tyr Cys Val Arg
            20                  25                  30

<210> SEQ ID NO 352
<211> LENGTH: 11
<212> TYPE: PRT
<213> ORGANISM: Mus musculus

<400> SEQUENCE: 352

Trp Gly Gln Gly Thr Leu Val Thr Val Ser Ala
1               5                   10

<210> SEQ ID NO 353
<211> LENGTH: 23
<212> TYPE: PRT
<213> ORGANISM: Mus musculus

<400> SEQUENCE: 353

Asp Ile Gln Met Thr Gln Ser Pro Ala Ser Leu Ser Ala Ser Val Gly
1               5                   10                  15

Glu Thr Val Thr Ile Thr Cys
            20

<210> SEQ ID NO 354
<211> LENGTH: 15
<212> TYPE: PRT
<213> ORGANISM: Mus musculus

<400> SEQUENCE: 354

Trp Tyr Gln Gln Lys Gln Gly Lys Ser Pro Gln Val Leu Val Tyr
1               5                   10                  15

<210> SEQ ID NO 355
<211> LENGTH: 32
<212> TYPE: PRT
<213> ORGANISM: Mus musculus

<400> SEQUENCE: 355

Gly Val Pro Ser Arg Phe Ser Gly Ser Gly Ser Gly Thr Gln Tyr Ser
1               5                   10                  15

Leu Lys Ile Asn Ser Leu Gln Pro Glu Asp Phe Gly Thr Tyr Tyr Cys
            20                  25                  30

<210> SEQ ID NO 356
<211> LENGTH: 10
<212> TYPE: PRT
<213> ORGANISM: Mus musculus

<400> SEQUENCE: 356

Phe Gly Ala Gly Thr Lys Leu Glu Leu Lys
1               5                   10

<210> SEQ ID NO 357
<211> LENGTH: 19
<212> TYPE: PRT
<213> ORGANISM: Mus musculus

<400> SEQUENCE: 357

Met Val Leu Gly Leu Lys Trp Val Phe Phe Val Val Leu Tyr Gln Gly
1               5                   10                  15

Val His Cys

<210> SEQ ID NO 358
<211> LENGTH: 20
<212> TYPE: PRT
<213> ORGANISM: Mus musculus

<400> SEQUENCE: 358

Met Ser Val Leu Thr Gln Val Leu Ala Leu Leu Leu Leu Trp Leu Thr
1               5                   10                  15

Gly Ala Arg Cys
            20

<210> SEQ ID NO 359
<211> LENGTH: 369
<212> TYPE: DNA
<213> ORGANISM: Mus musculus

<400> SEQUENCE: 359
gaggttcaac tgctgcagtc tgtggcagag cttgtgaggc caggggcctc agtcaagttg        60
tcctgcacag cttctggctt caacattaaa aacacctta tacactggct gaagcagagg        120
cctgagcagg gcctggagtg gattggaaag attgatcctg cgaatggtaa tattagatgt        180
gccccgaagt tccagggcaa ggccactata actgcagaca catcctccaa cacagcctac        240
ctgcagctca gcagcctgac atctggggac actgccatct attactgtgg tagaggtact        300
atgttagtag gtcacttcta ctggtacttc gatgtctggg gcacagggac cacggtcacc        360
gtctcctca                                                              369

<210> SEQ ID NO 360
<211> LENGTH: 339
<212> TYPE: DNA
<213> ORGANISM: Mus musculus

<400> SEQUENCE: 360
gacattgtga tgtcacagtc tccatcctcc ctagctgtgt cagttggaga gaagattact        60
atgagctgca gtccagtca gagccttta tatagtagca atcaaaagaa ctacttggcc        120
tggtaccagc agaaaccggg gcagtctcct aaactgctga tttactgggc atccactagg        180
gaatctgggg tccctgatcg cttctcaggc agtggatctg ggacagattt cactctcacc        240
atcagcagtg tgaagactga agacctggca atttttact gtcagcaata ttattactat        300
cctcccacgt tcggtgctgg gaccaagctg gagctgaga                             339

<210> SEQ ID NO 361
<211> LENGTH: 123
<212> TYPE: PRT
<213> ORGANISM: Mus musculus

<400> SEQUENCE: 361

Glu Val Gln Leu Leu Gln Ser Val Ala Glu Leu Val Arg Pro Gly Ala
1               5                   10                  15

Ser Val Lys Leu Ser Cys Thr Ala Ser Gly Phe Asn Ile Lys Asn Thr
            20                  25                  30

Phe Ile His Trp Leu Lys Gln Arg Pro Glu Gln Gly Leu Glu Trp Ile
        35                  40                  45

Gly Lys Ile Asp Pro Ala Asn Gly Asn Ile Arg Cys Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Gly Asp Thr Ala Ile Tyr Tyr Cys
                85                  90                  95

Gly Arg Gly Thr Met Leu Val Gly His Phe Tyr Trp Tyr Phe Asp Val
            100                 105                 110

-continued

```
Trp Gly Thr Gly Thr Thr Val Thr Val Ser Ser
        115                 120
```

```
<210> SEQ ID NO 362
<211> LENGTH: 113
<212> TYPE: PRT
<213> ORGANISM: Mus musculus

<400> SEQUENCE: 362
```

```
Asp Ile Val Met Ser Gln Ser Pro Ser Ser Leu Ala Val Ser Val Gly
1               5                   10                  15

Glu Lys Ile Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Lys Thr Glu Asp Leu Ala Ile Phe Tyr Cys Gln Gln
                85                  90                  95

Tyr Tyr Tyr Tyr Pro Pro Thr Phe Gly Ala Gly Thr Lys Leu Glu Leu
            100                 105                 110

Arg
```

```
<210> SEQ ID NO 363
<211> LENGTH: 5
<212> TYPE: PRT
<213> ORGANISM: Mus musculus

<400> SEQUENCE: 363
```

```
Asn Thr Phe Ile His
1               5
```

```
<210> SEQ ID NO 364
<211> LENGTH: 17
<212> TYPE: PRT
<213> ORGANISM: Mus musculus

<400> SEQUENCE: 364
```

```
Lys Ile Asp Pro Ala Asn Gly Asn Ile Arg Cys Ala Pro Lys Phe Gln
1               5                   10                  15

Gly
```

```
<210> SEQ ID NO 365
<211> LENGTH: 14
<212> TYPE: PRT
<213> ORGANISM: Mus musculus

<400> SEQUENCE: 365
```

```
Gly Thr Met Leu Val Gly His Phe Tyr Trp Tyr Phe Asp Val
1               5                   10
```

```
<210> SEQ ID NO 366
<211> LENGTH: 17
<212> TYPE: PRT
<213> ORGANISM: Mus musculus

<400> SEQUENCE: 366
```

```
Lys Ser Ser Gln Ser Leu Leu Tyr Ser Ser Asn Gln Lys Asn Tyr Leu
1               5                   10                  15
```

-continued

Ala

<210> SEQ ID NO 367
<211> LENGTH: 7
<212> TYPE: PRT
<213> ORGANISM: Mus musculus

<400> SEQUENCE: 367

Trp Ala Ser Thr Arg Glu Ser
1               5

<210> SEQ ID NO 368
<211> LENGTH: 9
<212> TYPE: PRT
<213> ORGANISM: Mus musculus

<400> SEQUENCE: 368

Gln Gln Tyr Tyr Tyr Tyr Pro Pro Thr
1               5

<210> SEQ ID NO 369
<211> LENGTH: 30
<212> TYPE: PRT
<213> ORGANISM: Mus musculus

<400> SEQUENCE: 369

Glu Val Gln Leu Leu Gln Ser Val Ala Glu Leu Val Arg Pro Gly Ala
1               5                   10                  15

Ser Val Lys Leu Ser Cys Thr Ala Ser Gly Phe Asn Ile Lys
            20                  25                  30

<210> SEQ ID NO 370
<211> LENGTH: 14
<212> TYPE: PRT
<213> ORGANISM: Mus musculus

<400> SEQUENCE: 370

Trp Leu Lys Gln Arg Pro Glu Gln Gly Leu Glu Trp Ile Gly
1               5                   10

<210> SEQ ID NO 371
<211> LENGTH: 32
<212> TYPE: PRT
<213> ORGANISM: Mus musculus

<400> SEQUENCE: 371

Lys Ala Thr Ile Thr Ala Asp Thr Ser Ser Asn Thr Ala Tyr Leu Gln
1               5                   10                  15

Leu Ser Ser Leu Thr Ser Gly Asp Thr Ala Ile Tyr Tyr Cys Gly Arg
            20                  25                  30

<210> SEQ ID NO 372
<211> LENGTH: 11
<212> TYPE: PRT
<213> ORGANISM: Mus musculus

<400> SEQUENCE: 372

Trp Gly Thr Gly Thr Thr Val Thr Val Ser Ser
1               5                   10

<210> SEQ ID NO 373
<211> LENGTH: 23
<212> TYPE: PRT

-continued

<213> ORGANISM: Mus musculus

<400> SEQUENCE: 373

Asp Ile Val Met Ser Gln Ser Pro Ser Ser Leu Ala Val Ser Val Gly
1               5                   10                  15

Glu Lys Ile Thr Met Ser Cys
            20

<210> SEQ ID NO 374
<211> LENGTH: 15
<212> TYPE: PRT
<213> ORGANISM: Mus musculus

<400> SEQUENCE: 374

Trp Tyr Gln Gln Lys Pro Gly Gln Ser Pro Lys Leu Leu Ile Tyr
1               5                   10                  15

<210> SEQ ID NO 375
<211> LENGTH: 32
<212> TYPE: PRT
<213> ORGANISM: Mus musculus

<400> SEQUENCE: 375

Gly Val Pro Asp Arg Phe Ser Gly Ser Gly Ser Gly Thr Asp Phe Thr
1               5                   10                  15

Leu Thr Ile Ser Ser Val Lys Thr Glu Asp Leu Ala Ile Phe Tyr Cys
            20                  25                  30

<210> SEQ ID NO 376
<211> LENGTH: 10
<212> TYPE: PRT
<213> ORGANISM: Mus musculus

<400> SEQUENCE: 376

Phe Gly Ala Gly Thr Lys Leu Glu Leu Arg
1               5                   10

<210> SEQ ID NO 377
<211> LENGTH: 19
<212> TYPE: PRT
<213> ORGANISM: Mus musculus

<400> SEQUENCE: 377

Met Lys Phe Ser Trp Val Ile Phe Phe Leu Met Ala Val Val Thr Gly
1               5                   10                  15

Val Asn Ser

<210> SEQ ID NO 378
<211> LENGTH: 20
<212> TYPE: PRT
<213> ORGANISM: Mus musculus

<400> SEQUENCE: 378

Met Asp Ser Gln Ala Gln Val Leu Met Leu Leu Leu Leu Trp Val Ser
1               5                   10                  15

Gly Thr Cys Gly
            20

<210> SEQ ID NO 379
<211> LENGTH: 369
<212> TYPE: DNA
<213> ORGANISM: Mus musculus -continued

<400> SEQUENCE: 379
gaggttcaac tgctgcagtc tgtggcagag cttgtgaggc cagggggcctc agtcaagttg      60 tcctgcacag cttctggctt caacattaaa aacacctta tacactggct gaagcagagg      120
cctgagcagg gcctggagtg gattggaaag attgatcctg cgaatggtaa tattagatgt      180
gccccgaagt tccagggcaa ggccactata actgcagaca catcctccaa cacagcctac      240
ctgcagctca gcagcctgac atctggggac actgccatct attactgtgg tagaggtact      300
atgttagtag gtcacttcta ctggtacttc gatgtctggg gcacagggac cacggtcacc      360
gtctcctca                                                             369

<210> SEQ ID NO 380
<211> LENGTH: 339
<212> TYPE: DNA
<213> ORGANISM: Mus musculus

<400> SEQUENCE: 380
gacattgtga tgtcacagtc tccatcctcc ctagctgtgt cagttggaga aagagattact      60 atgagctgca agtccagtca gagccttta tatagtagca atcaaaagaa ctacttggcc      120
tggtaccagc agaaaccggg gcagtctcct aaactgctga tttactgggc atccactagg      180
gaatctgggg tccctgatcg cttctcaggc agtggatctg ggacagattt cactctcacc      240
atcagcagtg tgaagactga agacctggca atttttttact gtcagcaata ttattactat      300
cctcccacgt tcggtgctgg gaccaagctg gagctgaga                            339

<210> SEQ ID NO 381
<211> LENGTH: 123
<212> TYPE: PRT
<213> ORGANISM: Mus musculus

<400> SEQUENCE: 381

Glu Val Gln Leu Leu Gln Ser Val Ala Glu Leu Val Arg Pro Gly Ala
1               5                   10                  15

Ser Val Lys Leu Ser Cys Thr Ala Ser Gly Phe Asn Ile Lys Asn Thr
            20                  25                  30

Phe Ile His Trp Leu Lys Gln Arg Pro Glu Gln Gly Leu Glu Trp Ile
        35                  40                  45

Gly Lys Ile Asp Pro Ala Asn Gly Asn Ile Arg Cys Ala Pro Lys Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Gly Asp Thr Ala Ile Tyr Tyr Cys
                85                  90                  95

Gly Arg Gly Thr Met Leu Val Gly His Phe Tyr Trp Tyr Phe Asp Val
            100                 105                 110

Trp Gly Thr Gly Thr Thr Val Thr Val Ser Ser
        115                 120

<210> SEQ ID NO 382
<211> LENGTH: 113
<212> TYPE: PRT
<213> ORGANISM: Mus musculus

<400> SEQUENCE: 382

Asp Ile Val Met Ser Gln Ser Pro Ser Ser Leu Ala Val Ser Val Gly
1               5                   10                  15

-continued

```
Glu Lys Ile Thr Met Ser Cys Lys Ser Ser Gln Ser Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Val Lys Thr Glu Asp Leu Ala Ile Phe Tyr Cys Gln Gln
                85                  90                  95

Tyr Tyr Tyr Tyr Pro Pro Thr Phe Gly Ala Gly Thr Lys Leu Glu Leu
            100                 105                 110

Arg
```

```
<210> SEQ ID NO 383
<211> LENGTH: 5
<212> TYPE: PRT
<213> ORGANISM: Mus musculus

<400> SEQUENCE: 383

Asn Thr Phe Ile His
1               5
```

```
<210> SEQ ID NO 384
<211> LENGTH: 17
<212> TYPE: PRT
<213> ORGANISM: Mus musculus

<400> SEQUENCE: 384

Lys Ile Asp Pro Ala Asn Gly Asn Ile Arg Cys Ala Pro Lys Phe Gln
1               5                   10                  15

Gly
```

```
<210> SEQ ID NO 385
<211> LENGTH: 14
<212> TYPE: PRT
<213> ORGANISM: Mus musculus

<400> SEQUENCE: 385

Gly Thr Met Leu Val Gly His Phe Tyr Trp Tyr Phe Asp Val
1               5                   10
```

```
<210> SEQ ID NO 386
<211> LENGTH: 17
<212> TYPE: PRT
<213> ORGANISM: Mus musculus

<400> SEQUENCE: 386

Lys Ser Ser Gln Ser Leu Leu Tyr Ser Ser Asn Gln Lys Asn Tyr Leu
1               5                   10                  15

Ala
```

```
<210> SEQ ID NO 387
<211> LENGTH: 7
<212> TYPE: PRT
<213> ORGANISM: Mus musculus

<400> SEQUENCE: 387

Trp Ala Ser Thr Arg Glu Ser
1               5
```

-continued

<210> SEQ ID NO 388
<211> LENGTH: 9
<212> TYPE: PRT
<213> ORGANISM: Mus musculus

<400> SEQUENCE: 388

Gln Gln Tyr Tyr Tyr Tyr Pro Pro Thr
1               5

<210> SEQ ID NO 389
<211> LENGTH: 30
<212> TYPE: PRT
<213> ORGANISM: Mus musculus

<400> SEQUENCE: 389

Glu Val Gln Leu Leu Gln Ser Val Ala Glu Leu Val Arg Pro Gly Ala
1               5                   10                  15

Ser Val Lys Leu Ser Cys Thr Ala Ser Gly Phe Asn Ile Lys
            20                  25                  30

<210> SEQ ID NO 390
<211> LENGTH: 14
<212> TYPE: PRT
<213> ORGANISM: Mus musculus

<400> SEQUENCE: 390

Trp Leu Lys Gln Arg Pro Glu Gln Gly Leu Glu Trp Ile Gly
1               5                   10

<210> SEQ ID NO 391
<211> LENGTH: 32
<212> TYPE: PRT
<213> ORGANISM: Mus musculus

<400> SEQUENCE: 391

Lys Ala Thr Ile Thr Ala Asp Thr Ser Ser Asn Thr Ala Tyr Leu Gln
1               5                   10                  15

Leu Ser Ser Leu Thr Ser Gly Asp Thr Ala Ile Tyr Tyr Cys Gly Arg
            20                  25                  30

<210> SEQ ID NO 392
<211> LENGTH: 11
<212> TYPE: PRT
<213> ORGANISM: Mus musculus

<400> SEQUENCE: 392

Trp Gly Thr Gly Thr Thr Val Thr Val Ser Ser
1               5                   10

<210> SEQ ID NO 393
<211> LENGTH: 23
<212> TYPE: PRT
<213> ORGANISM: Mus musculus

<400> SEQUENCE: 393

Asp Ile Val Met Ser Gln Ser Pro Ser Ser Leu Ala Val Ser Val Gly
1               5                   10                  15

Glu Lys Ile Thr Met Ser Cys
            20

<210> SEQ ID NO 394
<211> LENGTH: 15
<212> TYPE: PRT

-continued

<213> ORGANISM: Mus musculus

<400> SEQUENCE: 394

Trp Tyr Gln Gln Lys Pro Gly Gln Ser Pro Lys Leu Leu Ile Tyr
1               5                   10                  15

<210> SEQ ID NO 395
<211> LENGTH: 32
<212> TYPE: PRT
<213> ORGANISM: Mus musculus

<400> SEQUENCE: 395

Gly Val Pro Asp Arg Phe Ser Gly Ser Gly Ser Gly Thr Asp Phe Thr
1               5                   10                  15

Leu Thr Ile Ser Ser Val Lys Thr Glu Asp Leu Ala Ile Phe Tyr Cys
            20                  25                  30

<210> SEQ ID NO 396
<211> LENGTH: 10
<212> TYPE: PRT
<213> ORGANISM: Mus musculus

<400> SEQUENCE: 396

Phe Gly Ala Gly Thr Lys Leu Glu Leu Arg
1               5                   10

<210> SEQ ID NO 397
<211> LENGTH: 19
<212> TYPE: PRT
<213> ORGANISM: Mus musculus

<400> SEQUENCE: 397

Met Lys Phe Ser Trp Val Ile Phe Phe Leu Met Ala Val Val Thr Gly
1               5                   10                  15

Val Asn Ser

<210> SEQ ID NO 398
<211> LENGTH: 20
<212> TYPE: PRT
<213> ORGANISM: Mus musculus

<400> SEQUENCE: 398

Met Asp Ser Gln Ala Gln Val Leu Met Leu Leu Leu Leu Trp Val Ser
1               5                   10                  15

Gly Thr Cys Gly
            20

<210> SEQ ID NO 399
<211> LENGTH: 339
<212> TYPE: DNA
<213> ORGANISM: Mus musculus

<400> SEQUENCE: 399
gaggtccagg tgcaacaatc tggacctgag ctggtgaagc ctggggcttc agtgaagata        60
tcctgtaagg cttctggata cacgttcact ggctactaca tgaactgggt gaagcagagc       120
catggaaaga gccttgagtg gattggagat attaatccta caatggtgg cactgactac        180 aatcggaagt tcaagggcaa ggccacattg actgtagaca gtcctccag cacagcctac        240 atggagctcc gcagcctgac atctgaggac tctgcagtct attactgtgc aagagacttc       300
gctgtctggg gcacagggac cacggtcacc gtctcctca                              339

```
<210> SEQ ID NO 400
<211> LENGTH: 333
<212> TYPE: DNA
<213> ORGANISM: Mus musculus

<400> SEQUENCE: 400
gatgttgtga tgacccagac tccactcact ttgtcggtta ccattggaca accagcctcc       60
atctcttgca agtcaagtca gagcctctta gatagtgatg aaagacata tttgaattgg      120 ttgttacaga ggccaggcca gtctccaaag cgcctaatct atctggtgtc taaactggac      180
tctggagccc ctgacaggtt cactggcagt ggatcaggga cagatttcac actgaaaatc      240
agcagagtgg aggctgagga tttgggagtt tattattgct ggcaaggtac acattttccc      300
acgttcggag gggggaccaa gctggaaata aaa                                   333

<210> SEQ ID NO 401
<211> LENGTH: 113
<212> TYPE: PRT
<213> ORGANISM: Mus musculus

<400> SEQUENCE: 401

Glu Val Gln Val Gln Gln Ser Gly Pro Glu Leu Val Lys Pro Gly Ala
1               5                   10                  15

Ser Val Lys Ile Ser Cys Lys Ala Ser Gly Tyr Thr Phe Thr Gly Tyr
            20                  25                  30

Tyr Met Asn Trp Val Lys Gln Ser His Gly Lys Ser Leu Glu Trp Ile
        35                  40                  45

Gly Asp Ile Asn Pro Asn Asn Gly Gly Thr Asp Tyr Asn Arg Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Asp Phe Ala Val Trp Gly Thr Gly Thr Thr Val Thr Val Ser
            100                 105                 110

Ser

<210> SEQ ID NO 402
<211> LENGTH: 111
<212> TYPE: PRT
<213> ORGANISM: Mus musculus

<400> SEQUENCE: 402

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Ala Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Thr Phe Gly Gly Gly Thr Lys Leu Glu Ile Lys
            100                 105                 110
```

```
<210> SEQ ID NO 403
<211> LENGTH: 5
<212> TYPE: PRT
<213> ORGANISM: Mus musculus

<400> SEQUENCE: 403

Gly Tyr Tyr Met Asn
1               5

<210> SEQ ID NO 404
<211> LENGTH: 17
<212> TYPE: PRT
<213> ORGANISM: Mus musculus

<400> SEQUENCE: 404

Asp Ile Asn Pro Asn Asn Gly Gly Thr Asp Tyr Asn Arg Lys Phe Lys
1               5                   10                  15

Gly

<210> SEQ ID NO 405
<211> LENGTH: 4
<212> TYPE: PRT
<213> ORGANISM: Mus musculus

<400> SEQUENCE: 405

Asp Phe Ala Val
1

<210> SEQ ID NO 406
<211> LENGTH: 16
<212> TYPE: PRT
<213> ORGANISM: Mus musculus

<400> SEQUENCE: 406

Lys Ser Ser Gln Ser Leu Leu Asp Ser Asp Gly Lys Thr Tyr Leu Asn
1               5                   10                  15

<210> SEQ ID NO 407
<211> LENGTH: 7
<212> TYPE: PRT
<213> ORGANISM: Mus musculus

<400> SEQUENCE: 407

Leu Val Ser Lys Leu Asp Ser
1               5

<210> SEQ ID NO 408
<211> LENGTH: 8
<212> TYPE: PRT
<213> ORGANISM: Mus musculus

<400> SEQUENCE: 408

Trp Gln Gly Thr His Phe Pro Thr
1               5

<210> SEQ ID NO 409
<211> LENGTH: 30
<212> TYPE: PRT
<213> ORGANISM: Mus musculus

<400> SEQUENCE: 409

Glu Val Gln Val Gln Gln Ser Gly Pro Glu Leu Val Lys Pro Gly Ala
1               5                   10                  15
```

```
Ser Val Lys Ile Ser Cys Lys Ala Ser Gly Tyr Thr Phe Thr
            20                  25                  30

<210> SEQ ID NO 410
<211> LENGTH: 14
<212> TYPE: PRT
<213> ORGANISM: Mus musculus

<400> SEQUENCE: 410

Trp Val Lys Gln Ser His Gly Lys Ser Leu Glu Trp Ile Gly
1               5                   10

<210> SEQ ID NO 411
<211> LENGTH: 32
<212> TYPE: PRT
<213> ORGANISM: Mus musculus

<400> SEQUENCE: 411

Lys Ala Thr Leu Thr Val Asp Lys Ser Ser Ser Thr Ala Tyr Met Glu
1               5                   10                  15

Leu Arg Ser Leu Thr Ser Glu Asp Ser Ala Val Tyr Tyr Cys Ala Arg
            20                  25                  30

<210> SEQ ID NO 412
<211> LENGTH: 11
<212> TYPE: PRT
<213> ORGANISM: Mus musculus

<400> SEQUENCE: 412

Trp Gly Thr Gly Thr Thr Val Thr Val Ser Ser
1               5                   10

<210> SEQ ID NO 413
<211> LENGTH: 23
<212> TYPE: PRT
<213> ORGANISM: Mus musculus

<400> SEQUENCE: 413

Asp Val Val Met Thr Gln Thr Pro Leu Thr Leu Ser Val Thr Ile Gly
1               5                   10                  15

Gln Pro Ala Ser Ile Ser Cys
            20

<210> SEQ ID NO 414
<211> LENGTH: 15
<212> TYPE: PRT
<213> ORGANISM: Mus musculus

<400> SEQUENCE: 414

Trp Leu Leu Gln Arg Pro Gly Gln Ser Pro Lys Arg Leu Ile Tyr
1               5                   10                  15

<210> SEQ ID NO 415
<211> LENGTH: 32
<212> TYPE: PRT
<213> ORGANISM: Mus musculus

<400> SEQUENCE: 415

Gly Ala Pro Asp Arg Phe Thr Gly Ser Gly Ser Gly Thr Asp Phe Thr
1               5                   10                  15

Leu Lys Ile Ser Arg Val Glu Ala Glu Asp Leu Gly Val Tyr Tyr Cys
            20                  25                  30
```

```
<210> SEQ ID NO 416
<211> LENGTH: 10
<212> TYPE: PRT
<213> ORGANISM: Mus musculus

<400> SEQUENCE: 416

Phe Gly Gly Gly Thr Lys Leu Glu Ile Lys
1               5                   10

<210> SEQ ID NO 417
<211> LENGTH: 19
<212> TYPE: PRT
<213> ORGANISM: Mus musculus

<400> SEQUENCE: 417

Met Gly Trp Ser Trp Ile Phe Leu Phe Leu Leu Ser Gly Thr Ala Gly
1               5                   10                  15

Val Leu Ser

<210> SEQ ID NO 418
<211> LENGTH: 19
<212> TYPE: PRT
<213> ORGANISM: Mus musculus

<400> SEQUENCE: 418

Met Ser Pro Ala Gln Phe Leu Phe Leu Leu Val Leu Trp Ile Arg Glu
1               5                   10                  15

Thr Asn Gly

<210> SEQ ID NO 419
<211> LENGTH: 375
<212> TYPE: DNA
<213> ORGANISM: Homo sapiens

<400> SEQUENCE: 419
caggtgcagc tgcagcagtc cggcccggga ctggtgaagc ctagccagac actgtccctg      60
acctgcgcca tcagcggcga tagcgtgagc tccaattccg ccgcctggaa ttggatcagg     120 cagtcccta gcagaggcct ggagtggctg ggcagaacct actacagaag caagtggtac      180
aatgattacg ccgtgagcgt gaagtccagg atcaccatca accccgacac ctccaagaac     240
cagttctccc tgcagctgaa tagcgtgaca cctgaggata cagccgtgta ctactgtgcc     300
agagacgatt acgaccccgt gggcatgtac gccttcgata tctggggcca gggcaccctg     360
gtgacagtga gcagc                                                      375

<210> SEQ ID NO 420
<211> LENGTH: 330
<212> TYPE: DNA
<213> ORGANISM: Homo sapiens

<400> SEQUENCE: 420
ctgcctgtgc tgacccagcc ccctctgcc agcggaacac ccggacagag ggtgaccatc        60
tcctgctccg gcagcagctc caatatcggc agcaatacag tgaactggta ccagcagctg     120
cccggcaccg cccctaagct gctgatctac aggaacaccc agagaccctc cggcgtgcct     180
gatagatttt ccggcagcaa gagcggcacc agcgccagcc tggccatctc cggactgcag     240
agcgaggacg aggccgacta ctactgtgag gcctgggatg attccatgag gggcgccgcc     300
tttggcggcg gaacccaact gacagtgctg                                      330
```

-continued

```
<210> SEQ ID NO 421
<211> LENGTH: 125
<212> TYPE: PRT
<213> ORGANISM: Homo sapiens

<400> SEQUENCE: 421

Gln Val Gln Leu Gln Gln Ser Gly Pro Gly Leu Val Lys Pro Ser Gln
1               5                   10                  15

Thr Leu Ser Leu Thr Cys Ala Ile Ser Gly Asp Ser Val Ser Ser Asn
            20                  25                  30

Ser Ala Ala Trp Asn Trp Ile Arg Gln Ser Pro Ser Arg Gly Leu Glu
        35                  40                  45

Trp Leu Gly Arg Thr Tyr Tyr Arg Ser Lys Trp Tyr Asn Asp Tyr Ala
    50                  55                  60

Val Ser Val Lys Ser Arg Ile Thr Ile Asn Pro Asp Thr Ser Lys Asn
65                  70                  75                  80

Gln Phe Ser Leu Gln Leu Asn Ser Val Thr Pro Glu Asp Thr Ala Val
            85                  90                  95

Tyr Tyr Cys Ala Arg Asp Asp Tyr Asp Pro Val Gly Met Tyr Ala Phe
                100                 105                 110

Asp Ile Trp Gly Gln Gly Thr Leu Val Thr Val Ser Ser
            115                 120                 125

<210> SEQ ID NO 422
<211> LENGTH: 110
<212> TYPE: PRT
<213> ORGANISM: Homo sapiens

<400> SEQUENCE: 422

Leu Pro Val Leu Thr Gln Pro Pro Ser Ala Ser Gly Thr Pro Gly Gln
1               5                   10                  15

Arg Val Thr Ile Ser Cys Ser Gly Ser Ser Ser Asn Ile Gly Ser Asn
            20                  25                  30

Thr Val Asn Trp Tyr Gln Gln Leu Pro Gly Thr Ala Pro Lys Leu Leu
        35                  40                  45

Ile Tyr Arg Asn Thr Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Glu Ala Trp Asp Asp Ser Met
            85                  90                  95

Arg Gly Ala Ala Phe Gly Gly Gly Thr Gln Leu Thr Val Leu
                100                 105                 110

<210> SEQ ID NO 423
<211> LENGTH: 10
<212> TYPE: PRT
<213> ORGANISM: Homo sapiens

<400> SEQUENCE: 423

Gly Asp Ser Val Ser Ser Asn Ser Ala Ala
1               5                   10

<210> SEQ ID NO 424
<211> LENGTH: 9
<212> TYPE: PRT
<213> ORGANISM: Homo sapiens

<400> SEQUENCE: 424
```

```
Thr Tyr Tyr Arg Ser Lys Trp Tyr Asn
1               5

<210> SEQ ID NO 425
<211> LENGTH: 15
<212> TYPE: PRT
<213> ORGANISM: Homo sapiens

<400> SEQUENCE: 425

Ala Arg Asp Asp Tyr Asp Pro Val Gly Met Tyr Ala Phe Asp Ile
1               5                   10                  15

<210> SEQ ID NO 426
<211> LENGTH: 8
<212> TYPE: PRT
<213> ORGANISM: Homo sapiens

<400> SEQUENCE: 426

Ser Ser Asn Ile Gly Ser Asn Thr
1               5

<210> SEQ ID NO 427
<211> LENGTH: 3
<212> TYPE: PRT
<213> ORGANISM: Homo sapiens

<400> SEQUENCE: 427

Arg Asn Thr
1

<210> SEQ ID NO 428
<211> LENGTH: 11
<212> TYPE: PRT
<213> ORGANISM: Homo sapiens

<400> SEQUENCE: 428

Glu Ala Trp Asp Asp Ser Met Arg Gly Ala Ala
1               5                   10

<210> SEQ ID NO 429
<211> LENGTH: 25
<212> TYPE: PRT
<213> ORGANISM: Homo sapiens

<400> SEQUENCE: 429

Gln Val Gln Leu Gln Gln Ser Gly Pro Gly Leu Val Lys Pro Ser Gln
1               5                   10                  15

Thr Leu Ser Leu Thr Cys Ala Ile Ser
            20                  25

<210> SEQ ID NO 430
<211> LENGTH: 17
<212> TYPE: PRT
<213> ORGANISM: Homo sapiens

<400> SEQUENCE: 430

Trp Asn Trp Ile Arg Gln Ser Pro Ser Arg Gly Leu Glu Trp Leu Gly
1               5                   10                  15

Arg

<210> SEQ ID NO 431
<211> LENGTH: 38
<212> TYPE: PRT
```

-continued

```
<213> ORGANISM: Homo sapiens

<400> SEQUENCE: 431

Asp Tyr Ala Val Ser Val Lys Ser Arg Ile Thr Ile Asn Pro Asp Thr
1               5                   10                  15

Ser Lys Asn Gln Phe Ser Leu Gln Leu Asn Ser Val Thr Pro Glu Asp
            20                  25                  30

Thr Ala Val Tyr Tyr Cys
        35

<210> SEQ ID NO 432
<211> LENGTH: 11
<212> TYPE: PRT
<213> ORGANISM: Homo sapiens

<400> SEQUENCE: 432

Trp Gly Gln Gly Thr Leu Val Thr Val Ser Ser
1               5                   10

<210> SEQ ID NO 433
<211> LENGTH: 25
<212> TYPE: PRT
<213> ORGANISM: Homo sapiens

<400> SEQUENCE: 433

Leu Pro Val Leu Thr Gln Pro Pro Ser Ala Ser Gly Thr Pro Gly Gln
1               5                   10                  15

Arg Val Thr Ile Ser Cys Ser Gly Ser
            20                  25

<210> SEQ ID NO 434
<211> LENGTH: 17
<212> TYPE: PRT
<213> ORGANISM: Homo sapiens

<400> SEQUENCE: 434

Val Asn Trp Tyr Gln Gln Leu Pro Gly Thr Ala Pro Lys Leu Leu Ile
1               5                   10                  15

Tyr

<210> SEQ ID NO 435
<211> LENGTH: 36
<212> TYPE: PRT
<213> ORGANISM: Homo sapiens

<400> SEQUENCE: 435

Gln Arg Pro Ser Gly Val Pro Asp Arg Phe Ser Gly Ser Lys Ser Gly
1               5                   10                  15

Thr Ser Ala Ser Leu Ala Ile Ser Gly Leu Gln Ser Glu Asp Glu Ala
            20                  25                  30

Asp Tyr Tyr Cys
        35

<210> SEQ ID NO 436
<211> LENGTH: 10
<212> TYPE: PRT
<213> ORGANISM: Homo sapiens

<400> SEQUENCE: 436

Phe Gly Gly Gly Thr Gln Leu Thr Val Leu
1               5                   10
```

<210> SEQ ID NO 437
<211> LENGTH: 19
<212> TYPE: PRT
<213> ORGANISM: Homo sapiens

<400> SEQUENCE: 437

Met Lys His Leu Trp Phe Phe Leu Leu Leu Val Ala Ala Pro Arg Trp
1               5                   10                  15

Val Leu Ser

<210> SEQ ID NO 438
<211> LENGTH: 20
<212> TYPE: PRT
<213> ORGANISM: Homo sapiens

<400> SEQUENCE: 438

Met Val Leu Gln Thr Gln Val Phe Ile Ser Leu Leu Leu Trp Ile Ser
1               5                   10                  15

Gly Ala Tyr Gly
            20

<210> SEQ ID NO 439
<211> LENGTH: 9
<212> TYPE: PRT
<213> ORGANISM: Artificial Sequence
<220> FEATURE:
<223> OTHER INFORMATION: Light CDR3 consensus sequence
<220> FEATURE:
<221> NAME/KEY: MISC_FEATURE
<222> LOCATION: (5)..(5)
<223> OTHER INFORMATION: Tyr or Ser
<220> FEATURE:
<221> NAME/KEY: MISC_FEATURE
<222> LOCATION: (8)..(8)
<223> OTHER INFORMATION: Pro or Thr
<220> FEATURE:
<221> NAME/KEY: MISC_FEATURE
<222> LOCATION: (9)..(9)
<223> OTHER INFORMATION: Thr or no amino acid

<400> SEQUENCE: 439

Gln Gln Tyr Tyr Xaa Tyr Pro Xaa Xaa
1               5

<210> SEQ ID NO 440
<211> LENGTH: 6
<212> TYPE: PRT
<213> ORGANISM: Artificial Sequence
<220> FEATURE:
<223> OTHER INFORMATION: Heavy CDR1 consensus sequence
<220> FEATURE:
<221> NAME/KEY: MISC_FEATURE
<222> LOCATION: (3)..(3)
<223> OTHER INFORMATION: any amino acid

<400> SEQUENCE: 440

Ser Asp Xaa Ala Trp Asn
1               5

<210> SEQ ID NO 441
<211> LENGTH: 6
<212> TYPE: PRT
<213> ORGANISM: Artificial Sequence
<220> FEATURE:
<223> OTHER INFORMATION: Heavy CDR1 consensus sequence
<220> FEATURE:
<221> NAME/KEY: MISC_FEATURE
<222> LOCATION: (3)..(3)

```
<223> OTHER INFORMATION: Phe or Tyr

<400> SEQUENCE: 441

Ser Asp Xaa Ala Trp Asn
1               5

<210> SEQ ID NO 442
<211> LENGTH: 16
<212> TYPE: PRT
<213> ORGANISM: Artificial Sequence
<220> FEATURE:
<223> OTHER INFORMATION: Heavy CDR2 consensus sequence
<220> FEATURE:
<221> NAME/KEY: MISC_FEATURE
<222> LOCATION: (1)..(1)
<223> OTHER INFORMATION: any amino acid
<220> FEATURE:
<221> NAME/KEY: MISC_FEATURE
<222> LOCATION: (6)..(6)
<223> OTHER INFORMATION: any amino acid
<220> FEATURE:
<221> NAME/KEY: MISC_FEATURE
<222> LOCATION: (7)..(7)
<223> OTHER INFORMATION: any amino acid
<220> FEATURE:
<221> NAME/KEY: MISC_FEATURE
<222> LOCATION: (10)..(10)
<223> OTHER INFORMATION: any amino acid
<220> FEATURE:
<221> NAME/KEY: MISC_FEATURE
<222> LOCATION: (15)..(15)
<223> OTHER INFORMATION: any amino acid

<400> SEQUENCE: 442

Xaa Ile Thr Tyr Ser Xaa Xaa Thr Asn Xaa Asn Pro Ser Leu Xaa Ser
1               5                   10                  15

<210> SEQ ID NO 443
<211> LENGTH: 16
<212> TYPE: PRT
<213> ORGANISM: Artificial Sequence
<220> FEATURE:
<223> OTHER INFORMATION: Heavy CDR2 consensus sequence
<220> FEATURE:
<221> NAME/KEY: MISC_FEATURE
<222> LOCATION: (1)..(1)
<223> OTHER INFORMATION: Tyr or Phe
<220> FEATURE:
<221> NAME/KEY: MISC_FEATURE
<222> LOCATION: (6)..(6)
<223> OTHER INFORMATION: Gly or Asp
<220> FEATURE:
<221> NAME/KEY: MISC_FEATURE
<222> LOCATION: (7)..(7)
<223> OTHER INFORMATION: Tyr or His or Asn
<220> FEATURE:
<221> NAME/KEY: MISC_FEATURE
<222> LOCATION: (10)..(10)
<223> OTHER INFORMATION: Tyr or Phe
<220> FEATURE:
<221> NAME/KEY: MISC_FEATURE
<222> LOCATION: (15)..(15)
<223> OTHER INFORMATION: Lys or Ile or Arg

<400> SEQUENCE: 443

Xaa Ile Thr Tyr Ser Xaa Xaa Thr Asn Xaa Asn Pro Ser Leu Xaa Ser
1               5                   10                  15

<210> SEQ ID NO 444
<211> LENGTH: 7
<212> TYPE: PRT
<213> ORGANISM: Artificial Sequence
<220> FEATURE:
```

<223> OTHER INFORMATION: Heavy CDR3 consensus sequence
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (3)..(3)
<223> OTHER INFORMATION: any amino acid
<220> FEATURE:
<221> NAME/KEY: MISC_FEATURE
<222> LOCATION: (4)..(4)
<223> OTHER INFORMATION: any amino acid

<400> SEQUENCE: 444

Ser Xaa Xaa Xaa Phe Asp Tyr
1               5

<210> SEQ ID NO 445
<211> LENGTH: 7
<212> TYPE: PRT
<213> ORGANISM: Artificial Sequence
<220> FEATURE:
<223> OTHER INFORMATION: Heavy CDR3 consensus sequence
<220> FEATURE:
<221> NAME/KEY: MISC_FEATURE
<222> LOCATION: (2)..(2)
<223> OTHER INFORMATION: Thr or Gly
<220> FEATURE:
<221> NAME/KEY: MISC_FEATURE
<222> LOCATION: (3)..(3)
<223> OTHER INFORMATION: Thr or Ala or Asn
<220> FEATURE:
<221> NAME/KEY: MISC_FEATURE
<222> LOCATION: (4)..(4)
<223> OTHER INFORMATION: Tyr or Phe

<400> SEQUENCE: 445

Ser Xaa Xaa Xaa Phe Asp Tyr
1               5

<210> SEQ ID NO 446
<211> LENGTH: 16
<212> TYPE: PRT
<213> ORGANISM: Artificial Sequence
<220> FEATURE:
<223> OTHER INFORMATION: Light CDR1 consensus sequence
<220> FEATURE:
<221> NAME/KEY: MISC_FEATURE
<222> LOCATION: (5)..(5)
<223> OTHER INFORMATION: any amino acid
<220> FEATURE:
<221> NAME/KEY: MISC_FEATURE
<222> LOCATION: (6)..(6)
<223> OTHER INFORMATION: any amino acid
<220> FEATURE:
<221> NAME/KEY: MISC_FEATURE
<222> LOCATION: (7)..(7)
<223> OTHER INFORMATION: any amino acid

<400> SEQUENCE: 446

Arg Ser Ser Gln Xaa Xaa Xaa His Ser Asp Gly Asn Thr Tyr Leu Glu
1               5                   10                  15

<210> SEQ ID NO 447
<211> LENGTH: 16
<212> TYPE: PRT
<213> ORGANISM: Artificial Sequence
<220> FEATURE:
<223> OTHER INFORMATION: Light CDR1 consensus sequence
<220> FEATURE:
<221> NAME/KEY: MISC_FEATURE
<222> LOCATION: (5)..(5)

```
<223> OTHER INFORMATION: Ser or Thr
<220> FEATURE:
<221> NAME/KEY: MISC_FEATURE
<222> LOCATION: (6)..(6)
<223> OTHER INFORMATION: Ile or Val
<220> FEATURE:
<221> NAME/KEY: MISC_FEATURE
<222> LOCATION: (7)..(7)
<223> OTHER INFORMATION: Leu or Val or Ile

<400> SEQUENCE: 447

Arg Ser Ser Gln Xaa Xaa Xaa His Ser Asp Gly Asn Thr Tyr Leu Glu
1               5                   10                  15

<210> SEQ ID NO 448
<211> LENGTH: 17
<212> TYPE: PRT
<213> ORGANISM: Artificial Sequence
<220> FEATURE:
<223> OTHER INFORMATION: Light CDR1 consensus sequence
<220> FEATURE:
<221> NAME/KEY: MISC_FEATURE
<222> LOCATION: (1)..(1)
<223> OTHER INFORMATION: any amino acid
<220> FEATURE:
<221> NAME/KEY: MISC_FEATURE
<222> LOCATION: (5)..(5)
<223> OTHER INFORMATION: any amino acid
<220> FEATURE:
<221> NAME/KEY: MISC_FEATURE
<222> LOCATION: (6)..(6)
<223> OTHER INFORMATION: any amino acid
<220> FEATURE:
<221> NAME/KEY: MISC_FEATURE
<222> LOCATION: (7)..(7)
<223> OTHER INFORMATION: any amino acid
<220> FEATURE:
<221> NAME/KEY: MISC_FEATURE
<222> LOCATION: (8)..(8)
<223> OTHER INFORMATION: any amino acid
<220> FEATURE:
<221> NAME/KEY: MISC_FEATURE
<222> LOCATION: (10)..(10)
<223> OTHER INFORMATION: any amino acid
<220> FEATURE:
<221> NAME/KEY: MISC_FEATURE
<222> LOCATION: (11)..(11)
<223> OTHER INFORMATION: any amino acid
<220> FEATURE:
<221> NAME/KEY: MISC_FEATURE
<222> LOCATION: (12)..(12)
<223> OTHER INFORMATION: any amino acid or no amino acid
<220> FEATURE:
<221> NAME/KEY: MISC_FEATURE
<222> LOCATION: (13)..(13)
<223> OTHER INFORMATION: any amino acid
<220> FEATURE:
<221> NAME/KEY: MISC_FEATURE
<222> LOCATION: (14)..(14)
<223> OTHER INFORMATION: any amino acid
<220> FEATURE:
<221> NAME/KEY: MISC_FEATURE
<222> LOCATION: (15)..(15)
<223> OTHER INFORMATION: any amino acid
<220> FEATURE:
<221> NAME/KEY: MISC_FEATURE
<222> LOCATION: (17)..(17)
<223> OTHER INFORMATION: any amino acid

<400> SEQUENCE: 448

Xaa Ser Ser Gln Xaa Xaa Xaa Xaa Ser Xaa Xaa Xaa Xaa Xaa Xaa Leu
1               5                   10                  15

Xaa
```

```
<210> SEQ ID NO 449
<211> LENGTH: 17
<212> TYPE: PRT
<213> ORGANISM: Artificial Sequence
<220> FEATURE:
<223> OTHER INFORMATION: Light CDR1 consensus sequence
<220> FEATURE:
<221> NAME/KEY: MISC_FEATURE
<222> LOCATION: (1)..(1)
<223> OTHER INFORMATION: Lys or Arg
<220> FEATURE:
<221> NAME/KEY: MISC_FEATURE
<222> LOCATION: (5)..(5)
<223> OTHER INFORMATION: Ser or Thr
<220> FEATURE:
<221> NAME/KEY: MISC_FEATURE
<222> LOCATION: (6)..(6)
<223> OTHER INFORMATION: Leu or Ile or Val
<220> FEATURE:
<221> NAME/KEY: MISC_FEATURE
<222> LOCATION: (7)..(7)
<223> OTHER INFORMATION: Leu or Ile or Val
<220> FEATURE:
<221> NAME/KEY: MISC_FEATURE
<222> LOCATION: (8)..(8)
<223> OTHER INFORMATION: His or Asp or Tyr
<220> FEATURE:
<221> NAME/KEY: MISC_FEATURE
<222> LOCATION: (10)..(10)
<223> OTHER INFORMATION: Ser or Ala or Asp
<220> FEATURE:
<221> NAME/KEY: MISC_FEATURE
<222> LOCATION: (11)..(11)
<223> OTHER INFORMATION: Gly or Asn
<220> FEATURE:
<221> NAME/KEY: MISC_FEATURE
<222> LOCATION: (12)..(12)
<223> OTHER INFORMATION: Gln or no amino acid
<220> FEATURE:
<221> NAME/KEY: MISC_FEATURE
<222> LOCATION: (13)..(13)
<223> OTHER INFORMATION: Lys or Asn
<220> FEATURE:
<221> NAME/KEY: MISC_FEATURE
<222> LOCATION: (14)..(14)
<223> OTHER INFORMATION: Thr or Asn
<220> FEATURE:
<221> NAME/KEY: MISC_FEATURE
<222> LOCATION: (15)..(15)
<223> OTHER INFORMATION: Tyr or Cys
<220> FEATURE:
<221> NAME/KEY: MISC_FEATURE
<222> LOCATION: (17)..(17)
<223> OTHER INFORMATION: Ala or Asn or Glu

<400> SEQUENCE: 449

Xaa Ser Ser Gln Xaa Xaa Xaa Xaa Ser Xaa Xaa Xaa Xaa Xaa Xaa Leu
1               5                   10                  15

Xaa

<210> SEQ ID NO 450
<211> LENGTH: 9
<212> TYPE: PRT
<213> ORGANISM: Artificial Sequence
<220> FEATURE:
<223> OTHER INFORMATION: Light CDR3 consensus sequence
<220> FEATURE:
<221> NAME/KEY: MISC_FEATURE
<222> LOCATION: (1)..(1)
<223> OTHER INFORMATION: any amino acid
<220> FEATURE:
<221> NAME/KEY: MISC_FEATURE
<222> LOCATION: (4)..(4)
<223> OTHER INFORMATION: any amino acid
<220> FEATURE:
<221> NAME/KEY: MISC_FEATURE
```

-continued

```
<222> LOCATION: (6)..(6)
<223> OTHER INFORMATION: any amino acid
<220> FEATURE:
<221> NAME/KEY: MISC_FEATURE
<222> LOCATION: (8)..(8)
<223> OTHER INFORMATION: any amino acid or no amino acid

<400> SEQUENCE: 450

Xaa Gln Gly Xaa His Xaa Pro Xaa Thr
1               5

<210> SEQ ID NO 451
<211> LENGTH: 9
<212> TYPE: PRT
<213> ORGANISM: Artificial Sequence
<220> FEATURE:
<223> OTHER INFORMATION: Light CDR3 consensus sequence
<220> FEATURE:
<221> NAME/KEY: MISC_FEATURE
<222> LOCATION: (1)..(1)
<223> OTHER INFORMATION: Trp or Phe or Ser
<220> FEATURE:
<221> NAME/KEY: MISC_FEATURE
<222> LOCATION: (4)..(4)
<223> OTHER INFORMATION: Thr or Ser
<220> FEATURE:
<221> NAME/KEY: MISC_FEATURE
<222> LOCATION: (6)..(6)
<223> OTHER INFORMATION: Phe or Val
<220> FEATURE:
<221> NAME/KEY: MISC_FEATURE
<222> LOCATION: (8)..(8)
<223> OTHER INFORMATION: Pro or Tyr or no amino acid

<400> SEQUENCE: 451

Xaa Gln Gly Xaa His Xaa Pro Xaa Thr
1               5

<210> SEQ ID NO 452
<211> LENGTH: 9
<212> TYPE: PRT
<213> ORGANISM: Artificial Sequence
<220> FEATURE:
<223> OTHER INFORMATION: Light CDR3 consensus sequence
<220> FEATURE:
<221> NAME/KEY: MISC_FEATURE
<222> LOCATION: (5)..(5)
<223> OTHER INFORMATION: any amino acid
<220> FEATURE:
<221> NAME/KEY: MISC_FEATURE
<222> LOCATION: (8)..(8)
<223> OTHER INFORMATION: any amino acid
<220> FEATURE:
<221> NAME/KEY: MISC_FEATURE
<222> LOCATION: (9)..(9)
<223> OTHER INFORMATION: any amino acid or no amino acid

<400> SEQUENCE: 452

Gln Gln Tyr Tyr Xaa Tyr Pro Xaa Xaa
1               5
```